(12) United States Patent
Shuber

(10) Patent No.: US 11,788,152 B2
(45) Date of Patent: Oct. 17, 2023

(54) MULTIPLE-TIERED SCREENING AND SECOND ANALYSIS

(71) Applicant: Flagship Pioneering Innovations VI, LLC, Cambridge, MA (US)

(72) Inventor: Anthony P. Shuber, Cambridge, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 17/898,154

(22) Filed: Aug. 29, 2022

(65) Prior Publication Data

US 2023/0242991 A1    Aug. 3, 2023

Related U.S. Application Data

(60) Provisional application No. 63/312,741, filed on Feb. 22, 2022, provisional application No. 63/304,536, filed on Jan. 28, 2022.

(51) Int. Cl.
| | | |
|---|---|---|
| *C12Q 1/6886* | (2018.01) | |
| *C12Q 1/6869* | (2018.01) | |
| *G16B 5/20* | (2019.01) | |
| *G16B 20/20* | (2019.01) | |
| *G16B 40/00* | (2019.01) | |

(52) U.S. Cl.
CPC ......... *C12Q 1/6886* (2013.01); *C12Q 1/6869* (2013.01); *G16B 5/20* (2019.02); *C12Q 2600/118* (2013.01); *C12Q 2600/154* (2013.01); *C12Q 2600/156* (2013.01); *G16B 20/20* (2019.02); *G16B 40/00* (2019.02)

(58) Field of Classification Search
CPC ...... C12Q 1/6886; C12Q 1/6869; G16B 5/20; G16B 20/20; G16B 40/00
See application file for complete search history.

(56) References Cited

U.S. PATENT DOCUMENTS

| | | |
|---|---|---|
| 2006/0160105 A1 | 7/2006 | Dhallan |
| 2018/0237863 A1 | 8/2018 | Namsaraev et al. |
| 2019/0256921 A1 * | 8/2019 | Mueller ................ G16B 99/00 |
| 2019/0256931 A1 | 8/2019 | Babiarz et al. |
| 2020/0392586 A1 | 12/2020 | Frumkin et al. |

FOREIGN PATENT DOCUMENTS

| | | |
|---|---|---|
| WO | WO1997/09925 A2 | 3/1997 |
| WO | 2018209361 A2 | 11/2018 |
| WO | WO2021/202351 A1 | 10/2021 |
| WO | WO2022/029449 A1 | 2/2022 |
| WO | 2022133315 A1 | 6/2022 |

OTHER PUBLICATIONS

Notification of Transmittal of the International Search Report and the Written Opinion of the International Searching Authority for PCT Application No. PCT/US2023/061606 dated Jul. 26, 2023.
Notification of Transmittal of the International Search Report and the Written Opinion of the International Searching Authority for PCT Application No. PCT/US2023/013657 dated Aug. 1, 2023.

* cited by examiner

*Primary Examiner* — Jerry Lin
(74) *Attorney, Agent, or Firm* — Goodwin Procter LLP

(57) ABSTRACT

Disclosed herein are methods, non-transitory computer readable media, systems, and kits for performing a multiple tiered analysis for identifying individuals with a health condition for monitoring, treating, and/or enrolling the individuals in a clinical trial. Specifically, the multiple tiered analysis involves a first screen, which eliminates a large proportion of individuals who are identified as not at risk for a health condition, and a subsequent second analysis which detects presence of a health condition in the remaining individuals. The second analysis includes an intra-individual analysis, which involves combining sequence information from target nucleic acids and reference nucleic acids obtained from the individual. The target nucleic acids include signatures that may be informative for determining presence or absence of the health condition and the reference nucleic acids include baseline biological signatures of the individual. Altogether, the multiple tiered analysis achieves improved performance and accurate identification of individuals with the health condition.

10 Claims, 18 Drawing Sheets
Specification includes a Sequence Listing.

SEQUENCE LISTING

```
Sequence total quantity: 3
SEQ ID NO: 1            moltype = DNA  length = 11
FEATURE                 Location/Qualifiers
source                  1..11
                        mol_type = genomic DNA
                        organism = Homo sapiens
SEQUENCE: 1
acggtcgacg t                                                               11

SEQ ID NO: 2            moltype = DNA  length = 11
FEATURE                 Location/Qualifiers
source                  1..11
                        mol_type = genomic DNA
                        organism = Homo sapiens
SEQUENCE: 2
acggttgatg c                                                               11

SEQ ID NO: 3            moltype = DNA  length = 11
FEATURE                 Location/Qualifiers
source                  1..11
                        mol_type = genomic DNA
                        organism = Homo sapiens
SEQUENCE: 3
acggtcgacg t                                                               11
```

MULTIPLE-TIERED SCREENING AND SECOND ANALYSIS

CROSS-REFERENCE TO RELATED APPLICATIONS

This application claims priority to and the benefit of U.S. Provisional Application No. 63/312,741 filed Feb. 22, 2022, and U.S. Provisional Application No. 63/304,536 filed Jan. 28, 2022, which are incorporated herein by reference in their entirety.

REFERENCE TO A SEQUENCE LISTING XML

This application contains a Sequence Listing which has been submitted electronically in XML format. The Sequence Listing XML is incorporated herein by reference. Said XML file, created on Sep. 21, 2022, is named FLG-011-VL67010-US-02_SL.xml and is 3,698 in size.

BACKGROUND

Diagnostic technologies include simple, point of care (POC) tests applied to large populations to identify relatively common diseases as well as complex, centralized tests applied to select populations. However, although POC tests can be applied to large populations, they are incapable of diagnosing individuals for rare health conditions at a high enough accuracy to be feasible for implementation. Similarly, although complex, centralized testing can be deployed for rare population testing, such testing is often invasive, expensive, and fails when applied for detecting rare health conditions in large patient populations. For example, complex, centralized testing suffers from poor performance (e.g., high number of false positives and/or low positive predictive value) when attempting to diagnose rare health conditions in large patient populations.

SUMMARY

Disclosed herein are methods involving a multiple tiered analysis for identifying individuals with a health condition. In particular, the methods disclosed herein involving a multiple tiered analysis are useful for identifying individuals from a large population (e.g., millions of individuals) who have a rare health condition. The multiple tiered analysis involves a first screen, which eliminates a large proportion of individuals who are identified as not at risk for a health condition.

In various embodiments, the multiple tiered analysis involves an individual-specific analysis, hereafter referred to as an intra-individual analysis, for determining presence or absence of a health condition in the individual. The intra-individual analysis removes baseline biological signatures of the individual which are less informative or not informative of presence of absence of the health condition. By eliminating baseline biological signatures, the remaining signatures are used to more accurately predict presence or absence of a health condition in the individual. The intra-individual analysis is useful because it accounts for baseline biological signatures that may be unique for each individual. As a result, the intra-individual analysis generates a background-corrected signal for an individual that accounts for baseline biological signatures unique to the individual. Specifically, the intra-individual analysis involves combining sequence information from target nucleic acids with sequence information from reference nucleic acids obtained from the individual. The target nucleic acids include signatures that are informative for determining presence or absence of the health condition and the reference nucleic acids include baseline biological signatures of the individual. By combining sequence information from the target nucleic acids and the reference nucleic acids, the resulting combined signal is more informative for determining presence or absence of the health condition in comparison to sequence information of the target nucleic acids alone.

In various embodiments, the multiple tiered analysis further involves a second analysis which analyzes the background-corrected signal determined via the intra-individual analysis. The second analysis detects presence of a health condition in the remaining individuals.

Altogether, the multiple tiered analysis (e.g., including a screen, intra-individual analysis, and second analysis) achieves improved performance (e.g., high positive predictive value, negative predictive value, sensitivity, and specificity), thereby enabling accurate identification of individuals with the health condition.

Disclosed herein is a tiered, multipart method for detecting circulating tumor DNA in a biological sample of a subject, the method comprising: performing a first analysis of nucleic acid sequence information that was derived from a first assay performed on the biological sample to identify whether the biological sample is not at risk of containing circulating tumor DNA, and then if the biological sample is not identified as not at risk: obtaining target nucleic acids and reference nucleic acids from the biological sample or an additional biological sample obtained from the subject; performing bisulfite conversion of the target nucleic acids and the reference nucleic acids; selectively amplifying target regions of the bisulfite converted target nucleic acids and/or reference nucleic acids generating a dataset comprising methylation information from the target nucleic acids and methylation information from the reference nucleic acids; using a computer processor, combining the methylation information from the target nucleic acids and the methylation information from the reference nucleic acids to generate background-corrected methylation information for the target nucleic acids; and performing a second analysis comprising analyzing the background-corrected methylation information to detect the presence of the circulating tumor DNA in the biological sample.

In various embodiments, the biological sample or the additional biological sample is a blood sample. In various embodiments, obtaining target nucleic acids and reference nucleic acids comprises fractionating the biological sample or the additional sample, wherein the target nucleic acids are obtained from a first fraction of the biological sample or the additional biological sample, and wherein the reference nucleic acids are obtained from a second fraction of the biological sample or the additional biological sample. In various embodiments, the target nucleic acids comprise cell free DNA (cfDNA), and wherein the reference nucleic acids comprise genomic DNA from cells of the subject. In various embodiments, the cells of the subject comprise peripheral blood mononuclear cells (PBMCs) or polymorphonuclear cells.

In various embodiments, combining the methylation information from the target nucleic acids and the methylation information from the reference nucleic acids comprises: aligning the methylation information from the target nucleic acids and the methylation information from the reference nucleic acids; and determining a difference between the methylation information from the target nucleic acids and the methylation information from the reference nucleic acids. In various embodiments, the methylation information of the target nucleic acids and the methylation information of the reference nucleic acids both comprise methylation statuses for a plurality of genomic sites. In various embodiments, the plurality of genomic sites comprise a plurality of CpG sites shown in any of Tables 1-4.

Additionally disclosed herein is a tiered, multipart method for detecting circulating tumor DNA in a biological sample of a subject, the method comprising: performing a first analysis of nucleic acid sequence information that was derived from a first assay performed on the biological sample to identify whether the biological sample is not at risk of containing circulating tumor DNA, and then if the biological sample is not identified as not at risk: obtaining target nucleic acids and reference nucleic acids from the biological sample or an additional biological sample obtained from the subject; processing the target nucleic acids and reference nucleic acids to generate a dataset comprising methylation information from the target nucleic acids and methylation information from the reference nucleic acids, wherein processing the target nucleic acids and reference nucleic acids to generate the dataset comprises performing a second assay, wherein the second assay comprises one or more of: a. sequencing of target nucleic acids and/or reference nucleic acids via targeted sequencing, whole genome sequencing, or whole genome bisulfite sequencing; b. a nucleic acid amplification assay; and c. an assay that generates methylation information; using a computer processor, combining the methylation information from the target nucleic acids and the methylation information from the reference nucleic acids to generate background-corrected methylation information for the target nucleic acids, and performing a second analysis comprising analyzing the background-corrected methylation information to detect the presence of the circulating tumor DNA in the biological sample. In various embodiments, the biological sample or the additional biological sample is a blood sample. In various embodiments, obtaining target nucleic acids and reference nucleic acids comprises fractionating the biological sample or the additional sample, wherein the target nucleic acids are obtained from a first fraction of the biological sample or the additional biological sample, and wherein the reference nucleic acids are obtained from a second fraction of the biological sample or the additional biological sample. In various embodiments, the target nucleic acids comprise cell free DNA (cfDNA), and wherein the reference nucleic acids comprise genomic DNA from cells of the subject. In various embodiments, the cells of the subject comprise peripheral blood mononuclear cells (PBMCs) or polymorphonuclear cells.

In various embodiments, combining the methylation information from the target nucleic acids and the methylation information from the reference nucleic acids comprises: aligning the methylation information from the target nucleic acids and the methylation information from the reference nucleic acids; and determining a difference between the methylation information from the target nucleic acids and the methylation information from the reference nucleic acids. In various embodiments, the methylation information of the target nucleic acids and the methylation information of the reference nucleic acids both comprise methylation statuses for a plurality of genomic sites. In various embodiments, the plurality of genomic sites comprise a plurality of CpG sites shown in any of Tables 1-4.

Additionally disclosed herein is a tiered, multipart method for detecting circulating tumor DNA in a biological sample of a subject, the method comprising: performing a first analysis of nucleic acid sequence information that was derived from a first assay performed on the biological sample to identify whether the biological sample is not at risk of containing circulating tumor DNA, and then if the biological sample is not identified as not at risk: obtaining target nucleic acids and reference nucleic acids from the biological sample or an additional biological sample obtained from the subject; processing the target nucleic acids and reference nucleic acids to generate a dataset comprising methylation information from the target nucleic acids and methylation information from the reference nucleic acids; using a computer processor, combining the methylation information from the target nucleic acids and the methylation information from the reference nucleic acids to generate background-corrected methylation information for the target nucleic acids; and performing a second analysis comprising analyzing the background-corrected methylation information to detect the presence of the circulating tumor DNA in the biological sample.

In various embodiments, the biological sample or the additional biological sample is a blood sample. In various embodiments, obtaining target nucleic acids and reference nucleic acids comprises fractionating the biological sample or the additional sample, wherein the target nucleic acids are obtained from a first fraction of the biological sample or the additional biological sample, and wherein the reference nucleic acids are obtained from a second fraction of the biological sample or the additional biological sample. In various embodiments, the target nucleic acids comprise cell free DNA (cfDNA), and wherein the reference nucleic acids comprise genomic DNA from cells of the subject. In various embodiments, the cells of the subject comprise peripheral blood mononuclear cells (PBMCs) or polymorphonuclear cells.

In various embodiments, combining the methylation information from the target nucleic acids and the methylation information from the reference nucleic acids comprises: aligning the methylation information from the target nucleic acids and the methylation information from the reference nucleic acids; and determining a difference between the methylation information from the target nucleic acids and the methylation information from the reference nucleic acids. In various embodiments, the methylation information of the target nucleic acids and the methylation information of the reference nucleic acids both comprise methylation statuses for a plurality of genomic sites. In various embodiments, the plurality of genomic sites comprise a plurality of CpG sites shown in any of Tables 1-4. In various embodiments, processing the target nucleic acids and reference nucleic acids to generate the dataset further comprises performing a target enrichment assay. In various embodiments, the target enrichment assay comprises hybrid capture.

BRIEF DESCRIPTION OF THE DRAWINGS

These and other features, aspects, and advantages of the present invention will become better understood with regard to the following description and accompanying drawings. It is noted that wherever practicable, similar or like reference numbers may be used in the figures and may indicate similar or like functionality. For example, a letter after a reference numeral, such as "third party entity 155A," indicates that the text refers specifically to the element having that particular reference numeral. A reference numeral in the text without a following letter, such as "third party entity 155," refers to any or all of the elements in the figures bearing that reference numeral (e.g. "third party entity 155" in the text refers to reference numerals "third party entity 155A" and/or "third party entity 155B" in the figures).

FIG. 2D discloses SEQ ID NOS 1-3, respectively, in order of appearance.

DETAILED DESCRIPTION

Definitions

Figure 1A:
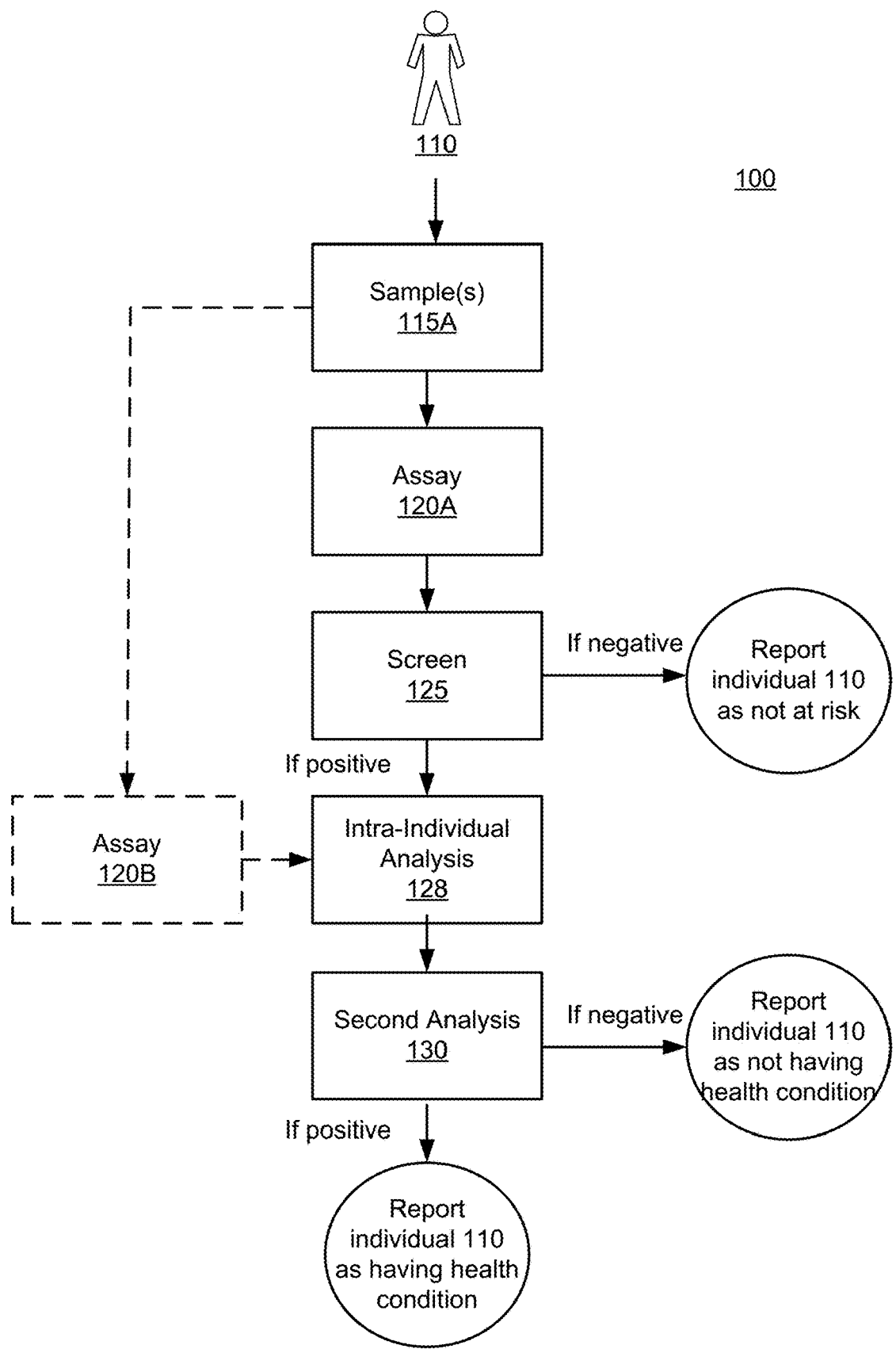
FIG. 1A depicts an overall flow process of the multiple-tiered process for identifying an individual with a health condition, in accordance with an embodiment.

Terms used in the claims and specification are defined as set forth below unless otherwise specified.

The terms "subject," "patient," and "individual" are used interchangeably and encompass a cell, tissue, or organism, human or non-human, male or female.

The term "sample" can include a single cell or multiple cells or fragments of cells or an aliquot of body fluid, such as a blood sample, taken from a subject, by means including venipuncture, excretion, ejaculation, massage, biopsy, needle aspirate, lavage sample, scraping, surgical incision, or intervention or other means known in the art. Examples of an aliquot of body fluid include amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour.

The term "obtaining information," "obtaining marker information," and "obtaining sequence information" encompasses obtaining information that is determined from at least one sample. Obtaining information (e.g., marker information or sequence information) encompasses obtaining a sample and processing the sample to experimentally determine the information (e.g., marker information or sequence information). The phrase also encompasses receiving the information, e.g., from a third party that has processed the sample to experimentally determine the information.

The terms "marker," "markers," "biomarker," and "biomarkers" encompass, without limitation, lipids, lipoproteins, proteins, cytokines, chemokines, growth factors, peptides, nucleic acids (e.g., DNA or RNA), genes, and oligonucleotides, together with their related complexes, metabolites, mutations, variants, polymorphisms, modifications, fragments, subunits, degradation products, elements, and other analytes or sample-derived measures. A marker can also include mutated proteins, mutated nucleic acids, variations in copy numbers, and/or transcript variants, in circumstances in which such mutations, variations in copy number and/or transcript variants are useful for generating a prediction model, or are useful in prediction models developed using related markers (e.g., non-mutated versions of the proteins or nucleic acids, alternative transcripts, etc.).

The term "screen" or a "first analysis" refers to a step in the first tier of a multiple tiered analysis. The screen achieves a high specificity and removes a large majority of true negatives (e.g., individuals not at risk of a health condition). In various embodiments, the "screen" refers to an in silico screen that involves application of a machine learning model. For example, such a machine learning model may analyze sequence information (e.g., methylation information) and predicts whether individuals are likely to be at risk of the health condition.

The phrase "second analysis" refers to a step in the second tier of a multiple tiered analysis. The second analysis is performed on individuals who were identified, using the screen, as at risk for a health condition. Thus, the second analysis achieves a higher positive predictive value than the screen, given that the screen removes a large proportion of the true negatives. In various embodiments, the "second analysis" refers to an in silico analysis that involves application of a machine learning model that analyzes sequence information (e.g., methylation information) and predicts whether individuals have the health condition.

The phrase "intra-individual analysis" refers to an analysis performed for an individual that removes baseline biological signatures that are less informative for determining whether the individual is at risk for a health condition. In various embodiments, the intra-individual analysis involves combining information from target nucleic acids and reference nucleic acids of an individual to generate a signal informative for determining presence or absence of one or more health conditions within the individual. By combining the information from the target nucleic acids and the reference nucleic acids, the generated signal can be more informative of presence or absence of a health condition in comparison to a signal derived from the target nucleic acids alone.

The phrase "target nucleic acids" refers to nucleic acids of an individual that contain at least signatures that may be informative for determining presence or absence of the health condition. The target nucleic acids may further include baseline biological signatures of the individual that are not informative or less informative. In various embodiments, target nucleic acids may be nucleic acids derived from a diseased cell that is associated with the health condition. For example, target nucleic acids may be cell-free nucleic acids originating from cancer cells. Target nucleic acids can be any of DNA, cDNA, or RNA. In particular embodiments, target nucleic acids include DNA.

The phrase "reference nucleic acids" refers to nucleic acids of an individual that contain baseline biological signatures of the individual. Here, the baseline biological signatures of the individual may be present when the individual is healthy, and therefore, the baseline biological signatures are less informative for determining presence or absence of the health condition in comparison to sequence information of the target nucleic acids. Reference nucleic acids can be any of DNA, cDNA, or RNA. In particular embodiments, reference nucleic acids include DNA.

It must be noted that, as used in the specification, the singular forms "a," "an" and "the" include plural referents unless the context clearly dictates otherwise.

Overview

Disclosed herein is a multiple-tiered process for detecting signals indicative of a health condition in an individual. For example, methods disclosed herein are useful for detecting circulating tumor DNA from one or more samples obtained from an individual. By detecting circulating tumor DNA from a sample obtained from the individual, the individual can be identified as having a particular health condition, such as cancer.

In various embodiments, the multiple-tiered process is a multipart method which includes performing a first analysis of nucleic acid sequence information that was derived from a first assay performed on a biological sample obtained from the individual. This first analysis identifies whether the biological sample is at risk or not at risk of containing circulating tumor DNA. In various embodiments, for a biological sample that is determined to be not at risk of containing circulating tumor DNA, the multipart method further includes performing an intra-individual analysis and a second analysis. In various embodiments, the intra-individual analysis includes obtaining target nucleic acids and reference nucleic acids from the biological sample or an additional biological sample obtained from the individual; processing the target nucleic acids and reference nucleic acids to generate a dataset comprising methylation information from the target nucleic acids and methylation information from the reference nucleic acids; and using a computer processor, combining the methylation information from the target nucleic acids and the methylation information from the reference nucleic acids to generate background-corrected methylation information for the target nucleic acids. Here, the background-corrected methylation information is more informative for determining presence or absence of a health condition within the individual. In various embodiments, performing the second analysis comprises analyzing the background-corrected methylation information to detect the presence of the circulating tumor DNA in the biological sample. By detecting presence of circulating tumor DNA in the biological sample, the individual can be identified as having cancer.

Additionally disclosed herein is a multiple-tiered process for screening a patient population and identifying a subset of the individuals in the population as having a health condition. The multiple tiered process includes at least a first tier of screening and removing a large proportion of individuals in the population that are not at risk for the health condition. Then, for individuals identified as at risk for the health condition, a second tier involving a second analysis is performed to identify candidate subjects who have the health condition. In various embodiments, prior to performing the second analysis, methods involve performing an intra-individual analysis for individuals identified as at risk for the health condition. For example, the intra-individual analysis can involve generating a signal by removing baseline biological signatures that are less informative for determining whether the individual is at risk for a health condition. Thus, the second analysis involves analyzing the generated signal, which is more informative for determining presence or absence of one or more health conditions within the individual.

In various embodiments, the first tier of screening can involve a simplified molecular test with high specificity to screen out the vast majority of true negatives. The second tier of screening can involve applying a molecular test of increased complexity to the resultant mixed true positive/false positive (TP/FP) population that achieves a much higher positive predictive value. Thus, given a large patient population (e.g., millions, tens of millions, or hundreds of millions of patients), the multiple-tiered process enables the rapid removal of a large proportion of individuals (e.g., greater than 80% of the patient population) representing true negatives, and enables the identification and diagnosis of a subset of the population representing true positives at a high positive predictive value (PPV). In various embodiments, the individuals identified as true positives, also referred to herein as candidate subjects, can undergo subsequent monitoring and/or treatment. In some embodiments, the candidate subjects and be selected for enrollment in a clinical trial (e.g., a clinical trial relevant for the health condition).

In particular embodiments, the multiple-tiered process disclosed herein is useful for detecting rare or low incidence health conditions. For example, the rare or low incidence health condition may have an incidence rate of 1 in 100, 1 in 1,000, 1 in 10,000 individuals, 1 in 100,000 individuals, 1 in 1,000,000 individuals, 1 in 10,000,000 individuals, 1 in 100,000,000 individuals or 1 in 1,000,000,000 individuals. Therefore, the disclosed multiple-tiered process represents a significant improvement over current methodologies that suffer from poor specificity or sensitivity which contributes to their inability to detect rare or low incidence conditions with sufficient positive predictive value.

In various embodiments, the multiple-tiered process can be performed for diagnosing a subset of the individuals in the population as having a plurality of health conditions. In various embodiments, the multiple-tiered process can be performed for diagnosing a subset of the individuals in the population as having one of two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more different health conditions. In particular embodiments, the health conditions are forms of cancer. In particular embodiments, the multiple-tiered process can be performed for diagnosing a subset of the individuals in the population as having one of ten or more different cancers. In particular embodiments, the multiple-tiered process can be performed for diagnosing a subset of the individuals in the population as having one of fifteen or more different cancers. In particular embodiments, the multiple-tiered process can be performed for diagnosing a subset of the individuals in the population as having one of twenty or more different cancers. In particular embodiments, the different cancers are early stage cancers or preclinical stage cancers. Further examples of health conditions are detailed herein.

In particular embodiments, the multiple-tiered process disclosed herein is useful for identifying a signal in samples obtained from individuals of a patient population. For example, the signal in a sample can be informative for a presence of a health condition. In particular embodiments, the signal is informative for a presence of a rare health condition that has a low incidence rate of 1 in 100, 1 in 1,000, 1 in 10,000 individuals, 1 in 100,000 individuals, 1 in 1,000,000 individuals, 1 in 10,000,000 individuals, 1 in 100,000,000 individuals or 1 in 1,000,000,000 individuals. Thus, the multiple-tiered process is useful for improving a likelihood that the detected signal is authentic. Here, the multiple-tiered process can include. (a) performing an analysis of sequence information of nucleic acids in a sample to determine whether the analysis generates a result correlative with presence of a human condition, and then if the result is detected: (b) analyzing the sequence information of the nucleic acids in the sample by performing a second analysis to determine if the second analysis generates the signal. In various embodiments, if the signal is detected, then the probability the signal in the sample is authentic is higher as compared to a probability that a signal is authentic when generated by an analogous method that omits step (a). In particular embodiments, the signal in a sample can be informative for an absence of a health condition. Here, the multiple-tiered process can include: (a) performing an analysis of sequence information of nucleic acids in a sample to determine whether the analysis generates a result correlative with absence of a human condition, and then if the result is detected: (b) analyzing the sequence information of the nucleic acids in the sample by performing a second analysis to determine if the second analysis generates the signal. In various embodiments, if the signal is detected, then the probability the signal in the sample is authentic is higher as compared to a probability that a signal is authentic when generated by an analogous method that omits step (a).

FIG. 1A depicts an overall flow process 100 of the multiple-tiered process for identifying an individual with a health condition, in accordance with an embodiment. Although FIG. 1A shows the flow process in relation to a single individual 110, in various embodiments, the flow process can be performed for more than a single individual 110 (e.g., for thousands, millions, tens of millions, or hundreds of millions of individuals).

FIG. 1A shows a first tier (e.g., assay 120A and screen 125), an intra-individual analysis 128 (optionally assay 120B), and a second tier (second analysis 130) of the multiple-tiered analysis. Generally, the second tier involves a more complex molecular test and analysis in comparison to the first tier. In various embodiments, the more complex molecular test of the second tier is more expensive to perform than the simpler molecular test of the first tier. By employing a cheaper and less complex test, the first tier can identify and remove of individuals that are not at risk of the health condition. The more complex molecular test and analysis of the second tier enables accurate identification of the remaining individuals that likely have the health condition. In various embodiments, between the first tier and the second tier, the method involves an intra-individual analysis that removes baseline biological signatures. For example, the intra-individual analysis can be performed to remove baseline biological signatures in sequencing information (hereafter referred to as "background-corrected information") prior to the performance of the second tier (e.g., a more complex molecular test in comparison to the first tier). Thus, the more complex molecular test of the second tier can be applied to analyze the background-corrected information to achieve an improved identification of individuals with a health condition.

Although FIG. 1A shows a first tier and a second tier of a multiple-tiered analysis, in various embodiments, there may be additional tiers for further classifying individuals. In various embodiments, the multiple-tiered analysis includes three or more tiers, includes four or more tiers, includes five or more tiers, includes six or more tiers, includes seven or more tiers, includes eight or more tiers, includes nine or more tiers, or includes ten or more tiers.

In various embodiments, the combination of the first tier and the second tier enables the ultimate high performance (e.g., high positive predictive value) of the multiple-tier analysis. In various embodiments, the first tier and the second tier interrogate different markers from samples obtained from individuals. This can be beneficial because different markers can provide different information. In some cases, different markers can be informative for different predictions (e.g., whether an individual is at risk of a health condition, or whether an individual has a health condition). As an example, the first tier may analyze protein markers from samples obtained from individuals whereas the second tier may analyze sequencing data derived from nucleic acids in the samples obtained from individuals.

In various embodiments, the first tier and second tier interrogate the same type of markers from samples obtained from individuals, but at different levels of detail. For example, the first tier may involve the analysis of methylation statuses for a limited, pre-selected set of genomic sites. The differential methylation of the limited, pre-selected set of genomic sites is sufficient to enable identification of individuals not at risk of the health condition. Additionally, the second tier may involve the analysis of methylation statuses for a larger set of genomic sites. In one scenario, the second tier involves analysis of methylation statuses for the whole genome (e.g., through whole genome bisulfite sequencing). The differential methylation of the larger set of genomic sites enables accurate identification of the remaining individuals who have the health condition. As another example, the first tier may involve the analysis of shallow sequencing data. Here, shallow sequencing data is sufficient to identify and remove individuals who are not at risk for a health condition. The second tier may involve analysis of sequencing data derived from deeper sequencing, which is sufficient to identify individuals who have the health condition.

As shown in FIG. 1A, one or more samples are obtained from the individual 110. In various embodiments, a sample is any of a blood sample, a stool sample, a urine sample, a mucous sample, or a saliva sample. In particular embodiments, the one or more samples obtained from the individual 110 are blood samples. The sample can be obtained by the individual or by a third party, e.g., a medical professional. Examples of medical professionals include physicians, emergency medical technicians, nurses, first responders, psychologists, phlebotomist, medical physics personnel, nurse practitioners, surgeons, dentists, and any other obvious medical professional as would be known to one skilled in the art. In various embodiments, the one or more samples can be obtained from the individual 110 by a reference lab.

In various embodiments, the sample obtained from the individual is a liquid biopsy sample obtained at a first point in time. In various embodiments, the liquid biopsy sample may include various biomarkers, examples of which include proteins, metabolites, and/or nucleic acids. In particular embodiments, the liquid biopsy sample includes cell-free DNA (cfDNA) fragments. In particular embodiments, the cfDNA fragments include genomic sequences corresponding to CpG islands for which methylation states are informative of the health condition.

In various embodiments, a plurality of liquid biopsy samples are obtained from the individual 110 at a plurality of different points in time. For example, a first liquid biopsy sample can be obtained at a first timepoint and at least a second liquid biopsy sample can be obtained from the individual 110 at a second timepoint. In such embodiments, the first liquid biopsy sample can be used for performing the screen (e.g., screen 125) and the second liquid biopsy can be used to perform a second analysis (e.g., second analysis 130) involving an intra-individual analysis. Obtaining a plurality of liquid biopsy samples from the individual at a plurality of different points in time includes obtaining a number M of liquid biopsy samples, wherein M is one of 2, 3, 4, . . . , N–1, N, wherein N is a positive integer.

An assay 120A is performed on the obtained sample(s) 115A to generate marker information. An example of marker information can include quantitative levels of a biomarker, such as a protein biomarker, nucleic acid biomarker, metabolite biomarker, that is present in the sample. Another examples of marker information is sequence information for a plurality of genomic sites. In various embodiments, given that the assay 120A may be performed on a large number of samples (e.g., millions of samples) obtained from a large patient population, the assay 120A be a simplified molecular test that generates marker information that can rapidly distinguish between individuals at risk and individuals not at risk for a health condition. For example, the marker information can include quantitative levels of a biomarker, such as a protein biomarker, nucleic acid biomarker, metabolite biomarker, that can rapidly guide the identification and removal of individuals not at risk for the health condition As another example, the marker information can be sequence information for a limited number of genomic sites that are sufficient for identifying individuals who are not at risk for the health condition (e.g., true negatives). In particular embodiments, the sequence information for a plurality of genomic sites includes methylation information, such as methylation statuses for the plurality of genomic sites. In various embodiments, the plurality of genomic sites include a plurality of CpG islands (CGIs) whose differential methylation status may be indicative of risk for the health condition. Further details regarding the assay 120A are described herein.

A screen 125 is performed to analyze the marker information generated by the assay 120A. For example, the screen 125 can involve an in silico analysis of the marker information. In various embodiments, the marker information includes quantitative values of biomarkers. Therefore, the screen 125 can identify and remove individuals whose quantitative values of biomarkers indicate that the individuals are not at risk of the health condition. In various embodiments, the marker information is sequence information for a plurality of genomic sites. Therefore, the screen 125 involves deploying a trained machine learning model that analyzes the sequence information for the plurality of genomic sites and predicts whether an individual is at risk for a health condition. If the screen 125 identifies the individual as not at risk for the health condition (as indicated in FIG. 1A as "If negative"), then the individual 110 can be reported as not at risk for the health condition. Thus, the individual 110 need not undergo subsequent analysis and need not be further tracked.

Alternatively, if the screen identifies the individual as at risk for the health condition (as indicated in FIG. 1A as "If positive" following screen 125), then the individual 110 undergoes at least another tier of testing. As shown in FIG. 1A, a second analysis 130 can be performed for individuals identified as at risk for the health condition.

Referring to the intra-individual analysis 128, the analysis is conducted for a specific individual, such as an individual identified via the screen 125 as at risk for the health condition. Therefore, for a particular patient, the intra-individual analysis is performed to remove baseline biological signatures that are present in the patient irrespective of whether the patient has a health condition or does not have the health condition. These baseline biological signatures would be confounding signals if analyzed to predict whether the patient has a presence or absence of the health condition. Performing the intra-individual analysis 128 eliminates these confounding baseline biological signatures while keeping signatures that are more informative for determining presence or absence of the health condition. For example, in processing nucleic acid sequencing information to generate a signal that may be detected, the resulting signal may comprise a mixture of baseline biological signatures (e.g., germline methylation in a patient) that represent a form of background noise and signatures informative of a health condition (e.g., cancer). Such background noise can obscure a signal informative of a health condition. Advantageously, in certain embodiments, methods described herein contemplate subtracting such background noise from a patient's nucleic acid sequencing information, thereby improving the signal-to-noise ratio of the signal informative of a health condition.

In contrast to an inter-individual analysis, where, for example, to determine a presence or absence of one or more health conditions within a patient, an average of baseline signatures from a group of normal subjects are removed from the nucleic acid sequencing information of the patient, it has been discovered that performing an intra-individual analysis can significantly improve the sensitivity or specificity of detecting a signal informative for determining presence or absence of the health condition.

Generally, the intra-individual analysis 128 involves generating information from at least target nucleic acids and reference nucleic acids from one or more samples obtained from the patient. In various embodiments, the intra-individual analysis 128 is performed on sequence information. Such sequence information may be generated by assay 120A, as shown in FIG. 1A. In such scenarios, the sequence information generated by the assay 120A can be used to perform both the screen 125 and the intra-individual analysis 128. In various embodiments, the intra-individual analysis 128 is performed on sequence information generated by an assay (e.g., assay 120B) different from assay 120A. As shown in FIG. 1A, the performance of assay 120B is optional (as indicated by the dotted line). In various embodiments, the assay 120B is performed on sample 115A, which is the same sample 115A on which assay 120A was performed. In various embodiments, the assay 120B is performed on a second sample obtained from individual 110, where the second sample is different from sample 115A. For example, the second sample can be obtained from the individual 110 at a different timepoint than when the sample 115A was obtained from the individual 110. Thus, the screen 125 and the intra-individual analysis 128 are performed on information generated from assays performed on different samples. Further detailed embodiments of the samples and/or assays that are used to perform the intra-individual analysis 128 are described below in reference to FIGS. 1B and 1C.

In various embodiments, the intra-individual analysis 128 involves combining information from target nucleic acids and the reference nucleic acids to generate a signal informative for determining presence or absence of one or more health conditions within the patient. By combining the information from the target nucleic acids and the reference nucleic acids, the generated signal can be more informative of presence or absence of a health condition in comparison to a signal derived from the target nucleic acids alone. For example, the information from the reference nucleic acids can represent baseline biology of the patient. By combining the information from the target nucleic acids and the reference nucleic acids, the baseline biology of the patient, which may not be informative for the presence or absence of a health condition, is removed from the generated signal. Thus, information of the target nucleic acids that are not attributable to the patient's baseline biology remains and is included in the generated signal for determining presence or absence of one or more health conditions in the patient.

Referring next to the second analysis 130 shown in FIG. 1A, the second analysis 130 may reveal that the individual does not have the health condition. If the individual is predicted to not have the health condition (e.g., "if negative" as shown in FIG. 1A), then the individual is reported as not having the health condition. In various embodiments, the individual reported as not having the health condition can be further monitored, given that the screen 125 identified the individual as at risk for the health condition (or not identified as not at risk). Alternatively, if the individual is predicted to have the health condition (e.g., "if positive" as shown in FIG. 1A following second analysis 130), the individual is reported as having the health condition. In various embodiments, the individual is monitored for progression of the health condition. In various embodiments, the individual is provided a treatment to control or revert the health condition. In various embodiments, the individual is selected for enrollment in a clinical trial.

Generally, the multiple-tiered analysis (e.g., multiple-tiered analysis involving the screen 125 and second analysis 130 or multiple-tiered analysis involving each of the screen 125, intra-individual analysis 128, and second analysis 130) enables the rapid identification of a large proportion of individuals (e.g., greater than 80% of the patient population) representing true negatives, and further enables the accurate identification and diagnosis of a subset of the population representing true positives. The overall multiple-tiered analysis (e.g., multiple-tiered analysis involving the screen 125 and second analysis 130 or multiple-tiered analysis involving each of the screen 125, intra-individual analysis 128, and second analysis 130) achieves one or more performance metrics, such as metrics of sensitivity, specificity, positive predictive value (PPV), and/or negative predictive value (NPV). Sensitivity is the true positive rate, reported as a proportion of correctly identified positives. Specificity is the true negative rate reported as a proportion of correctly identified negatives. Positive predictive value refers to the number of true positives divided by the sum of true positives and false positives. Negative predictive value refers to the true negative rate divided by the sum of true negatives and false negatives.

In various embodiments, the overall multiple-tiered analysis (e.g., multiple-tiered analysis involving the screen 125 and second analysis 130 or multiple-tiered analysis involving each of the screen 125, intra-individual analysis 128, and second analysis 130) achieves at least 60% sensitivity in detecting presence of a health condition. In various embodiments, the overall multiple-tiered analysis achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sensitivity. In particular embodiments, the overall multiple-tiered analysis achieves at least 70% sensitivity. In particular embodiments, the overall multiple-tiered analysis achieves at least 71% sensitivity. In particular embodiments, the overall multiple-tiered analysis achieves at least 72% sensitivity. In particular embodiments, the overall multiple-tiered analysis achieves at least 73% sensitivity. In particular embodiments, the overall multiple-tiered analysis achieves at least 74% sensitivity. In particular embodiments, the overall multiple-tiered analysis achieves at least 75% sensitivity.

In various embodiments, the overall multiple-tiered analysis (e.g., multiple-tiered analysis involving the screen 125 and second analysis 130 or multiple-tiered analysis involving each of the screen 125, intra-individual analysis 128, and second analysis 130) achieves at least 60% specificity in excluding individuals without the health condition. In various embodiments, the overall multiple-tiered analysis achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% specificity. In particular embodiments, the overall multiple-tiered analysis achieves at least 99% specificity. In particular embodiments, the overall multiple-tiered analysis achieves at least 99.5% specificity. In particular embodiments, the overall multiple-tiered analysis achieves at least 99.9% specificity.

In various embodiments, the overall multiple-tiered analysis (e.g., multiple-tiered analysis involving the screen 125 and second analysis 130 or multiple-tiered analysis involving each of the screen 125, intra-individual analysis 128, and second analysis 130) achieves a particular sensitivity and a particular specificity. The combination of the sensitivity and specificity limits both the number of false positives and the number of false negatives. In various embodiments, the overall multiple-tiered analysis achieves between 70% to 90% sensitivity and between 90% to 100% specificity. In various embodiments, the overall multiple-tiered analysis achieves between 75% to 89% sensitivity and between 90% to 100% specificity. In various embodiments, the overall multiple-tiered analysis achieves between 80% to 88% sensitivity and between 90% to 100% specificity. In various embodiments, the overall multiple-tiered analysis achieves between 83% to 87% sensitivity and between 90% to 100% specificity. In various embodiments, the overall multiple-tiered analysis achieves between 84% to 86% sensitivity and between 90% to 100% specificity. In various embodiments, the overall multiple-tiered analysis achieves about 85% sensitivity and between 90% to 100% specificity.

In various embodiments, the overall multiple-tiered analysis (e.g., multiple-tiered analysis involving the screen 125 and second analysis 130 or multiple-tiered analysis involving each of the screen 125, intra-individual analysis 128, and second analysis 130) achieves between 70% to 90% sensitivity and between 91% to 99% specificity. In various embodiments, the overall multiple-tiered analysis achieves between 70% to 90% sensitivity and between 92% to 98% specificity. In various embodiments, the overall multiple-tiered analysis achieves between 70% to 90% sensitivity and between 93% to 97% specificity. In various embodiments, the overall multiple-tiered analysis achieves between 70% to 90% sensitivity and between 97% to 96% specificity. In various embodiments, the overall multiple-tiered analysis achieves between 70% to 90% sensitivity and about 95% specificity.

In various embodiments, the overall multiple-tiered analysis (e.g., multiple-tiered analysis involving the screen 125 and second analysis 130 or multiple-tiered analysis involving each of the screen 125, intra-individual analysis 128, and second analysis 130) achieves between 75% to 89% sensitivity and between 91% to 99% specificity. In various embodiments, the overall multiple-tiered analysis achieves between 80% to 88% sensitivity and between 92% to 98% specificity. In various embodiments, the overall multiple-tiered analysis achieves between 83% to 87% sensitivity and between 93% to 97% specificity. In various embodiments, the overall multiple-tiered analysis achieves between 84% to 86% sensitivity and between 94% to 96% specificity. In various embodiments, the overall multiple-tiered analysis achieves about 85% sensitivity and about 95% specificity.

In various embodiments, the overall multiple-tiered analysis (e.g., multiple-tiered analysis involving the screen 125 and second analysis 130 or multiple-tiered analysis involving each of the screen 125, intra-individual analysis 128, and second analysis 130) achieves at least 60% positive predictive value. In various embodiments, the overall multiple-tiered analysis achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% positive predictive value. In particular embodiments, the overall multiple-tiered analysis achieves at least 80% positive predictive value. In particular embodiments, the overall multiple-tiered analysis achieves at least 81% positive predictive value. In particular embodiments, the overall multiple-tiered analysis achieves at least 82% positive predictive value. In particular embodiments, the overall multiple-tiered analysis achieves at least 83% positive predictive value. In particular embodiments, the overall multiple-tiered analysis achieves at least 84% positive predictive value. In particular embodiments, the overall multiple-tiered analysis achieves at least 85% positive predictive value.

In various embodiments, the overall multiple-tiered analysis (e.g., multiple-tiered analysis involving the screen 125 and second analysis 130 or multiple-tiered analysis involving each of the screen 125, intra-individual analysis 128, and second analysis 130) achieves at least 60% negative predictive value. In various embodiments, the overall multiple-tiered analysis achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% negative predictive value. In particular embodiments, the overall multiple-tiered analysis achieves at least 98% negative predictive value. In particular embodiments, the overall multiple-tiered analysis achieves at least 99% negative predictive value. In particular embodiments, the overall multiple-tiered analysis achieves at least 99.4% negative predictive value.

In various embodiments, individuals that are identified as having the health condition can undergo additional analysis. The additional analysis can refer to classification of the individuals identified as having the health condition as candidate subjects who are selected for enrollment in a clinical trial. Thus, the multiple-tiered analysis disclosed herein enables the accurate identification of individuals (from amongst a large patient population) who have a health condition and therefore, meet the eligibility criteria for enrollment in a clinical trial. The multiple-tiered analysis enables clinical trials to avoid enrollment of individuals who do not have the health condition, thereby reducing the consumption of resources that otherwise would have been mistakenly dedicated to these individuals.

In various embodiments, the additional analysis refers to a longitudinal monitoring of the individuals identified as having the health condition. For example, at a subsequent timepoint, an additional sample may be obtained from the individual identified as having the health condition and an assay (e.g., assay 120A or assay 120B) can be performed to generate marker information. The marker information can be analyzed by performing one or both of the screen and second analysis. The results from the screen and/or second analysis can be compared to the results of the prior screen and/or second analysis to understand the longitudinal changes to the individual's health condition. In some scenarios, the longitudinal changes can guide an interventional therapy that is provided to the individual. Further details of the longitudinal analysis is described herein.

Figure 1B:
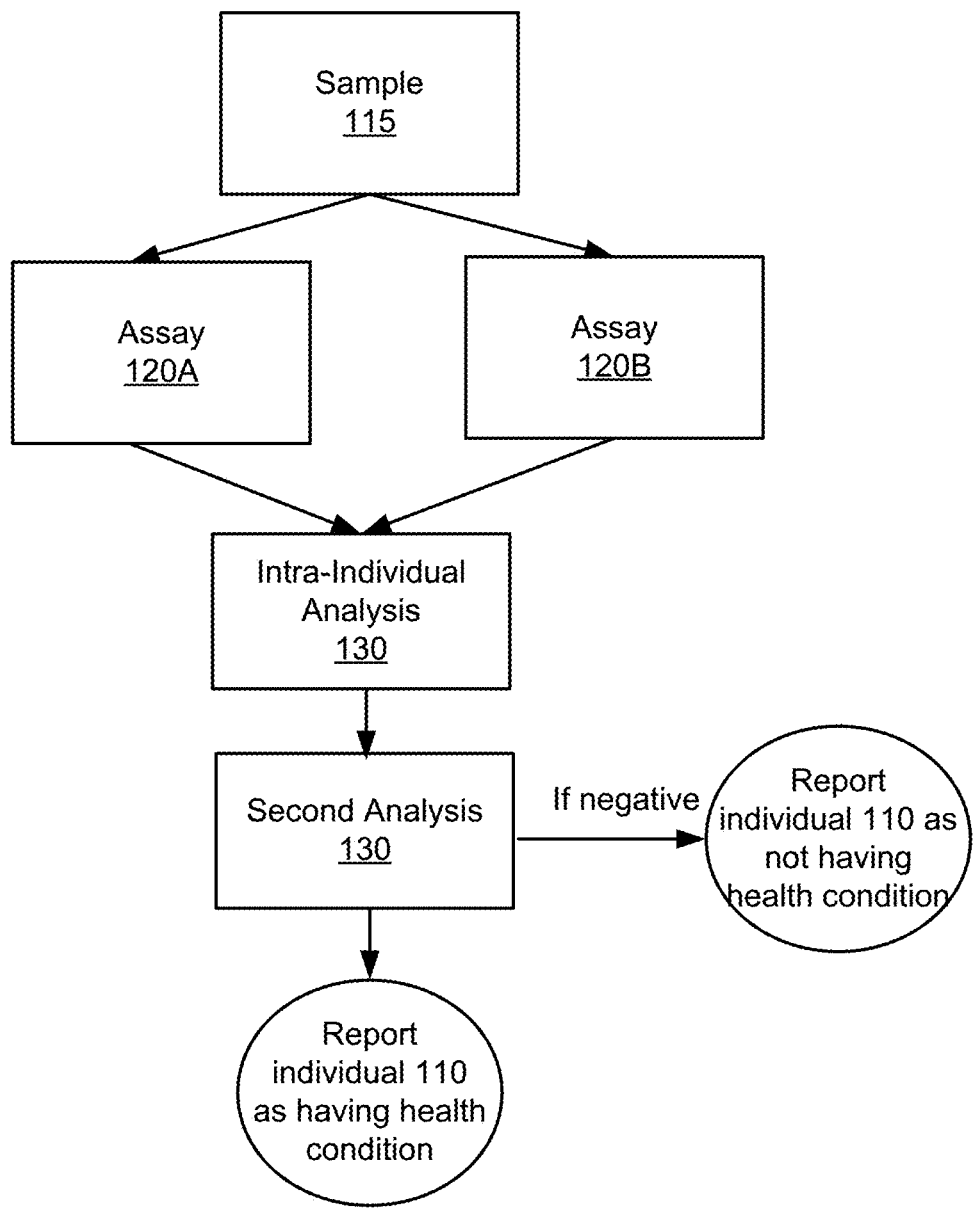
FIG. 1B depicts an overall flow process involving an intra-individual analysis and second analysis, in accordance with a first embodiment.
Figure 1C:
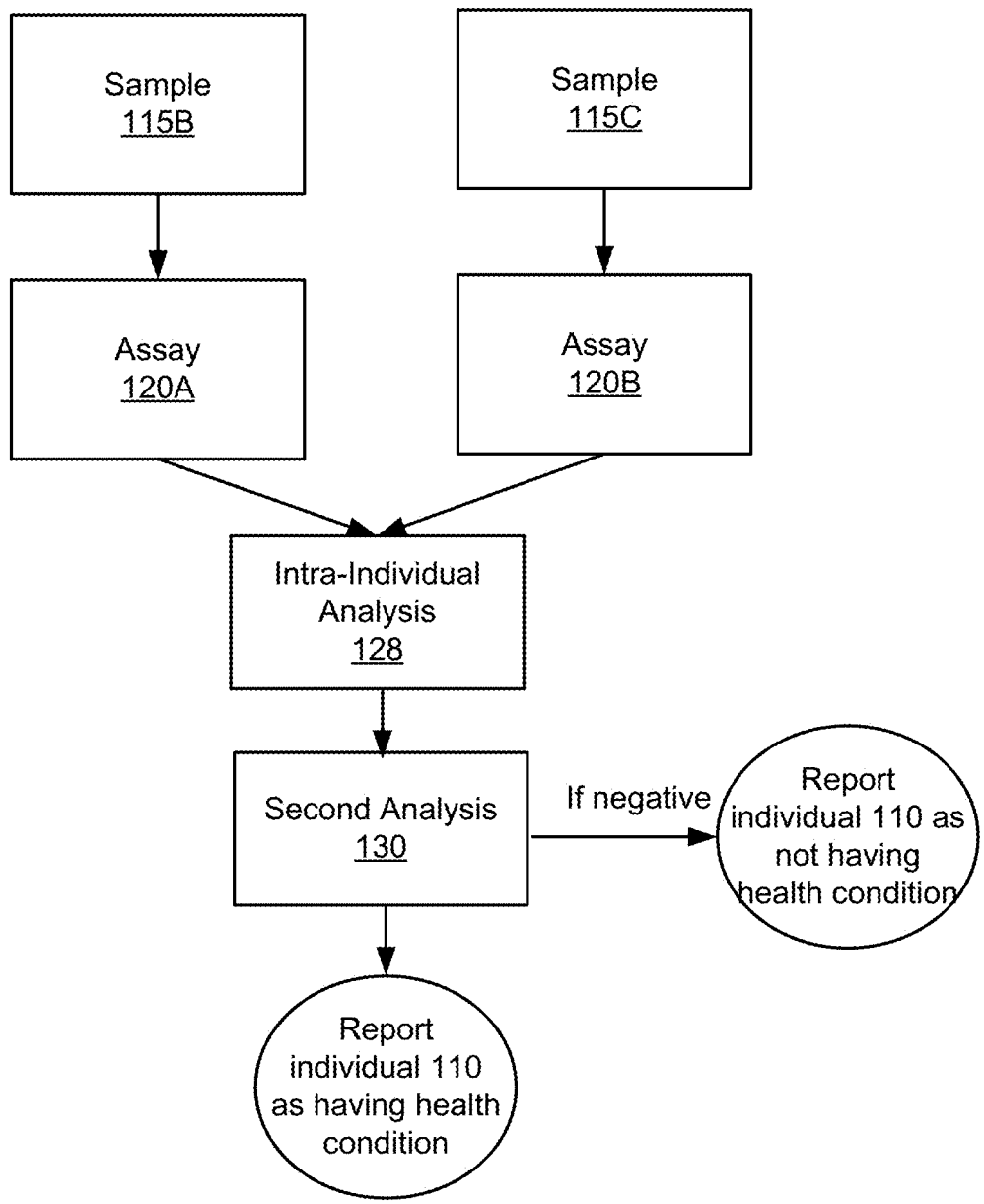
FIG. 1C depicts an overall flow process involving an intra-individual analysis and second analysis, in accordance with a second embodiment.

Reference is now made to FIGS. 1B and 1C, each of which shows an overall flow process involving an intra-individual analysis and second analysis. In general, the intra-individual analysis 128 and second analysis 130 are conducted for individual patients that were previously determined (e.g., via screen 125 as shown in FIG. 1A) as at risk for the health condition or not identified as not at risk. The intra-individual analysis 128 removes baseline biological signatures that are specific for an individual patient to generate a background-corrected signal. Thus, the second analysis 130 involves analyzing the background-corrected signal to determine whether the individual has the health condition. Although FIGS. 1B and 1C each shows the flow process in relation to a single individual, in various embodiments, the flow process can be performed for more than a single individual (e.g., for thousands, millions, tens of millions, or hundreds of millions of individuals).

Referring first to FIG. 1B, it shows an embodiment in which the intra-individual analysis 128 and second analysis 130 are conducted using a single sample 115. In various embodiments, the sample 115 is a blood sample, a stool sample, a urine sample, a mucous sample, or a saliva sample. In particular embodiments, the sample 115 obtained from the individual is a blood sample. The sample 115 can be obtained by the individual or by a third party, e.g., a medical professional. Examples of medical professionals include physicians, emergency medical technicians, nurses, first responders, psychologists, phlebotomist, medical physics personnel, nurse practitioners, surgeons, dentists, and any other obvious medical professional as would be known to one skilled in the art. In various embodiments, the sample 115 can be obtained from the individual by a reference lab. In various embodiments, the single sample 115 may be the same sample (e.g., sample 115A shown in FIG. 1A) obtained from the individual that was previously used for performing the assay 120A and the screen 125.

In various embodiments, target nucleic acids and reference nucleic acids can be obtained from the single sample 115. Target nucleic acids may include signatures that are informative of determining presence or absence of a health condition, and can further include baseline biological signatures. Here, target nucleic acids in the blood sample may be derived from a diseased cell which is associated with the health condition. For example, target nucleic acids can include cell-free DNA in the blood that originates from a diseased cell. In particular embodiments, target nucleic acids are cell-free DNA in the blood that originates from a cancer cell. Reference nucleic acids in the sample 115 refer to nucleic acids that contain baseline biological signatures of the individual. For example, baseline biological signatures of the individual may be present in nucleic acids irrespective of whether the nucleic acids originate from a diseased source, or a non-diseased source. The baseline biological signatures of the reference nucleic acids are generally less informative for determining presence or absence of a health condition in comparison to the informative signatures present in the target nucleic acids. In various embodiments, reference nucleic acids refer to cellular genomic DNA derived from a healthy cell from the individual. In various embodiments, reference nucleic acids found in the sample derive from a cell in a healthy organ of the individual. Example organs include the brain, heart, thorax, lung, abdomen, colon, cervix, pancreas, kidney, liver, muscle, lymph nodes, esophagus, intestine, spleen, stomach, and gall bladder. In particular embodiments, reference nucleic acids are found in the sample and refer to cellular genomic DNA derived from peripheral blood mononuclear cells (PBMCs) (e.g., lymphocytes or monocytes) or polymorphonuclear cells (e.g., eosinophils or neutrophils).

In various embodiments, target nucleic acids and reference nucleic acids are separately obtained from the single sample 115. In various embodiments, the sample is processed to separate the target nucleic acids and reference nucleic acids. For example, the sample may be processed through any one of centrifugation, filtration, gel electrophoresis, bead capture, or matrix extraction. In particular embodiments, target nucleic acids are cell-free nucleic acids and therefore, can be obtained from the supernatant of the separated sample. In particular embodiments, reference nucleic acids are cellular genomic nucleic acids and therefore, can be obtained from a different portion of the separated sample that contains cells.

As shown in FIG. 1B, the single sample 115 can be used to perform two separate assays, such as assay 120A and assay 120B. In various embodiments, a first assay 120A is performed to generate information derived from target nucleic acids of the sample 115. In various embodiments, the second assay 120B is performed to generate information derived from reference nucleic acids of the sample 115. As described in further detail herein, the intra-individual analysis 128 is performed to combine the information derived from the target nucleic acids and the information derived from the reference nucleic acids. Thus, the intra-individual analysis 128 generates background-corrected information that is analyzed through the second analysis 130 to determine whether the individual has a health condition.

Reference is now made to FIG. 1C, which shows an alternative embodiment in which two samples (e.g., labeled as sample 115B and sample 115C) are used to perform the intra-individual analysis 128 and second analysis 130. Here, samples 115B and 115C can be obtained from an individual previously identified via the screen 125 as at risk for the health condition or not identified as not at risk for the health condition. In various embodiments, one of the samples contains target nucleic acids and the other of the samples contains reference nucleic acids. Therefore, in such embodiments, target nucleic acids can be obtained from one of the samples, and reference nucleic acids can be obtained from the other of the samples. Separate assays (e.g., assay 120A and assay 120B) can be performed on the target nucleic acids and the reference nucleic acids.

In the particular embodiment shown in FIG. 1C, samples 115B and 115C are obtained from the individual and used to perform the intra-individual analysis 128 and second analysis 130. In various embodiments, one of the samples can be sample 115A that, as shown in FIG. 1A, was used to perform the assay 120A and screen 125. Thus, this enables the reusability of prior samples as opposed to having to obtain new samples from the individual. In various embodiments, a plurality of samples 115 are obtained from the individual 110 at a plurality of different points in time. For example, a first sample 115A can be obtained at a first timepoint, a second sample 115B can be obtained from the individual 110 at a second timepoint, a third sample 115C can be obtained from the individual 110 at a third timepoint, and so on. Obtaining a plurality of samples 115 from the individual at a plurality of different points in time includes obtaining a number M of samples 115, wherein M is one of: 2, 3, 4, ..., N−1, N, wherein N is a positive integer. In such embodiments, target nucleic acids and reference nucleic acids can be obtained at the different points in time, thereby enabling intra-individual analyses 128 and second analyses 130 across the different points in time. This can enable the tracking of progression of a health condition over the different points in time.

In various embodiments, samples 115 may be processed to extract the target nucleic acids and reference nucleic acids. In various embodiments, samples can undergo cellular disruption methods (e.g., to obtain genomic DNA) involving chemical methods or mechanical methods. Example chemical methods include osmotic shock, enzymatic digestion, detergents, or alkali treatment. Example mechanical methods include homogenization, ultrasonication or cavitation, pressure cell, or ball mill. In various embodiments, samples can undergo removal of membrane lipids or proteins or nucleic acid purification. Example chemical methods for removing membrane lipids or proteins and methods for nucleic acid purification include guanidine thiocyanate (GuSCN)-phenol-chloroform extraction, alkaline extraction, cesium chloride gradient centrifugation with ethidium bromide, Chelex® extraction, or cetyltrimethylammonium bromide extraction. Example physical methods for removing membrane lipids or proteins and methods for nucleic acid purification include solid-phase extraction methods using any of silica matrices, glass particles, diatomaceous earth, magnetic beads, anion exchange material, or cellulose matrix. Further details of nucleic acid extraction methods are described in Ali et al, Current Nucleic Acid Extraction Methods and Their Implications to Point-of-Care Diagnostics, Biomed Res. Int. 2017; 2017:9306564, which is hereby incorporated by reference in its entirety.

As shown in FIGS. 1B and 1C, one or more assays (e.g., assay 120A and/or assay 120B) are performed on the obtained sample 115A and/or sample 115B to generate sequence information. Although methods shown in FIGS. 1B and 1C include the performance of assay 120A, which is also performed in FIG. 1A, in some embodiments, methods of FIGS. 1B and 1C need not perform assay 120A and instead, perform an assay different from the assay 120A performed in FIG. 1A. For the intra-individual analysis 128, generally, assays 120 are performed to generate sequence information for target nucleic acids and to generate sequence information for reference nucleic acids. In particular embodiments, sequence information includes statuses for a plurality of genomic sites, such as epigenetic statuses for a plurality of CpG sites. In various embodiments, epigenetic statuses refer to methylation statuses. In particular embodiments, sequence information of the target nucleic acids and sequence information of the reference nucleic includes statuses for two or more, three or more, four or more, five or more, six or more, seven or more, eight or more, nine or more, or ten or more common genomic sites. In particular embodiments, sequence information of the target nucleic acids and sequence information of the reference nucleic each includes statuses for 15 or more, 20 or more, 25 or more, 30 or more, 40 or more, 50 or more, 100 or more, 200 or more, 300 or more, 400 or more, 500 or more, 750 or more, 1000 or more, 2000 or more, 3000 or more, 4000 or more, 5000 or more, 6000 or more, 7000 or more, 8000 or more, 9000 or more, 10000 or more, 11000 or more, 12000 or more, 13000 or more, 14000 or more, 15000 or more, 16000 or more, 17000 or more, 18000 or more, 19000 or more, or 20000 or more genomic sites. In particular embodiments, sequence information of the target nucleic acids and sequence information of the reference nucleic each includes statuses for 15 or more, 20 or more, 25 or more, 30 or more, 40 or more, 50 or more, 100 or more, 200 or more, 300 or more, 400 or more, 500 or more, 750 or more, 1000 or more, 2000 or more, 3000 or more, 4000 or more, 5000 or more, 6000 or more, 7000 or more, 8000 or more, 9000 or more, 10000 or more, 11000 or more, 12000 or more, 13000 or more, 14000 or more, 15000 or more, 16000 or more, 17000 or more, 18000 or more, 19000 or more, or 20000 or more of the same genomic sites or overlapping genomic sites. In various embodiments, the plurality of genomic sites include a plurality of CpG islands (CGIs) whose differential methylation status may be indicative of a health condition. Further details regarding the assays 120 are described herein.

The intra-individual analysis 128 involves combining the sequence information of the target nucleic acids and the sequence information of the reference nucleic acids to generate a signal informative for determining presence or absence of a health condition. Here, the signal informative for determining presence or absence of a health condition is more informative for determining presence or absence of the health condition in comparison to the sequence information of the target nucleic acids alone. In particular embodiments, the signal informative for determining presence or absence of the health condition includes informative signatures from the target nucleic acids (e.g., signatures derived from diseased cells) and excludes baseline biological signatures (e.g., baseline biological signatures present in reference nucleic acids). Further details of the intra-individual analysis 128, and specifically the generation of the background-corrected signal informative for determining presence or absence of the health condition, is described herein.

In various embodiments, the second analysis 130 involves analyzing the background-corrected signal from the intra-individual analysis 128 to predict whether the individual has the health condition. Thus, as shown in both FIGS. 1B and 1C, the output of the second analysis 130 can be a determination of whether the individual has the health condition. In various embodiments, the determination can be useful for guiding the decision-making for treating the individual. For example, if the determination reveals that the individual has the health condition, the individual can be provided a therapy (e.g., a prophylactic therapy or a preventative therapy) to treat the health condition.

System Environment Overview

Figure 1D:
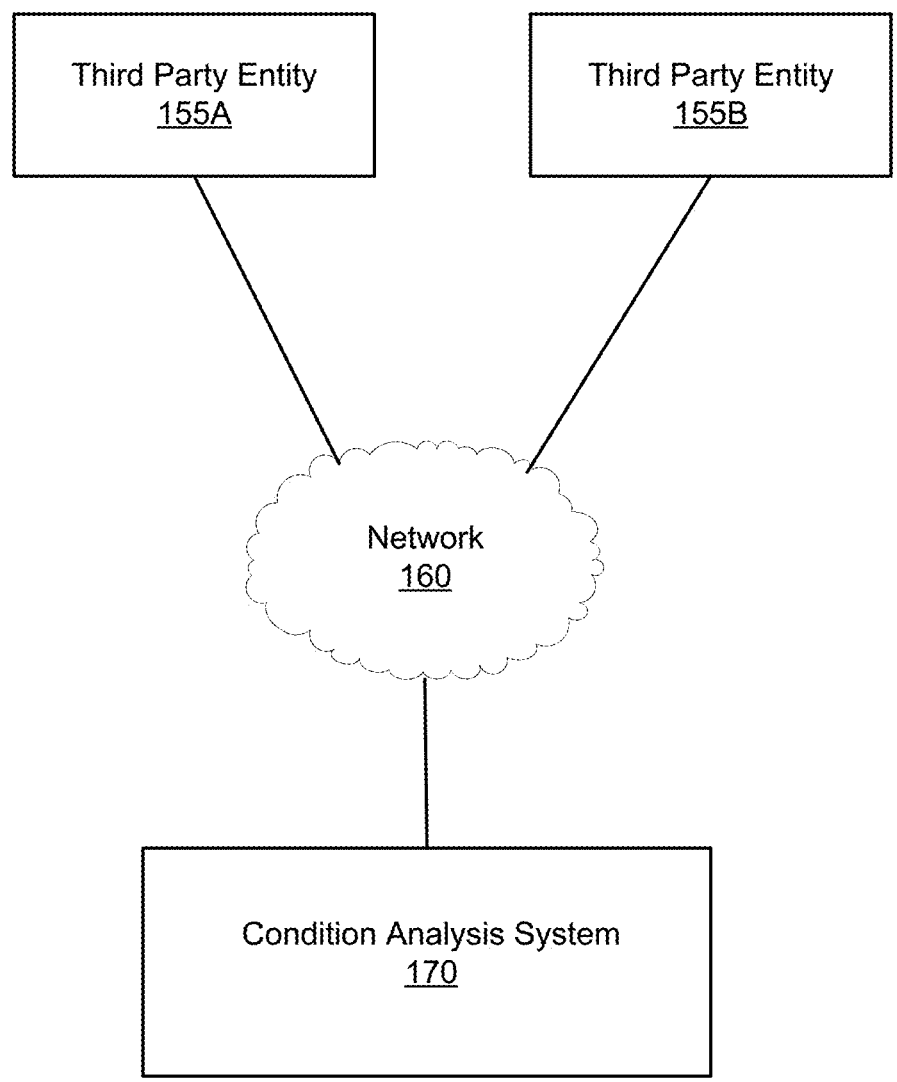
FIG. 1D depicts an overall system environment including a condition analysis system, in accordance with an embodiment.

FIG. 1D depicts an overall system environment 150 including a condition analysis system 170 for performing a multiple-tiered analysis, in accordance with an embodiment. The overall system environment 150 includes a condition analysis system 170 for at least performing one or more steps shown in FIG. 1A, and one or more third party entities 155A and 155B in communication with one another through a network 160. FIG. 1B depicts one embodiment of the overall system environment 150 in which two third party entities 155A and 155B are involved. In other embodiments, additional or fewer third party entities 155 in communication with the condition analysis system 170 can be included. The third party entities 155 may communicate with the condition analysis system 170 to enable the condition analysis system 170 to perform a screen and/or second analysis.

Third Part Entity

A third party entity 155 represents a partner entity of the condition analysis system 170 that can operate upstream, downstream, or both upstream and downstream of the operations of the condition analysis system 170. As one example, the third party entity 155 operates upstream of the condition analysis system 170 and provides samples obtained from patients to the condition analysis system 170. Thus, the condition analysis system 170 can perform assays, a screen, intra-individual analysis, and/or a second analysis to determine whether the patients are at risk for a health condition or have a health condition. As another example, the third party entity 155 may process samples obtained from patients by performing one or more assays on the samples to generate data. Thus, the third party entity 155 can provide the data derived from the assays to the condition analysis system 170 such that the condition analysis system 170 can perform a screen, intra-individual analysis, and/or second analysis.

As another example, the third party entity 155 operates downstream of the condition analysis system 170. In this scenario, the condition analysis system 170 may perform a screen and determine whether a patient is at risk for a health condition. The condition analysis system 170 can provide an indication to the third party entity 155 that identifies the patient at risk for the health condition. The third party entity 155 takes appropriate action. For example, the third party entity 155 notifies the patient regarding a follow-up appointment such that an additional sample can be obtained from the patient at the follow-up appointment for subsequent analysis. Further description and examples of the interactions between third party entities 155 and the condition analysis system 170 are detailed herein.

Network

This disclosure contemplates any suitable network 160 that enables connection between the condition analysis system 170 and third party entities 155. The network 160 may comprise any combination of local area and/or wide area networks, using both wired and/or wireless communication systems. In one embodiment, the network 160 uses standard communications technologies and/or protocols. For example, the network 160 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 160 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 160 may be represented using any suitable format, such as hypertext markup language (HTML) or extensible markup language (XML). In some embodiments, all or some of the communication links of the network 160 may be encrypted using any suitable technique or techniques.

Condition Analysis System

Figure 2A:
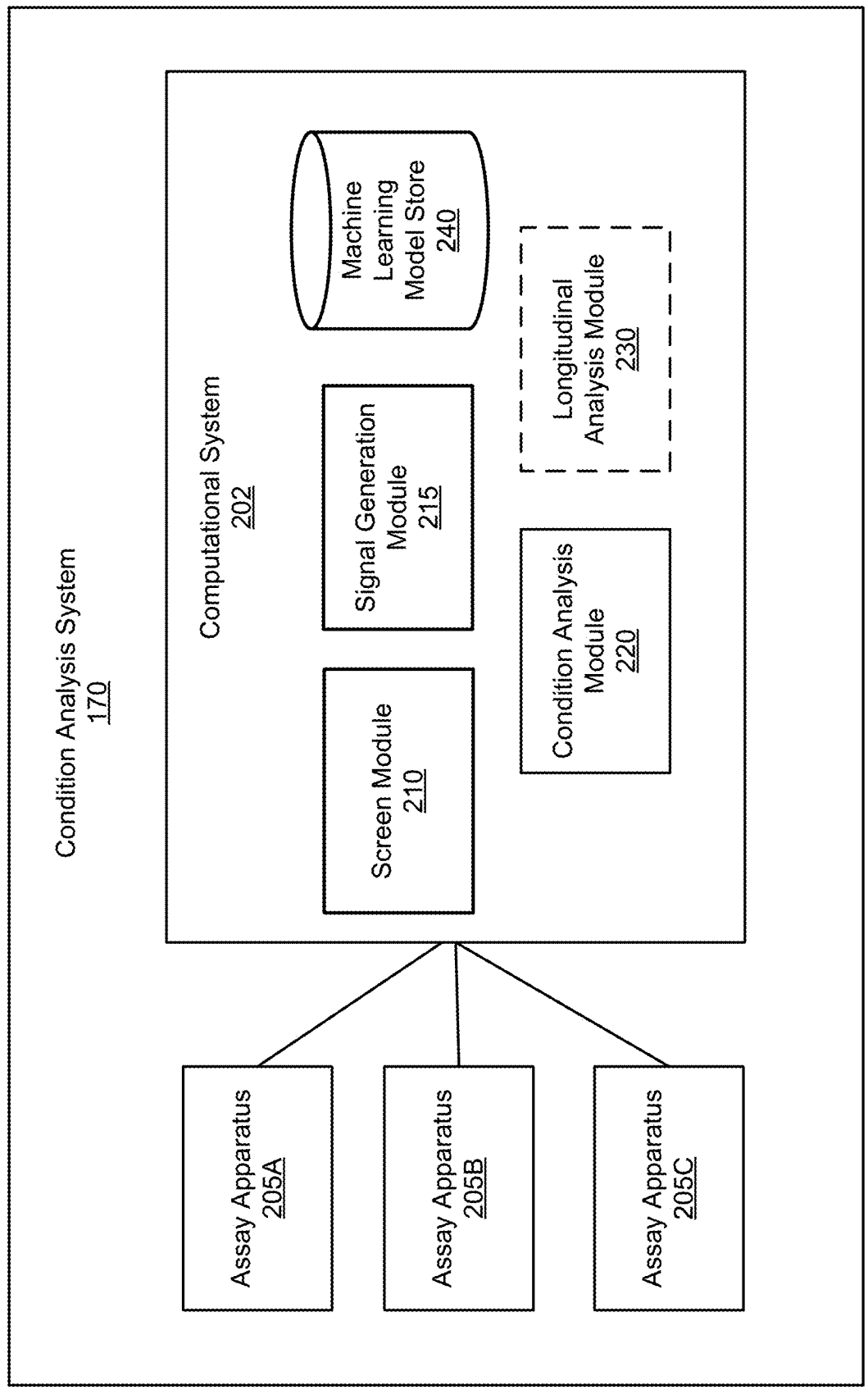
FIG. 2A depicts a block diagram of the condition analysis system, in accordance with an embodiment.

FIG. 2A depicts a block diagram of the condition analysis system, in accordance with an embodiment. The block diagram of the condition analysis system 170 is introduced to show an embodiment in which the condition analysis system 170 includes one or more assay apparatuses 205 communicatively coupled to a computational system 202. The computational system 202 can further include computational modules, such as a screen module 210, signal generation module 215, condition analysis module 220, and optionally, a longitudinal analysis module 230. The computational system 202 can further include data stores such as a machine learning model store 240 for storing one or more trained machine learning models. FIG. 2A depicts an embodiment in which the condition analysis system 170 performs one or more assays (e.g., assay 120A or 120B described in FIG. 1A), performs the screen (e.g., screen 125 described in FIG. 1A), performs the intra-individual analysis (e.g., intra-individual analysis 128 described in FIG. 1A), and performs the second analysis (e.g., second analysis 130 described in FIG. 1A).

In various embodiments, the condition analysis system 170 may be differently configured than shown in FIG. 2A. For example, although the condition analysis system 170 shown in FIG. 2A includes three different assay apparatuses 205, in various embodiments, the condition analysis system 170 includes fewer or additional assay apparatuses. In particular embodiments, the condition analysis system 170 does not include an assay apparatus. In such embodiments, the condition analysis system 170 includes only the computational system 202. In these embodiments in which the condition analysis system 170 does not include an assay apparatus, the condition analysis system 170 may perform the screen (e.g., screen 125 described in FIG. 1A), intra-individual analysis (e.g., intra-individual analysis 128 described in FIG. 1A), and the second analysis (e.g., second analysis 130 described in FIG. 1A). However, the condition analysis system 170 does not perform an assay. The assay apparatus 205 may be operated and used by a different entity, such as a third party entity (e.g., third party entity 155 described in FIG. 1B). Thus, the third party entity can perform assays using one or more assay apparatus 205 and then transmits the data generated from the assays to the condition analysis system 170 for performing the screen and/or second analysis.

Assays

Methods disclosed herein involve performing an assay to generate marker information. Assays described in this section can refer to either assay 120A, assay 120B, or both assay 120A and assay 120B shown in FIGS. 1A-1C. Referring to FIG. 2A, performing an assay can involve employing one or more assay apparatuses 205 to perform the assay. In various embodiments, marker information refers to quantitative values of biomarkers, such as protein biomarkers, nucleic acid biomarkers, or metabolite biomarkers. Thus, the quantitative values of biomarkers in a sample can be used to determine whether the individual is at risk for a health condition. In various embodiments, to determine quantitative values of protein biomarkers, performing an assay can include performing one or more of an immunoassay, a protein-binding assay, an antibody-based assay, an antigen-binding protein-based assay, a protein-based array, an enzyme-linked immunosorbent assay (ELISA), or a Western blot. To determine quantitative values of nucleic acid biomarkers, performing an assay can include performing one or more of quantitative PCR (qPCR) or digital PCR (dPCR). To determine quantitative values of metabolites, performing an assay can include performing NMR, mass spectrometry, LC-MS, or UPLC-MS/MS.

In various embodiments, marker information refers to sequence information for a plurality of genomic sites. The sequence information can then be analyzed to generate a prediction for an individual (e.g., whether an individual is at risk for a health condition or whether the individual has the health condition). In particular embodiments, performing the assay results in generation of methylation sequence information. Methylation sequence information includes methylation statuses for a plurality of genomic sites. In various embodiments, the plurality of genomic sites are previously identified and selected. For example, the plurality of genomic sites may be one or more CpG sites whose differential methylation are informative for determining whether an individual is at risk for a health condition. A CpG site is portion of a genome that has cytosine and guanine separated by only one phosphate group and is often denoted as "5'-C-phosphate-G-3'", or "CpG" for short. Regions with a high frequency of CpG sites are commonly referred to as "CG islands" or "CGIs". It has been found that certain CGIs and certain features of certain CGIs in tumor cells tend to be different from the same CGIs or features of the CGIs in healthy cells. Herein, such CGIs and features of the genome are referred to herein as "cancer informative CGIs."

Figure 2B:
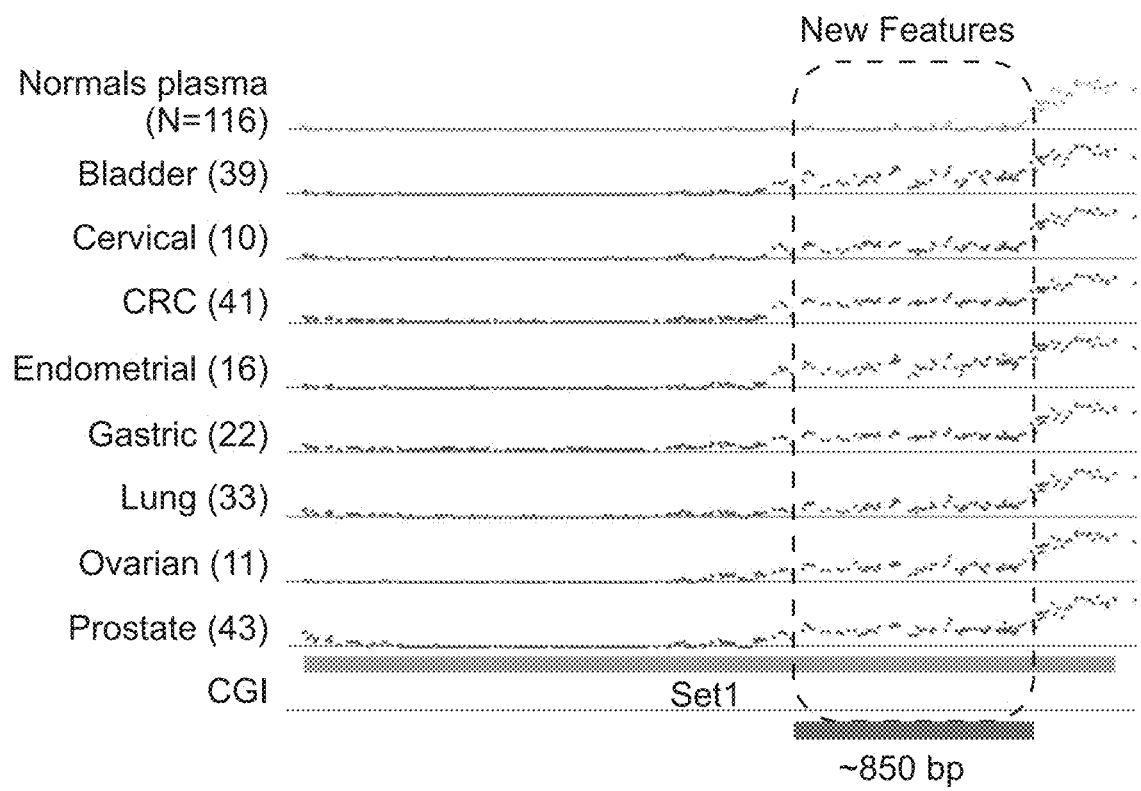
FIG. 2B depicts example methylation information useful for determining whether an individual is at risk for a health condition, in accordance with an embodiment.

Reference is made to FIG. 2B, which depicts example methylation information useful for determining whether an individual is at risk for a health condition, in accordance with an embodiment. Specifically, FIG. 2B shows that across various types of cancers (e.g., bladder, cervical, colorectal, endometrial, gastric, lung, ovarian, and prostate cancers), sub-regions within a particular CGI can exhibit differential methylation in comparison to normal plasma. Thus, FIG. 2B depicts an example cancer informative CGI such that performing the assay results in the generation of methylation sequence information corresponding to the cancer informative CGI.

In various embodiments, performing an assay to generate sequence information for a plurality of genomic sites includes the steps of processing nucleic acids of a sample, enriching the processed nucleic acids for pre-selected genomic sequences (e.g., pre-selected informative CGIs), amplifying the genomic sequences to generate amplicons, and quantifying the amplicons including the genomic sequences (e.g., via sequencing or via quantitative methods such as an ELISA, quantitative PCR, or DNA or RNA-based assay). In various embodiments, performing an assay to generate sequence information for a plurality of genomic sites involves a subset of the previously mentioned steps. For example, enriching the processed nucleic acids can be omitted. Therefore, performing an assay may include processing nucleic acids of a sample, amplifying the pre-selected genomic sequences, and quantifying the amplicons including the genomic sequences.

Referring again to any of FIGS. 1A-1C, in various embodiments, assay 120A and assay 120B may both involve performing steps of processing nucleic acids of a sample, enriching the processed nucleic acids for pre-selected genomic sequences (e.g., pre-selected informative CGIs), amplifying the genomic sequences to generate amplicons, and quantifying the amplicons including the genomic sequences. In some embodiments, assay 120A and assay 120B may differ. For example, assay 120A can exclude the step of enriching nucleic acids and therefore, includes the steps of processing nucleic acids, amplifying the genomic sequences, and quantifying the amplicons. Assay 120B includes the steps of processing nucleic acids, enriching genomic sequences, amplifying the genomic sequences, and quantifying the amplicons. In various embodiments, assay 120A involves quantifying the amplicons by performing an ELISA assay or by performing quantitative PCR whereas assay 120B involves quantifying the amplicons by performing next generation sequencing.

In various embodiments, performing an assay (e.g., assay 120A or assay 120B) involves processing nucleic acids (e.g., cfDNA fragments) from a sample (e.g., liquid biopsy sample). In various embodiments, processing nucleic acids includes treating the nucleic acids to capture methylation modifications. In various embodiments, processing nucleic acids to capture methylation modifications includes performing bisulfite conversion. Bisulfite conversion enables highly efficient conversion of unmethylated cytosines to uracils of DNA from samples such as whole blood or plasma, cultured cells, tissue samples, genomic DNA, and formalin-fixed, paraffin-embedded (FFPE) tissues. Bisulfite conversion can be performed using commercially available technologies, such as Zymo Gold available from Zymo Research (Irvine, CA) or EpiTect Fast available from Qiagen (Germantown, MD). Other techniques include but are not limited to enzymatic methods. In various embodiments, processing nucleic acids to capture methylation modifications includes performing any of nucleic acid amplification, polymerase chain reaction (PCR), methylation specific PCR, bisulfite pyrosequencing, single-strand conformation polymorphism (SSCP) analysis, methylation-sensitive single-strand conformation analysis restriction analysis, high resolution melting analysis, methylation-sensitive single-nucleotide primer extension, restriction analysis, microarray technology, next generation methylation sequencing, nanopore sequencing, and combinations thereof.

In various embodiments, performing the assay includes enriching for specific genomic sequences, such as genomic sequences of pre-selected CGIs. In various embodiments, enrichment of pre-selected CGIs can be accomplished via hybrid capture. Examples of such hybrid capture probe sets include the KAPA HyperPrep Kit and SeqCAP Epi Enrichment System from Roche Diagnostics (Pleasanton, CA). For example, hybrid capture probe sets can be designed to target (e.g., hybridize with) selected genomic sequences, thereby capturing and enriching the selected genomic sequences.

In various embodiments, performing the assay includes a step of nucleic acid amplification. Examples of such assays include, but are not limited to performing PCR assays, Real-time PCR assays, Quantitative real-time PCR (qPCR) assays, digital PCR (dPCR), Allele-specific PCR assays, Reverse-transcription PCR assays and reporter assays. For example, given the processed nucleic acids (e.g., bisulfite converted nucleic acids) that are enriched for pre-selected genomic sequences, a PCR assay is performed to amplify the pre-selected genomic sequences to generate amplicons. Here, PCR primers are added to initiate the amplification. In various embodiments, the PCR primers are whole genome primers that enable whole genome amplification. In various embodiments, the PCR primers are gene-specific primers that result in amplification of sequences of specific genes. In various embodiments, the PCR primers are allele-specific primers. For example, allele specific primers can target a genomic sequence corresponding to a pre-selected CGI, such that performing nucleic acid amplification results in amplification of the genomic sequence of the pre-selected CGI.

In various embodiments, performing the assay includes quantifying the nucleic acids including the pre-selected genomic sequences (e.g., informative CGIs). In some embodiments, quantifying the nucleic acids to generate sequence information comprises performing an enzyme-linked immunosorbent assay (ELISA). In some embodiments, quantifying the nucleic acids to generate sequence information comprises performing quantitative PCR (qPCR) or digital PCR (dPCR). Therefore, the number of methylated, unmethylated, or partially methylated pre-selected genomic sequences can be quantified.

In various embodiments, quantifying the nucleic acids comprises sequencing the nucleic acids including the pre-selected genomic sequences. Thus, the sequenced reads can be aligned to a reference library and methylation sequence information including methylation statuses of the informative CGIs can be determined. Therefore, the number of methylated, unmethylated, or partially methylated pre-selected genomic sequences can be quantified via the sequenced reads.

Figure 2C:
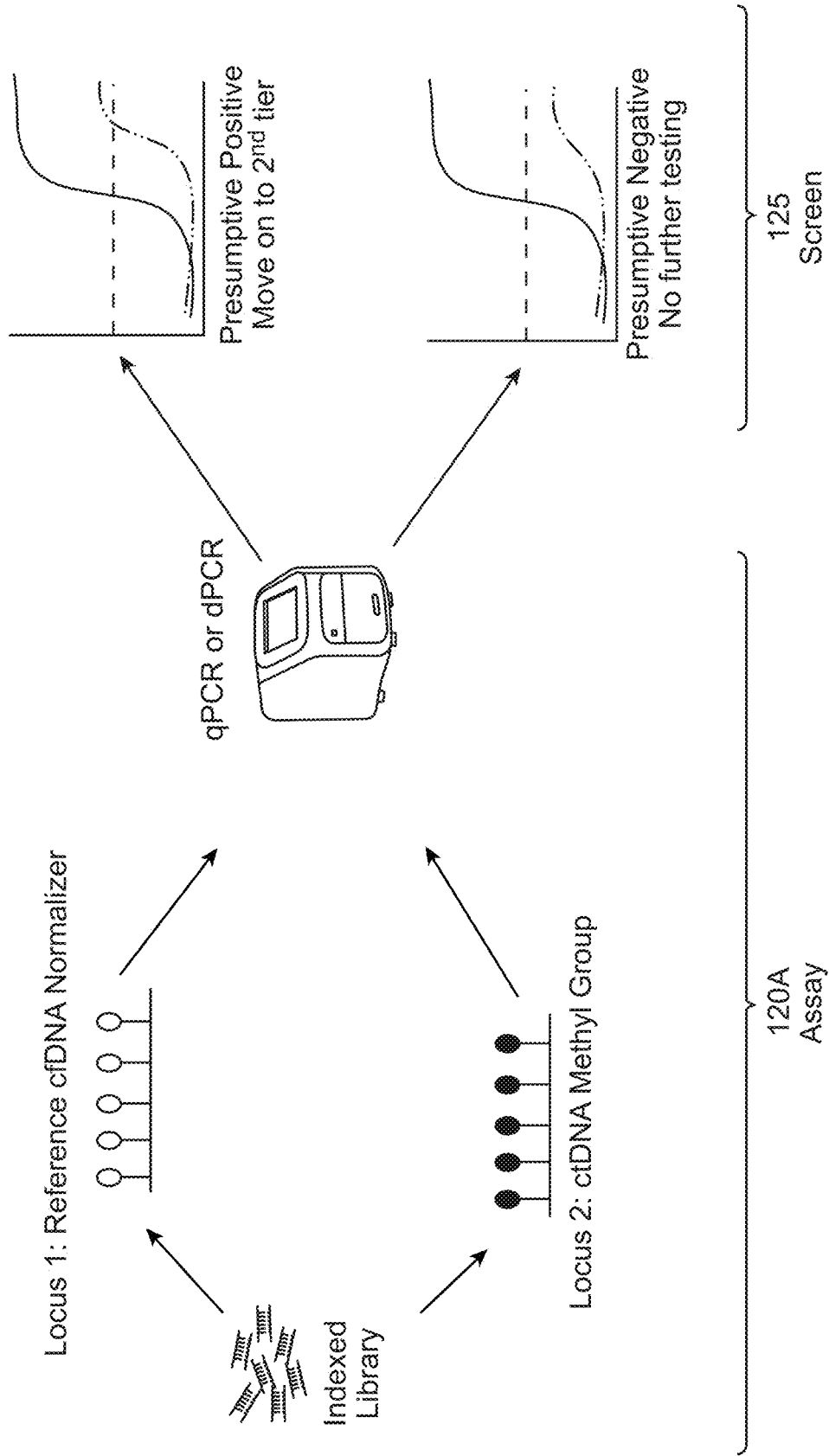
FIG. 2C shows an example flow process for determining whether an individual is at risk for a health condition, in accordance with an embodiment.

FIG. 2C shows an example flow process for determining whether an individual is at risk for a health condition, in accordance with an embodiment. Here, specific genomic regions of an indexed library of nucleic acids (e.g., DNA) are targeted. For example, locus 1 can refer to a reference genomic location. Here, a reference genomic location serves as a control. For example, the reference genomic location is not differentially methylated in healthy individuals in comparison to individuals with the health condition. Locus 2 can refer to a pre-selected genomic location, such as a pre-selected informative CGI.

Performing the assay further includes performing nucleic acid amplification (e.g., PCR) to generate marker information. In various embodiments, nucleic acid amplification includes either qPCR or dPCR. This quantifies the number of methylated, unmethylated, or partially methylated sequences at locus 1 (reference) and at locus 2. In various embodiments, performing the assay includes performing an ELISA to quantify the number of methylated, unmethylated, or partially methylated sequences at locus 1 (reference) and at locus 2.

Assays for Generating Sequencing Information for Performing Intra-Individual Analysis In particular embodiments, assays disclosed herein (e.g., assay 120A or 120B shown in FIGS. 1A-1C) are useful for generating sequencing information for performing an intra-individual analysis. For example, an assay is performed to generate sequence information for target nucleic acids and/or reference nucleic acids.

In various embodiments, sequence information of target nucleic acids and/or sequence information of reference nucleic acids refer to statuses for a plurality of genomic sites. Sequence information of target nucleic acids refers to epigenetic statuses (e.g., methylation statuses) across a plurality of genomic sites in the target nucleic acids. Sequence information of reference nucleic acids refers to epigenetic statuses (e.g., methylation statuses) across a plurality of genomic sites in the reference nucleic acids. In various embodiments, the plurality of genomic sites are previously identified and selected. For example, the plurality of genomic sites may be one or more CpG sites whose differential methylation are informative for determining whether an individual has a health condition. A CpG site is portion of a genome that has cytosine and guanine separated by only one phosphate group and is often denoted as "5'-C-phosphate-G-3'", or "CpG" for short. Regions with a high frequency of CpG sites are commonly referred to as "CG islands" or "CGIs". It has been found that certain CGIs and certain features of certain CGIs in tumor cells tend to be different from the same CGIs or features of the CGIs in healthy cells. Herein, such CGIs and features of the genome are referred to herein as "cancer informative CGIs." Cancer informative CGI can be a "CGI identifier" or reference number to allow referencing CGIs during data processing by their respective unique CGI identifiers. Example CGIs include, but are not limited to, the CGIs shown in the accompanying tables (referred to herein as Tables 1-4) which lists, for each CGI, its respective location in the human genome. Additional example CGIs are disclosed in WO2018209361 (see Table 1) and WO2022133315 (see Table 2 entitled "TOO Methylation Sites" and Table 3 entitled "Pan Cancer Methylation Sites"), each of which is hereby incorporated by reference in its entirety.

In various embodiments, performing an assay to generate sequence information for a plurality of genomic sites includes the steps of processing nucleic acids of a sample, enriching the processed nucleic acids for pre-selected genomic sequences (e.g., pre-selected informative CGIs), amplifying the genomic sequences to generate amplicons, and quantifying the amplicons including the genomic sequences (e.g., via sequencing such as next generation sequencing or via quantitative methods such as an ELISA, quantitative PCR, allele-specific PCR, or DNA or RNA-based assay). In various embodiments, performing an assay to generate sequence information for a plurality of genomic sites involves a subset of the previously mentioned steps. For example, enriching the processed nucleic acids can be omitted. Therefore, performing an assay may include processing nucleic acids of a sample, amplifying the pre-selected genomic sequences, and quantifying the amplicons including the genomic sequences.

In various embodiments, performing an assay (e.g., assay 120A or assay 120B) involves processing target nucleic acids and/or reference nucleic acids. In various embodiments, processing target nucleic acids and/or reference nucleic acids to capture methylation modifications includes performing bisulfite conversion. Bisulfite conversion enables highly efficient conversion of unmethylated cytosines to uracils of DNA from samples such as whole blood or plasma, cultured cells, tissue samples, genomic DNA, and formalin-fixed, paraffin-embedded (FFPE) tissues. Bisulfite conversion can be performed using commercially available technologies, such as Zymo Gold available from Zymo Research (Irvine, CA) or EpiTect Fast available from Qiagen (Germantown, MD). Other techniques include but are not limited to enzymatic methods. In various embodiments, processing target nucleic acids and/or reference nucleic acids to capture methylation modifications includes performing any of nucleic acid amplification, polymerase chain reaction (PCR), methylation specific PCR, bisulfite pyrosequencing, single-strand conformation polymorphism (SSCP) analysis, methylation-sensitive single-strand conformation analysis restriction analysis, high resolution melting analysis, methylation-sensitive single-nucleotide primer extension, restriction analysis, microarray technology, next generation methylation sequencing, nanopore sequencing, and combinations thereof.

In various embodiments, performing the assay includes enriching for specific sequences in the target nucleic acids and/or reference nucleic acids. In various embodiments, the specific sequences refer to sequences of pre-selected CGIs. In various embodiments, enrichment of pre-selected CGIs can be accomplished via hybrid capture. Examples of such hybrid capture probe sets include the KAPA HyperPrep Kit and SeqCAP Epi Enrichment System from Roche Diagnostics (Pleasanton, CA). For example, hybrid capture probe sets can be designed to hybridize with particular sequences of the target nucleic acids and/or reference nucleic acids, thereby capturing and enriching the particular sequences.

In various embodiments, performing the assay includes performing nucleic acid amplification to amplify the particular sequences of the target nucleic acids and/or reference nucleic acids. Examples of such assays include, but are not limited to performing PCR assays, Real-time PCR assays, Quantitative real-time PCR (qPCR) assays, digital PCR (dPCR), Allele-specific PCR assays, Reverse-transcription PCR assays and reporter assays. For example, given the processed nucleic acids (e.g., bisulfite converted nucleic acids) that are enriched for pre-selected sequences, a PCR assay is performed to amplify the pre-selected sequences to generate amplicons. Here, PCR primers are added to initiate the amplification. In various embodiments, the PCR primers are whole genome primers that enable whole genome amplification. In various embodiments, the PCR primers are gene-specific primers that result in amplification of sequences of specific genes. In various embodiments, the PCR primers are allele-specific primers. For example, allele specific primers can target a genomic sequence corresponding to a pre-selected CGI, such that performing nucleic acid amplification results in amplification of the sequence of the pre-selected CGI.

In various embodiments, performing the assay includes quantifying the nucleic acids including the pre-selected sequences (e.g., informative CGIs). In some embodiments, quantifying the nucleic acids to generate sequence information comprises performing any of real-time PCR assay, quantitative real-time PCR (qPCR) assay, digital PCR (dPCR) assay, allele-specific PCR assay, or reverse-transcription PCR assay. Therefore, the number of methylated, hypermethylated, unmethylated, or partially methylated pre-selected sequences are quantified.

In various embodiments, quantifying the nucleic acids comprises sequencing the nucleic acids including the pre-selected sequences. Thus, the sequenced reads are aligned to a reference library and sequence information including methylation statuses of the informative CGIs of amplicons derived from the target nucleic acids and/or reference nucleic acids can be determined. Therefore, the number of methylated, hypermethylated, unmethylated, or partially methylated pre-selected sequences of the target nucleic acids and the reference nucleic acids can be quantified via the sequenced reads.

Screen

The description in this section pertains to the performance of a screen, such as screen 125 described in FIG. 1A, which can be performed by the screen module 210 described in FIG. 2A. Generally, a screen is performed on marker information generated by the assay (e.g., assay 120A). In various embodiments, the screen is performed to determine whether a biological sample is at risk or not at risk of containing a signal indicative of a health condition. For example, the screen is performed to determine whether a biological sample is at risk or not at risk of containing circulating tumor DNA. Circulating DNA within the biological sample may indicate that the individual (e.g., individual from whom the biological sample is obtained) may be at risk of a health condition, such as cancer. In various embodiments, the screen is performed to classify the individual as at risk for having a health condition, or not at risk for having the health condition.

In various embodiments, the marker information represents quantified values of biomarkers. For example, depending on the type of biomarker, the quantified values may be generated via one or more of: an immunoassay, a protein-binding assay, an antibody-based assay, an antigen-binding protein-based assay, a protein-based array, an enzyme-linked immunosorbent assay (ELISA), a Western blot, quantitative PCR (qPCR) or digital PCR (dPCR), NMR, mass spectrometry, LC-MS, or UPLC-MS/MS.

In various embodiments, performing the screen involves comparing the quantified values of biomarkers to one or more reference values or to threshold values. For example, a reference value can be a statistical measure of quantified biomarker values corresponding to individuals known to be at risk for the health condition. Therefore, if the comparison identifies that the quantified values of biomarkers for an individual is statistically significantly different from the reference value corresponding to individuals known to be at risk for the health condition, then the screen can identify the individual as not at risk for the health condition.

In various embodiments, the marker information represents sequencing information for one or more genomic locations, such as one or more CpG islands. In various embodiments, performing the screen involves comparing methylation information at one or more pre-selected genomic locations to quantified values of reference genomic locations. For example, referring again to FIG. 2C, an assay may have been performed that generates methylation information for locus 1 corresponding to a reference genomic location and for locus 2 corresponding to a pre-selected genomic location (e.g., a pre-selected informative CGI). Thus, the methylation information at locus 1 is compared to methylation information at locus 2. Based on the comparison, the screen can identify the individual as at risk for the health condition, or not at risk for the health condition.

As an example, the methylation information for one or more pre-selected genomic locations and methylation information for reference genomic locations can be cycle threshold (Ct) values. Cycle threshold refers to the number of PCR cycles needed for a sample to amplify and cross a threshold. In various embodiments, if a difference between the Ct value of the methylation sequences of the pre-selected genomic locations and the Ct value of the reference genomic locations is greater than a threshold, then the screen identifies the individual as at risk for the health condition. If a difference between the Ct value of the methylation sequences of the pre-selected genomic locations and the Ct value of the reference genomic locations is less than a threshold, then the screen identifies the individual as not at risk for the health condition.

In various embodiments, a screen is performed on sequence information generated via sequencing (e.g., next generation sequencing) of sequences at the one or more genomic locations, such as one or more CpG islands. In various embodiments, such a screen is performed using a system comprising a computer storage and a processing system. The screen can further involve the implementation of a machine learning model. For example, the computer storage can store sequence information corresponding to a processed sample, the processed sample including cell-free DNA fragments originating from a liquid biopsy of an individual and having been processed to enrich for cancer informative CGIs, the sequencer information comprising, for each sequenced cell-free DNA fragment corresponding to the cancer informative CGIs, a respective position on the genome for the cell-free DNA fragment and methylation information for the cell-free DNA fragment. The processing system can compute values of the cancer informative CGIs for the individual and applies the values as input to a trained machine learning model. The machine learning model provides a predicted output as to whether the individual is at risk for the health condition based on the values of the cancer informative CGIs.

In various embodiments, the screen achieves at least 60% sensitivity in detecting presence of a health condition. In various embodiments, the screen achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sensitivity. In particular embodiments, the screen achieves at least 75% sensitivity. In particular embodiments, the screen achieves at least 76% sensitivity. In particular embodiments, the screen achieves at least 77% sensitivity. In particular embodiments, the screen achieves at least 78% sensitivity. In particular embodiments, the screen achieves at least 79% sensitivity. In particular embodiments, the screen achieves at least 80% sensitivity.

In various embodiments, the screen achieves at least 60% specificity in excluding individuals without the health condition. In various embodiments, the screen achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% specificity. In particular embodiments, the screen achieves at least 90% specificity. In particular embodiments, the screen achieves at least 91% specificity. In particular embodiments, the screen achieves at least 92% specificity. In particular embodiments, the screen achieves at least 93% specificity. In particular embodiments, the screen achieves at least 94% specificity. In particular embodiments, the screen achieves at least 95% specificity.

In various embodiments, the screen achieves at least 15% positive predictive value. In various embodiments, the screen achieves at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, or at least 40% positive predictive value. In particular embodiments, the screen achieves at least 20% positive predictive value. In particular embodiments, the screen achieves at least 21% positive predictive value. In particular embodiments, the screen achieves at least 22% positive predictive value. In particular embodiments, the screen achieves at least 23% positive predictive value. In particular embodiments, the screen achieves at least 24% positive predictive value. In particular embodiments, the screen achieves at least 25% positive predictive value.

In various embodiments, the screen achieves at least 60% negative predictive value. In various embodiments, the screen achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% negative predictive value. In particular embodiments, the screen achieves at least 95% negative predictive value. In particular embodiments, the screen achieves at least 96% negative predictive value. In particular embodiments, the screen achieves at least 97% negative predictive value. In particular embodiments, the screen achieves at least 98% negative predictive value. In particular embodiments, the screen achieves at least 99% negative predictive value.

Intra-Individual Analysis

The description in this section pertains to the performance of an intra-individual analysis, such as an intra-individual analysis 128 described in FIG. 1, which can be performed by the condition analysis system 1709 (and more specifically, the signal generation module 215) described in FIG. 2A. Generally, an intra-individual analysis is performed on sequence information of target nucleic acids and sequence information of reference nucleic acids. As described herein, the sequence information of target nucleic acids and sequence information of reference nucleic acids are generated by performing one or more assays (e.g., assay 120A and/or assay 120B). In particular embodiments, the sequence information of target nucleic acids comprise sequence information of cell free DNA. In particular embodiments, the sequence information of reference nucleic acids comprise sequence information of cells, such as peripheral blood mononuclear cells (PBMCs) or polymorphonuclear cells.

The intra-individual analysis involves combining the sequence information of target nucleic acids and sequence information of reference nucleic acids to generate a signal informative for determining presence or absence of a health condition. Here, the step of combining the sequence information of target nucleic acids and sequence information of reference nucleic acids can be performed by the signal generation module 210 shown in FIG. 2A.

In various embodiments, combining the sequence information of target nucleic acids and sequence information of reference nucleic acids involves differentiating between signatures present or absent in the sequence information of target nucleic acids and signatures present or absent in the sequence information of the reference nucleic acids. For example, if particular signatures are present in the sequence information of target nucleic acids, and the signatures are also present in the sequence information of reference nucleic acids, the signatures in both the target nucleic acids and reference nucleic acids may represent baseline biological signatures. Thus, these signatures may be excluded from the resulting signal informative of determining presence or absence of the health condition. As another example, if particular signatures are present in the sequence information of target nucleic acids, but those signatures are absent in the sequence information of reference nucleic acids, the signatures may not be baseline biological signatures. Thus, these signatures may be included in the resulting signal informative of determining presence or absence of the health condition.

In various embodiments, combining the sequence information of the target nucleic acids and the sequence information of the reference nucleic acids includes aligning the sequence information of the target nucleic acids and the sequence information of the reference nucleic acids. For example, aligning the sequence information involves aligning sequences of a plurality of pre-selected genomic sites for the target nucleic acids and sequences of the same or overlapping plurality of pre-selected genomic sites for the reference nucleic acids.

In various embodiments, both the sequence information of the target nucleic acids and the sequence information of the reference nucleic acids are aligned to a reference genome library (e.g., a reference assembly) with known sequences. Therefore, sequence information of the target nucleic acids are aligned to the sequence information of the reference nucleic acids via the reference genome library. In various embodiments, the sequence information of the target nucleic acids is aligned directly with the sequence information of the reference nucleic acids. In such embodiments, a reference genome library need not be used.

In various embodiments, combining the sequence information of the target nucleic acids and the sequence information of the reference nucleic acids includes determining a difference between the sequence information of the target nucleic acids to the sequence information of the reference nucleic acids.

In various embodiments, differences between the sequence information of the target nucleic acids and the sequence information of the reference nucleic acids are performed on a per-position basis. For example, at a first position of a genomic site, the difference between the sequence information of the target nucleic acids at the first position and the sequence information of the reference nucleic acid at the same first position is determined. The process can then be further repeated for additional positions (e.g., for additional positions across the plurality of genomic sites). In various embodiments, the differences are determined on a per-position basis if the sequence information of the target nucleic acids and reference nucleic acids were generated using a sequencing assay (e.g., next generation sequencing) which provides base-level resolution of the sequences.

In various embodiments, differences between the sequence information of the target nucleic acids and the sequence information of the reference nucleic acids are performed on a per-CGI basis. For example, at a first CGI of a genomic site, the difference between the sequence information of the target nucleic acids at the first CGI and the sequence information of the reference nucleic acid at the same CGI or overlapping portion of the first CGI is determined. The process can then be further repeated for additional CGIs (e.g., for additional CGIs across the plurality of genomic sites). In various embodiments, the differences are determined on a per-CGI basis if the sequence information of the target nucleic acids and reference nucleic acids were generated using a quantitative assay (e.g., qPCR assay).

In various embodiments, differences between the sequence information of the target nucleic acids and the sequence information of the reference nucleic acids are performed on a per-allele basis. For example, at a first allele of a genomic site, the difference between the sequence information of the target nucleic acids at the first allele and the sequence information of the reference nucleic acid at the same allele or overlapping portion of the first allele is determined. The process can then be further repeated for additional alleles (e.g., for additional alleles across the plurality of genomic sites). In various embodiments, the differences are determined on a per-allele basis if the sequence information of the target nucleic acids and reference nucleic acids were generated using a quantitative assay (e.g., qPCR assay or allele-specific PCR assay).

Figure 2D:
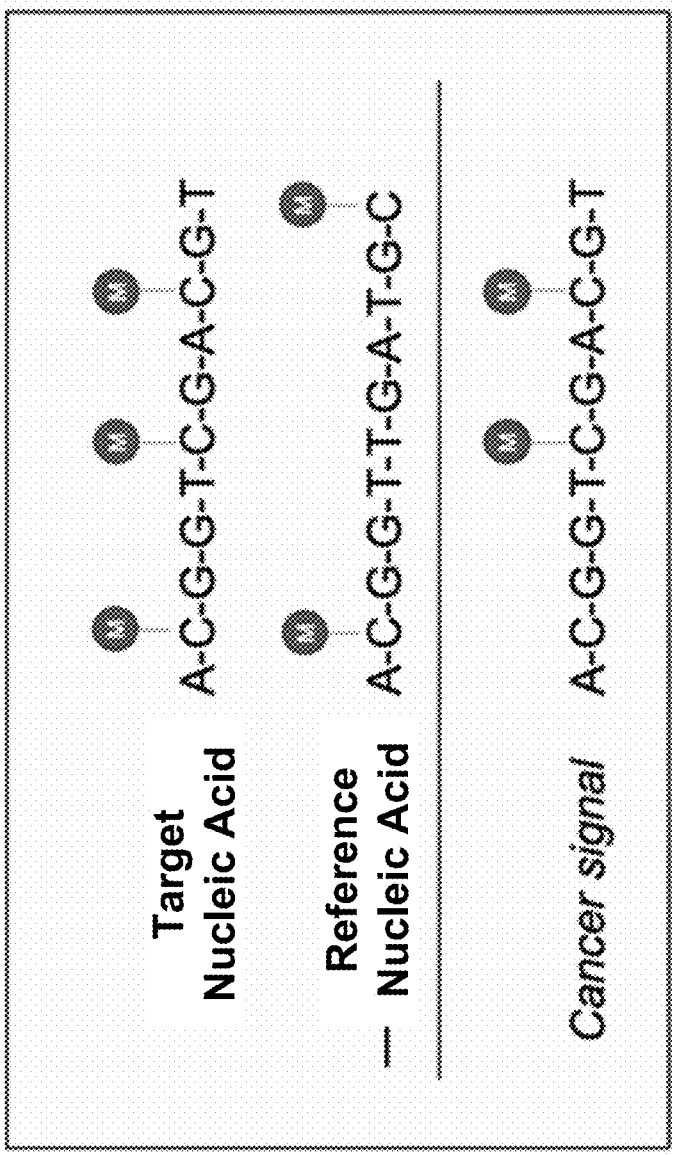
FIG. 2D depicts an example process of combining sequence information of target nucleic acids and reference nucleic acids to generate a signal informative for determining presence or absence of a health condition, in accordance with an embodiment.

Reference is now made to FIG. 2D, which depicts an example combining of sequence information of target nucleic acids and reference nucleic acids to generate a signal informative for a health condition, in accordance with an embodiment. The sequence information of the target nucleic acids and the sequence information of the reference nucleic acids include methylation statuses across a plurality of genomic sites. FIG. 2D shows an example genomic site in which nucleotide bases may be differentially methylated in the target nucleic acid and the reference nucleic acid. For example, as shown in FIG. 2D, the nucleotide base at the second position is methylated (as represented by the presence of a cytosine base which arises following bisulfite conversion) in both the target nucleic acid and the reference nucleic acid. Given that the methylation at the second position occurs in both the target nucleic acid and the reference nucleic acid, this may be a baseline biological signature. Conversely, the target nucleic acid may additionally be methylated at the sixth position and the ninth position, whereas the reference nucleic acid is unmethylated at the sixth position and the ninth position. Here, given that the reference nucleic acid is not methylated at the sixth and ninth position, the presence of the methylated nucleotide bases in the target nucleic acid may represent signatures that are informative of presence or absence of the health condition. Additionally, at the eleventh nucleotide position, the target nucleic acid is unmethylated whereas the reference nucleic acid is methylated. Here, the methylation of the reference nucleic acid can be interpreted as a baseline biological signature.

The differences between the methylation status at each position of the target nucleic acid and the reference nucleic acid can represent the cancer signal. As shown in FIG. 2D, the cancer signal includes methylation statuses at the genomic site, wherein the sixth and ninth position are methylated. Thus, the cancer signal includes signatures from the target nucleic acids that are likely informative of the health condition (e.g., methylated statuses of the sixth and ninth nucleotide bases), and further excludes baseline biological signatures (e.g., baseline biological signatures present in reference nucleic acids such as methylated statuses of the second and eleventh nucleotide bases).

The intra-individual analysis may further involve analyzing the signal representing the combination of the sequence information of the target nucleic acids and the sequence information of the reference nucleic acids to determine whether a health condition is present or absent in the individual. Here, the step of analyzing the signal to determine presence of absence of the health condition can be performed by the signal generation module 215 shown in FIG. 2A. In various embodiments, a machine learning model is deployed to analyze a signal informative for determining presence or absence of the health condition. The machine learning model analyzes the signal, which represents the difference between epigenetic statuses (e.g., methylation statuses) of the plurality of genomic sites of target nucleic acids and epigenetic statuses (e.g., methylation statuses) of the plurality of genomic sites of reference nucleic acids. Therefore, trained machine learning models analyze the signal across the plurality of genomic sites to output a prediction as to whether the individual has a presence or absence of the health condition.

In particular embodiments, machine learning models analyze methylation statuses of a plurality of genomic sites in cell-free DNA to generate predictions. The methylation statuses can correspond to a set of cancer informative CpG islands (CGIs), wherein the cancer informative CGIs are selected from a group consisting of a ranked set of candidate CGIs. In various embodiments, a machine learning model analyzes methylation statuses for at least 50 CGIs. In various embodiments, a machine learning model analyzes methylation statuses for at least 100 CGIs. In various embodiments, a machine learning model analyzes methylation statuses for at least 150 CGIs. In various embodiments, a machine learning model analyzes methylation statuses for at least 200 CGIs. In various embodiments, a machine learning model analyzes methylation statuses for at least 250 CGIs. In various embodiments, a machine learning model analyzes methylation statuses for at least 300 CGIs. In various embodiments, a machine learning model analyzes methylation statuses for at least 400 CGIs. In various embodiments, a machine learning model analyzes methylation statuses for at least 500 CGIs. In various embodiments, a machine learning model analyzes methylation statuses for at least 600 CGIs. In various embodiments, a machine learning model analyzes methylation statuses for at least 700 CGIs. In various embodiments, a machine learning model analyzes methylation statuses for at least 800 CGIs. In various embodiments, a machine learning model analyzes methylation statuses for at least 900 CGIs. In various embodiments, a machine learning model analyzes methylation statuses for at least 1000 CGIs. In various embodiments, a machine learning model analyzes methylation statuses for at least 2500 CGIs. In various embodiments, a machine learning model analyzes methylation statuses for at least 5000 CGIs. In various embodiments, a machine learning model analyzes methylation statuses for at least 7500 CGIs. In various embodiments, a machine learning model analyzes methylation statuses for at least 10000 CGIs. In various embodiments, a machine learning model analyzes methylation statuses for at least 15000 CGIs. In various embodiments, a machine learning model analyzes methylation statuses for at least 20000 CGIs. In various embodiments, a machine learning model analyzes methylation statuses for at least 25000 CGIs.

In various embodiments, a machine learning model analyzes methylation statuses for CGIs across the whole genome. For example, a machine learning model may be implemented to analyze sequencing data generated from whole genome sequencing (e.g., whole genome bisulfite sequencing).

In particular embodiments, the intra-individual analysis further reveals, for an individual predicted to have a presence of the health condition, a tissue of origin of the health condition. The intra-individual analysis may identify a tissue of origin of the health condition according to the methylation statuses of the cancer informative CGIs. For example, particular methylation patterns across the cancer informative CGIs are attributable to certain tissues, examples of which include the nervous tissue (e.g., brain, spinal cord, nerves), muscle tissue (cardiac muscle, smooth muscle, skeletal muscle), epithelial tissue (e.g., GI tract lining, skin), and connective tissue (e.g., fat, bone, tendon, and ligaments). As a particular example, in patients with brain cancer, a first set of CGIs may be frequently methylated. Therefore, if a similar methylation pattern is observed across the first set of CGIs for an individual, the intra-individual analysis can identify that the individual has cancer, and furthermore, that the cancer is localized to the brain.

Second Analysis

The description in this section pertains to the performance of a second analysis, such as second analysis 130 described in FIG. 1A, which can be performed by the condition analysis module 220 described in FIG. 2A. Generally, a second analysis is performed on sequence information generated by the assay (e.g., assay 120A or assay 120B). In various embodiments, the second analysis is performed to determine whether a biological sample obtained from an individual contains a signal indicative of a health condition. For example, the screen is performed to determine whether a biological sample contains circulating tumor DNA. Circulating DNA within the biological sample may indicate that the individual (e.g., individual from whom the biological sample is obtained) has a health condition, such as cancer. In various embodiments, the second analysis is performed to classify the individual as having a health condition (e.g., cancer), or not having the health condition (e.g., cancer).

In various embodiments, a second analysis is performed on sequence information generated via sequencing (e.g., next generation sequencing) of sequences at the one or more genomic locations, such as one or more CpG islands. In various embodiments, the sequence information is generated as a result of whole genome sequencing and therefore, a second analysis is performed on sequences of one or more genomic locations across the whole genome.

In various embodiments, the second analysis is performed using a system comprising a computer storage and a processing system. The second analysis can involve the implementation of a machine learning model. For example, the computer storage can store sequence information corresponding to a processed sample, the processed sample including cell-free DNA fragments originating from a liquid biopsy of an individual and having been processed to enrich for cancer informative CGIs, the sequencer information comprising, for each sequenced cell-free DNA fragment corresponding to the cancer informative CGIs, a respective position on the genome for the cell-free DNA fragment and methylation information for the cell-free DNA fragment.

In particular embodiments, the second analysis further reveals, for individuals who are determined to have the health condition, a tissue of origin of the health condition. The second analysis may identify a tissue of origin of the health condition according to the methylation statuses of the cancer informative CGIs. For example, particular methylation patterns across the cancer informative CGIs are attributable to certain tissues, examples of which include the nervous tissue (e.g., brain, spinal cord, nerves), muscle tissue (cardiac muscle, smooth muscle, skeletal muscle), epithelial tissue (e.g., GI tract lining, skin), and connective tissue (e.g., fat, bone, tendon, and ligaments). As a particular example, in patients with brain cancer, a first set of CGIs may be frequently methylated. Therefore, if a similar methylation pattern is observed across the first set of CGIs for an individual who is under analysis, the second analysis can identify that the individual has cancer, and furthermore, that the cancer is localized to the brain.

In various embodiments, the second analysis achieves at least 60% sensitivity in detecting presence of a health condition. In various embodiments, the screen achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sensitivity. In particular embodiments, the second analysis achieves at least 85% sensitivity. In particular embodiments, the second analysis achieves at least 86% sensitivity. In particular embodiments, the second analysis achieves at least 87% sensitivity. In particular embodiments, the second analysis achieves at least 88% sensitivity. In particular embodiments, the second analysis achieves at least 89% sensitivity. In particular embodiments, the second analysis achieves at least 90% sensitivity.

In various embodiments, the second analysis achieves at least 60% specificity in excluding individuals without the health condition. In various embodiments, the second analysis achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% specificity. In particular embodiments, the second analysis achieves at least 90% specificity. In particular embodiments, the second analysis achieves at least 91% specificity. In particular embodiments, the second analysis achieves at least 92% specificity. In particular embodiments, the second analysis achieves at least 93% specificity. In particular embodiments, the second analysis achieves at least 94% specificity. In particular embodiments, the second analysis achieves at least 95% specificity.

In various embodiments, the second analysis achieves at least 60% positive predictive value. In various embodiments, the second analysis achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% positive predictive value. In particular embodiments, the second analysis achieves at least 80% positive predictive value. In particular embodiments, the second analysis achieves at least 81% positive predictive value. In particular embodiments, the second analysis achieves at least 82% positive predictive value. In particular embodiments, the second analysis achieves at least 83% positive predictive value. In particular embodiments, the second analysis achieves at least 84% positive predictive value. In particular embodiments, the second analysis achieves at least 85% positive predictive value.

In various embodiments, the second analysis achieves at least 60% negative predictive value. In various embodiments, the second analysis achieves at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% negative predictive value. In particular embodiments, the second analysis achieves at least 90% negative predictive value. In particular embodiments, the second analysis achieves at least 91% negative predictive value. In particular embodiments, the second analysis achieves at least 92% negative predictive value. In particular embodiments, the second analysis achieves at least 93% negative predictive value. In particular embodiments, the second analysis achieves at least 94% negative predictive value. In particular embodiments, the second analysis achieves at least 95% negative predictive value. In particular embodiments, the second analysis achieves at least 96% negative predictive value. In particular embodiments, the second analysis achieves at least 97% negative predictive value. In particular embodiments, the second analysis achieves at least 98% negative predictive value. In particular embodiments, the second analysis achieves at least 99% negative predictive value.

Longitudinal Analysis

Reference is now made to the longitudinal analysis module 230, which represents an optional module of the condition analysis system 170 as shown in FIG. 2A (as indicated by the dotted lines). In various embodiments, the longitudinal analysis enables the monitoring of an individual who has been identified as having the health condition, and determines whether the health condition for the individual has progressed. In various embodiments, the longitudinal analysis involves analyzing whether a first biological sample obtained from the individual at a first timepoint differs from a second biological sample obtained from the individual at a second timepoint. For example, the longitudinal analysis can involve determining a difference in a signal indicative of a health condition in the first biological sample and the second biological sample. The signal may be the presence or quantity of circulating tumor DNA which is indicative of cancer. Thus, the longitudinal analysis can involve determining a change in circulating tumor DNA that is present in the first biological sample and the second biological sample, which may be an indication of the change (e.g., progression) in the health condition (e.g., cancer). In various embodiments, if the longitudinal analysis module 230 determines that the health condition of the individual has progressed, an intervention can be recommended and/or provided to the individual to slow the progression of the health condition.

In various embodiments, the longitudinal analysis module 230 analyzes marker information derived from an additional sample obtained from the individual at a timepoint subsequent to when the individual was identified as having the health condition. For example, the individual may have been previously identified as having the health condition through a screen (e.g., screen 125 in FIG. 1A) and second analysis (e.g., second analysis 130 in FIG. 1A). Here, the screen and/or second analysis may have involved the analysis of sequence information, such as methylation statuses of a plurality of informative CGIs In various embodiments, the longitudinal analysis module 230 analyzes sequence information identifying methylation statuses of the plurality of informative CGIs derived from the additional sample obtained at the subsequent timepoint and compares it to the methylation statuses of the plurality of informative CGIs derived from the previous sample. In various embodiments, such sequence information may be background-corrected sequence information e.g., corrected via an intra-individual analysis that combines sequence information from target nucleic acids and reference nucleic acids. Thus, the longitudinal analysis module 230 generates a longitudinal understanding of how the methylation statuses of the plurality of informative CGIs has changed over time. This longitudinal understanding is informative for determining the progression of the health condition. In various embodiments, if the longitudinal methylation patterns of the plurality of the informative CGIs indicate that the health condition in the individual is progressing, the individual can be provided an intervention to slow or halt the progression of the health condition. In various embodiments, an intervention may be a surgical intervention, a therapeutic intervention (e.g., a chemotherapeutic, a gene therapy, gene editing), or a lifestyle intervention (e.g., change in behavior or habits).

Interactions Between Third Party Entities and Condition analysis system

Figure 3A:
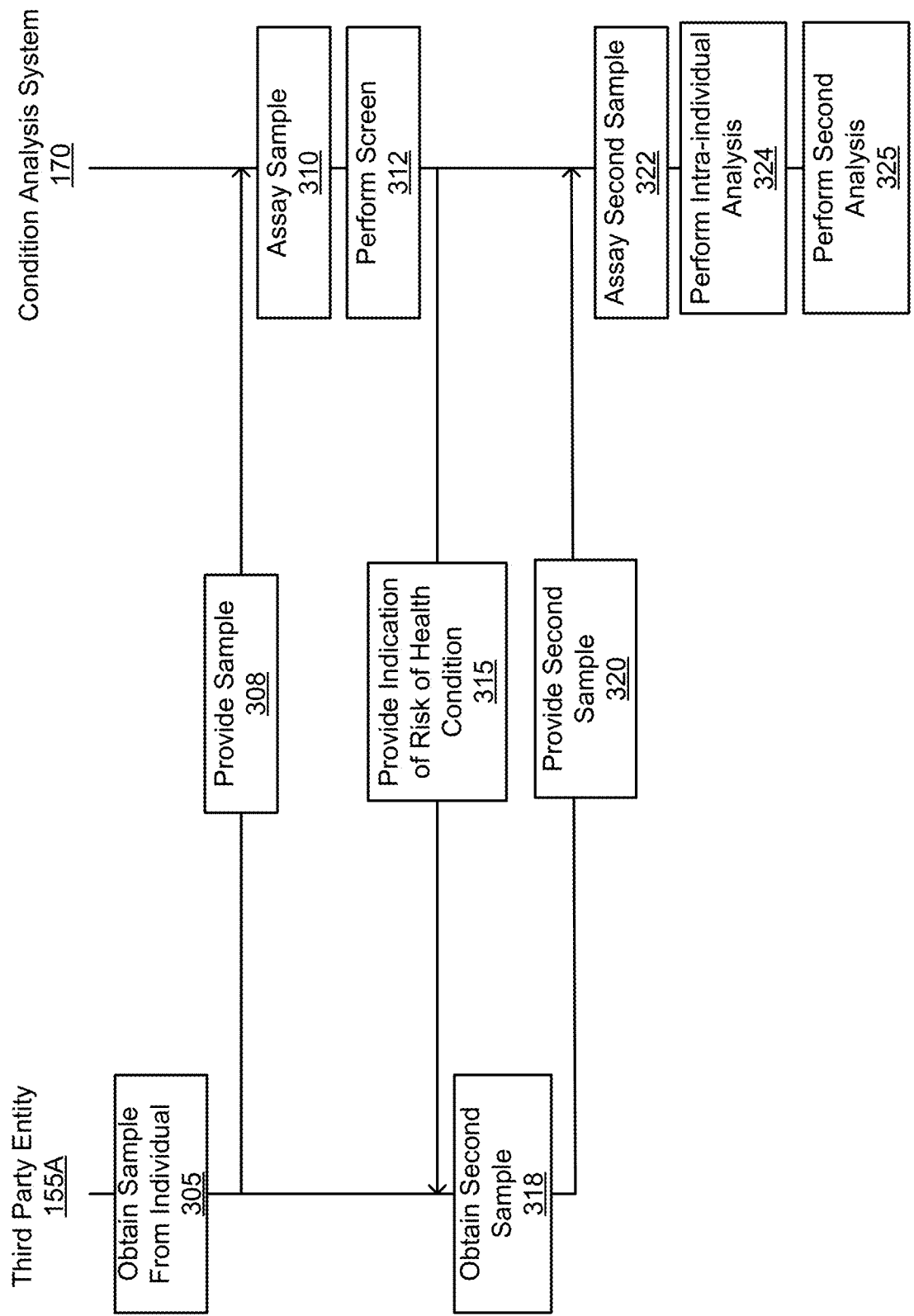
FIG. 3A shows an interaction diagram between a third party entity and a condition analysis system for performing the multiple tier analysis, in accordance with a first embodiment.

FIG. 3A shows an interaction diagram between a third party entity and a condition analysis system for performing the multiple tier analysis, in accordance with a first embodiment. Here, FIG. 3A shows the embodiment in which the third party entity 155A obtains samples from an individual, and the condition analysis system 170 performs one or more assays, the screen, the intra-individual analysis, and the second analysis.

Specifically, the process begins at step 305 where the third party entity 155A obtains a sample from an individual. The third party entity 155A provides 308 the sample to the condition analysis system 170. The condition analysis system assays 310 the sample to generate marker information. In various embodiments, the marker information includes methylation statuses for a plurality of genomic sites, such as a plurality of selected CpG islands. Thus, the condition analysis system 170 performs a screen 312 by analyzing the methylation statuses using a trained machine learning model. The screen can identify the individual as at risk for the health condition, or not at risk for the health condition. If the individual is determined to not be at risk for the health condition, the process terminates and subsequent analysis is not performed.

If the individual is determined to be at risk for the health condition, the condition analysis system 170 provides 315 an indication that the individual is at risk for the health condition to the third party entity 155A. At step 318, the third party entity 155A obtains a second sample from the individual who was determined to be at risk for the health condition. The third party entity 155A provides 320 the second sample to the condition analysis system 170. The condition analysis system 170 assays 322 the second sample to generate methylation information. In one embodiment, the assaying the second sample involves performing whole genome bisulfite sequencing. In one embodiment, assaying the second sample involves performing a hybrid capture. In various embodiments, step 322 involves assaying the second sample to generate sequence information for target nucleic acids and sequence information for reference nucleic acids. For example, the sequence information for the target nucleic acids may include methylation information of the target nucleic acids. The sequence information for the reference nucleic acids may include methylation information of the reference nucleic acids. At step 324, the condition analysis system 170 performs an intra-individual analysis to remove baseline biological signatures and generate background-corrected information. Thus, at step 325, the condition analysis system 170 performs the second analysis by analyzing the background-corrected information and determines a presence or absence of the health condition in the individual. If the individual is determined to have the health condition, the individual can be monitored, provided treatment, and/or selected as a candidate subject for enrollment in a clinical trial.

Figure 3B:
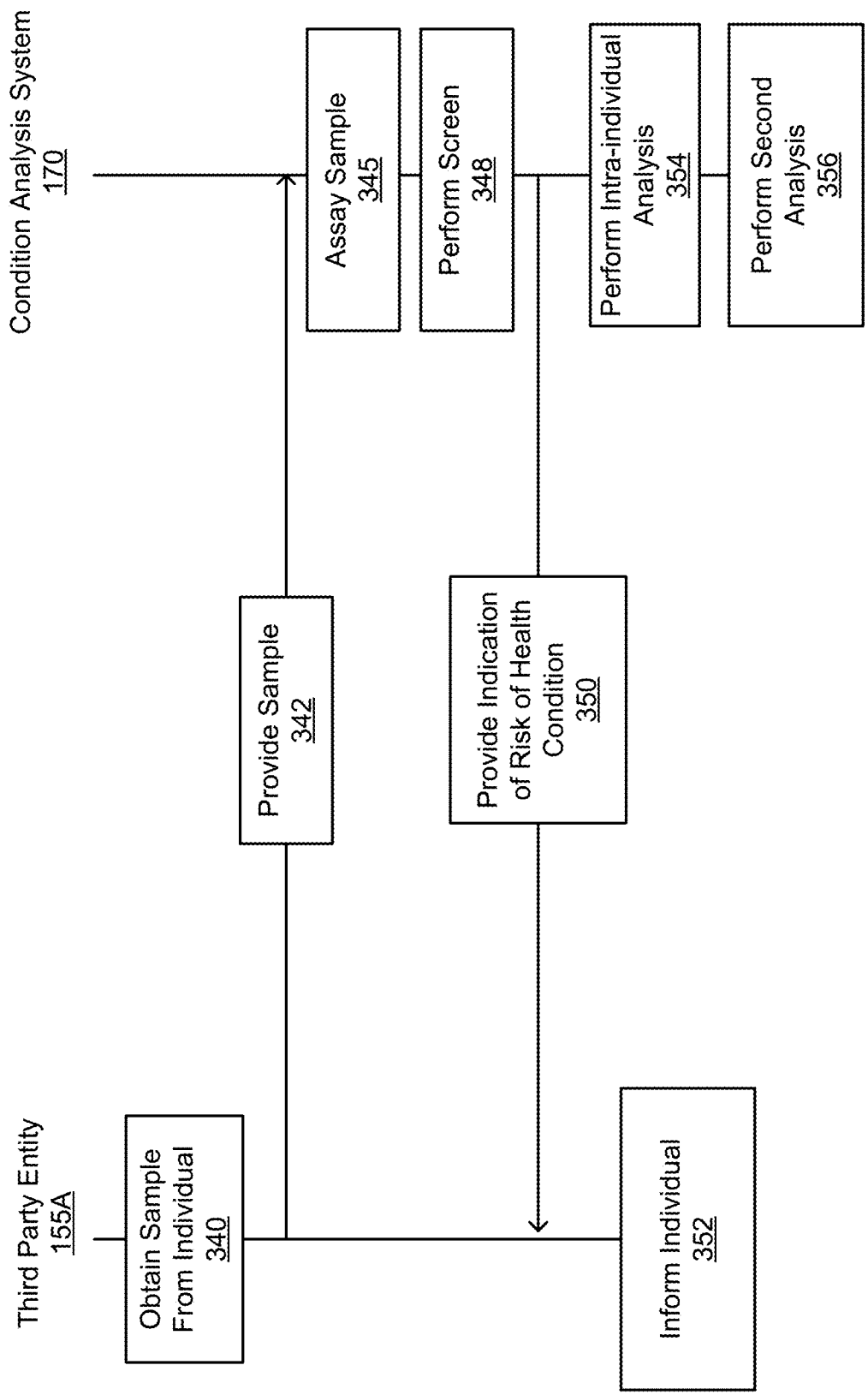
FIG. 3B shows an interaction diagram between a third party entity and a condition analysis system for performing the multiple tier analysis, in accordance with a second embodiment.

FIG. 3B shows an interaction diagram between a third party entity and a condition analysis system for performing the multiple tier analysis, in accordance with a second embodiment. Here, the multiple-tiered analysis can be performed using samples collected from an individual at a single collection timepoint. As shown in FIG. 3B, at step 340, the third party entity 155A obtains a sample from the individual. The third party entity 155A provides 342 the sample to the condition analysis system 170 for processing and analysis. For example, the condition analysis system 170 assays 345 the sample to generate marker information. The condition analysis system 170 further performs 348 a screen by analyzing the marker information to determine whether the individual is at risk for the health condition.

If the individual is determined to be at risk for the health condition, a subsequent intr-individual analysis is performed at step 354 and a second analysis is performed at step 356. Optionally, the condition analysis system 170 provides 350 an indication that the individual is at risk for the health condition back to the third party entity 155A. The third party entity 155A can then inform the individual 352 of the indication. However, in other embodiments, steps 350 and 352 need not occur.

In various embodiments, the condition analysis system 170 performs the intra-individual analysis at step 354 after assaying one or more samples from the individual to generate sequence information for target nucleic acids and sequence information for reference nucleic acids. For example, the sequence information for the target nucleic acids may include methylation information of the target nucleic acids. The sequence information for the reference nucleic acids may include methylation information of the reference nucleic acids. The condition analysis system 170 performs the intra-individual analysis to remove baseline biological signatures and generate background-corrected information. At step 356, the condition analysis system 170 performs the second analysis by analyzing the background-corrected information generated as a result of step 354 and determines a presence or absence of the health condition in the individual. If the individual is determined to have the health condition, the individual can be monitored, provided treatment, and/or selected as a candidate subject for enrollment in a clinical trial.

Figure 3C:
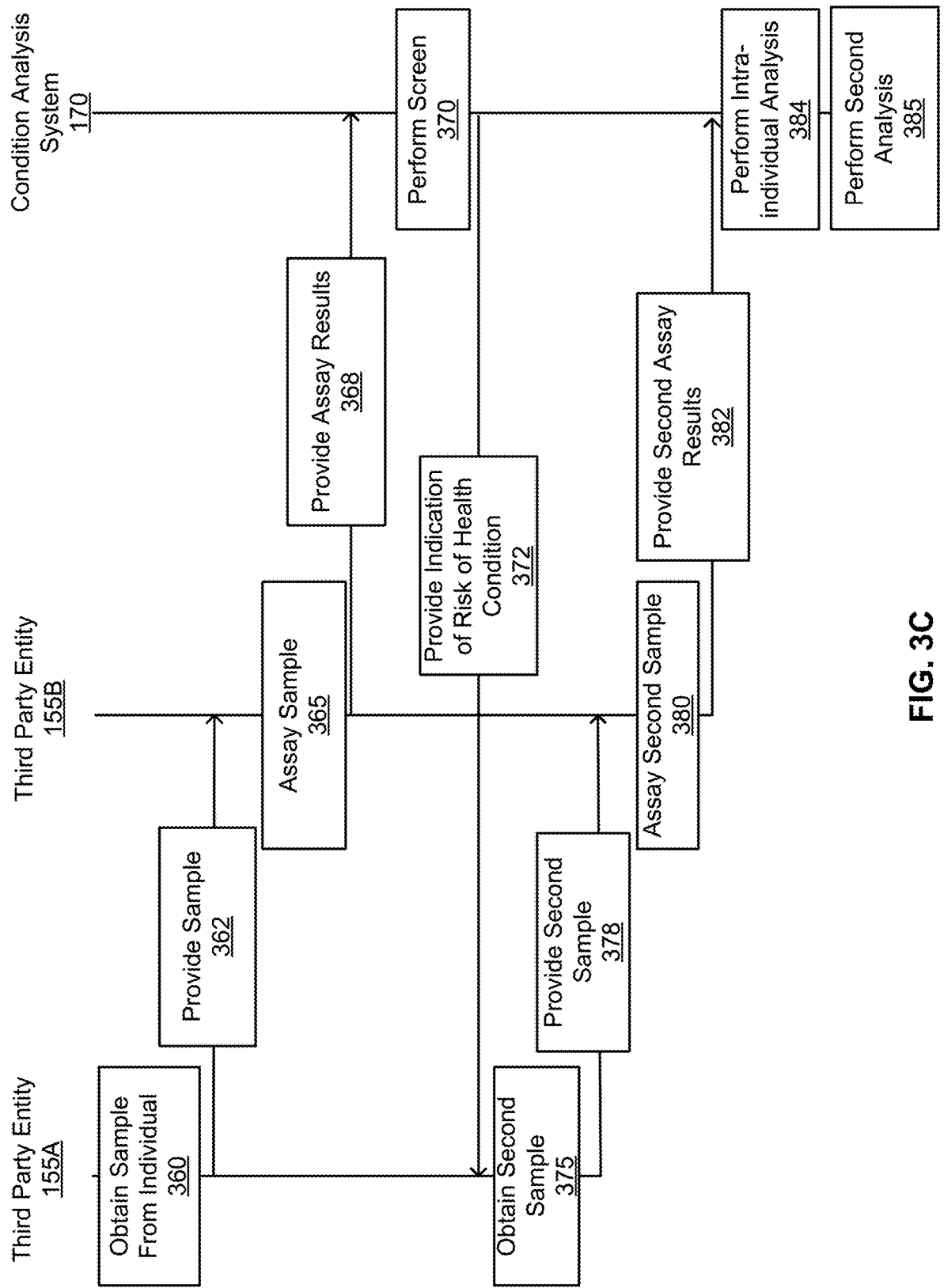
FIG. 3C shows an interaction diagram between a first third party entity, a second third party entity, and a condition analysis system for performing the multiple tier analysis, in accordance with an embodiment.

FIG. 3C shows an interaction diagram between a first third party entity, a second third party entity, and a condition analysis system for performing the multiple tier analysis, in accordance with an embodiment. Here, the first third party entity 155A obtains one or more samples from an individual, the second third party entity 155B performs assays on the one or more samples obtained from the individual, and the condition analysis system 170 performs the screen and/or second analysis.

Specifically, at step 360, the third party entity 155A obtains a sample from the individual. The third party entity 155B provides 362 the sample to a third party entity 155B. Here, third party entity 155B assays 365 the sample to generate methylation information. The third party entity 155B provides 368 the assay results, including the generated methylation information, to the condition analysis system 170. The condition analysis system performs 370 the screen to determine whether the individual is at risk or not at risk for the health condition by analyzing the generated methylation information.

If the individual is determined to be not at risk for the health condition, the process terminates at this point. If the individual is determined to be at risk for the health condition, the condition analysis system 170 can provide 372 an indication to the third party entity 155A that the individual is at risk. Therefore, the third party entity 155A can obtain 375 a second sample from the individual (e.g., during a second visit by the individual). The third party entity 155A provides 378 the second sample to the third party entity 155B who assays 380 the second sample. In various embodiments, the third party entity 155B performs a whole genome bisulfite sequencing. In various embodiments, the third party entity 155B performs hybrid capture. In various embodiments, the third party entity 155B generates methylation information as a result of assaying the second sample. In various embodiments, the third party entity 155B generates sequence information for target nucleic acids and sequence information for reference nucleic acids. The sequence information for the target nucleic acids and the sequence information for the reference nucleic acids may include methylation information. Thus, the third party entity 155B provides 382 results of the second assay, including the methylation information of target nucleic acids and reference nucleic acids, to the condition analysis system 170.

At step 384, the condition analysis system performs an intra-individual analysis to remove baseline biological signatures and generate background-corrected information. The condition analysis system 170 performs 385 a second analysis by analyzing the background-corrected information to determine whether the individual has the health condition. If the individual is determined to have the health condition, the individual can be monitored, provided treatment, and/or selected as a candidate subject for enrollment in a clinical trial.

Example Methods for Conducting an Intra-Individual Analysis

Figure 4:
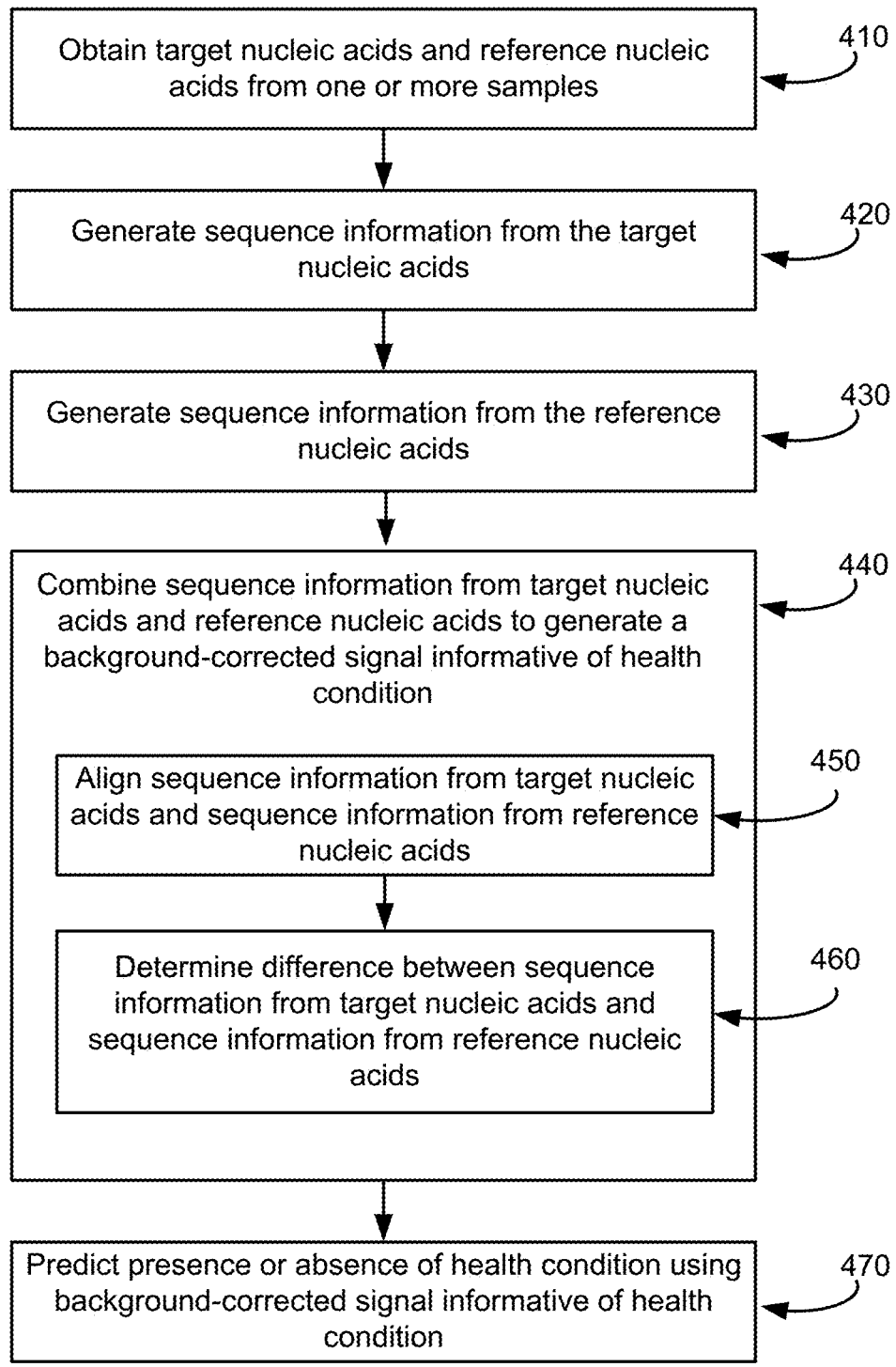
FIG. 4 shows an example flow process involving an intra-individual analysis, in accordance with an embodiment.

FIG. 4 shows an example flow process involving an intra-individual analysis, in accordance with an embodiment. Step 410 involves obtaining target nucleic acids and reference nucleic acids from one or more samples.

Step 420 involves generating sequence information from the target nucleic acids. Here, sequence information from the target nucleic acids may include signatures informative for determining presence or absence of the health condition, but it may also include baseline biological signatures that are present irrespective of whether the nucleic acids originate from a diseased source or a non-diseased source. Step 430 involves generating sequence information from the reference nucleic acids. Sequence information of the reference nucleic acids include baseline biological signatures, which are less informative for determining presence or absence of the health condition in comparison to sequence information of the target nucleic acids.

Step 440 involves combining sequence information from target nucleic acids and sequence information from reference nucleic acids to generate a background-corrected signal informative for determining presence or absence of the health condition. As shown in FIG. 4, step 440 can include both steps 450 and 460. Step 450 involves aligning sequence information from target nucleic acids with sequence information from reference nucleic acids. Step 460 involves determining a difference between sequence information from target nucleic acids and sequence information from reference nucleic acids. In various embodiments, step 460 involves determining a difference on a per-position basis.

Step 470 involves predicting presence or absence of a health condition using the background-corrected signal informative of the health condition. Thus, if the individual is determined to have presence of the health condition, the individual can be provided treatment to prophylactically or therapeutically treat the health condition.

Machine Learning Models for Analyzing Sequence Information

As disclosed herein, trained machine learning models can be deployed to analyze sequence information to predict whether an individual is at risk for a health condition, or whether an individual has the health condition. In various embodiments, the sequence information includes methylation statuses of plurality of genomic sites. Therefore, trained machine learning models analyze differential methylation of the plurality of genomic sites to output predictions.

In various embodiments, a trained machine learning model is deployed as part of a screen (e.g., screen 125 as shown in FIG. 1A). Thus, the trained machine learning model can analyze sequence information generated via an assay (e.g., assay 120A shown in FIG. 1A) to determine whether individuals are at risk of a health condition. In various embodiments, a trained machine learning model is deployed as part of a second analysis (e.g., second analysis 130 shown in FIG. 1A). Therefore, the trained machine learning model can analyze sequence information, such as background-corrected sequence information generated via an intra-individual analysis (e.g., intra-individual analysis 128 shown in FIG. 1A) to determine whether an individual has the health condition.

In various embodiments, a machine learning model is any one of a regression model (e.g., linear regression, logistic regression, or polynomial regression), decision tree, random forest, support vector machine, Naïve Bayes model, k-means cluster, or neural network (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, deep bi-directional recurrent networks).

The machine learning model can be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, and dimensionality reduction techniques such as manifold learning, principal component analysis, factor analysis, autoencoder regularization, and independent component analysis, or combinations thereof. In various embodiments, the machine learning model is trained using supervised learning algorithms, unsupervised learning algorithms, semi-supervised learning algorithms (e.g., partial supervision), weak supervision, transfer, multi-task learning, or any combination thereof.

In various embodiments, the machine learning model has one or more parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, and coefficients in a regression model. The model parameters of the machine learning model are trained (e.g., adjusted) using the training data to improve the predictive power of the machine learning model.

In particular embodiments, machine learning models analyze methylation statuses of a plurality of genomic sites in cell-free DNA to generate predictions. The methylation statuses can correspond to a set of cancer informative CpG islands (CGIs), wherein the cancer informative CGIs are selected from a group consisting of a ranked set of candidate CGIs. In various embodiments, a machine learning model analyzes methylation statuses for at least 50 CGIs. In various embodiments, a machine learning model analyzes methylation statuses for at least 100 CGIs. In various embodiments, a machine learning model analyzes methylation statuses for at least 150 CGIs. In various embodiments, a machine learning model analyzes methylation statuses for at least 200 CGIs. In various embodiments, a machine learning model analyzes methylation statuses for at least 250 CGIs. In various embodiments, a machine learning model analyzes methylation statuses for at least 300 CGIs. In various embodiments, a machine learning model analyzes methylation statuses for at least 400 CGIs. In various embodiments, a machine learning model analyzes methylation statuses for at least 500 CGIs. In various embodiments, a machine learning model analyzes methylation statuses for at least 600 CGIs. In various embodiments, a machine learning model analyzes methylation statuses for at least 700 CGIs. In various embodiments, a machine learning model analyzes methylation statuses for at least 800 CGIs. In various embodiments, a machine learning model analyzes methylation statuses for at least 900 CGIs. In various embodiments, a machine learning model analyzes methylation statuses for at least 1000 CGIs. In various embodiments, a machine learning model analyzes methylation statuses for at least 2500 CGIs. In various embodiments, a machine learning model analyzes methylation statuses for at least 5000 CGIs. In various embodiments, a machine learning model analyzes methylation statuses for at least 7500 CGIs. In various embodiments, a machine learning model analyzes methylation statuses for at least 10000 CGIs. In various embodiments, a machine learning model analyzes methylation statuses for at least 15000 CGIs. In various embodiments, a machine learning model analyzes methylation statuses for at least 20000 CGIs. In various embodiments, a machine learning model analyzes methylation statuses for at least 25000 CGIs.

In various embodiments, a machine learning model analyzes methylation statuses for CGIs across the whole genome. For example, a machine learning model may be implemented to analyze sequencing data generated from whole genome sequencing (e.g., whole genome bisulfite sequencing).

Additionally disclosed herein are particular genomic sites, such as CpG islands (CGIs) whose methylation statuses can be informative for determining whether an individual is at risk of a health condition or whether the individual has a health condition. These informative CGIs can represent a signal in a sample. In some embodiments, methylation statuses of the informative CGIs representing a signal in a sample can be indicative of a presence of the health condition. In some embodiments, methylation statuses of the informative CGIs representing a signal in a sample can be indicative of an absence of the health condition. In various embodiments, methods disclosed herein, such as methods involving the multiple-tiered analysis, are useful for detecting or identifying the signal (e.g., methylation statuses of the informative CGIs) in a sample. In various embodiments, methods disclosed herein, such as methods involving the multiple-tiered analysis, are useful for increasing the probability that the detected signal (e.g., methylation statuses of the informative CGIs) in the sample is authentic. Thus, a signal (e.g., methylation statuses of the informative CGIs) detected by the multiple-tiered analysis can be confidently trusted as present in the sample.

Methylation statuses of cancer informative CGIs can be useful for predicting whether an individual has a health condition. In various embodiments, the methylation statuses of cancer informative CGIs are background-corrected methylation statuses of cancer informative CGIs. For example, background-corrected methylation statuses of cancer informative CGIs can be determined via an intra-individual analysis. For example, background-corrected methylation statuses of cancer informative CGIs can be determined by combining methylation information of cancer informative CGIs of target nucleic acids and methylation information of cancer informative CGIs of reference nucleic acids.

In various embodiments, each cancer informative CGI can be a "CGI identifier" or reference number to allow referencing CGIs during data processing by their respective unique CGI identifiers. The accompanying tables (e.g., Tables 1-4) lists, for each CGI, its respective location in the human genome. Additional example CGIs are disclosed in WO2018209361 (see Table 1) and WO2022133315 (see Table 2 entitled "TOO Methylation Sites" and Table 3 entitled "Pan Cancer Methylation Sites"), each of which is hereby incorporated by reference in its entirety.

Health Conditions

The disclosure provides methods for performing a multiple-tiered analysis (e.g., screening and/or intra-individual analysis) to identify presence of a health condition in one or more patients. In various embodiments, the patient may be suspected of having a health condition, but may not have been previously diagnosed with a health disorder. In various embodiments, the patient is healthy and is not yet suspected of having a health condition.

In various embodiments, the health condition can be a disease or disorder. Examples of diseases and/or disorders can include, for example, a cancer, inflammatory disease, neurodegenerative disease, autoimmune disorder, neuromuscular disease, metabolic disorder (e.g., diabetes), cardiac disease, or fibrotic disease (e.g., idiopathic pulmonary fibrosis).

In particular embodiments, the health condition is a cancer. In various embodiments, the cancer is an early stage cancer. In various embodiments, the cancer is a preclinical phase cancer. In various embodiments, the cancer is a stage I cancer. In various embodiments, the cancer is a stage II cancer. Thus, the methods disclosed herein enable the screening and diagnosis of an individual for an early stage or preclinical stage cancer.

In various embodiments, the cancer is any of an acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the inflammatory disease can be any one of acute respiratory distress syndrome (ARDS), acute lung injury (ALI), alcoholic liver disease, allergic inflammation of the skin, lungs, and gastrointestinal tract, allergic rhinitis, ankylosing spondylitis, asthma (allergic and non-allergic), atopic dermatitis (also known as atopic eczema), atherosclerosis, celiac disease, chronic obstructive pulmonary disease (COPD), chronic respiratory distress syndrome (CRDS), colitis, dermatitis, diabetes, eczema, endocarditis, fatty liver disease, fibrosis (e.g., idiopathic pulmonary fibrosis, scleroderma, kidney fibrosis, and scarring), food allergies (e.g., allergies to peanuts, eggs, dairy, shellfish, tree nuts, etc.), gastritis, gout, hepatic steatosis, hepatitis, inflammation of body organs including joint inflammation including joints in the knees, limbs or hands, inflammatory bowel disease (IBD) (including Crohn's disease or ulcerative colitis), intestinal hyperplasia, irritable bowel syndrome, juvenile rheumatoid arthritis, liver disease, metabolic syndrome, multiple sclerosis, myasthenia gravis, neurogenic lung edema, nephritis (e.g., glomerular nephritis), non-alcoholic fatty liver disease (NAFLD) (including non-alcoholic steatosis and non-alcoholic steatohepatitis (NASH)), obesity, prostatitis, psoriasis, psoriatic arthritis, rheumatoid arthritis (RA), sarcoidosis sinusitis, splenitis, seasonal allergies, sepsis, systemic lupus erythematosus, uveitis, and UV-induced skin inflammation.

In various embodiments, the neurodegenerative disease can be any one of Alzheimer's disease, Parkinson's disease, traumatic CNS injury, Down Syndrome (DS), glaucoma, amyotrophic lateral sclerosis (ALS), frontotemporal dementia (FTD), and Huntington's disease. In addition, the neurodegenerative disease can also include Absence of the Septum Pellucidum, Acid Lipase Disease, Acid Maltase Deficiency, Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, AIDS, Alexander Disease, Alper's Disease, Alternating Hemiplegia, Anencephaly, Aneurysm, Angelman Syndrome, Angiomatosis, Anoxia, Antiphosphipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Autism, Autonomic Dysfunction, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Injuries, Bradbury-Eggleston Syndrome, Brain or Spinal Tumors, Brain Aneurysm, Brain injury, Brown-Sequard Syndrome, Bulbospinal Muscular Atrophy, Cadasil, Canavan Disease, Causalgia, Cavernomas, Cavernous Angioma, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Palsy, Cerebro-Oculo-Facio-Skeletal Syndrome, Charcot-Marie-Tooth Disease, Chiari Malformation, Chorea, Chronic Inflammatory Demyelinating Polyneuropathy (CIDP), Coffin Lowry Syndrome, Colpocephaly, Congenital Facial Diplegia, Congenital Myasthenia, Congenital Myopathy, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Dancing Eyes-Dancing Feet Syndrome, Dandy-Walker Syndrome, Dawson Disease, Dementia, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Dysautonomia, Dysgraphia, Dyslexia, Dysphagia, Dyssynergia Cerebellaris Myoclonica, Dystonias, Early Infantile Epileptic Encephalopathy, Empty Sella Syndrome, Encephalitis, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Essential Tremor, Extrapontine Myelinolysis, Fabry Disease, Fahr's Syndrome, Fainting, Familial Dysautonomia, Familial Hemangioma, Familial Periodic Paralyzes, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gangliosidoses, Gaucher's Disease, Gerstmann's Syndrome, Gerstmann-Straussler-Scheinker Disease, Giant Cell Arteritis, Giant Cell Inclusion Disease, Globoid Cell Leukodystrophy, Glossopharyngeal Neuralgia, Glycogen Storage Disease, Guillain-Barre Syndrome, Hallervorden-Spatz Disease, Head Injury, Hemicrania Continua, Hemifacial Spasm, Hemiplegia Alterans, Hereditary Neuropathy, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Hydromyelia, Hypernychthemeral Syndrome, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaac's Syndrome, Joubert syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kluver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus, Lyme Disease, Machado-Joseph Disease, Macrencephaly, Melkersson-Rosenthal Syndrome, Meningitis, Menkes Disease, Meralgia Paresthetica, Metachromatic Leukodystrophy, Microcephaly, Migraine, Miller Fisher Syndrome, Mini-Strokes, Mitochondrial Myopathies, Motor Neuron Diseases, Moyamoya Disease, Mucolipidoses, Mucopolysaccharidoses, Multiple sclerosis (MS), Multiple System Atrophy, Muscular Dystrophy, Myasthenia Gravis, Myoclonus, Myopathy, Myotonia, Narcolepsy, Neuroacanthocytosis, Neurodegeneration with Brain Iron Accumulation, Neurofibromatosis, Neuroleptic Malignant Syndrome, Neurosarcoidosis, Neurotoxicity, Nevus Cavernosus, Niemann-Pick Disease, Non 24 Sleep Wake Disorder, Normal Pressure Hydrocephalus, Occipital Neuralgia, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Perineural Cysts, Periodic Paralyzes, Peripheral Neuropathy, Periventricular Leukomalacia, Pervasive Developmental Disorders, Pinched Nerve, Piriformis Syndrome, Plexopathy, Polymyositis, Pompe Disease, Porencephaly, Postherpetic Neuralgia, Postinfectious Encephalomyelitis, Post-Polio Syndrome, Postural Hypotension, Postural Orthostatic Tachyardia Syndrome (POTS), Primary Lateral Sclerosis, Prion Diseases, Progressive Multifocal Leukoencephalopathy, Progressive Sclerosing Poliodystrophy, Progressive Supranuclear Palsy, Prosopagnosia, Pseudotumor Cerebri, Ramsay Hunt Syndrome I, Ramsay Hunt Syndrome II, Rasmussen's Encephalitis, Reflex Sympathetic Dystrophy Syndrome, Refsum Disease, Refsum Disease, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Saint Vitus Dance, Sandhoff Disease, Schizencephaly, Septo-Optic Dysplasia, Shingles, Shy-Drager Syndrome, Sjogren's Syndrome, Sleep Apnea, Sleeping Sickness, Sotos Syndrome, Spasticity, Spinal Cord Infarction, Spinal Cord Injury, Spinal Cord Tumors, Spinocerebellar Atrophy, Spinocerebellar Degeneration, Stiff-Person Syndrome, Striatonigral Degeneration, Stroke, Sturge-Weber Syndrome, SUNCT Headache, Syncope, Syphilitic Spinal Sclerosis, Syringomyelia, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tinnitus, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, Wolman's Disease, X-Linked Spinal and Bulbar Muscular Atrophy, and Zellweger Syndrome.

In various embodiments, the autoimmune disease or disorder can be any one of: arthritis, including rheumatoid arthritis, acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, juvenile-onset rheumatoid arthritis, osteoarthritis, arthritis deformans, polyarthritis chronica primaria, reactive arthritis, and ankylosing spondylitis; inflammatory hyperproliferative skin diseases; psoriasis, such as plaque psoriasis, pustular psoriasis, and psoriasis of the nails; atopy, including atopic diseases such as hay fever and Job's syndrome; dermatitis, including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis; x-linked hyper IgM syndrome; allergic intraocular inflammatory diseases; urticaria, such as chronic allergic urticaria, chronic idiopathic urticaria, and chronic autoimmune urticaria; myositis; polymyositis/dermatomyositis; juvenile dermatomyositis; toxic epidermal necrolysis; scleroderma, including systemic scleroderma; sclerosis, such as systemic sclerosis, multiple sclerosis (MS), spino-optical MS, primary progressive MS (PPMS), relapsing remitting MS (RRMS), progressive systemic sclerosis, atherosclerosis, arteriosclerosis, sclerosis disseminata, and ataxic sclerosis; neuromyelitis optica (NMO); inflammatory bowel disease (IBD), including Crohn's disease, autoimmune-mediated gastrointestinal diseases, colitis, ulcerative colitis, colitis ulcerosa, microscopic colitis, collagenous colitis, colitis polyposa, necrotizing enterocolitis, transmural colitis, and autoimmune inflammatory bowel disease; bowel inflammation; pyoderma gangrenosum; erythema nodosum; primary sclerosing cholangitis; respiratory distress syndrome, including adult or acute respiratory distress syndrome (ARDS); meningitis; inflammation of all or part of the uvea; iritis; choroiditis; an autoimmune hematological disorder; rheumatoid spondylitis; rheumatoid synovitis; hereditary angioedema; cranial nerve damage, as in meningitis; herpes gestationis; pemphigoid gestationis; pruritis scroti; autoimmune premature ovarian failure; sudden hearing loss due to an autoimmune condition; IgE-mediated diseases, such as anaphylaxis and allergic and atopic rhinitis; encephalitis, such as Rasmussen's encephalitis and limbic and/or brainstem encephalitis; uveitis, such as anterior uveitis, acute anterior uveitis, granulomatous uveitis, nongranulomatous uveitis, phacoantigenic uveitis, posterior uveitis, or autoimmune uveitis; glomerulonephritis (GN) with and without nephrotic syndrome, such as chronic or acute glomerulonephritis, primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN; proliferative nephritis; autoimmune polyglandular endocrine failure; balanitis, including balanitis circumscripta plasmacellularis; balanoposthitis; erythema annulare centrifugum; erythema dyschromicum perstans; eythema multiform; granuloma annulare; lichen nitidus; lichen sclerosus et atrophicus; lichen simplex chronicus; lichen spinulosus; lichen planus; lamellar ichthyosis; epidermolytic hyperkeratosis; premalignant keratosis; pyoderma gangrenosum; allergic conditions and responses; allergic reaction; eczema, including allergic or atopic eczema, asteatotic eczema, dyshidrotic eczema, and vesicular palmoplantar eczema; asthma, such as asthma bronchiale, bronchial asthma, and auto-immune asthma; conditions involving infiltration of T cells and chronic inflammatory responses; immune reactions against foreign antigens such as fetal A-B-O blood groups during pregnancy; chronic pulmonary inflammatory disease; autoimmune myocarditis; leukocyte adhesion deficiency; lupus, including lupus nephritis, lupus cerebritis, pediatric lupus, non-renal lupus, extra-renal lupus, discoid lupus and discoid lupus erythematosus, alopecia lupus, systemic lupus erythematosus (SLE), cutaneous SLE, subacute cutaneous SLE, neonatal lupus syndrome (NLE), and lupus erythematosus disseminatus; juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, and diabetic large-artery disorder; immune responses associated with acute and delayed hypersensitivity mediated by cytokines and T-lymphocytes; tuberculosis; sarcoidosis; granulomatosis, including lymphomatoid granulomatosis; Wegener's granulomatosis; agranulocytosis; vasculitides, including vasculitis, large-vessel vasculitis, polymyalgia rheumatica and giant-cell (Takayasu's) arteritis, medium-vessel vasculitis, Kawasaki's disease, polyarteritis nodosa/periarteritis nodosa, microscopic polyarteritis, immunovasculitis, CNS vasculitis, cutaneous vasculitis, hypersensitivity vasculitis, necrotizing vasculitis, systemic necrotizing vasculitis, ANCA-associated vasculitis, Churg-Strauss vasculitis or syndrome (CSS), and ANCA-associated small-vessel vasculitis; temporal arteritis; aplastic anemia; autoimmune aplastic anemia; Coombs positive anemia; Diamond Blackfan anemia; hemolytic anemia or immune hemolytic anemia, including autoimmune hemolytic anemia (AIHA), pernicious anemia (anemia perniciosa); Addison's disease, pure red cell anemia or aplasia (PRCA); Factor VIII deficiency; hemophilia A; autoimmune neutropenia; pancytopenia; leukopenia; diseases involving leukocyte diapedesis; CNS inflammatory disorders; multiple organ injury syndrome, such as those secondary to septicemia, trauma or hemorrhage; antigen-antibody complex-mediated diseases; anti-glomerular basement membrane disease; anti-phospholipid antibody syndrome; allergic neuritis; Behcet's disease/syndrome; Castleman's syndrome; Goodpasture's syndrome; Reynaud's syndrome; Sjogren's syndrome; Stevens-Johnson syndrome; pemphigoid, such as pemphigoid bullous and skin pemphigoid, pemphigus, pemphigus vulgaris, pemphigus *foliaceus*, pemphigus mucus-membrane pemphigoid, and pemphigus erythematosus; autoimmune polyendocrinopathies; Reiter's disease or syndrome; thermal injury; preeclampsia; an immune complex disorder, such as immune complex nephritis, and antibody-mediated nephritis; polyneuropathies; chronic neuropathy, such as IgM polyneuropathies and IgM-mediated neuropathy; thrombocytopenia (as developed by myocardial infarction patients, for example), including thrombotic thrombocytopenic purpura (TTP), post-transfusion purpura (PTP), heparin-induced thrombocytopenia, autoimmune or immune-mediated thrombocytopenia, idiopathic thrombocytopenic purpura (ITP), and chronic or acute ITP; scleritis, such as idiopathic cerato-scleritis, and episcleritis; autoimmune disease of the testis and ovary including, autoimmune orchitis and oophoritis; primary hypothyroidism; hypoparathyroidism; autoimmune endocrine diseases, including thyroiditis, autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes, autoimmune polyglandular syndromes, and polyglandular endocrinopathy syndromes; paraneoplastic syndromes, including neurologic paraneoplastic syndromes; Lambert-Eaton myasthenic syndrome or Eaton-Lambert syndrome; stiff-man or stiff-person syndrome; encephalomyelitis, such as allergic encephalomyelitis, encephalomyelitis allergica, and experimental allergic encephalomyelitis (EAE); myasthenia gravis, such as thymoma-associated myasthenia gravis; cerebellar degeneration; neuromyotonia; opsoclonus or opsoclonus myoclonus syndrome (OMS); sensory neuropathy; multifocal motor neuropathy; Sheehan's syndrome; hepatitis, including autoimmune hepatitis, chronic hepatitis, lupoid hepatitis, giant-cell hepatitis, chronic active hepatitis, and autoimmune chronic active hepatitis; lymphoid interstitial pneumonitis (LIP); bronchiolitis obliterans (non-transplant) vs NSIP; Guillain-Barre syndrome; Berger's disease (IgA nephropathy); idiopathic IgA nephropathy; linear IgA dermatosis; acute febrile neutrophilic dermatosis; subcorneal pustular dermatosis; transient acantholytic dermatosis; cirrhosis, such as primary biliary cirrhosis and pneumonocirrhosis; autoimmune enteropathy syndrome; Celiac or Coeliac disease; celiac sprue (gluten enteropathy); refractory sprue; idiopathic sprue; cryoglobulinemia; amylotrophic lateral sclerosis (ALS; Lou Gehrig's disease); coronary artery disease; autoimmune ear disease, such as autoimmune inner ear disease (AIED); autoimmune hearing loss; polychondritis, such as refractory or relapsed or relapsing polychondritis; pulmonary alveolar proteinosis; Cogan's syndrome/non-syphilitic interstitial keratitis; Bell's palsy; Sweet's disease/syndrome; rosacea autoimmune; zoster-associated pain; amyloidosis; a non-cancerous lymphocytosis; a primary lymphocytosis, including monoclonal B cell lymphocytosis (e.g., benign monoclonal gammopathy and monoclonal gammopathy of undetermined significance, MGUS); peripheral neuropathy; channelopathies, such as epilepsy, migraine, arrhythmia, muscular disorders, deafness, blindness, periodic paralysis, and channelopathies of the CNS; autism; inflammatory myopathy; focal or segmental or focal segmental glomerulosclerosis (FSGS); endocrine opthalmopathy; uveoretinitis; chorioretinitis; autoimmune hepatological disorder; fibromyalgia; multiple endocrine failure; Schmidt's syndrome; adrenalitis; gastric atrophy; presenile dementia; demyelinating diseases, such as autoimmune demyelinating diseases and chronic inflammatory demyelinating polyneuropathy; Dressler's syndrome; alopecia areata; alopecia totalis; CREST syndrome (calcinosis, Raynaud's phenomenon, esophageal dysmotility, sclerodactyly, and telangiectasia); male and female autoimmune infertility (e.g., due to anti-spermatozoan antibodies); mixed connective tissue disease; Chagas' disease; rheumatic fever; recurrent abortion; farmer's lung; erythema multiforme; post-cardiotomy syndrome; Cushing's syndrome; bird-fancier's lung; allergic granulomatous angiitis; benign lymphocytic angiitis; Alport's syndrome; alveolitis, such as allergic alveolitis and fibrosing alveolitis; interstitial lung disease; transfusion reaction; leprosy; malaria; Samter's syndrome; Caplan's syndrome; endocarditis; endomyocardial fibrosis; diffuse interstitial pulmonary fibrosis; interstitial lung fibrosis; pulmonary fibrosis; idiopathic pulmonary fibrosis; cystic fibrosis; endophthalmitis; erythema elevatum et diutinum; erythroblastosis fetalis; eosinophilic fasciitis; Shulman's syndrome; Felty's syndrome; flariasis; cyclitis, such as chronic cyclitis, heterochronic cyclitis, iridocyclitis (acute or chronic), or Fuch's cyclitis; Henoch-Schonlein purpura; sepsis; endotoxemia; pancreatitis; thyroxicosis; Evan's syndrome; autoimmune gonadal failure; Sydenham's chorea; post-streptococcal nephritis; thromboangitis ubiterans; thyrotoxicosis; tabes dorsalis; choroiditis; giant-cell polymyalgia; chronic hypersensitivity pneumonitis; keratoconjunctivitis sicca; epidemic keratoconjunctivitis; idiopathic nephritic syndrome; minimal change nephropathy; benign familial and ischemia-reperfusion injury; transplant organ reperfusion; retinal autoimmunity; joint inflammation; bronchitis; chronic obstructive airway/pulmonary disease; silicosis; aphthae; aphthous stomatitis; arteriosclerotic disorders; aspermiogenese; autoimmune hemolysis; Boeck's disease; cryoglobulinemia; Dupuytren's contracture; endophthalmia phacoanaphylactica; enteritis allergica; erythema nodo sum leprosum; idiopathic facial paralysis; febris rheumatica; Hamman-Rich's disease; sensoneural hearing loss, haemoglobinuria paroxysmatica; hypogonadism; ileitis regionalis; leucopenia; mononucleosis infectiosa; traverse myelitis; primary idiopathic myxedema; nephrosis; ophthalmia symphatica; orchitis granulomatosa; pancreatitis; polyradiculitis acuta; pyoderma gangrenosum; Quervain's thyreoiditis; acquired splenic atrophy; non-malignant thymoma; vitiligo; toxic-shock syndrome; food poisoning; conditions involving infiltration of T cells; leukocyte-adhesion deficiency; immune responses associated with acute and delayed hypersensitivity mediated by cytokines and T-lymphocytes; diseases involving leukocyte diapedesis; multiple organ injury syndrome; antigen-antibody complex-mediated diseases; antiglomerular basement membrane disease; allergic neuritis; autoimmune polyendocrinopathies; oophoritis; primary myxedema; autoimmune atrophic gastritis; sympathetic ophthalmia; rheumatic diseases; mixed connective tissue disease; nephrotic syndrome; insulitis; polyendocrine failure; autoimmune polyglandular syndrome type I; adult-onset idiopathic hypoparathyroidism (AOIH); cardiomyopathy such as dilated cardiomyopathy; epidermolisis bullosa acquisita (EBA); hemochromatosis; myocarditis; nephrotic syndrome; primary sclerosing cholangitis; purulent or nonpurulent sinusitis; acute or chronic sinusitis; ethmoid, frontal, maxillary, or sphenoid sinusitis; an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils; anaphylaxis; seronegative spondyloarthritides; polyendocrine autoimmune disease; sclerosing cholangitis; chronic mucocutaneous candidiasis; Bruton's syndrome; transient hypogammaglobulinemia of infancy; Wiskott-Aldrich syndrome; ataxia telangiectasia syndrome; angiectasis; autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization; allergic hypersensitivity disorders; glomerulonephritides; reperfusion injury; ischemic reperfusion disorder; reperfusion injury of myocardial or other tissues; lymphomatous tracheobronchitis; inflammatory dermatoses; dermatoses with acute inflammatory components; multiple organ failure; bullous diseases; renal cortical necrosis; acute purulent meningitis or other central nervous system inflammatory disorders; ocular and orbital inflammatory disorders; granulocyte transfusion-associated syndromes; cytokine-induced toxicity; narcolepsy; acute serious inflammation; chronic intractable inflammation; pyelitis; endarterial hyperplasia; peptic ulcer; valvulitis; and endometriosis. In particular embodiments, the autoimmune disorder in the subject can include one or more of: systemic lupus erythematosus (SLE), lupus nephritis, chronic graft versus host disease (cGVHD), rheumatoid arthritis (RA), Sjogren's syndrome, vitiligo, inflammatory bowed disease, and Crohn's Disease. In particular embodiments, the autoimmune disorder is systemic lupus erythematosus (SLE). In particular embodiments, the autoimmune disorder is rheumatoid arthritis.

Exemplary metabolic disorders include, for example, diabetes, insulin resistance, lysosomal storage disorders (e.g., Gauchers disease, Krabbe disease, Niemann Pick disease types A and B, multiple sclerosis, Fabry's disease, Tay Sachs disease, and Sandhoff Variant A, B), obesity, cardiovascular disease, and dyslipidemia. Other exemplary metabolic disorders include, for example, 17-alpha-hydroxylase deficiency, 17-beta hydroxysteroid dehydrogenase 3 deficiency, 18 hydroxylase deficiency, 2-hydroxyglutaric aciduria, 2-methylbutyryl-CoA dehydrogenase deficiency, 3-alpha hydroxyacyl-CoA dehydrogenase deficiency, 3-hydroxyisobutyric aciduria, 3-methylcrotonyl-CoA carboxylase deficiency, 3-methylglutaconyl-CoA hydratase deficiency (AUH defect), 5-oxoprolinase deficiency, 6-pyruvoyl-tetrahydropterin synthase deficiency, abdominal obesity metabolic syndrome, abetalipoproteinemia, acatalasemia, aceruloplasminemia, acetyl CoA acetyltransferase 2 deficiency, acetyl-carnitine deficiency, acrodermatitis enteropathica, adenine phosphoribosyltransferase deficiency, adenosine deaminase deficiency, adenosine monophosphate deaminase 1 deficiency, adenylosuccinase deficiency, adrenomyeloneuropathy, adult polyglucosan body disease, albinism deafness syndrome, alkaptonuria, Alpers syndrome, alpha-1 antitrypsin deficiency, alpha-ketoglutarate dehydrogenase deficiency, alpha-mannosidosis, aminoacylase 1 deficiency, anemia sideroblastic and spinocerebellar ataxia, arginase deficiency, argininosuccinic aciduria, aromatic L-amino acid decarboxylase deficiency, arthrogryposis renal dysfunction cholestasis syndrome, Arts syndrome, aspartylglycosaminuria, atypical Gaucher disease due to saposin C deficiency, autoimmune polyglandular syndrome type 2, autosomal dominant optic atrophy and cataract, autosomal erythropoietic protoporphyria, autosomal recessive spastic ataxia 4, Barth syndrome, Bartter syndrome, Bartter syndrome antenatal type 1, Bartter syndrome antenatal type 2, Bartter syndrome type 3, Bartter syndrome type 4, Beta ketothiolase deficiency, biotinidase deficiency, Bjornstad syndrome, carbamoyl phosphate synthetase 1 deficiency, carnitine palmitoyl transferase 1A deficiency, carnitine-acylcarnitine translocase deficiency, carnosinemia, central diabetes insipidus, cerebral folate deficiency, cerebrotendinous xanthomatosis, ceroid lipofuscinosis neuronal 1, Chanarin-Dorfman syndrome, Chediak-Higashi syndrome, childhood hypophosphatasia, cholesteryl ester storage disease, chondrocalcinosisc, chylomicron retention disease, citrulline transport defect, congenital bile acid synthesis defect, type 2, Crigler Najjar syndrome, cytochrome c oxidase deficiency, D-2-hydroxyglutaric aciduria, D-bifunctional protein deficiency, D-glycericacidemia, Danon disease, dicarboxylic aminoaciduria, dihydropteridine reductase deficiency, dihydropyrimidinase deficiency, diabetes insipidus, dopamine beta hydroxylase deficiency, Dowling-Degos disease, erythropoietic uroporphyria associated with myeloid malignancy, Familial chylomicronemia syndrome, Familial HDL deficiency, Familial hypocalciuric hypercalcemia type 1, Familial hypocalciuric hypercalcemia type 2, Familial hypocalciuric hypercalcemia type 3, Familial LCAT deficiency, Familial partial lipodystrophy type 2, Fanconi Bickel syndrome, Farber disease, fructose-1,6-bisphosphatase deficiency, gamma-cystathionase deficiency, Gaucher disease, Gilbert syndrome, Gitelman syndrome, glucose transporter type 1 deficiency syndrome, glutamine deficiency, congenital, Glutaric acidemia. glutathione synthetase deficiency, glycine N-methyltransferase deficiency, Glycogen storage disease hepatic lipase deficiency, homocysteinemia, Hurler syndrome, hyperglycerolemia, Imerslund-Grasbeck syndrome, iminoglycinuria, infantile neuroaxonal dystrophy, Kearns-Sayre syndrome, Krabbe disease, lactate dehydrogenase deficiency, Lesch Nyhan syndrome, Menkes disease, methionine adenosyltransferase deficiency, mitochondrial complex deficiency, muscular phosphorylase kinase deficiency, neuronal ceroid lipofuscinosis, Niemann-Pick disease type A, Niemann-Pick disease type B, Niemann-Pick disease type C1, Niemann-Pick disease type C2, ornithine transcarbamylase deficiency, Pearson syndrome, Perrault syndrome, phosphoribosylpyrophosphate synthetase superactivity, primary carnitine deficiency, hyperoxaluria, purine nucleoside phosphorylase deficiency, pyruvate carboxylase deficiency, pyruvate dehydrogenase complex deficiency, pyruvate dehydrogenase phosphatase deficiency, yruvate kinase deficiency, Refsum disease, diabetes mellitus, Scheie syndrome, Sengers syndrome, Sialidosis Sjogren-Larsson syndrome, Tay-Sachs disease, transcobalamin 1 deficiency, trehalase deficiency, Walker-Warburg syndrome, Wilson disease, Wolfram syndrome, and Wolman disease.

Computer Implementation

The methods of the invention, including the methods of performing a multiple-tiered analysis (e.g., screening and/or intra-individual analysis) to identify presence or absence of a health condition in a patient, are, in some embodiments, performed on one or more computers. In particular embodiments, the steps of performing a screen (e.g., screen 125 shown in FIG. 1A), performing an intra-individual analysis (e.g., intra-individual analysis 128 show in FIG. 1A), and performing a second analysis (e.g., second analysis 130 shown in FIG. 1A) are performed on one or more computers. The steps of performing an assay (e.g., assay 120A and/or assay 120B shown in FIG. 1A) are not performed on one or more computers.

In various embodiments, the performance of the screen, the intra-individual analysis, and/or the second analysis can be implemented in hardware or software, or a combination of both. In one embodiment of the invention, a machine-readable storage medium is provided, the medium comprising a data storage material encoded with machine readable data which, when using a machine programmed with instructions for using said data, is capable of displaying data (e.g., methylation data) and results of the screen, intra-individual analysis, and/or second analysis (e.g., indication of risk or presence of the health condition in the individual). Such data can be used for a variety of purposes, such as patient eligibility for enrollment in a clinical trial, patient monitoring, treatment considerations, and the like. The invention can be implemented in computer programs executing on programmable computers, comprising a processor, a data storage system (including volatile and non-volatile memory and/or storage elements), a graphics adapter, a pointing device, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

In some embodiments, the methods of the invention, including methods of performing a multiple-tiered analysis to identify presence of a health condition in a patient, are performed on one or more computers in a distributed computing system environment (e.g., in a cloud computing environment). In this description, "cloud computing" is defined as a model for enabling on-demand network access to a shared set of configurable computing resources. Cloud computing can be employed to offer on-demand access to the shared set of configurable computing resources. The shared set of configurable computing resources can be rapidly provisioned via virtualization and released with low management effort or service provider interaction, and then scaled accordingly. A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Example Computer

Figure 5:
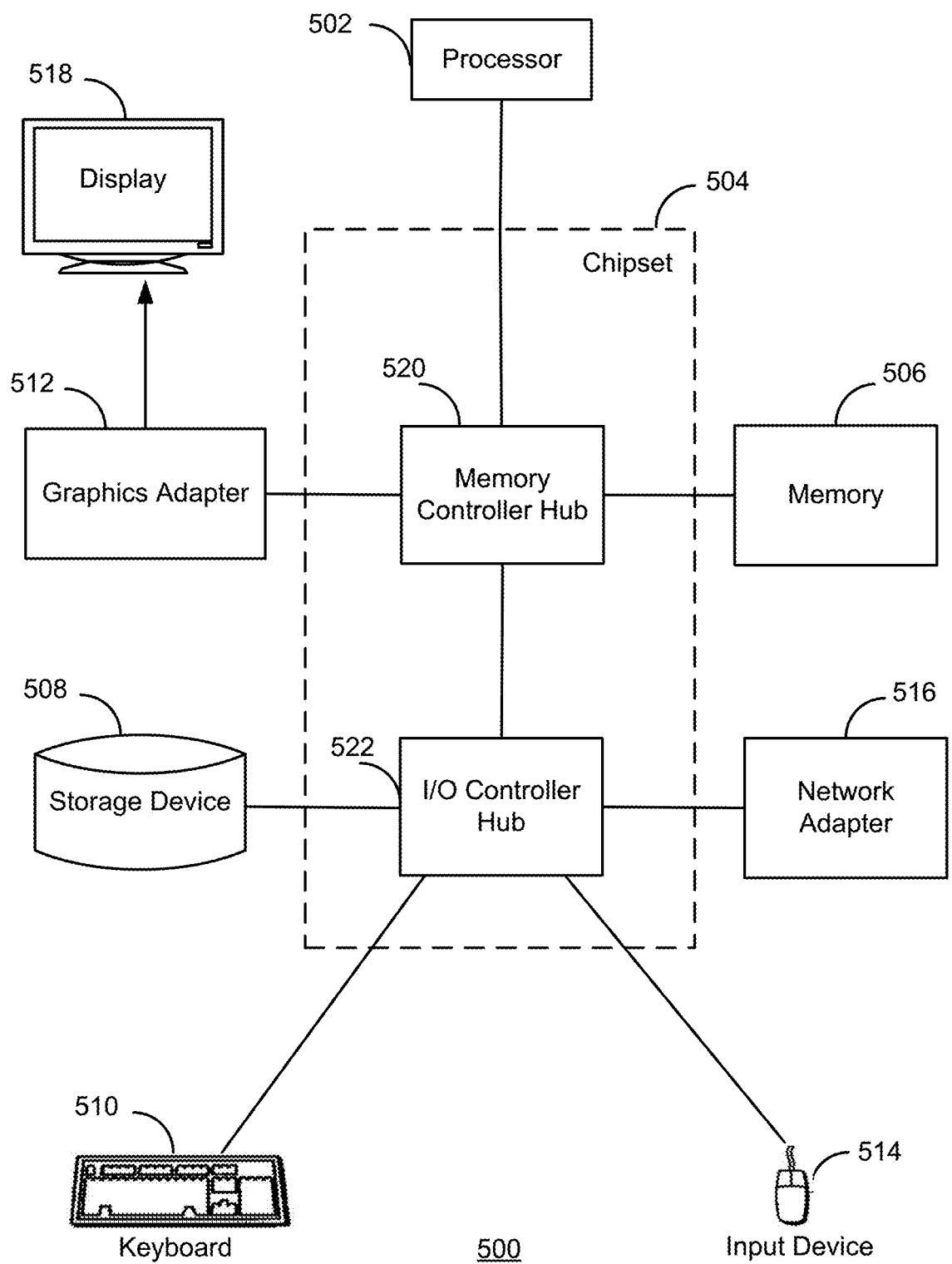
FIG. 5 illustrates an example computer for implementing the entities shown in FIGS. 1A-1D, 2A-2C, and 3A-3C.

FIG. 5 illustrates an example computer for implementing the entities shown in FIGS. 1A-ID, 2A-2C, and 3A-3C. In particular embodiments, the example computer 500 can represent computational system 202 described in FIG. 2A. The computer 500 includes at least one processor 502 coupled to a chipset 504. The chipset 504 includes a memory controller hub 520 and an input/output (I/O) controller hub 422. A memory 506 and a graphics adapter 512 are coupled to the memory controller hub 520, and a display 518 is coupled to the graphics adapter 512. A storage device 508, an input device 514, and network adapter 516 are coupled to the I/O controller hub 522. Other embodiments of the computer 500 have different architectures.

The storage device 508 is a non-transitory computer-readable storage medium such as a hard drive, compact disk read-only memory (CD-ROM), DVD, or a solid-state memory device. The memory 506 holds instructions and data used by the processor 502. The input interface 514 is a touch-screen interface, a mouse, track ball, or other type of pointing device, a keyboard, or some combination thereof, and is used to input data into the computer 500. In some embodiments, the computer 500 may be configured to receive input (e.g., commands) from the input interface 514 via gestures from the user. The graphics adapter 512 displays images and other information on the display 518. The network adapter 516 couples the computer 500 to one or more computer networks.

The computer 500 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 508, loaded into the memory 506, and executed by the processor 502. A module can be implemented as computer program code processed by the processing system(s) of one or more computers. Computer program code includes computer-executable instructions and/or computer-interpreted instructions, such as program modules, which instructions are processed by a processing system of a computer. Generally, such instructions define routines, programs, objects, components, data structures, and so on, that, when processed by a processing system, instruct the processing system to perform operations on data or configure the processor or computer to implement various components or data structures in computer storage. A data structure is defined in a computer program and specifies how data is organized in computer storage, such as in a memory device or a storage device, so that the data can accessed, manipulated, and stored by a processing system of a computer.

The types of computers 500 used by the entities of FIG. 1D can vary depending upon the embodiment and the processing power required by the entity. For example, the condition analysis system 170 can run in a single computer 500 or multiple computers 500 communicating with each other through a network such as in a server farm. The computers 500 can lack some of the components described above, such as graphics adapters 512, and displays 518.

Kit Implementation

Also disclosed herein are kits for performing a multiple-tiered analysis (e.g., screening and/or intra-individual analysis). Such kits can include equipment to draw a sample from a patient. For example, kits can include syringes and/or needles for obtaining a sample from a patient. Kits can include detection reagents for determining marker information using the sample obtained from the patient.

For example, detection reagents can include antibody reagents for performing a protein immunoassay. As another example, detection reagents can be a set of primers that, when combined with the sample, allows detection of a plurality of sites in cell-free DNA in the sample. In particular embodiments, the detection reagents enable detection of methylated or unmethylated target sites (e.g., methylated or unmethylated informative CpGs including one or more CGIs selected from Tables 1-4. Additional example CGIs are disclosed in WO2018209361 (see Table 1) and WO2022133315 (see Table 2 entitled "TOO Methylation Sites" and Table 3 entitled "Pan Cancer Methylation Sites"), each of which is hereby incorporated by reference in its entirety. For example, the detection reagents may be primers that target specific known sequences of target sites, thereby enabling nucleic acid amplification of the target sites. Thus, the use of the detection reagents results in generation of methylation information of the patient corresponding to the target sites.

A kit can include instructions for use of one or more sets of detection reagents. For example, a kit can include instructions for performing at least one detection assay such as a nucleic acid amplification assay (e.g., polymerase chain reaction assay including any of real-time PCR assays, quantitative real-time PCR (qPCR) assays, allele-specific PCR assays, and reverse-transcription PCR assays), nucleic acid sequencing (e.g., targeted gene sequencing, targeted amplicon sequencing, whole genome sequencing, or whole genome bisulfite sequencing), hybrid capture, an immunoassay, a protein-binding assay, an antibody-based assay, an antigen-binding protein-based assay, a protein-based array, an enzyme-linked immunosorbent assay (ELISA), reporter assays, flow cytometry, a protein array, a blot, a Western blot, nephelometry, turbidimetry, chromatography, NMR, mass spectrometry, LC-MS, UPLC-MS/MS, enzymatic activity, proximity extension assay, and an immunoassay selected from RIA, immunofluorescence, immunochemiluminescence, immunoelectrochemiluminescence, immunoelectrophoretic, a competitive immunoassay, and immunoprecipitation.

Kits can further include instructions for accessing computer program instructions stored on a computer storage medium. In various embodiments, the computer program instructions, when executed by a processor of a computer system, cause the processor to perform a screen and/or perform a second analysis to detect presence of a health condition in a patient. For example, kits can include instructions that, when executed by a processor of a computer system, cause the processor to perform an analysis of sequence information comprising data of the plurality of sites to identify whether the patient is not at risk of having a health condition; and then if the patient has not been identified as not at risk and analyze sequence information of the patient not identified as not at risk derived from whole genome sequencing to detect the presence of the health condition in the patient.

In various embodiments, the kits include instructions for practicing the methods disclosed herein (e.g., performing an assay, screen, or diagnostic assay). These instructions can be present in the kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Yet another means would be a computer readable medium, e.g., diskette, CD, hard-drive, network data storage, etc., on which the information has been recorded. Yet another means that can be present is a website address which can be used via the internet to access the information at a removed site. Any convenient means can be present in the kits.

Systems

Further disclosed herein are systems for performing a multiple-tiered analysis (e.g., screening and/or intra-individual analysis). In various embodiments, such a system can include one or more sets of detection reagents for determining genomic information using a sample obtained from the patient, an apparatus configured to receive a mixture of the one or more sets of detection reagents and the sample obtained from a subject to generate marker information (an example of which is methylation information) of the patient corresponding to a plurality of target sites, and a computer system communicatively coupled to the apparatus to obtain the methylation information and to perform a screen, intra-individual analysis, and/or second analysis.

The one or more sets of detection reagents enable the determination of marker information using the sample obtained from the patient. For example, detection reagents can include antibody reagents for performing a protein immunoassay. For example, detection reagents can be a set of primers that, when combined with the sample, allows detection of a plurality of sites in cell-free DNA in the sample. In particular embodiments, the detection reagents enable detection of methylated or methylated target sites (e.g., methylated or unmethylated informative CpGs including one or more CGI's selected from Tables 1-4. Additional example CGIs are disclosed in WO2018209361 (see Table 1) and WO2022133315 (see Table 2 entitled "TOO Methylation Sites" and Table 3 entitled "Pan Cancer Methylation Sites"), each of which is hereby incorporated by reference in its entirety.

The apparatus is configured to determine the methylation information from a mixture of the detection reagents and sample. For example, the apparatus can be configured to perform one or more of a nucleic acid amplification assay (e.g., polymerase chain reaction assay), nucleic acid sequencing (e.g., targeted gene sequencing, whole genome sequencing, or whole genome bisulfite sequencing), and hybrid capture to determine methylation information.

The mixture of the detection reagents and sample may be presented to the apparatus through various conduits, examples of which include wells of a well plate (e.g., 96 well plate), a vial, a tube, and integrated fluidic circuits. As such, the apparatus may have an opening (e.g., a slot, a cavity, an opening, a sliding tray) that can receive the container including the reagent test sample mixture and perform a reading. Examples of an apparatus include one or more of a sequencer, an incubator, plate reader (e.g., a luminescent plate reader, absorbance plate reader, fluorescence plate reader), a spectrometer, or a spectrophotometer.

The computer system, such as example computer 500 described in FIG. 5, communicates with the apparatus to receive the methylation information. The computer system performs an insilico screen and/or second analysis determine whether the patient is at risk of a health condition, or whether the health condition is present in the patient.

Additional Embodiments

Disclosed herein is a tiered, multipart method for detecting one or more early stage cancers in a subject, comprising: performing an analysis of sequence information of the subject that has been obtained from a biological sample of the subject to identify whether the subject is not at risk of having one or more of the early stage cancers; and then if the patient has not been identified as not at risk: analyzing the sequence information of the subject not identified as not at risk by performing a second analysis to detect the presence of at least one specific cancer in the subject. In various embodiments, the one or more of the early stage cancers is fifteen or more different cancers. In various embodiments, the one or more of the early stage or preclinical phase cancers is a set of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the one or more of the early stage or preclinical phase cancer is a single cancer type. In various embodiments, the single cancer type is any one of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the early stage cancer is a preclinical phase cancer. In various embodiments, the preclinical phase cancer is stage I or stage II cancer. In various embodiments, the method has more than a 70% ability to detect the at least one of multiple early stage cancers. In various embodiments, the method has more than a 70% ability to detect the at least one of multiple early stage cancers at more than 95%, more than 96%, more than 97%, more than 98%, more than 99%, more than 99.5%, or more than 99.9% specificity. In various embodiments, the method achieves at least a 80%, at least a 81%, at least a 82%, at least a 83%, at least a 84%, or at least a 85% positive predictive value when detecting the at least one of multiple early stage cancers. In various embodiments, the method achieves at least a 95%, at least a 96%, at least a 97%, at least a 98%, at least a 99%, at least a 99.3%, or at least a 99.4% negative predictive value when detecting the at least one of multiple early stage cancers.

In various embodiments, performing the analysis of the sequence information of the subject to identify whether the subject is not at risk has at least a 90%, at least a 95%, or at least a 99% negative predictive value. In various embodiments, the analyzing sequence information of the subject to identify whether the subject has a detectable cancer or precancer has at least a 80%, at least a 81%, at least a 82%, at least a 83%, at least a 84%, or at least a 85% positive predictive value. In various embodiments, the analyzing sequence information of the subject to identify whether the subject has a detectable cancer or precancer has at least a 90%, at least a 91%, at least a 92%, at least a 93%, at least a 94%, at least a 95%, at least a 96%, or at least a 97% negative predictive value.

In various embodiments, the sequence information comprises methylation sequence information. In various embodiments, the methylation sequence information comprises methylation statuses for a plurality of genomic sites. In various embodiments, the plurality of genomic sites comprise a plurality of CpG sites. In various embodiments, performing an analysis of sequence information of the subject comprises applying a trained machine learning model. In various embodiments, the sequence information is obtained from an assay, wherein the assay comprises performing one or more of: a. sequencing of nucleic acids in the sample; b. hybrid capture; c. methylation-specific PCR; d. an assay that generates methylation information; and e. sequencing a clone library generated from a template immortalized library.

In various embodiments, performing the assay that generates sequence information comprises: obtaining bisulfite converted cell free DNA (cfDNA); selectively amplifying target regions of the bisulfite converted cfDNA; and sequencing amplicons comprising the amplified target regions to generate the methylation information. In various embodiments, the target regions of the bisulfite converted cfDNA comprise previously identified regions that are differentially methylated in cancer. In various embodiments, the target regions of the bisulfite converted cfDNA comprise one or more CGIs shown in Tables 1-4. Additional example CGIs are disclosed in WO2018209361 (see Table 1) and WO2022133315 (see Table 2 entitled "TOO Methylation Sites" and Table 3 entitled "Pan Cancer Methylation Sites"), each of which is hereby incorporated by reference in its entirety. In various embodiments, the biological sample is obtained from the subject while the subject is asymptomatic. In various embodiments, the biological sample comprises any one of: a blood sample, a stool sample, a urine sample, a mucous sample, a saliva sample.

In various embodiments, the biological sample is a blood sample. In various embodiments, the biological sample does not comprise an invasive biopsy sample. In various embodiments, the assay performed on the biological sample processes one or more of: nucleic acids, cell free DNA including selected CpGs with a selected methylation state; and RNA. In various embodiments, the second analysis comprises whole genome sequencing, optionally whole genome bisulfite sequencing.

In various embodiments, methods disclosed herein further comprise determining a tissue of origin of the at least one specific cancer in the subject using the sequence information of the subject. In various embodiments, methods disclosed herein further comprise: performing an analysis of additional sequence information of the subject that has been obtained from an additional biological sample of the subject obtained subsequent to a timepoint that the biological sample was obtained; determining one or more changes between the additional sequence information of the subject and the sequence information; and determining a progression of the at least one specific cancer in the subject based on the determined one or more changes. In various embodiments, methods disclosed herein further comprise: determining whether to provide an intervention to the subject based on the determined progression of the at least one specific cancer. In various embodiments, determining one or more changes between the additional sequence information of the subject and the sequence information comprises determining changes one or more changes in methylation status across a plurality of genomic sites.

Additionally disclosed herein is a tiered, multipart method for detecting a health condition in a subject, comprising: performing an analysis of sequence information of the subject that has been obtained from a biological sample of the subject to identify whether the subject is not at risk of having the health condition; and then if the patient has not been identified as not at risk: analyzing the sequence information of the subject not identified as not at risk by performing a second analysis to detect the presence of the health condition in the subject. Additionally disclosed herein is a tiered, multipart method for detecting a health condition in a subject, comprising: performing an analysis of marker information of the subject that has been obtained from a biological sample of the subject to identify whether the subject is not at risk of having the health condition; and then if the patient has not been identified as not at risk: analyzing sequence information of the subject not identified as not at risk by performing a second analysis to detect the presence of the health condition in the subject. In various embodiments, marker information comprises quantitative levels of protein biomarkers.

Additionally disclosed herein is a tiered, multipart method for improving the probability a signal in a sample is authentic, comprising: (a) performing an analysis of sequence information of nucleic acids in the sample to determine whether the analysis generates a result correlative with presence or absence of a human condition, and then if the result is detected: (b) analyzing the sequence information of the nucleic acids in the sample by performing second analysis to determine if the second analysis generates the signal, wherein if the signal is detected, then the probability the signal in the sample is authentic is higher as compared to a probability that a signal is authentic when generated by an analogous method, where the analogous method differs by omitting step (a). In various embodiments, the method achieves at least a 80%, at least a 81%, at least a 82%, at least a 83%, at least a 84%, or at least a 85% positive predictive value when detecting the health condition. In various embodiments, the health condition is a disease risk. In various embodiments, the health condition is a rare disease or disorder. In various embodiments, the health condition has an incidence of 1 in 100, 1 in 1,000, 1 in 10,000 individuals, 1 in 100,000 individuals, 1 in 1,000,000 individuals, 1 in 10,000,000 individuals, or 1 in 100,000,000 individuals.

Additionally disclosed herein is a method for diagnosing a subject with at least one of multiple early stage cancers, the method comprising: obtaining sequence information derived from a first assay performed on a sample obtained from the subject; performing a screen by analyzing the sequence information to classify the subject as at risk for one or more multiple early stage cancers or not at risk for one or more multiple early stage cancers; responsive to a classification of the subject as at risk for one or more multiple early stage cancers, obtaining sequence information derived from a second assay performed on the sample or an additional sample obtained from the subject to generate the sequence information derived from the second assay; and performing a second analysis of the sequence information derived from the second assay for the subject to further classify the subject at risk for one or more multiple early stage cancers as a candidate subject for monitoring or treatment. Additionally disclosed herein is a method for diagnosing a subject at risk for at least one of multiple early stage cancers, the method comprising: obtaining sequence information derived from a first assay performed on a sample obtained from the subject; performing a screen by analyzing the sequence information to classify the subject as at risk for one or more multiple early stage cancers or not at risk for one or more multiple early stage cancers; if the subject is classified as not at risk for one or more multiple early stage cancers, reporting that the subject is not at risk for one or more multiple early stage cancers; if the subject is classified as at risk for one or more multiple early stage cancers: obtaining sequence information derived from a second assay performed on the sample or an additional sample obtained from the subject to generate the sequence information derived from the second assay; and performing a second analysis of the sequence information derived from the second assay for the subject to further classify the subject at risk for the one or more multiple early stage cancers as a candidate subject for monitoring.

Additionally disclosed herein is a method for identifying a candidate population of subjects having an early stage cancer for enrollment in a clinical trial, the method comprising: for each of one or more subjects in a plurality of subjects: obtaining sequence information derived from a first assay performed on a sample obtained from the subject; performing a screen by analyzing the sequence information to classify the subject as at risk for one or more multiple early stage cancers or not at risk for one or more multiple early stage cancers; responsive to a classification of the subject as at risk for one of multiple early stage cancers, obtaining sequence information derived from a second assay performed on the sample or an additional sample obtained from the subject to generate the sequence information derived from the second assay; and performing a second analysis of the sequence information derived from the second assay for the subject to further classify the subject at risk for one or more multiple early stage cancers as a candidate subject for inclusion in the candidate population.

In various embodiments, the sequence information derived from the first assay comprises methylation sequence information. In various embodiments, the methylation sequence information derived from the first assay comprises methylation statuses for a plurality of genomic sites. In various embodiments, the plurality of genomic sites comprise a plurality of CpG sites. In various embodiments, performing a screen by analyzing the obtained sequence information derived from the first assay comprises applying a first trained machine learning model. In various embodiments, the sequence information derived from the second assay comprises methylation sequence information. In various embodiments, the methylation sequence information from the second assay comprises methylation statuses for a plurality of genomic sites identified as relevant for the subject. In various embodiments, the plurality of genomic sites comprise a plurality of CpG sites. In various embodiments, performing a second analysis of the obtained sequence information derived from the second assay comprises applying a second trained machine learning model. In various embodiments, obtaining sequence information derived from the first assay comprises: performing or having performed the first assay to generate the sequence information derived from the first assay. In various embodiments, performing or having performed the first assay comprises performing or having performed one or more of: a. sequencing of nucleic acids in the sample; b. hybrid capture; c. methylation-specific PCR; d. an assay that generates methylation information; and e. sequencing a clone library generated from a template immortalized library.

In various embodiments, performing the assay that generates sequence information comprises: obtaining bisulfite converted cell free DNA (cfDNA); selectively amplifying target regions of the bisulfite converted cfDNA; and sequencing amplicons comprising the amplified target regions to generate the methylation information. In various embodiments, the target regions of the bisulfite converted cfDNA comprise previously identified regions that are differentially methylated in cancer. In various embodiments, the target regions of the bisulfite converted cfDNA comprise one or more CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety. In various embodiments, the sample or additional sample is obtained from the subject while the subject is asymptomatic. In various embodiments, the sample or additional sample comprises any one of: a blood sample, a stool sample, a urine sample, a mucous sample, a saliva sample. In various embodiments, the sample or the additional sample are blood samples. In various embodiments, the first assay performed on the sample or the second assay performed on the sample or the additional sample processes one or more of: nucleic acids; cell free DNA including selected CpGs with a selected methylation state; and RNA.

In various embodiments, a cost of the second assay is greater than a cost of the first assay. In various embodiments, the second assay comprises whole genome sequencing. In various embodiments, the whole genome sequencing comprises whole genome bisulfite sequencing. In various embodiments, the second analysis achieves a higher sensitivity at a higher specificity in comparison to the screen. In various embodiments, methods disclosed herein further comprise determining a tissue of origin of the at least one specific cancer in the subject using the sequence information of the subject. In various embodiments, methods disclosed herein further comprise: performing an analysis of additional sequence information of the subject that has been obtained from an additional biological sample of the subject obtained subsequent to a timepoint that the biological sample was obtained; determining one or more changes between the additional sequence information of the subject and the sequence information; and determining a progression of the at least one specific cancer in the subject based on the determined one or more changes. In various embodiments, methods disclosed herein further comprise: determining whether to provide an intervention to the subject based on the determined progression of the at least one specific cancer.

In various embodiments, determining one or more changes between the additional sequence information of the subject and the sequence information comprises determining changes one or more changes in methylation status across a plurality of genomic sites. In various embodiments, methods disclosed herein further comprise: for each of one or more other subjects in the plurality of subjects: obtaining sequence information derived from a first assay performed on a sample obtained from the subject; performing a screen by analyzing the sequence information to classify the subject as at risk for one or more multiple early stage cancers or not at risk for one or more multiple early stage cancers; and responsive to a classification of the subject as not at risk for one or more multiple early stage cancers, reporting that the subject is not at risk for one or more multiple early stage cancers and withholding the subject from the candidate population. In various embodiments, methods disclosed herein further comprise: obtaining sequence information derived from a third assay performed on a yet additional sample obtained from the subject; and performing a second analysis of sequence information derived from the third assay for the subject to further classify the subject.

In various embodiments, the obtained sequence information derived from the third assay comprises methylation sequence information. In various embodiments, the methylation sequence information comprises methylation statuses for a plurality of individually informative sites for the subject. In various embodiments, the yet additional sample is obtained at a different time than a time that either the sample or additional sample were obtained. In various embodiments, the one or more multiple early stage cancers is fifteen or more different cancers. In various embodiments, the one or more multiple early stage cancers is a set of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the one or more multiple early stage cancers is a single cancer type. In various embodiments, the single cancer type is any one of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer. In various embodiments, the early stage cancer is a preclinical phase cancer In various embodiments, the preclinical phase cancer is stage I or stage H cancer. In various embodiments, the method has more than a 70% ability to detect the at least one of multiple early stage cancers at more than 95%, more than 96%, more than 97%, more than 98%, more than 99%, more than 99.5%, or more than 99.9% specificity. In various embodiments, the method achieves at least a 80%, at least a 81%, at least a 82%, at least a 83%, at least a 84%, or at least a 85% positive predictive value when detecting the at least one of multiple early stage cancers. In various embodiments, the method achieves at least a 95%, at least a 96%, at least a 97%, at least a 98%, at least a 99%, at least a 99.3%, or at least a 99.4% negative predictive value when detecting the at least one of multiple early stage cancers. In various embodiments, the screen has at least a 90%, at least a 95%, or at least a 99% negative predictive value. In various embodiments, the second analysis has at least a 80%, at least a 81%, at least a 82%, at least a 83%, at least a 84%, or at least a 85% positive predictive value. In various embodiments, the second analysis has at least a 90%, at least a 91%, at least a 92%, at least a 93%, at least a 94%, at least a 95%, at least a 96%, or at least a 97% negative predictive value.

Additionally disclosed herein is a non-transitory computer readable medium comprising instructions that, when executed by a processor, cause the processor to: perform an analysis of sequence information of the subject that has been obtained from a biological sample of the subject to identify whether the subject is not at risk of having one or more of the early stage cancers; and then if the patient has not been identified as not at risk: analyze the sequence information of the subject not identified as not at risk by performing a second analysis to detect the presence of at least one specific cancer in the subject. In various embodiments, the one or more of the early stage cancers is fifteen or more different cancers. In various embodiments, the one or more of the early stage or preclinical phase cancers is a set of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the one or more of the early stage or preclinical phase cancer is a single cancer type. In various embodiments, the single cancer type is any one of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer. In various embodiments, the early stage cancer is a preclinical phase cancer In various embodiments, the preclinical phase cancer is stage I or stage II cancer.

In various embodiments, the performance of the analysis and the analysis of the sequence information has more than a 70% ability to detect the at least one of multiple early stage cancers. In various embodiments, the performance of the analysis and the analysis of the sequence information has more than a 70% ability to detect the at least one of multiple early stage cancers at more than 95%, more than 96%, more than 97%, more than 98%, more than 99%, more than 99.5%, or more than 99.9% specificity. In various embodiments, the performance of the analysis and the analysis of the sequence information achieves at least a 80%, at least a 81%, at least a 82%, at least a 83%, at least a 84%, or at least a 85% positive predictive value when detecting the at least one of multiple early stage cancers. In various embodiments, the performance of the analysis and the analysis of the sequence information achieves at least a 95%, at least a 96%, at least a 97%, at least a 98%, at least a 99%, at least a 99.3%, or at least a 99.4% negative predictive value when detecting the at least one of multiple early stage cancers. In various embodiments, the performance of the analysis has at least a 90%, at least a 95%, or at least a 99% negative predictive value. In various embodiments, the analysis of the sequence information to identify whether the subject has a detectable cancer or precancer has at least a 80%, at least a 81%, at least a 82%, at least a 83%, at least a 84%, or at least a 85% positive predictive value. In various embodiments, the analysis of the sequence information to identify whether the subject has a detectable cancer or precancer has at least a 90%, at least a 91%, at least a 92%, at least a 93%, at least a 94%, at least a 95%, at least a 96%, or at least a 97% negative predictive value.

In various embodiments, the sequence information comprises methylation sequence information. In various embodiments, the methylation sequence information comprises methylation statuses for a plurality of genomic sites. In various embodiments, the plurality of genomic sites comprise a plurality of CpG sites. In various embodiments, the instructions that cause the processor to perform an analysis of sequence information of the subject comprises further comprises instructions that, when executed by the processor, cause the processor to apply a trained machine learning model. In various embodiments, the sequence information is obtained from an assay, wherein the assay comprises performing one or more of: a. sequencing of nucleic acids in the sample; b. hybrid capture; c. methylation-specific PCR; d. an assay that generates methylation information; and e. sequencing a clone library generated from a template immortalized library. In various embodiments, performing the assay that generates sequence information comprises: obtaining bisulfite converted cell free DNA (cfDNA); selectively amplifying target regions of the bisulfite converted cfDNA; and sequencing amplicons comprising the amplified target regions to generate the methylation information.

In various embodiments, the target regions of the bisulfite converted cfDNA comprise previously identified regions that are differentially methylated in cancer. In various embodiments, the target regions of the bisulfite converted cfDNA comprise one or more CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety. In various embodiments, the biological sample is obtained from the subject while the subject is asymptomatic. In various embodiments, the biological sample comprises any one of: a blood sample, a stool sample, a urine sample, a mucous sample, a saliva sample. In various embodiments, the biological sample is a blood sample. In various embodiments, the biological sample does not comprise an invasive biopsy sample. In various embodiments, the assay performed on the biological sample processes one or more of: nucleic acids; cell free DNA including selected CpGs with a selected methylation state; and RNA.

In various embodiments, the second analysis comprises whole genome sequencing, optionally whole genome bisulfite sequencing. In various embodiments, the non-transitory computer readable medium further comprising instructions that, when executed by the processor, cause the processor to determine a tissue of origin of the at least one specific cancer in the subject using the sequence information of the subject. In various embodiments, the non-transitory computer readable medium further comprising instructions that, when executed by the processor, cause the processor to: perform an analysis of additional sequence information of the subject that has been obtained from an additional biological sample of the subject obtained subsequent to a timepoint that the biological sample was obtained; determine one or more changes between the additional sequence information of the subject and the sequence information; and determine a progression of the at least one specific cancer in the subject based on the determined one or more changes. In various embodiments, the non-transitory computer readable medium further comprising instructions that, when executed by the processor, cause the processor to: determine whether to provide an intervention to the subject based on the determined progression of the at least one specific cancer. In various embodiments, the instructions that cause to processor to determine one or more changes between the additional sequence information of the subject and the sequence information further comprises instructions that, when executed by the processor, cause the processor to determine changes one or more changes in methylation status across a plurality of genomic sites.

Additionally disclosed herein is a non-transitory computer readable medium comprising instructions that, when executed by a processor, cause the processor to: perform an analysis of sequence information of the subject that has been obtained from a biological sample of the subject to identify whether the subject is not at risk of having the health condition; and then if the patient has not been identified as not at risk: analyze the sequence information of the subject not identified as not at risk by performing a second analysis to detect the presence of the health condition in the subject. Additionally disclosed herein is a non-transitory computer readable medium comprising instructions that, when executed by a processor, cause the processor to: perform an analysis of marker information of the subject that has been obtained from a biological sample of the subject to identify whether the subject is not at risk of having the health condition; and then if the patient has not been identified as not at risk: analyze sequence information of the subject not identified as not at risk by performing a second analysis to detect the presence of the health condition in the subject. In various embodiments, marker information comprises quantitative levels of protein biomarkers.

Additionally disclosed herein is a non-transitory computer readable medium comprising instructions that, when executed by a processor, cause the processor to: (a) perform an analysis of sequence information of nucleic acids in the sample to determine whether the analysis generates a result correlative with presence or absence of a human condition, and then if the result is detected: (b) analyze the sequence information of the nucleic acids in the sample by performing a second analysis to determine if the second analysis generates the signal, wherein if the signal is detected, then the probability the signal in the sample is authentic is higher as compared to a probability that a signal is authentic when generated by an analogous method, where the analogous method differs by omitting step (a). In various embodiments, the steps performed by the processor achieve at least a 80%, at least a 81%, at least a 82%, at least a 83%, at least a 84%, or at least a 85% positive predictive value when detecting the health condition. In various embodiments, the health condition is a disease risk. In various embodiments, the health condition is a rare disease or disorder. In various embodiments, the health condition has an incidence of 1 in 100, 1 in 1,000, 1 in 10,000 individuals, 1 in 100,000 individuals, 1 in 1,000,000 individuals, 1 in 10,000,000 individuals, or 1 in 100,000,000 individuals.

Additionally disclosed herein is a non-transitory computer readable medium comprising instructions that, when executed by a processor, cause the processor to: obtain sequence information derived from a first assay performed on a sample obtained from a subject; perform a screen by analyzing the sequence information to classify the subject as at risk for a health condition or not at risk for a health condition; responsive to a classification of the subject as at risk for a health condition, obtain sequence information derived from a second assay performed on the sample or an additional sample obtained from the subject to generate the sequence information derived from the second assay; and performing a second analysis of the sequence information derived from the second assay for the subject to further classify the subject at risk for the health condition as a candidate subject for monitoring. Additionally disclosed herein is a non-transitory computer readable medium comprising instructions that, when executed by a processor, cause the processor to: obtain sequence information derived from a first assay performed on a sample obtained from the subject; perform a screen by analyzing the sequence information to classify the subject as at risk for the health condition or not at risk for the health condition; if the subject is classified as not at risk for the health condition, report that the subject is not at risk for the health condition; if the subject is classified as at risk for the health condition: obtain sequence information derived from a second assay performed on the sample or an additional sample obtained from the subject to generate the sequence information derived from the second assay; and perform a second analysis of the sequence information derived from the second assay for the subject to further classify the subject at risk for the health condition as a candidate subject for monitoring.

Additionally disclosed herein is a non-transitory computer readable medium comprising instructions that, when executed by a processor, cause the processor to: for each of one or more subjects in a plurality of subjects: obtain sequence information derived from a first assay performed on a sample obtained from the subject; perform a screen by analyzing the sequence information to classify the subject as at risk for a health condition or not at risk for a health condition; responsive to a classification of the subject as at risk for a health condition, obtain sequence information derived from a second assay performed on the sample or an additional sample obtained from the subject to generate the sequence information derived from the second assay; and perform a second analysis of the sequence information derived from the second assay for the subject to further classify the subject at risk for a health condition as a candidate subject for inclusion in the candidate population.

Additionally disclosed herein is a system comprising: a processor; a data storage comprising sequence information that has been obtained from a biological sample of a subject; a non-transitory computer readable medium comprising instructions that, when executed by the processor, cause the processor to: perform an analysis of sequence information of the subject that has been obtained from a biological sample of the subject to identify whether the subject is not at risk of having one or more of the early stage cancers; and then if the patient has not been identified as not at risk: analyze the sequence information of the subject not identified as not at risk by performing a second analysis to detect the presence of at least one specific cancer in the subject. In various embodiments, the one or more of the early stage cancers is fifteen or more different cancers. In various embodiments, the one or more of the early stage or preclinical phase cancers is a set of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the one or more of the early stage or preclinical phase cancer is a single cancer type. In various embodiments, the single cancer type is any one of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the early stage cancer is a preclinical phase cancer. In various embodiments, the preclinical phase cancer is stage I or stage II cancer. In various embodiments, the performance of the analysis and the analysis of the sequence information has more than a 70% ability to detect the at least one of multiple early stage cancers. In various embodiments, the performance of the analysis and the analysis of the sequence information has more than a 70% ability to detect the at least one of multiple early stage cancers at more than 95%, more than 96%, more than 97%, more than 98%, more than 99%, more than 99.5%, or more than 99.9% specificity. In various embodiments, the performance of the analysis and the analysis of the sequence information achieves at least a 80%, at least a 81%, at least a 82%, at least a 83%, at least a 84%, or at least a 85% positive predictive value when detecting the at least one of multiple early stage cancers. In various embodiments, the performance of the analysis and the analysis of the sequence information achieves at least a 95%, at least a 96%, at least a 97%, at least a 98%, at least a 99%, at least a 99.3%, or at least a 99.4% negative predictive value when detecting the at least one of multiple early stage cancers. In various embodiments, the performance of the analysis has at least a 90%, at least a 95%, or at least a 99% negative predictive value. In various embodiments, the analysis of the sequence information to identify whether the subject has a detectable cancer or precancer has at least a 80%, at least a 81%, at least a 82%, at least a 83%, at least a 84%, or at least a 85% positive predictive value. In various embodiments, the analysis of the sequence information to identify whether the subject has a detectable cancer or precancer has at least a 90%, at least a 91%, at least a 92%, at least a 93%, at least a 94%, at least a 95%, at least a 96%, or at least a 97% negative predictive value.

In various embodiments, the sequence information comprises methylation sequence information. In various embodiments, the methylation sequence information comprises methylation statuses for a plurality of genomic sites. In various embodiments, the plurality of genomic sites comprise a plurality of CpG sites. In various embodiments, the instructions that cause the processor to perform an analysis of sequence information of the subject comprises further comprises instructions that, when executed by the processor, cause the processor to apply a trained machine learning model.

In various embodiments, the sequence information is obtained from an assay, wherein the assay comprises performing one or more of: a. sequencing of nucleic acids in the sample; b. hybrid capture; c. methylation-specific PCR; d. an assay that generates methylation information; and e. sequencing a clone library generated from a template immortalized library.

In various embodiments, performing the assay that generates sequence information comprises: obtaining bisulfite converted cell free DNA (cfDNA); selectively amplifying target regions of the bisulfite converted cfDNA; and sequencing amplicons comprising the amplified target regions to generate the methylation information. In various embodiments, the target regions of the bisulfite converted cfDNA comprise previously identified regions that are differentially methylated in cancer. In various embodiments, the target regions of the bisulfite converted cfDNA comprise one or more CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety. In various embodiments, the biological sample is obtained from the subject while the subject is asymptomatic. In various embodiments, the biological sample comprises any one of: a blood sample, a stool sample, a urine sample, a mucous sample, a saliva sample. In various embodiments, the biological sample is a blood sample. In various embodiments, the biological sample does not comprise an invasive biopsy sample. In various embodiments, the assay performed on the biological sample processes one or more of: nucleic acids; cell free DNA including selected CpGs with a selected methylation state; and RNA.

In various embodiments, the second analysis comprises whole genome sequencing, optionally whole genome bisulfite sequencing. In various embodiments, the non-transitory computer readable medium further comprises instructions that, when executed by the processor, cause the processor to determine a tissue of origin of the at least one specific cancer in the subject using the sequence information of the subject. In various embodiments, the non-transitory computer readable medium further comprises instructions that, when executed by the processor, cause the processor to: perform an analysis of additional sequence information of the subject that has been obtained from an additional biological sample of the subject obtained subsequent to a timepoint that the biological sample was obtained; determine one or more changes between the additional sequence information of the subject and the sequence information; and determine a progression of the at least one specific cancer in the subject based on the determined one or more changes.

In various embodiments, the non-transitory computer readable medium further comprises instructions that, when executed by the processor, cause the processor to: determine whether to provide an intervention to the subject based on the determined progression of the at least one specific cancer. In various embodiments, the instructions that cause to processor to determine one or more changes between the additional sequence information of the subject and the sequence information further comprises instructions that, when executed by the processor, cause the processor to determine changes one or more changes in methylation status across a plurality of genomic sites.

Additionally disclosed herein is a system comprising: a processor; a data storage comprising sequence information that has been obtained from a biological sample of a subject; a non-transitory computer readable medium comprising instructions that, when executed by the processor, cause the processor to: perform an analysis of sequence information of the subject that has been obtained from a biological sample of the subject to identify whether the subject is not at risk of having the health condition; and then if the patient has not been identified as not at risk: analyze the sequence information of the subject not identified as not at risk by performing a second analysis to detect the presence of the health condition in the subject.

Additionally disclosed herein is a system comprising: a processor; a data storage comprising marker information that has been obtained from a biological sample of a subject; a non-transitory computer readable medium comprising instructions that, when executed by the processor, cause the processor to: perform an analysis of marker information of the subject that has been obtained from a biological sample of the subject to identify whether the subject is not at risk of having the health condition; and then if the patient has not been identified as not at risk: analyze sequence information of the subject not identified as not at risk by performing a second analysis to detect the presence of the health condition in the subject. In various embodiments, the marker information comprises quantitative levels of protein biomarkers.

Additionally disclosed herein is a system comprising: a processor; a data storage comprising marker information that has been obtained from a biological sample of a subject; a non-transitory computer readable medium comprising instructions that, when executed by the processor, cause the processor to: (a) perform an analysis of sequence information of nucleic acids in the sample to determine whether the analysis generates a result correlative with presence or absence of a human condition, and then if the result is detected: and (b) analyze the sequence information of the nucleic acids in the sample by performing second analysis to determine if the second analysis generates the signal, wherein if the signal is detected, then the probability the signal in the sample is authentic is higher as compared to a probability that a signal is authentic when generated by an analogous method, where the analogous method differs by omitting step (a). In various embodiments, the steps performed by the processor achieve at least a 80%, at least a 81%, at least a 82%, at least a 83%, at least a 84%, or at least a 85% positive predictive value when detecting the health condition. In various embodiments, the health condition is a disease risk. In various embodiments, the health condition is a rare disease or disorder. In various embodiments, the health condition has an incidence of 1 in 100, 1 in 1,000, 1 in 10,000 individuals, 1 in 100,000 individuals, 1 in 1,000,000 individuals, 1 in 10,000,000 individuals, or 1 in 100,000,000 individuals.

Additionally disclosed herein is a system comprising: a processor; a data storage comprising sequence information derived from a first assay performed on a sample obtained from a subject; a non-transitory computer readable medium comprising instructions that, when executed by the processor, cause the processor to: perform a screen by analyzing the sequence information to classify the subject as at risk for a health condition or not at risk for a health condition; responsive to a classification of the subject as at risk for a health condition, obtain sequence information derived from a second assay performed on the sample or an additional sample obtained from the subject to generate the sequence information derived from the second assay; and perform a second analysis of the sequence information derived from the second assay for the subject to further classify the subject at risk for the health condition as a candidate subject for monitoring.

Additionally disclosed herein is a system comprising: a processor; a data storage comprising sequence information derived from a first assay performed on a sample obtained from a subject; a non-transitory computer readable medium comprising instructions that, when executed by the processor, cause the processor to: perform a screen by analyzing the sequence information to classify the subject as at risk for a health condition or not at risk for a health condition; if the subject is classified as not at risk for the health condition, report that the subject is not at risk for the health condition; if the subject is classified as at risk for a health condition, obtain sequence information derived from a second assay performed on the sample or an additional sample obtained from the subject to generate the sequence information derived from the second assay; and perform a second analysis of the sequence information derived from the second assay for the subject to further classify the subject at risk for the health condition as a candidate subject for monitoring.

Additionally disclosed herein is a system comprising: a processor; a data storage comprising sequence information derived from a first assay performed on a sample obtained from a subject; a non-transitory computer readable medium comprising instructions that, when executed by the processor, cause the processor to: for each of one or more subjects in the plurality of subjects: perform a screen by analyzing the sequence information to classify the subject as at risk for a health condition or not at risk for a health condition; responsive to a classification of the subject as at risk for the health condition, obtain sequence information derived from a second assay performed on the sample or an additional sample obtained from the subject to generate the sequence information derived from the second assay; and perform a second analysis of the sequence information derived from the second assay for the subject to further classify the subject at risk for the health condition as a candidate subject for inclusion in the candidate population.

Additionally disclosed herein is a kit comprising: a. equipment to draw a sample from a subject; b. a set of detection reagents that, when combined with the sample, allows detection of biomarkers in the sample; and c. instructions for accessing computer program instructions stored on a computer storage medium that, when processed by a processor of a computer system, cause the processor to: perform an analysis of sequence information to identify whether the subject is not at risk of having one or more early stage cancers; and then if the patient has not been identified as not at risk: analyze sequence information of the subject not identified as not at risk derived from second analysis to detect the presence of the one or more early stage cancers in the subject. In various embodiments, the one or more of the early stage cancers is fifteen or more different cancers. In various embodiments, the one or more of the early stage or preclinical phase cancers is a set of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the one or more of the early stage or preclinical phase cancer is a single cancer type. In various embodiments, the single cancer type is any one of acute lymphoblastic leukemia, acute myeloid leukemia, adrenocortical carcinoma, soft tissue sarcoma, lymphoma, anal cancer, gastrointestinal cancer, brain cancer, skin cancer, bile duct cancer, bladder cancer, bone cancer, breast cancer, lung cancer, cardiac cancer, central nervous system cancer, cervical cancer, chronic lymphocytic leukemia, chronic myelogenous leukemia, chronic myeloproliferative neoplasms, colorectal cancer, uterine cancer, esophageal cancer, head and neck cancer, eye cancer, fallopian tube cancer, gallbladder cancer, gastric cancer, germ cell tumor, gestational trophoblastic cancer, hairy cell leukemia, liver cancer, Hodgkin lymphoma, intraocular melanoma, pancreatic cancer, kidney cancer, leukemia, mesothelioma, metastatic cancer, mouth cancer, multiple endocrine neoplasia syndromes, multiple myeloma neoplasms, myelodysplastic neoplasms, ovarian cancer, parathyroid cancer, penile cancer, pheochromocytoma, pituitary cancer, plasma cell neoplasm, primary peritoneal cancer, prostate cancer, rectal cancer, retinoblastoma, sarcoma, small intestine cancer, testicular cancer, throat cancer, thymoma and thymic carcinoma, thyroid cancer, urethral cancer, uterine cancer, vaginal cancer, and vulvar cancer.

In various embodiments, the early stage cancer is a preclinical phase cancer In various embodiments, the preclinical phase cancer is stage I or stage II cancer. In various embodiments, the performance of the analysis and the analysis of the sequence information has more than a 70% ability to detect the at least one of multiple early stage cancers. In various embodiments, the performance of the analysis and the analysis of the sequence information has more than a 70% ability to detect the at least one of multiple early stage cancers at more than 95%, more than 96%, more than 97%, more than 98%, more than 99%, more than 99.5%, or more than 99.9% specificity. In various embodiments, the performance of the analysis and the analysis of the sequence information achieves at least a 80%, at least a 81%, at least a 82%, at least a 83%, at least a 84%, or at least a 85% positive predictive value when detecting the at least one of multiple early stage cancers. In various embodiments, the performance of the analysis and the analysis of the sequence information achieves at least a 95%, at least a 96%, at least a 97%, at least a 98%, at least a 99%, at least a 99.3%, or at least a 99.4% negative predictive value when detecting the at least one of multiple early stage cancers. In various embodiments, the performance of the analysis has at least a 90%, at least a 95%, or at least a 99% negative predictive value. In various embodiments, the analysis of the sequence information to identify whether the subject has a detectable cancer or precancer has at least a 80%, at least a 81%, at least a 82%, at least a 83%, at least a 84%, or at least a 85% positive predictive value. In various embodiments, the analysis of the sequence information to identify whether the subject has a detectable cancer or precancer has at least a 90%, at least a 91%, at least a 92%, at least a 93%, at least a 94%, at least a 95%, at least a 96%, or at least a 97% negative predictive value.

In various embodiments, the sequence information comprises methylation sequence information. In various embodiments, the methylation sequence information comprises methylation statuses for a plurality of genomic sites. In various embodiments, the plurality of genomic sites comprise a plurality of CpG sites. In various embodiments, the instructions that cause the processor to perform an analysis of sequence information of the subject comprises further comprises instructions that, when executed by the processor, cause the processor to apply a trained machine learning model.

In various embodiments, the sequence information is obtained from an assay, wherein the assay comprises performing one or more of: a. sequencing of nucleic acids in the sample; b. hybrid capture; c. methylation-specific PCR; d. an assay that generates methylation information; and e. sequencing a clone library generated from a template immortalized library. In various embodiments, performing the assay that generates sequence information comprises: obtaining bisulfite converted cell free DNA (cfDNA); selectively amplifying target regions of the bisulfite converted cfDNA; and sequencing amplicons comprising the amplified target regions to generate the methylation information.

In various embodiments, the target regions of the bisulfite converted cfDNA comprise previously identified regions that are differentially methylated in cancer. In various embodiments, target regions of the bisulfite converted cfDNA comprise one or more CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety. In various embodiments, the biological sample is obtained from the subject while the subject is asymptomatic. In various embodiments, the biological sample comprises any one of: a blood sample, a stool sample, a urine sample, a mucous sample, a saliva sample. In various embodiments, the biological sample is a blood sample. In various embodiments, the biological sample does not comprise an invasive biopsy sample.

In various embodiments, the assay performed on the biological sample processes one or more of: nucleic acids, cell free DNA including selected CpGs with a selected methylation state; and RNA. In various embodiments, the second analysis comprises whole genome sequencing, optionally whole genome bisulfite sequencing. In various embodiments, the non-transitory computer readable medium further comprises instructions that, when executed by the processor, cause the processor to determine a tissue of origin of the at least one specific cancer in the subject using the sequence information of the subject. In various embodiments, the computer program instructions further comprise instructions that, when executed by the processor, cause the processor to; perform an analysis of additional sequence information of the subject that has been obtained from an additional biological sample of the subject obtained subsequent to a timepoint that the biological sample was obtained; determine one or more changes between the additional sequence information of the subject and the sequence information; and determine a progression of the at least one specific cancer in the subject based on the determined one or more changes.

In various embodiments, the computer program instructions further comprise instructions that, when executed by the processor, cause the processor to: determine whether to provide an intervention to the subject based on the determined progression of the at least one specific cancer. In various embodiments, the computer program instructions that cause to processor to determine one or more changes between the additional sequence information of the subject and the sequence information further comprise instructions that, when executed by the processor, cause the processor to determine changes one or more changes in methylation status across a plurality of genomic sites.

Additionally disclosed herein is a kit comprising: a. equipment to draw a sample from a subject; b. a set of detection reagents that, when combined with the sample, allows detection of biomarkers in the sample; and c. instructions for accessing computer program instructions stored on a computer storage medium that, when processed by a processor of a computer system, cause the processor to: perform an analysis of sequence information of the subject that has been obtained from the sample of the subject to identify whether the subject is not at risk of having the health condition; and then if the patient has not been identified as not at risk: analyze the sequence information of the subject not identified as not at risk by performing a second analysis to detect the presence of the health condition in the subject.

Additionally disclosed herein is a kit comprising: a. equipment to draw a sample from a subject; b. a set of detection reagents that, when combined with the sample, allows detection of biomarkers in the sample; and c. instructions for accessing computer program instructions stored on a computer storage medium that, when processed by a processor of a computer system, cause the processor to: perform an analysis of marker information of the subject that has been obtained from a biological sample of the subject to identify whether the subject is not at risk of having the health condition; and then if the patient has not been identified as not at risk: analyze sequence information of the subject not identified as not at risk by performing a second analysis to detect the presence of the health condition in the subject. In various embodiments, the marker information comprises quantitative levels of protein biomarkers.

Additionally disclosed herein is a kit comprising: a. equipment to draw a sample from a subject; b. a set of detection reagents that, when combined with the sample, allows detection of biomarkers in the sample; and c. instructions for accessing computer program instructions stored on a computer storage medium that, when processed by a processor of a computer system, cause the processor to: (a) perform an analysis of sequence information of nucleic acids in the sample to determine whether the analysis generates a result correlative with presence or absence of a human condition, and then if the result is detected: and (b) analyze the sequence information of the nucleic acids in the sample by performing second analysis to determine if the second analysis generates the signal, wherein if the signal is detected, then the probability the signal in the sample is authentic is higher as compared to a probability that a signal is authentic when generated by an analogous method, where the analogous method differs by omitting step (a). In various embodiments, the steps performed by the processor achieve at least an 80%, at least a 81%, at least a 82%, at least a 83%, at least a 84%, or at least a 85% positive predictive value when detecting the health condition. In various embodiments, the health condition is a disease risk. In various embodiments, the health condition is a rare disease or disorder. In various embodiments, the health condition has an incidence of 1 in 100, 1 in 1,000, 1 in 10,000 individuals, 1 in 100,000 individuals, 1 in 1,000,000 individuals, 1 in 10,000,000 individuals, or 1 in 100,000,000 individuals.

Additionally disclosed herein is a kit comprising: a. equipment to draw a sample from a subject; b. a set of primers that, when combined with the sample, allows detection of a plurality of sites in cell-free DNA in the sample; and c. instructions for accessing computer program instructions stored on a computer storage medium that, when processed by a processor of a computer system, cause the processor to: perform a screen by analyzing the sequence information to classify the subject as at risk for a health condition or not at risk for a health condition; responsive to a classification of the subject as at risk for a health condition, obtain sequence information derived from a second assay performed on the sample or an additional sample obtained from the subject to generate the sequence information derived from the second assay; and perform a second analysis of the sequence information derived from the second assay for the subject to further classify the subject at risk for the health condition a candidate subject for monitoring.

Additionally disclosed herein is a kit comprising: a. equipment to draw a sample from a subject; b. a set of primers that, when combined with the sample, allows detection of a plurality of sites in cell-free DNA in the sample; and c. instructions for accessing computer program instructions stored on a computer storage medium that, when processed by a processor of a computer system, cause the processor to: perform a screen by analyzing the sequence information to classify the subject as at risk for a health condition or not at risk for a health condition; if the subject is classified as not at risk for a health condition, report that the subject is not at risk for a health condition; if the subject is classified as at risk for a health condition: obtain sequence information derived from a second assay performed on the sample or an additional sample obtained from the subject to generate the sequence information derived from the second assay; and perform a second analysis of the sequence information derived from the second assay for the subject to further classify the subject at risk for a health condition as a candidate subject for monitoring.

Additionally disclosed herein is a kit comprising: a. equipment to draw a sample from a subject; b. a set of primers that, when combined with the sample, allows detection of a plurality of sites in cell-free DNA in the sample; and c. instructions for accessing computer program instructions stored on a computer storage medium that, when processed by a processor of a computer system, cause the processor to: for each of one or more subjects in the plurality of subjects: perform a screen by analyzing the sequence information to classify the subject as at risk for a health condition or not at risk for a health condition; responsive to a classification of the subject as at risk for a health condition, obtain sequence information derived from a second assay performed on the sample or an additional sample obtained from the subject to generate the sequence information derived from the second assay; and perform a second analysis of the sequence information derived from the second assay for the subject to further classify the subject at risk for a health condition as a candidate subject for inclusion in the candidate population.

Disclosed herein is a method for determining a signal informative of a health condition from an individual, the method comprising: obtaining target nucleic acids and reference nucleic acids from one or more samples from the individual; generating sequence information from the target nucleic acids and sequence information from the reference nucleic acids; and combining the sequence information from the target nucleic acids and the sequence information from the reference nucleic acids to generate the signal informative of the health condition. In various embodiments, the health condition is a cancer. In various embodiments, the health condition is an early stage cancer or preclinical phase cancer.

In various embodiments, obtaining target nucleic acids and reference nucleic acids from one or more samples comprises obtaining the target nucleic acids and the reference nucleic acids from a single sample. In various embodiments, the single sample is any one of a blood sample, a stool sample, a urine sample, a mucous sample, or a saliva sample. In various embodiments, obtaining target nucleic acids and reference nucleic acids comprises fractionating the single sample, wherein the target nucleic acids are obtained from a first fraction of the single sample, and wherein the reference nucleic acids are obtained from a second fraction of the single sample. In various embodiments, the target nucleic acids comprise cell free DNA (cfDNA). In various embodiments, the reference nucleic acids comprise genomic DNA from cells of the individual. In various embodiments, the cells of the individual comprise peripheral blood mononuclear cells (PBMCs) or polymorphonuclear cells. In various embodiments, obtaining target nucleic acids and reference nucleic acids from one or more samples comprises obtaining the target nucleic acids and the reference nucleic acids from different samples. In various embodiments, the target nucleic acids are obtained from a blood sample, and wherein the reference nucleic acids are obtained from a tissue sample. In various embodiments, the target nucleic acids comprise cell free DNA (cfDNA). In various embodiments, the reference nucleic acids comprise genomic DNA from cells of the individual.

In various embodiments, combining the sequence information from the target nucleic acids and the sequence information from the reference nucleic acids comprises aligning the sequence information from the target nucleic acids and the sequence information from the reference nucleic acids. In various embodiments, combining the sequence information from the target nucleic acids and the sequence information from the reference nucleic acids comprises determining a difference between the sequence information from the target nucleic acids and the sequence information from the reference nucleic acids. In various embodiments, combining the sequence information from the target nucleic acids and the sequence information from the reference nucleic acids comprises subtracting the sequence information from the reference nucleic acids from the sequence information from the target nucleic acids.

In various embodiments, the sequence information from the target nucleic acids comprises methylation sequence information of the target nucleic acids. In various embodiments, the sequence information from the reference nucleic acids comprises methylation sequence information of the reference nucleic acids. In various embodiments, the methylation sequence information of the target nucleic acids and the methylation sequence information of the reference nucleic acids both comprise methylation statuses for a plurality of genomic sites. In various embodiments, the plurality of genomic sites comprise a plurality of CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety.

In various embodiments, generating sequence information from the target nucleic acids and sequence information from the reference nucleic acids comprises performing an assay, wherein the assay comprises one or more of a. sequencing of target nucleic acids and/or reference nucleic acids via targeted sequencing, whole genome sequencing, or whole genome bisulfite sequencing; b. a nucleic acid amplification assay; and c. an assay that generates methylation information. In various embodiments, the nucleic acid amplification assay is a PCR assay. In various embodiments, the PCR assay comprises a real-time PCR assay, quantitative real-time PCR (qPCR) assay, digital PCR (dPCR) assay, allele-specific PCR assay, or reverse-transcription PCR assay. In various embodiments, generating sequence information from the target nucleic acids and sequence information from the reference nucleic acids comprises performing a target enrichment assay. In various embodiments, the target enrichment assay comprises hybrid capture.

In various embodiments, performing the assay comprises: obtaining bisulfite converted target nucleic acids and/or reference nucleic acids; and selectively amplifying target regions of the bisulfite converted target nucleic acids and/or reference nucleic acids. In various embodiments, performing the assay further comprises: determining quantitative values of sequences of the amplicons comprising the amplified target regions to generate the sequence information of the target nucleic acids and/or sequence information of the reference nucleic acids. In various embodiments, the quantitative values comprise cycle threshold (Ct) values.

In various embodiments, performing the assay further comprises: sequencing amplicons comprising the amplified target regions to generate the sequence information of the target nucleic acids and/or sequence information of the reference nucleic acids. In various embodiments, the target regions comprise previously identified regions that are differentially methylated in presence of the health condition. In various embodiments, the target regions comprise one or more CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety.

In various embodiments, methods disclosed herein further comprise determining a tissue of origin of the health condition using the signal informative of the health condition. In various embodiments, methods disclosed herein further comprise determining progression of the health condition using the signal informative of the health condition.

Additionally disclosed is a method of identifying a cancer signal from an individual, the method comprising: obtaining a sample from the individual, wherein the sample comprises cfDNA and a PBMC DNA; determining the methylation status at a plurality of CpG sites of the cfDNA and the PBMC DNA; and comparing the methylation status at the plurality of CPG sites of the cfDNA and the PBMC DNA to generate the signal informative of the health condition. In various embodiments, the methylation status was determined from sequencing or nucleic acid amplification. In various embodiments, the nucleic acid amplification comprises a PCR assay. In various embodiments, the PCR assay comprises a real-time PCR assay, quantitative real-time PCR (qPCR) assay, digital PCR (dPCR) assay, allele-specific PCR assay, or reverse-transcription PCR assay. In various embodiments, the CPG sites comprise previously identified CPG sites that are differentially methylated in presence of the health condition. In various embodiments, the CPG sites comprise one or more CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety.

Additionally disclosed herein is a non-transitory computer readable medium comprising instructions that, when executed by a processor, cause the processor to: generate sequence information from target nucleic acids and sequence information from reference nucleic acids, wherein the target nucleic acids and reference nucleic acids are obtained from one or more samples from an individual; and combine the sequence information from the target nucleic acids and the sequence information from the reference nucleic acids to generate the signal informative of the health condition. In various embodiments, the health condition is a cancer. In various embodiments, the health condition is an early stage cancer or preclinical phase cancer.

In various embodiments, the target nucleic acids and reference nucleic acids are obtained from a single sample. In various embodiments, the single sample is any one of a blood sample, a stool sample, a urine sample, a mucous sample, or a saliva sample. In various embodiments, the single sample previously underwent fractionation, wherein the target nucleic acids are obtained from a first fraction of the single sample, and wherein the reference nucleic acids are obtained from a second fraction of the single sample. In various embodiments, the target nucleic acids comprise cell free DNA (cfDNA). In various embodiments, the reference nucleic acids comprise genomic DNA from cells of the individual. In various embodiments, the cells of the individual comprise peripheral blood mononuclear cells (PBMCs) or polymorphonuclear cells. In various embodiments, the target nucleic acids and reference nucleic acids are obtained from different samples. In various embodiments, the target nucleic acids are obtained from a blood sample, and wherein the reference nucleic acids are obtained from a tissue sample. In various embodiments, the target nucleic acids comprise cell free DNA (cfDNA). In various embodiments, the reference nucleic acids comprise genomic DNA from cells of the individual.

In various embodiments, the instructions that cause the processor to combine the sequence information from the target nucleic acids and the sequence information from the reference nucleic acids further comprises instructions that, when executed by the processor, cause the processor to align the sequence information from the target nucleic acids and the sequence information from the reference nucleic acids. In various embodiments, the instructions that cause the processor to combine the sequence information from the target nucleic acids and the sequence information from the reference nucleic acids further comprises instructions that, when executed by the processor, cause the processor to determine a difference between the sequence information from the target nucleic acids and the sequence information from the reference nucleic acids. In various embodiments, the instructions that cause the processor to combine the sequence information from the target nucleic acids and the sequence information from the reference nucleic acids further comprises instructions that, when executed by the processor, cause the processor to subtract the sequence information from the reference nucleic acids from the sequence information from the target nucleic acids.

In various embodiments, the sequence information from the target nucleic acids comprises methylation sequence information of the target nucleic acids. In various embodiments, the sequence information from the reference nucleic acids comprises methylation sequence information of the reference nucleic acids. In various embodiments, the methylation sequence information of the target nucleic acids and the methylation sequence information of the reference nucleic acids both comprise methylation statuses for a plurality of genomic sites. In various embodiments, the plurality of genomic sites comprise a plurality of CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety.

In various embodiments, non-transitory computer readable media disclosed herein further comprise instructions that, when executed by a processor, cause the processor to: determine a tissue of origin of the health condition using the signal informative of the health condition. In various embodiments, non-transitory computer readable media disclosed herein further comprise instructions that, when executed by a processor, cause the processor to: determine progression of the health condition using the signal informative of the health condition.

Additionally disclosed herein is a system comprising: a processor; a data storage comprising sequence information from target nucleic acids and sequence information from reference nucleic acids, wherein the target nucleic acids and reference nucleic acids are obtained from one or more samples from an individual; a non-transitory computer readable medium comprising instructions that, when executed by the processor, cause the processor to: combine the sequence information from the target nucleic acids and the sequence information from the reference nucleic acids to generate the signal informative of the health condition. In various embodiments, the health condition is a cancer. In various embodiments, the health condition is an early stage cancer or preclinical phase cancer. In various embodiments, the target nucleic acids and reference nucleic acids are obtained from a single sample. In various embodiments, the single sample is any one of a blood sample, a stool sample, a urine sample, a mucous sample, or a saliva sample. In various embodiments, the single sample previously underwent fractionation, wherein the target nucleic acids are obtained from a first fraction of the single sample, and wherein the reference nucleic acids are obtained from a second fraction of the single sample. In various embodiments, the target nucleic acids comprise cell free DNA (cfDNA). In various embodiments, the reference nucleic acids comprise genomic DNA from cells of the individual. In various embodiments, the cells of the individual comprise peripheral blood mononuclear cells (PBMCs) or polymorphonuclear cells. In various embodiments, the target nucleic acids and reference nucleic acids are obtained from different samples. In various embodiments, the target nucleic acids are obtained from a blood sample, and wherein the reference nucleic acids are obtained from a tissue sample. In various embodiments, the target nucleic acids comprise cell free DNA (cfDNA). In various embodiments, the reference nucleic acids comprise genomic DNA from cells of the individual.

In various embodiments, the instructions that cause the processor to combine the sequence information from the target nucleic acids and the sequence information from the reference nucleic acids further comprises instructions that, when executed by the processor, cause the processor to align the sequence information from the target nucleic acids and the sequence information from the reference nucleic acids. In various embodiments, the instructions that cause the processor to combine the sequence information from the target nucleic acids and the sequence information from the reference nucleic acids further comprises instructions that, when executed by the processor, cause the processor to determine a difference between the sequence information from the target nucleic acids and the sequence information from the reference nucleic acids. In various embodiments, the instructions that cause the processor to combine the sequence information from the target nucleic acids and the sequence information from the reference nucleic acids further comprises instructions that, when executed by the processor, cause the processor to subtract the sequence information of the reference nucleic acids from the sequence information of the target nucleic acids.

In various embodiments, the sequence information from the target nucleic acids comprises methylation sequence information of the target nucleic acids. In various embodiments, the sequence information from the reference nucleic acids comprises methylation sequence information of the reference nucleic acids. In various embodiments, the methylation sequence information of the target nucleic acids and the methylation sequence information of the reference nucleic acids both comprise methylation statuses for a plurality of genomic sites. In various embodiments, the plurality of genomic sites comprise a plurality of CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety.

In various embodiments, systems disclosed herein further comprise instructions that, when executed by a processor, cause the processor to: determine a tissue of origin of the health condition using the signal informative of the health condition. In various embodiments, systems disclosed herein further comprise instructions that, when executed by a processor, cause the processor to: determine progression of the health condition using the signal informative of the health condition.

Additionally disclosed herein is a kit comprising: a. equipment to draw one or more samples from an individual; b. a set of detection reagents for generating sequence information for target nucleic acids and sequence information for reference nucleic acids in the one or more samples; and c. instructions for accessing computer program instructions stored on a computer storage medium that, when executed by a processor of a computer system, cause the processor to: combine the sequence information from the target nucleic acids and the sequence information from the reference nucleic acids to generate the signal informative of the health condition. In various embodiments, the health condition is a cancer. In various embodiments, the health condition is an early stage cancer or preclinical phase cancer.

In various embodiments, the target nucleic acids and reference nucleic acids are obtained from a single sample. In various embodiments, the single sample is any one of a blood sample, a stool sample, a urine sample, a mucous sample, or a saliva sample. In various embodiments, the single sample was previously fractionated, wherein the target nucleic acids are obtained from a first fraction of the single sample, and wherein the reference nucleic acids are obtained from a second fraction of the single sample. In various embodiments, the target nucleic acids comprise cell free DNA (cfDNA). In various embodiments, the reference nucleic acids comprise genomic DNA from cells of the individual. In various embodiments, the cells of the individual comprise peripheral blood mononuclear cells (PBMCs) or polymorphonuclear cells. In various embodiments, the target nucleic acids and reference nucleic acids are obtained from different samples. In various embodiments, the target nucleic acids are obtained from a blood sample, and wherein the reference nucleic acids are obtained from a tissue sample. In various embodiments, the target nucleic acids comprise cell free DNA (cfDNA). In various embodiments, the reference nucleic acids comprise genomic DNA from cells of the individual.

In various embodiments, the computer program instructions that cause the processor to combine the sequence information from the target nucleic acids and the sequence information from the reference nucleic acids further comprises instructions that, when executed by the processor, cause the processor to align the sequence information from the target nucleic acids and the sequence information from the reference nucleic acids. In various embodiments, the computer program instructions that cause the processor to combine the sequence information from the target nucleic acids and the sequence information from the reference nucleic acids further comprises instructions that, when executed by the processor, cause the processor to determine a difference between the sequence information from the target nucleic acids and the sequence information from the reference nucleic acids. In various embodiments, the computer program instructions that cause the processor to combine the sequence information from the target nucleic acids and the sequence information from the reference nucleic acids further comprises instructions that, when executed by the processor, cause the processor to subtract the sequence information of the reference nucleic acids from the sequence information of the target nucleic acids.

In various embodiments, the sequence information from the target nucleic acids comprises methylation sequence information of the target nucleic acids. In various embodiments, the sequence information from the reference nucleic acids comprises methylation sequence information of the reference nucleic acids. In various embodiments, the methylation sequence information of the target nucleic acids and the methylation sequence information of the reference nucleic acids both comprise methylation statuses for a plurality of genomic sites. In various embodiments, the plurality of genomic sites comprise a plurality of CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety.

In various embodiments, generating sequence information from the target nucleic acids and sequence information from the reference nucleic acids comprises performing an assay, wherein the assay comprises one or more of a. sequencing of target nucleic acids and/or reference nucleic acids via targeted sequencing, whole genome sequencing, or whole genome bisulfite sequencing; b. a nucleic acid amplification assay; and c. an assay that generates methylation information. In various embodiments, the nucleic acid amplification assay is a PCR assay. In various embodiments, the PCR assay comprises a real-time PCR assay, quantitative real-time PCR (qPCR) assay, digital PCR (dPCR) assay, allele-specific PCR assay, or reverse-transcription PCR assay. In various embodiments, generating sequence information from the target nucleic acids and sequence information from the reference nucleic acids comprises performing a target enrichment assay. In various embodiments, the target enrichment assay comprises hybrid capture.

In various embodiments, performing the assay comprises: obtaining bisulfite converted target nucleic acids and/or reference nucleic acids; and selectively amplifying target regions of the bisulfite converted target nucleic acids and/or reference nucleic acids. In various embodiments, performing the assay further comprises: determining quantitative values of sequences of the amplicons comprising the amplified target regions to generate the sequence information of the target nucleic acids and/or sequence information of the reference nucleic acids. In various embodiments, the quantitative values comprise cycle threshold (Ct) values. In various embodiments, performing the assay further comprises: sequencing amplicons comprising the amplified target regions to generate the sequence information of the target nucleic acids and/or sequence information of the reference nucleic acids.

In various embodiments, the target regions comprise previously identified regions that are differentially methylated in presence of the health condition. In various embodiments, the target regions comprise one or more CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety. In various embodiments, the computer program instructions further comprise instructions that, when executed by a processor, cause the processor to: determine a tissue of origin of the health condition using the signal informative of the health condition. In various embodiments, the computer program instructions further comprise instructions that, when executed by a processor, cause the processor to: determine progression of the health condition using the signal informative of the health condition.

Additionally disclosed herein is a kit of identifying a cancer signal from an individual, the method comprising: a. equipment to draw one or more samples from an individual, wherein the one or more samples comprise cfDNA and a PBMC DNA; b. a set of detection reagents for determining methylation statuses at a plurality of CpG sites of the cfDNA and the PBMC DNA; and c. instructions for accessing computer program instructions stored on a computer storage medium that, when executed by a processor of a computer system, cause the processor to: compare the methylation status at the plurality of CPG sites of the cfDNA and the PBMC DNA to generate the signal informative of the health condition. In various embodiments, the methylation status was determined from sequencing or nucleic acid amplification. In various embodiments, the nucleic acid amplification comprises a PCR assay. In various embodiments, the PCR assay comprises a real-time PCR assay, quantitative real-time PCR (qPCR) assay, digital PCR (dPCR) assay, allele-specific PCR assay, or reverse-transcription PCR assay. In various embodiments, the CPG sites comprise previously identified CPG sites that are differentially methylated in presence of the health condition. In various embodiments, the CPG sites comprise one or more CGIs shown in Tables 1-4. Additional example CGIs are disclosed in WO2018209361 (see Table 1) or WO2022133315 (see Table 2 entitled "TOO Methylation Sites" and Table 3 entitled "Pan Cancer Methylation Sites"), each of which is hereby incorporated by reference in its entirety.

EXAMPLES

Below are examples of specific embodiments for carrying out the present invention. The examples are offered for illustrative purposes only and are not intended to limit the scope of the present invention in any way. Efforts have been made to ensure accuracy with respect to numbers used (e.g., percentages, etc.), but some experimental error and deviation should be allowed for.

Figure 6A:
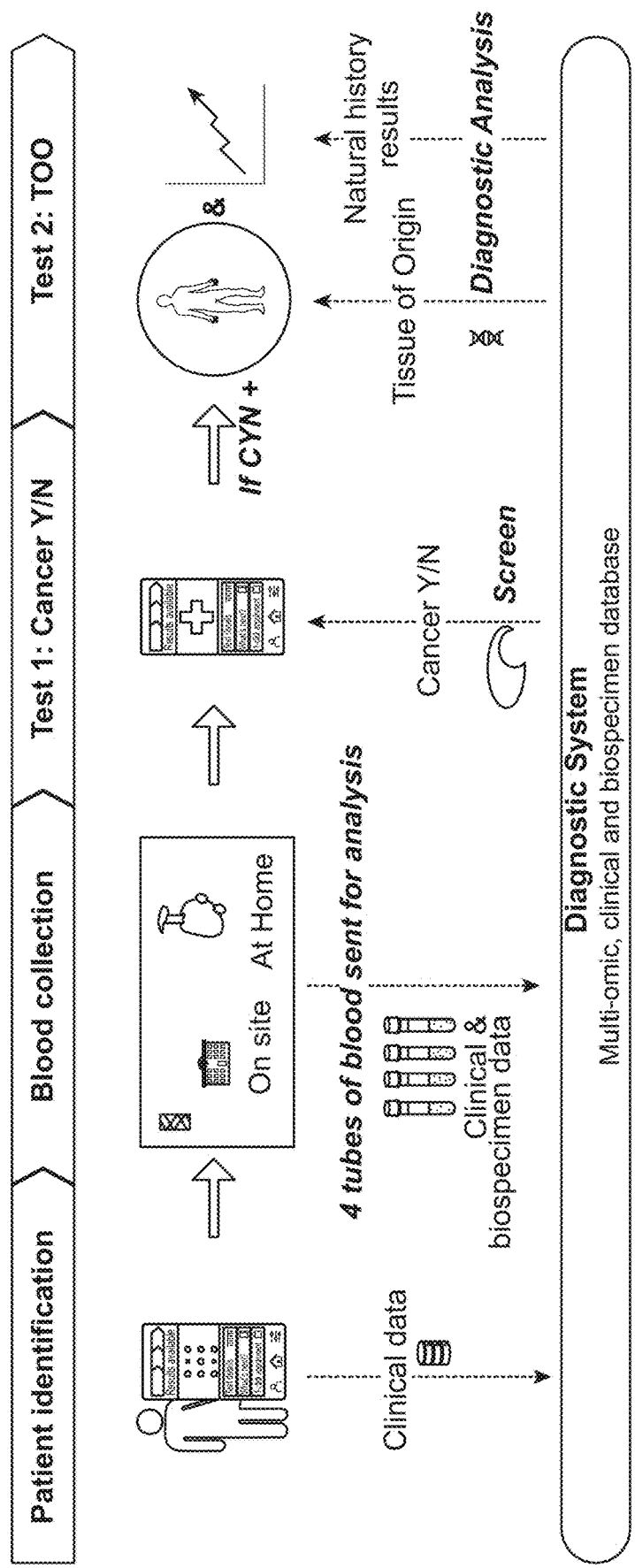
FIG. 6A shows a first example process involving a condition analysis system for performing a multiple tier analysis.

Example 1: Example Scenario Involving a 2-Tier Analysis Using a Single Blood Collection FIG. 6A shows a first example process involving a condition analysis system (e.g., condition analysis system 170 shown in FIG. 1B) for performing a multiple tier analysis. Here, the process involves a single blood collection from a patient. The multiple tier analysis is then performed on the blood samples obtained from the patient during the single blood collection.

Specifically, as shown in FIG. 6A, a patient is identified and clinical data of the patient is provided to the condition analysis system. Multiple blood samples are collected from the patient. FIG. 6A shows that four separate tubes of blood are collected and sent to the condition analysis system. The blood collection can be performed by a third party (e.g., on site at a reference lab, or at home). The condition analysis system processes the four blood samples by conducting an assay to generate methylation data. The condition analysis system performs a screen (e.g., "Test 1" in FIG. 6A) of the patient using the methylation data to determine whether the patient is at risk of a health condition, such as cancer.

If the patient is determined to not be at risk of cancer, then the patient does not undergo a second analysis. Alternatively, as shown in FIG. 6A, if the patient is determined to be at risk of cancer, then at least a second analysis (e.g., "Test 2") is performed. Here, the condition analysis system performs a second assay, such as whole genome bisulfite sequencing, and a second analysis to determine whether the patient at risk of cancer has a detectable presence of cancer. The second analysis further reveals a tissue of origin of the cancer. The condition analysis system diagnoses the patient with cancer, and therefore, the patient undergoes further monitoring and/or treatment.

Example 2: Example Scenario Involving a Two-Tiered Blood Collection and Testing

Figure 6B:
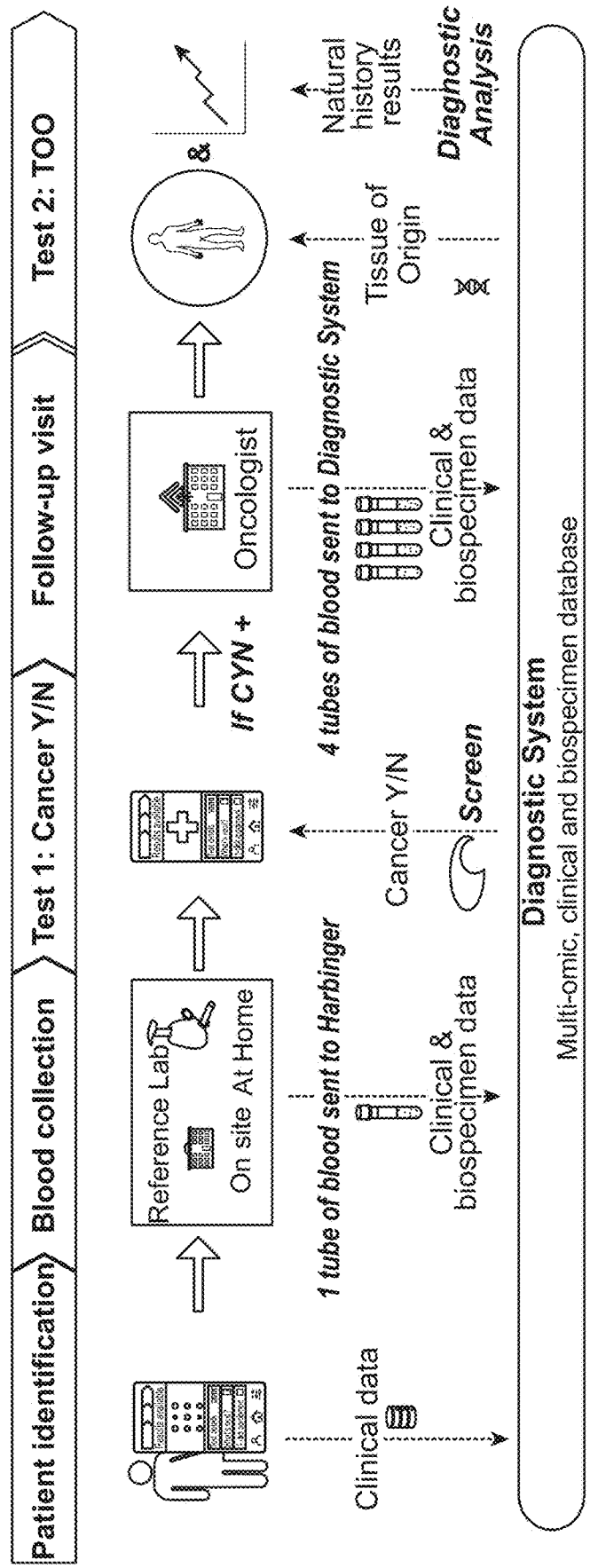
FIG. 6B shows a second example process involving a condition analysis system for performing a multiple tier analysis.

FIG. 6B shows a second example process involving a condition analysis system for performing a multiple tier analysis. Here, the process involves a two different blood collections from a patient. The multiple tier analysis is then performed on the blood samples obtained at different time-points from the patient. In particular, a first assay and the screen are performed using blood samples obtained from the patient at a first timepoint. A second assay and the second analysis are performed using blood samples obtained from the patient at a second timepoint.

Specifically, as shown in FIG. 6B, a patient is identified and clinical data of the patient is provided to the condition analysis system. A blood sample is collected from the patient. FIG. 6B shows that a single tube of blood is collected from the patient and sent to the condition analysis system. The blood collection can be performed by a third party (e.g., on site at a reference lab, or at home). The condition analysis system processes the blood sample by conducting an assay to generate methylation data. The condition analysis system performs a screen (e.g., "Test 1" in FIG. 6B) of the patient using the methylation data to determine whether the patient is at risk of a health condition, such as cancer.

If the patient is determined to not be at risk of cancer, then the patient does not undergo a second analysis. Alternatively, as shown in FIG. 6B, if the patient is determined to be at risk of cancer, then an indication is provided that identifies that the patient is at risk of cancer. Thus, the patient subsequently attends a follow-up visit (e.g., with an oncologist), during which blood samples are obtained from the patient at a second timepoint. FIG. 6B shows that 4 tubes of blood are obtained from the patient and sent to the condition analysis system for analysis. Here, the condition analysis system performs a second assay, such as whole genome bisulfite sequencing, and a second analysis to determine whether the patient at risk of cancer has a detectable presence of cancer. The second analysis further reveals a tissue of origin of the cancer. The condition analysis system diagnoses the patient with cancer, and therefore, the patient undergoes further monitoring and/or treatment.

Figure 6C:
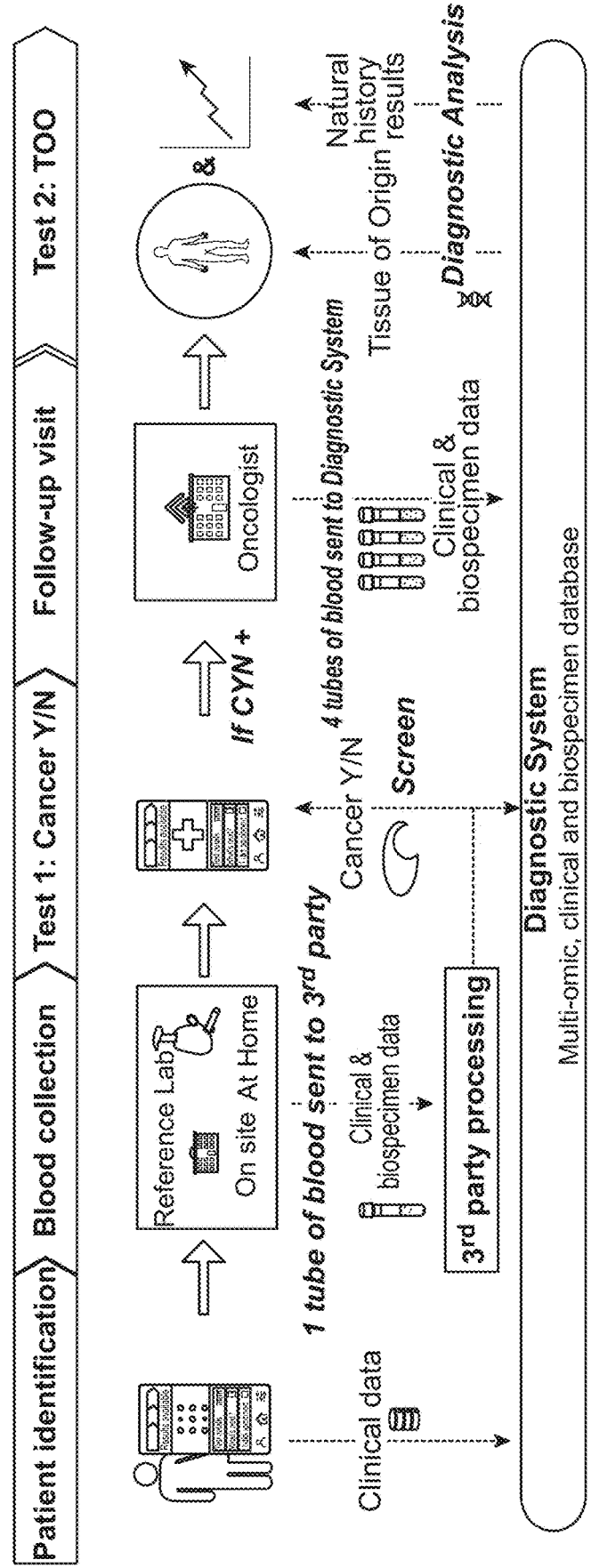
FIG. 6C shows a third example process involving a condition analysis system for performing a multiple tier analysis.

Example 3: Example Scenario Involving Third Party Processing of Samples Obtained Via a Two Tiered Blood Collection FIG. 6C shows a third example process involving a condition analysis system for performing a multiple tier analysis. Here, the process involves a two different blood collections from a patient. The multiple tier analysis is then performed on the blood samples obtained at different time-points from the patient. Additionally, a third party is involved in the processing of blood samples obtained from the patient.

Specifically, as shown in FIG. 6C, a patient is identified and clinical data of the patient is provided to the condition analysis system. A blood sample is collected from the patient. FIG. 6C shows that a single tube of blood is collected from the patient and sent to a third party. The blood collection is performed on site at a reference lab, or at home. The third party processes the blood sample by conducting an assay to generate methylation data. The third party sends the methylation data to the condition analysis system. The condition analysis system performs a screen (e.g., "Test 1"

in FIG. 5B) of the patient using the methylation data to determine whether the patient is at risk of a health condition, such as cancer.

If the patient is determined to not be at risk of cancer, then the patient does not undergo a second analysis. Alternatively, as shown in FIG. 6C, if the patient is determined to be at risk of cancer, then an indication is provided that identifies that the patient is at risk of cancer. Thus, the patient subsequently attends a follow-up visit (e.g., with an oncologist), during which blood samples are obtained from the patient at a second timepoint. FIG. 6C shows that 4 tubes of blood are obtained from the patient and sent to the condition analysis system for performing a second assay. Alternatively, the tubes of blood can be sent to the third party such that the third party performs the second assay. Here, the second assay involves whole genome bisulfite sequencing. The condition analysis system obtains methylation data from the second assay (either performed by the condition analysis system or performed by a third party), and the condition analysis system performs the second analysis to determine whether the patient at risk of cancer has a detectable presence of cancer. The second analysis further reveals a tissue of origin of the cancer. The condition analysis system diagnoses the patient with cancer, and therefore, the patient undergoes further monitoring and/or treatment.

Figure 7:
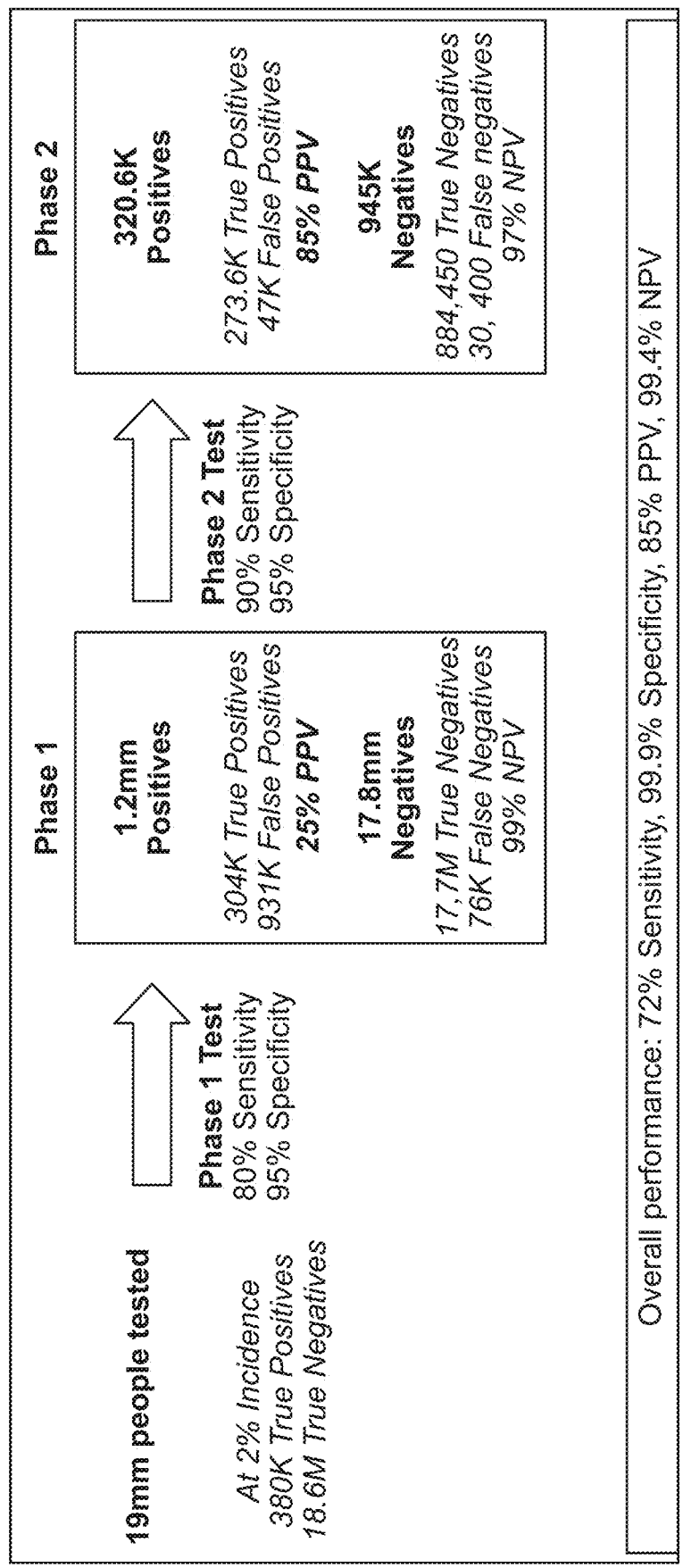
FIG. 7 shows example performance of different tiers of the multiple tier analysis for diagnosing individuals with a health condition.

Example 4: Overall Performance of Two-Tier Screening and Diagnosis of Patients with Prostate Cancer FIG. 7 shows example performance of different tiers of the multiple tier analysis for diagnosing individuals with a health condition (e.g., prostate cancer). Here, the process begins with 19 million individuals who underwent testing. At a 2% incidence rate, of the 19 million individuals, 380,000 are true positives, and 18.6 million are true negatives.

The multi-tiered analysis involves performing a screen by analyzing methylation data (generated via an assay) of the patients. Here, the screen is designed to achieve 80% sensitivity and 95% specificity, thereby identifying 1.2 million out of the original 19 million individuals as at risk for prostate cancer. Additionally, the screen identifies 17.8 million out of the original 19 million individuals as not at risk for prostate cancer. Thus, these 17.8 million individuals need not undergo further analysis. Altogether, the screen achieves a 25% positive predictive rate and a 99% negative predictive rate.

The 1.2 million individuals identifies as at risk for prostate cancer further undergo a second test in the form of the second analysis. The second analysis achieves a 90% sensitivity and a 95% specificity. Of the 1.2 million individuals, ~320,000 individuals are identified as having prostate cancer. This represents a 85% positive predictive rate as 273,600 individuals were true positives and 47,000 were false positives. Additionally, the second analysis identifies 945,000 negatives, of which 884,450 were true negatives, and 30,400 were false negatives, thereby representing a 97% negative predictive value.

Altogether, the overall performance of the multi-tier screen and second analysis includes 72% sensitivity, 99.9% specificity, 85% positive predictive value, and 99.4% negative predictive value.

Example steps for performing the multiple-tier analysis shown in FIG. 7 is detailed below.

Prepare Target Specimen

The target specimen type (e.g. DNA, RNA, protein, exosomes, metabolites, etc.) is isolated from a patient's biological source (e.g. tissue, blood, plasma, serum, saliva, feces, etc.). That specimen can be isolated by a CRO or private or service laboratory or hospital or isolated internally using an internal procedure. Target specimens are assayed for quality and quantity measurements.

Phase 1 Testing

Phase 1 testing is a relatively quick, non-invasive assay with simple technology, using small amounts of the target specimen. The result of this assay can be both qualitative and quantitative. Phase 1 testing is typically lower specificity (e.g. 95% specificity, 5% false positives) but higher sensitivity (e.g. 80% sensitivity, 20% false negatives) in order to screen a large proportion of the testing population rapidly and inexpensively. The phase 1 assay will overall increase the incidence of the target population (e.g. diseased) for the phase 2 assay, which will then increase the positive predictive value (PPV). Examples of the Phase 1 assay include but are not limited to ELISA assays, PCR assays, Real-time PCR assays, Quantitative real-time PCR (qPCR) assays, Allele-specific PCR assays, Reverse-transcription PCR assays and reporter assays.

Phase 1 Protocol:

An example protocol of an Allele-specific Real-Time PCR assay is as follows:

1. This assay runs DNA samples in triplicate with 2 ng input in 5 uL for the reference and mutation assays.
2. Combine 900 nmol/L unspecific primer(s), 100 nmol/L target probe(s), 2× polymerase enzyme(s), 2× dNTPs, 2× passive reference dyes, 10 uL water and 2 ng sample DNA at a pre-specified reaction volume as the reference control assay.
3. Combine 450 nmol/L allele-specific primer(s), 100 nmol/L target probe(s), 2× polymerase enzyme(s), 2× dNTPs, 2× passive reference dyes, 10 uL water and 2 ng sample DNA at a pre-specified reaction volume as the mutation assay.
4. Mix each reaction 10× and centrifuge to collect volume at the bottom of the well or tube.
5. Run the real-time PCR on a calibrated Real-Time PCR system under the following conditions: (1) 95° C. for 10 minutes followed by (2) 50 cycles of 90° C. for 15 seconds and 60° C. for 1 minute with fluorescence detection using FAM/VIC fluorophores.
6. Cycle threshold (Ct) values are recorded by the system and exported into an analysis program (e.g. Excel).
7. Average the Ct values between sample replicates for the reference and mutation assays.
8. Calculate the ΔCt between the sample average allele-specific Ct minus the sample average unspecific (reference) Ct.
9. Positive mutation results are identified by the ΔCt cut off >3 cycles and will move forward to phase 2 testing.

Allele-specific real-time PCR can be performed by combining library DNA with PCR reagents and primers specific for target sequences. The primers are designed to have single-base discrimination between tumor and non-tumor sequences. Perform real-time PCR (or digital PCR) for 30-50 cycles and monitor the output for signal via fluorescence from amplified target DNA or probe sequence. Cycle threshold values (Ct) are recorded and exported for analysis. The delta-Ct between negative control, positive control, and sample are calculated to determine presence or absence of target tumor sequences. Slight modifications of this protocol will allow for end-point PCR detection of RNA or DNA of tumor sequences. Phase 1 detection will be designed to remove 90-95% of non-cancer patient samples from moving forward for further testing.

ELISA assay detection of target molecules can be performed by coating an immunoassay well with monoclonal antibody designed to specifically detect target molecules, followed by blocking against non-specific binding. Next, target sample is introduced to the well, incubated and washed away. Any bound target can then be bound by a polyclonal antibody specific for the target. Additional secondary antibodies with color or fluorescent tags can be used to detect the presence of target molecules.

Phase 2 Testing

Phase 2 testing is a more complex, potentially invasive assay with complex technology, potentially using larger amounts of the target specimen. The result of this assay is both qualitative and quantitative. Phase 2 testing is typically higher specificity (e.g. 95% specificity, 10% false positives) but lower sensitivity (e.g. 90% sensitivity, 10% false negatives) in order to limit false positives. By screening out a large volume of the testing population, the target population has higher target incidence than the general population, which increases positive predictive value (PPV).

Phase 2 Protocol:

Examples of the phase 2 assay include but are not limited to Next Generation Sequencing assays utilizing target enrichment technologies, targeted amplicon sequencing technologies, whole genome sequencing, and whole genome bisulfite sequencing.

The target specimen for library construction is dsDNA isolated from formalin-fixed paraffin-embedded (FFPE) tissue. Alternatively, cfDNA is isolated from blood. For FFPE, the dsDNA is first mechanically sheared by the Covaris instrument utilizing adaptive focused acoustics to a target insert size of 200 base pairs. Post-shearing, a solid-phase reversible immobilization (SPRI) selection is done to remove smaller DNA fragments remaining in solution. For blood DNA, cfDNA is isolated. The fragmented DNA is then end-repaired and A-tailed (ERAT) to produce 5'-phosphorylated, 3'-dA-tailed dsDNA fragments. After ERAT, dsDNA unique dual index adapters with 3'-dTMP overhangs are then ligated to 3'-dA-tailed dsDNA fragments. Indices allow for sample multiplex for the downstream assay. Post-ligation, a solid-phase reversible immobilization (SPRI) selection is done to remove unwanted DNA fragments, excess adapters and molecules. PCR amplification is performed with a high-fidelity, low-bias polymerase at 10 cycles. Post-PCR, a SPRI selection is done to remove unwanted DNA fragments, excess primers, excess adapters and excess molecules. After library construction, the library quality and quantity are evaluated using the Agilent TapeStation and Qubit Fluorometer, respectively.

Libraries that pass quality control checks move forward to target enrichment through hybridization capture. Target enrichment by hybridization capture is defined as a positive selection strategy to enrich low abundance regions of interest from NGS libraries, allowing for more accurate sequencing analysis of these target regions. Indexed libraries are multi-plexed and hybridized to a custom, sequence specific, biotinylated probeset. The vast excess of probes drives their hybridization to complementary library fragments. The library fragment-biotinylated probe hybrid is pulled down by streptavidin beads, thereby capturing the target regions of interest. The streptavidin bead-bound library is sequentially washed with buffers to remove non-specifically associated library fragments. Following washes and recovery of captured libraries, samples are enriched for on target fragments and depleted for off-target fragments. Depletion of off-target fragments reduces overall library yield, requiring post-capture library amplification by PCR. The final amplified library is enriched for regions of interest. The hybrid captured library quality and quantity is evaluated using the Agilent TapeStation and Qubit Fluorometer, respectively. Additionally, the enrichment efficiency is evaluated using an iSeq Sequencing run and calculation of percent of reads within target enrichment panel. Measuring percent on-target is a good first approximation of target enrichment efficiency because the reads aligning to the target enrichment (bait) region indicate efficient hybridization and subsequent capture.

Target enriched libraries that pass quality control checks move forward to NovaSeq sequencing. Captured libraries with non-overlapping indices from library construction are pooled to multiplex for sequencing. Sequencing is completed on the NovaSeq 6000 instrument using paired end 150×150 base sequencing with a 10% PhiX spike-in. Sequencing data generated is then demultiplexed utilizing the assigned index, aligned to the human genome and trimmed to enrich for insert sample data only. This cleaned-up data is then processed through a quality pipeline to collapse duplicate reads and evaluate the sequencing data generated. Once the data is collapsed, the data is processed through a proprietary biomarker analysis pipeline to identify differences from the reference alignment (e.g. mutations, chemical modifications, etc). A report is then generated with the specific biomarker analysis per sample that confirms the results of the phase 1 assay or identifies true false positives from the phase 1 assay.

Interpreting Results for Phase 1 and Phase 2 Assays

Two positive signals from the phase 1 assay and phase 2 assay can be determined as a true positive sample with an 85% probability of being accurate.

One negative signal from the phase 1 assay can be determined as a true negative sample with a 99% probability of being accurate.

One positive signal from the phase 1 assay and one negative signal from the phase 2 assay can be determined as an indeterminate sample with a 97% probability of a false positive in phase 1 assay.

Figure 8:
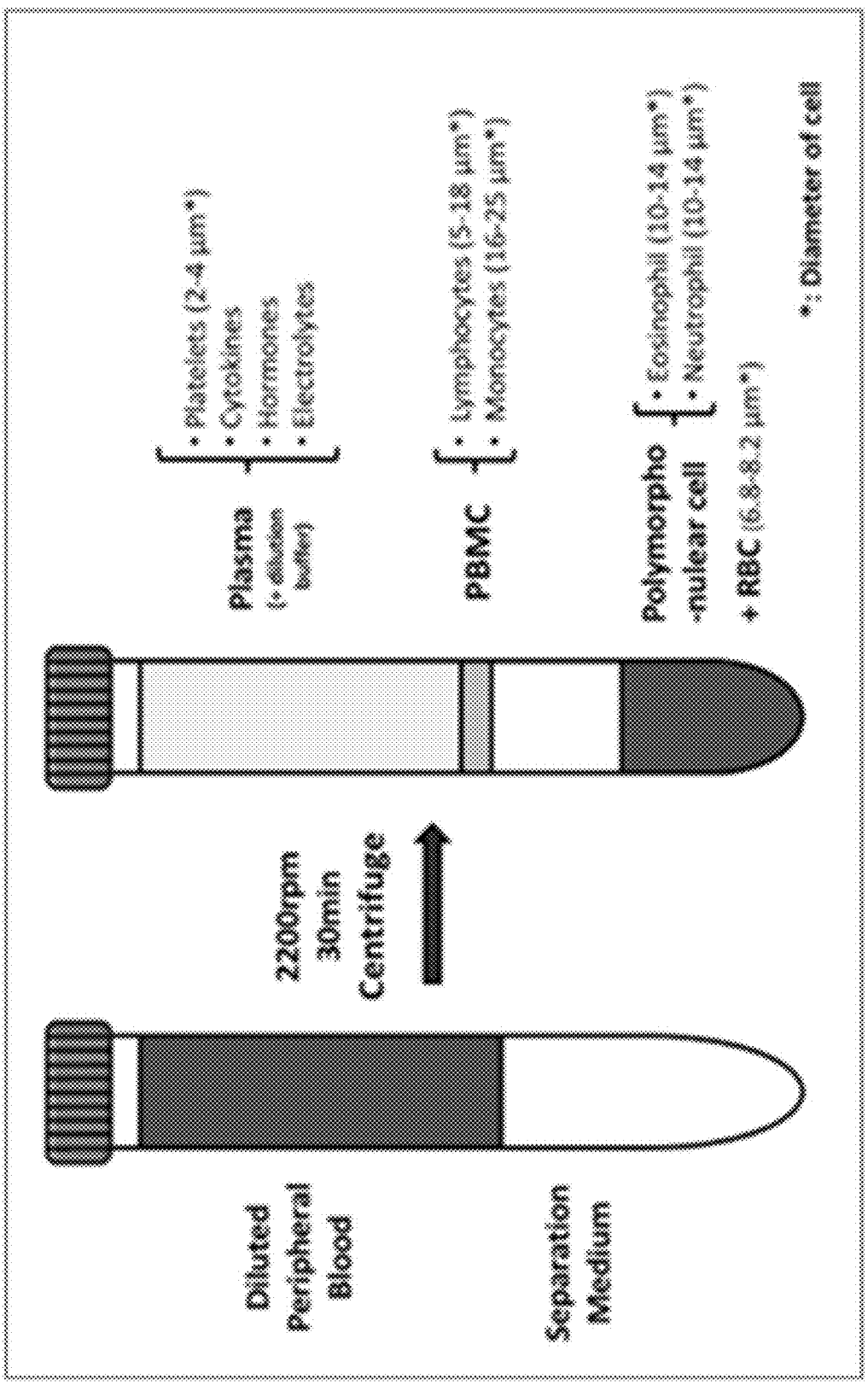
FIG. 8 shows an example sample from which target nucleic acids and reference nucleic acids are obtained.

Example 5: Example Samples and Assays for Conducting an Intra-Individual Analysis Blood samples are obtained from individuals. FIG. 8 shows an example sample from which target nucleic acids and reference nucleic acids are obtained. Shown on the left in FIG. 8 is a tube of blood obtained from an individual, the tube including diluted peripheral blood of the individual and separation medium. The tube undergoes centrifugation to separate different components of the diluted peripheral blood. For example, at a speed of 2200 rpm, the diluted peripheral blood is fractionated into plasma (including platelets, cytokines, hormones, and electrolytes), peripheral blood mononuclear cells (PBMCs), the separation medium, and polymorphonuclear cells. Here, target nucleic acids in the form of cell free DNA is found in the plasma whereas reference nucleic acids in the form of cellular genomic DNA is found in PBMCs.

Examples of an assay for generating sequence information from the target nucleic acids and the reference nucleic acids include but are not limited to Allele-specific PCR assays, Next Generation Sequencing assays, such as target enrichment technologies, targeted amplicon sequencing technologies, and whole genome sequencing.

An example protocol of an Allele-specific Real-Time PCR assay is as follows:
1. This assay runs all cfDNA samples in triplicate with 2 ng input in 5 uL for the reference and hypermethylation assays.
2. Combine 900 nmol/L unspecific primer(s), 100 nmol/L target probe(s), 2× polymerase enzyme(s), 2× dNTPs, 2× passive reference dyes, 10 uL water and 2 ng sample DNA at a pre-specified reaction volume as the reference control assay.
3. Combine 450 nmol/L allele-specific primer(s), 100 nmol/L target probe(s), 2× polymerase enzyme(s), 2× dNTPs, 2× passive reference dyes, 10 uL water and 2 ng sample DNA at a pre-specified reaction volume as the mutation assay.
4. Mix each reaction 10× and centrifuge to collect volume at the bottom of the well or tube.
5. Run the real-time PCR on a calibrated Real-Time PCR system under the following conditions: (1) 95° C. for 10 minutes followed by (2) 50 cycles of 90° C. for 15 seconds and 60° C. for 1 minute with fluorescence detection using FAM/VIC fluorophores.
6. Cycle threshold (Ct) values are recorded by the system and exported into an analysis program (e.g. Excel).
7. Average the Ct values between sample replicates for the reference and mutation assays.
8. Calculate the DCt between the sample average allele-specific Ct minus the sample average unspecific (reference) Ct.
9. Positive hypermethylation results are identified by the DCt cut off >3 cycles and will be compared to the patients individual PBMC natural signal.

An example protocol of an Allele-specific Real-Time PCR assay is as follows: Allele-specific real-time PCR can be performed by combining library from cfDNA with PCR reagents and primers specific for target sequences. The primers are designed to have single-base discrimination between tumor and non-tumor sequences. Perform real-time PCR (or digital PCR) for 30-50 cycles and monitor the output for signal via fluorescence from amplified target DNA or probe sequence. Cycle threshold values (Ct) are recorded and exported for analysis. The delta-Ct between negative control, positive control, and sample are calculated to determine presence or absence or absence of target tumor sequences. Slight modifications of this protocol will allow for end-point PCR detection of RNA or DNA of tumor sequences.

An example protocol of a next generation sequencing (NGS) Target Enrichment assay is as follows. The target specimen for library construction is dsDNA isolated from PBMCs. The dsDNA is first mechanically sheared by the Covaris instrument utilizing adaptive focused acoustics to a target insert size of 200 base pairs. Post-shearing, a solid-phase reversible immobilization (SPRI) selection is done to remove smaller DNA fragments remaining in solution. The fragmented DNA is then end-repaired and A-tailed (ERAT) to produce 5'-phosphorylated, 3'-dA-tailed dsDNA fragments. After ERAT, dsDNA unique dual index adapters with 3'-dTMP overhangs are then ligated to 3'-dA-tailed dsDNA fragments. Indices allow for sample multiplex for the downstream assay. Post-ligation, a solid-phase reversible immobilization (SPRI) selection is done to remove unwanted DNA fragments, excess adapters and molecules. PCR amplification is performed with a high-fidelity, low-bias polymerase at 10 cycles. Post-PCR, a SPRI selection is done to remove unwanted DNA fragments, excess primers, excess adapters and excess molecules. After library construction, the library quality and quantity are evaluated using the Agilent TapeStation and Qubit Fluorometer, respectively.

Libraries that pass quality control checks move forward to target enrichment through hybridization capture. Target enrichment by hybridization capture is defined as a positive selection strategy to enrich low abundance regions of interest from NGS libraries, allowing for more accurate sequencing analysis of these target regions. Indexed libraries are multi-plexed and hybridized to a custom, sequence specific, biotinylated probeset. The vast excess of probes drives their hybridization to complementary library fragments. The library fragment-biotinylated probe hybrid is pulled down by streptavidin beads, thereby capturing the target regions of interest. The streptavidin bead-bound library is sequentially washed with buffers to remove non-specifically associated library fragments. Following washes and recovery of captured libraries, samples are enriched for on target fragments and depleted for off-target fragments. Depletion of off-target fragments reduces overall library yield, requiring post-capture library amplification by PCR. The final amplified library is enriched for regions of interest. The hybrid captured library quality and quantity is evaluated using the Agilent TapeStation and Qubit Fluorometer, respectively. Additionally, the enrichment efficiency is evaluated using an iSeq Sequencing run and calculation of percent of reads within target enrichment panel. Measuring percent on-target is a good first approximation of target enrichment efficiency because the reads aligning to the target enrichment (bait) region indicate efficient hybridization and subsequent capture.

Target enriched libraries that pass quality control checks move forward to NovaSeq sequencing. Captured libraries with non-overlapping indices from library construction are pooled to multiplex for sequencing. Sequencing is completed on the NovaSeq 6000 instrument using paired end 150×150 base sequencing with a 10% PhiX spike-in. Sequencing data generated is then demultiplexed utilizing the assigned index, aligned to the human genome and trimmed to enrich for insert sample data only. This cleaned-up data is then processed through a quality pipeline to collapse duplicate reads and evaluate the sequencing data generated. Once the data is collapsed, the data is processed through a proprietary analysis pipeline to identify differences from the reference alignment (e.g. mutations, chemical modifications, etc.). A report is then generated with the specific signal informative for determining presence or absence of a health condition.

TABLE 1

List of CGIs

| Reference | Pos (hg19 coordinates) |
|---|---|
| 1 | chr13: 108518334-108518633 |
| 2 | chr6: 137242315-137245442 |
| 3 | chr2: 177016416-177016632 |
| 4 | chr5: 2738953-2741237 |
| 5 | chr4: 111553079-111554210 |
| 6 | chr15: 96909815-96910030 |
| 7 | chr6: 42072032-42072701 |
| 8 | chr10: 123922850-123923542 |
| 9 | chr16: 86612188-86613821 |
| 10 | chr19: 47151768-47153125 |
| 11 | chr1: 110610265-110613303 |
| 12 | chr5: 3594467-3603054 |
| 13 | chr9: 126773246-126780953 |
| 14 | chr3: 138656627-138659107 |
| 15 | chr4: 4859632-4860191 |
| 16 | chr10: 118895963-118898037 |

TABLE 1-continued

List of CGIs

| Reference | Pos (hg19 coordinates) |
|---|---|
| 17 | chr7: 103086344-103086840 |
| 18 | chr19: 407011-409511 |
| 19 | chr10: 22764708-22767050 |
| 20 | chr16: 86549069-86550512 |
| 21 | chr9: 96713326-96718186 |
| 22 | chr8: 139508795-139509774 |
| 23 | chr2: 73143055-73148260 |
| 24 | chr8: 26721642-26724566 |
| 25 | chr9: 129386112-129389231 |
| 26 | chr12: 49483601-49484255 |
| 27 | chr16: 54325040-54325703 |
| 28 | chr8: 72468560-72469561 |
| 29 | chr18: 70533965-70536871 |
| 30 | chr9: 98111364-98112362 |
| 31 | chr1: 50882997-50883426 |
| 32 | chr10: 88122924-88127364 |
| 33 | chr11: 31839363-31839813 |
| 34 | chr10: 101290025-101290338 |
| 35 | chr6: 41528266-41528900 |
| 36 | chr16: 51183699-51188763 |
| 37 | chr5: 140346105-140346931 |
| 38 | chr9: 23820691-23822135 |
| 39 | chr20: 690575-691099 |
| 40 | chr1: 177133392-177133846 |
| 41 | chr5: 45695394-45696510 |
| 42 | chr2: 45395869-45398186 |
| 43 | chr20: 48184193-48184833 |
| 44 | chr6: 6002471-6005125 |
| 45 | chr14: 101192851-101193499 |
| 46 | chr8: 4848968-4852635 |
| 47 | chr8: 53851701-53854426 |
| 48 | chr12: 186863-187610 |
| 49 | chr5: 54519054-54519628 |
| 50 | chr6: 108485671-108490539 |
| 51 | chr3: 157815581-157816095 |
| 52 | chr11: 626728~628037 |
| 53 | chr2: 177012371-177012675 |
| 54 | chr17: 59531723-59535254 |
| 55 | chr16: 55364823-55365483 |
| 56 | chr8: 99960497-99961438 |
| 57 | chr7: 42267546-42267823 |
| 58 | chr17: 14202632-14203258 |
| 59 | chr10: 102891010-102891794 |
| 60 | chr5: 174158680-174159729 |
| 61 | chr14: 33402094-33404079 |
| 62 | chr2: 177036254-177037213 |
| 63 | chr10: 106399567-106402812 |
| 64 | chr6: 166579973-166583423 |
| 65 | chr11: 123066517-123066986 |
| 66 | chr11: 44327240-44327932 |
| 67 | chr14: 95237622-95238211 |
| 68 | chr9: 102590742-102591303 |
| 69 | chr15: 76630029-76630970 |
| 70 | chr4: 24801109-24801902 |
| 71 | chr8: 97169731-97170432 |
| 72 | chr3: 6902823-6903516 |
| 73 | chr22: 48884884-48887043 |
| 74 | chr15: 45408573-45409528 |
| 75 | chr9: 100610696-100611517 |
| 76 | chr4: 174448333-174448845 |
| 77 | chr16: 20084707-20085305 |
| 78 | chr4: 174439812-174440249 |
| 79 | chr6: 10381558-10382354 |
| 80 | chr15: 35046443-35047480 |
| 81 | chr10: 119494493-119494991 |
| 82 | chr5: 72676120-72678421 |
| 83 | chr11: 44325657-44326517 |
| 84 | chr17: 46670522-46671458 |
| 85 | chr14: 92789494-92790712 |
| 86 | chr4: 174459200-174460054 |
| 87 | chr2: 80549578-80549798 |
| 88 | chr7: 153748407-153750444 |
| 89 | chr6: 1389139-1391393 |
| 90 | chr16: 49314037-49316543 |
| 91 | chr2: 105459127-105461770 |
| 92 | chr21: 38079941-38081833 |
| 93 | chr4: 174427891-174428192 |
| 94 | chr14: 60973772-60974123 |
| 95 | chr8: 99985733-99986983 |
| 96 | chr2: 63281034-63281347 |
| 97 | chr12: 101109863-101111622 |
| 98 | chr1: 119549144-119551320 |
| 99 | chr5: 38257825-38259136 |
| 100 | chr5: 54522302-54523533 |
| 101 | chr1: 165324191-165326328 |
| 102 | chr15: 33602816-33604003 |
| 103 | chr10: 118030732-118034230 |
| 104 | chr2: 45240372-45241579 |
| 105 | chr4: 174430386-174430861 |
| 106 | chr6: 50810642-50810994 |
| 107 | chr5: 122430676-122431443 |
| 108 | chr10: 109674196-109674964 |
| 109 | chr8: 97172634-97173880 |
| 110 | chr8: 11536767-11538961 |
| 111 | chr5: 180486154-180486892 |
| 112 | chr2: 38301276-38304518 |
| 113 | chr10: 1778784-1780018 |
| 114 | chr12: 54424610-54425173 |
| 115 | chr17: 46669434-46669811 |
| 116 | chr11: 8190226-8190671 |
| 117 | chr8: 25900562-25905842 |
| 118 | chr12: 81102034-81102716 |
| 119 | chr7: 27199661-27200960 |
| 120 | chr10: 119311204-119312104 |
| 121 | chr12: 130387609-130389139 |
| 122 | chr7: 155258827-155261403 |
| 123 | chr6: 117591533-117592279 |
| 124 | chr10: 111216604-111217083 |
| 125 | chr1: 29585897-29586598 |
| 126 | chr2: 144694666-144695180 |
| 127 | chr12: 48397889-48398731 |
| 128 | chr5: 2748368-2757024 |
| 129 | chr12: 114845861-114847650 |
| 130 | chr2: 80529677-80530846 |
| 131 | chr5: 1874907-1879032 |
| 132 | chr6: 100905952-100906686 |
| 133 | chr15: 96904722-96905050 |
| 134 | chr5: 134374385-134376751 |
| 135 | chr2: 66652691-66654218 |
| 136 | chr12: 54440642-54441543 |
| 137 | chr6: 108495654-108495986 |
| 138 | chr17: 70112824-70114271 |
| 139 | chr3: 87841796-87842563 |
| 140 | chr7: 96650221-96651551 |
| 141 | chr4: 110222970-110224257 |
| 142 | chr6: 78172231-78174088 |
| 143 | chr7: 155164557-155167854 |
| 144 | chr12: 113900750-113906442 |
| 145 | chr9: 112081402-112082905 |
| 146 | chr12: 114886354-114886579 |
| 147 | chr5: 3590644-3592000 |
| 148 | chr2: 119592602-119593845 |
| 149 | chr20: 21485932-21496714 |
| 150 | chr18: 11148307-11149936 |
| 151 | chr17: 46824785-46825372 |
| 152 | chr10: 100992156-100992687 |
| 153 | chr14: 36986362-36990576 |
| 154 | chr18: 55094825-55096310 |
| 155 | chr15: 96895306-96895729 |
| 156 | chr17: 36717727-36718593 |
| 157 | chr2: 223183013-223185468 |
| 158 | chr7: 30721372-30722445 |
| 159 | chr1: 53527572-53528974 |
| 160 | chr18: 56939624-56941540 |
| 161 | chr5: 175085004-175085756 |
| 162 | chr10: 50817601-50820356 |
| 163 | chr14: 60975732-60978180 |
| 164 | chr15: 89920793-89922768 |
| 165 | chr9: 122131086-122132214 |
| 166 | chr1: 217311467-217311773 |
| 167 | chr14: 38724254-38725537 |
| 168 | chr14: 61103978-61104663 |

TABLE 1-continued

List of CGIs

| Reference | Pos (hg19 coordinates) |
|---|---|
| 169 | chr18: 73167402-73167920 |
| 170 | chr1: 50880916-50881516 |
| 171 | chr2: 241758141-241760783 |
| 172 | chr11: 31825743-31826967 |
| 173 | chr7: 27260101-27260467 |
| 174 | chr20: 41817475-41819212 |
| 175 | chr3: 238391-240140 |
| 176 | chr7: 121950249-121950927 |
| 177 | chr5: 72526203-72526497 |
| 178 | chr15: 96903311-96903711 |
| 179 | chr10: 26504383-26507434 |
| 180 | chr6: 100915602-100915883 |
| 181 | chr1: 18962842-18963481 |
| 182 | chr3: 127794369-127796136 |
| 183 | chr7: 27203915-27206462 |
| 184 | chr8: 25899335-25899692 |
| 185 | chr12: 114838312-114838889 |
| 186 | chr6: 38682949-38683265 |
| 187 | chr11: 31841315-31842003 |
| 188 | chr4: 174451828-174452962 |
| 189 | chr9: 129372737-129378106 |
| 190 | chr2: 176964062-176965509 |
| 191 | chr2: 176931575-176932663 |
| 192 | chr12: 114833911-114834210 |
| 193 | chr11: 79148358-79152200 |
| 194 | chr2: 177024501-177025692 |
| 195 | chr5: 172672311-172672971 |
| 196 | chr7: 27291119-27292197 |
| 197 | chr1: 180198119-180204975 |
| 198 | chr14: 37126786-37128274 |
| 199 | chr2: 200333687-200334172 |
| 200 | chr14: 58331676-58333121 |
| 201 | chr3: 147131066-147131333 |
| 202 | chr13: 109147798-109149019 |
| 203 | chr14: 48143433-48145589 |
| 204 | chr6: 100905444-100905697 |
| 205 | chr17: 14200579-14200996 |
| 206 | chr6: 1379693-1380014 |
| 207 | chr1: 34642382-34643024 |
| 208 | chr2: 119599059-119599299 |
| 209 | chr2: 119613031-119615565 |
| 210 | chr4: 85413997-85414874 |
| 211 | chr9: 17906419-17907488 |
| 212 | chr12: 29302034-29302954 |
| 213 | chr20: 10200088-10200384 |
| 214 | chr8: 57358126-57359415 |
| 215 | chr10: 63212495-63213009 |
| 216 | chr2: 176936246-176936809 |
| 217 | chr11: 20618197-20619920 |
| 218 | chr18: 19744936-19752363 |
| 219 | chr14: 29234889-29235908 |
| 220 | chr17: 46673532-46674181 |
| 221 | chr4: 144620822-144622218 |
| 222 | chr16: 82660651-82661813 |
| 223 | chr3: 192125821-192127994 |
| 224 | chr2: 119599458-119600966 |
| 225 | chr22: 44257942-44258612 |
| 226 | chr19: 13616752-13617267 |
| 227 | chr3: 147138916-147139564 |
| 228 | chr9: 969529-973276 |
| 229 | chr18: 55103154-55108853 |
| 230 | chr4: 174422024-174422443 |
| 231 | chr4: 57521621-57522703 |
| 232 | chr15: 79724099-79725643 |
| 233 | chr14: 37135513-37136348 |
| 234 | chr10: 23480697-23482455 |
| 235 | chr2: 45169505-45171884 |
| 236 | chr18: 30349690-30352302 |
| 237 | chr6: 99291327-99291737 |
| 238 | chr9: 21970913-21971190 |
| 239 | chr4: 107146-107898 |
| 240 | chr12: 117798076-117799448 |
| 241 | chr2: 219736132-219736592 |
| 242 | chr10: 118892161-118892639 |
| 243 | chr11: 27743472-27744564 |
| 244 | chr12: 65218245-65219143 |
| 245 | chr12: 75601081-75601752 |
| 246 | chr7: 54612324-54612558 |
| 247 | chr6: 100912071-100913337 |
| 248 | chr10: 102905714-102906693 |
| 249 | chr8: 87081653-87082046 |
| 250 | chr6: 50818180-50818431 |
| 251 | chr1: 91189139-91189400 |
| 252 | chr2: 118981769-118982466 |
| 253 | chr10: 50602989-50606783 |
| 254 | chr17: 59528979-59530266 |
| 255 | chr4: 147559205-147561901 |
| 256 | chr1: 4713989-4716555 |
| 257 | chr13: 102568425-102569495 |
| 258 | chr16: 6068914-6070401 |
| 259 | chr22: 29709281-29712013 |
| 260 | chr10: 100993820-100994188 |
| 261 | chr6: 391188-393790 |
| 262 | chr2: 176977284-176977540 |
| 263 | chr4: 4868440-4869173 |
| 264 | chr6: 137809342-137810204 |
| 265 | chr12: 54321301-54321721 |
| 266 | chr2: 105468851-105473488 |
| 267 | chr8: 55366180-55367628 |
| 268 | chr12: 72665683-72667551 |
| 269 | chr4: 54966163-54968063 |
| 270 | chr5: 134366913-134367438 |
| 271 | chr1: 226075150-226075680 |
| 272 | chr20: 17206528-17206952 |
| 273 | chr4: 172733734-172735118 |
| 274 | chr18: 55019707-55021605 |
| 275 | chr2: 162279835-162280709 |
| 276 | chr6: 1381743-1385211 |
| 277 | chr7: 103968783-103969959 |
| 278 | chr6: 150358872-150359394 |
| 279 | chr2: 119914126-119916663 |
| 280 | chr7: 27278945-27279469 |
| 2.81 | chr12: 114851957-114852360 |
| 282 | chr16: 24267040-24267527 |
| 283 | chr6: 7229877-7230865 |
| 284 | chr2: 45227644-45228783 |
| 285 | chr4: 174450046-174451469 |
| 286 | chr4: 154712073-154712706 |
| 287 | chr3: 22413492-22414365 |
| 288 | chr20: 21694472-21695344 |
| 289 | chr6: 1378445~1379318 |
| 290 | chr8: 70981873-70984888 |
| 291 | chr12: 53107912-53108471 |
| 292 | chr10: 102996034-102996646 |
| 293 | chr3: 157821232-157821604 |
| 294 | chr4: 111554965-111555504 |
| 295 | chr13: 58206526-58208930 |
| 296 | chr10: 22634000-22634862 |
| 297 | chr9: 22005887-22006229 |
| 298 | chr5: 159399004-159399928 |
| 299 | chr2: 31805293-31806403 |
| 300 | chr6: 100903491-100903713 |
| 301 | chr5: 77268350-77268787 |
| 302 | chr14: 85997468-85998637 |
| 303 | chr5: 92923487-92924497 |
| 304 | chr11: 64480199-64481344 |
| 305 | chr13: 28366549-28368505 |
| 306 | chr5: 77805753-77806313 |
| 307 | chr9: 79633326-79636030 |
| 308 | chr4: 93226348-93227007 |
| 309 | chr2: 223170486-223171140 |
| 310 | chr1: 91172102-91172771 |
| 311 | chr1: 1181756-1182470 |
| 312 | chr8: 65281903-65283043 |
| 313 | chr10: 94825546-94826320 |
| 314 | chr6: 108491033-108491410 |
| 315 | chr21: 38076762-38077685 |
| 316 | chr1: 91183240-91184540 |
| 317 | chr3: 147136903-147137328 |
| 318 | chr15: 96911511-96911808 |
| 319 | chr14: 57274607-57276840 |
| 320 | chr13: 112726281-112728419 |

TABLE 1-continued

List of CGIs

| Reference | Pos (hg19 coordinates) |
|---|---|
| 321 | chr2: 171672310-171675447 |
| 322 | chr8: 11559596-11562956 |
| 323 | chr10: 48438411-48439320 |
| 324 | chr18: 59000683-59001692 |
| 325 | chr15: 91642908-91643702 |
| 326 | chr5: 3592391-3592644 |
| 327 | chr19: 56988313-56989741 |
| 328 | chr6: 26614013-26614851 |
| 329 | chr11: 27742059-27742273 |
| 330 | chr3: 147113608-147114479 |
| 331 | chr14: 57264638-57265561 |
| 332 | chr7: 155302253-155303158 |
| 333 | chr11: 31848487-31848776 |
| 334 | chr16: 54970301-54972846 |
| 335 | chr19: 30715549-30715753 |
| 336 | chr9: 96710811-96711717 |
| 337 | chr18: 77557780-77558948 |
| 338 | chr20: 21686199-21687689 |
| 339 | chr11: 31847132-31847958 |
| 340 | chr16: 86530747-86532994 |
| 341 | chr1: 203044722-203045390 |
| 342 | chr15: 53096014-53096482 |
| 343 | chr7: 97361132-97363018 |
| 344 | chr14: 29236835-29237832 |
| 345 | chr13: 79182859-79183880 |
| 346 | chr11: 69517840-69519929 |
| 347 | chr1: 231296559-231297345 |
| 348 | chr19: 8675333-8675699 |
| 349 | chr1: 63795363-63796140 |
| 350 | chr4: 90228714-90229010 |
| 351 | chr3: 62362610-62363082 |
| 352 | chr19: 5827754-5828405 |
| 353 | chr10: 125732220-125732843 |
| 354 | chr9: 136293566-136294160 |
| 355 | chr1: 63782394-63790471 |
| 356 | chr4: 4867386-4867673 |
| 357 | chr9: 133534534-133542394 |
| 358 | chr15: 100913438-100914022 |
| 359 | chr10: 101279941-101280382 |
| 360 | chr13: 53419897-53422872 |
| 361 | chr1: 77747314-77748224 |
| 362 | chr14: 36974548-36975425 |
| 363 | chr12: 57618769-57619402 |
| 364 | chr7: 49813008-49815752 |
| 365 | chr4: 188916605-188916876 |
| 366 | chr11: 31831620-31839038 |
| 367 | chr8: 132052203-132054749 |
| 368 | chr2: 237071794-237078762 |
| 369 | chr20: 39994545-39995810 |
| 370 | chr11: 132812662-132813075 |
| 371 | chr5: 170735169-170739863 |
| 372 | chr1: 221051966-221053673 |
| 373 | chr5: 72529099-72529976 |
| 374 | chr14: 36973169-36973740 |
| 375 | chr4: 158141404-158141836 |
| 376 | chr14: 103655241-103655928 |
| 377 | chr1: 65731411-65731849 |
| 378 | chr1: 38218190-38218977 |
| 379 | chr3: 128719865-128721245 |
| 380 | chr15: 33009530-33011696 |
| 381 | chr2: 162275161-162275596 |
| 382 | chr7: 155241323-155243757 |
| 383 | chr19: 46001830-46002686 |
| 384 | chr6: 137814355-137815202 |
| 385 | chr7: 70596228-70598382 |
| 386 | chr15: 96959341-96960531 |
| 387 | chr16: 66612749-66613412 |
| 388 | chr6: 110299365-110301267 |
| 389 | chr15: 27215951-27216856 |
| 390 | chr11: 88241710-88242562 |
| 391 | chr2: 124782252-124783255 |
| 392 | chr17: 70111979-70112308 |
| 393 | chr2: 63283936-63284147 |
| 394 | chr17: 46800945-46801288 |
| 395 | chr6: 1393049-1394170 |
| 396 | chr3: 137489594-137491004 |
| 397 | chr15: 60296135-60298520 |
| 398 | chr12: 106979429-106981086 |
| 399 | chr12: 54360374-54360660 |
| 400 | chr14: 36991594-36992488 |
| 401 | chr4: 156129168-156130209 |
| 402 | chr4: 54975387-54976202 |
| 403 | chr3: 137482964-137484454 |
| 404 | chr10: 118893527-118894432 |
| 405 | chr18: 76737005-76741244 |
| 406 | chr10: 110671724-110672326 |
| 407 | chr5: 71014917-71015715 |
| 408 | chr6: 50787286-50788091 |
| 409 | chr19: 3868586-3869217 |
| 410 | chr4: 5894071-5895116 |
| 411 | chr11: 131780328-131781532 |
| 412 | chr6: 101846766-101847135 |
| 413 | chr11: 71952112-71952528 |
| 414 | chr5: 172663616-172664584 |
| 415 | chr9: 23822412-23822667 |
| 416 | chr4: 5891981-5892365 |
| 417 | chr1: 217310749-217311178 |
| 418 | chr10: 108923780-108924805 |
| 419 | chr6: 100038655-100039477 |
| 420 | chr7: 121945345-121946235 |
| 421 | chr3: 147126988-147128999 |
| 422 | chr7: 121956543-121957341 |
| 423 | chr4: 156680095-156681386 |
| 424 | chr4: 85404986-85405252 |
| 425 | chr1: 221064889-221065600 |
| 426 | chr17: 73749618-73750178 |
| 427 | chr8: 55370170-55372525 |
| 428 | chr6: 70992040-70992912 |
| 429 | chr16: 55513220-55513526 |
| 430 | chr6: 106433984-106434459 |
| 431 | chr14: 29254365-29255069 |
| 432 | chr6: 33655966-33656238 |
| 433 | chr9: 19788215-19789288 |
| 434 | chr11: 115630398-115631117 |
| 435 | chr1: 34628783-34630976 |
| 436 | chr14: 101923575-101925995 |
| 437 | chr17: 72855621-72858012 |
| 438 | chr2: 223162946-223163912 |
| 439 | chr4: 85417659-85420799 |
| 440 | chr1: 156390403-156391581 |
| 441 | chr3: 147130342-147130577 |
| 442 | chr2: 119602616-119604486 |
| 443 | chr9: 120175253-120177496 |
| 444 | chr4: 174443365-174443948 |
| 445 | chr5: 145724294-145724551 |
| 446 | chr11: 32454874-32457311 |
| 447 | chr2: 176949511-176949795 |
| 448 | chr1: 18436551-18437673 |
| 449 | chr3: 26665950-26666164 |
| 450 | chr3: 170303044-170303249 |
| 451 | chr2: 223176493-223177515 |
| 452 | chr2: 182321761-182323029 |
| 453 | chr18: 44789742-44790678 |
| 454 | chr17: 46796234-46797292 |
| 455 | chr18: 44772992-44775577 |
| 456 | chr8: 101117922-101118693 |
| 457 | chr7: 27134097-27134303 |
| 458 | chr10: 102507482-102509646 |
| 459 | chr19: 39754973-39756540 |
| 460 | chr7: 26415746-26416891 |
| 461 | chr14: 37116188-37117628 |
| 462 | chr4: 174421347-174421559 |
| 463 | chr6: 85472702-85474132 |
| 464 | chr20: 22557517-22559240 |
| 465 | chr6: 117198089-117198705 |
| 466 | chr10: 71331926-71333392 |
| 467 | chr19: 36334994-36335321 |
| 468 | chr4: 46995128-46995872 |
| 469 | chr9: 135455164-135458586 |
| 470 | chr8: 65290108-65290946 |
| 471 | chr10: 94828102-94829040 |
| 472 | chr1: 116380359-116382364 |

TABLE 1-continued

List of CGIs

| Reference | Pos (hg19 coordinates) |
|---|---|
| 473 | chr15: 47476369-47477499 |
| 474 | chr3: 147115764-147116421 |
| 475 | chr17: 59485573-59485780 |
| 476 | chr10: 23983366-23984978 |
| 477 | chr2: 176949993-176950336 |
| 478 | chr9: 137967110-137967727 |
| 479 | chr2: 176957054-176958279 |
| 480 | chr11: 119293320-119293943 |
| 481 | chr11: 132813562-132814395 |
| 482 | chr2: 237068071-237068834 |
| 483 | chr10: 27547668-27548402 |
| 484 | chr4: 4866438-4866813 |
| 485 | chr21: 19617098-19617874 |
| 486 | chr1: 91185156-91185577 |
| 487 | chr19: 15292399-15292632 |
| 488 | chr1: 145075483-145075845 |
| 489 | chr2: 19560963-19561650 |
| 490 | chr14: 57260878-57262123 |
| 491 | chr8: 55378928-55380186 |
| 492 | chr6: 99290279-99290771 |
| 493 | chr19: 13124959-13125259 |
| 494 | chr15: 27112030-27113479 |
| 495 | chr8: 145925410-145926101 |
| 496 | chr11: 124629723-124629926 |
| 497 | chr4: 109093038-109094546 |
| 498 | chr3: 62356773-62357315 |
| 499 | chr14: 37131181-37132785 |
| 500 | chr10: 124905634-124906161 |
| 501 | chr7: 35296921-35298218 |
| 502 | chr19: 36248979-36249307 |
| 503 | chr12: 15475318-15475901 |
| 504 | chr5: 87985470-87985810 |
| 505 | chr12: 54423427-54423712 |
| 506 | chr7: 96653467-96654199 |
| 507 | chr2: 45155195-45157049 |
| 508 | chr15: 96896928-96897301 |
| 509 | chr12: 58004982-58005351 |
| 510 | chr2: 176933131-176933449 |
| 511 | chr2: 176962179-176962487 |
| 512 | chr20: 25063838-25065525 |
| 513 | chr12: 5153012-5154346 |
| 514 | chr3: 154146347-154146965 |
| 515 | chr1: 165323486-165323811 |
| 516 | chr21: 38065179-38066185 |
| 517 | chr10: 119000435-119001530 |
| 518 | chr12: 45444202-45445386 |
| 519 | chr4: 158143296-158144053 |
| 520 | chr5: 76932317-76933523 |
| 521 | chr5: 172659049-172660277 |
| 522 | chr2: 223168653-223169008 |
| 523 | chr1: 248020330-248021252 |
| 524 | chr18: 904578~909574 |
| 525 | chr12: 127940451-127940907 |
| 526 | chr9: 135461934-135462909 |
| 527 | chr17: 48041282-48043064 |
| 528 | chr4: 94755786-94756310 |
| 529 | chr10: 130338695-130338994 |
| 530 | chr2: 119616133-119616826 |
| 531 | chr2: 177042751-177043444 |
| 532 | chr2: 105478600-105479188 |
| 533 | chr5: 172670829-172671824 |
| 534 | chr2: 176952695-176953297 |
| 535 | chr13: 28549839-28550246 |
| 536 | chr13: 112720564-112723582 |
| 537 | chr6: 100895773-100896062 |
| 538 | chr7: 136553854-136556194 |
| 539 | chr6: 127441553-127441760 |
| 540 | chr1: 119526782-119527192 |
| 541 | chr12: 49484920-49485178 |
| 542 | chr9: 23850910-23851522 |
| 543 | chr2: 220299483-220300243 |
| 544 | chr5: 1881924-1887743 |
| 545 | chr8:57360585-57360815 |
| 546 | chr18: 74961556-74963822 |
| 547 | chr5: 172660720-172661133 |
| 548 | chr17: 75277317-75278172 |
| 549 | chr10: 99789614-99791320 |
| 550 | chr2: 176944087-176948446 |
| 551 | chr4: 154709512-154710827 |
| 552 | chr5: 140798757-140799359 |
| 553 | chr3: 44063314-44063837 |
| 554 | chr15: 79574830-79575211 |
| 555 | chr2: 223161531-223161919 |
| 556 | chr6: 134210639-134211218 |
| 557 | chr10: 102899177-102899489 |
| 558 | chr13:79181944-79182222 |
| 559 | chr7: 71800757-71802768 |
| 560 | chr3: 186078710-186080111 |
| 561 | chr1: 24229115-24229537 |
| 562 | chr16:48844551-48845264 |
| 563 | chr7: 113724924-113727795 |
| 564 | chr22:44726724-44727590 |
| 565 | chr4: 15779998-15780729 |
| 566 | chr4: 41869174-41869459 |
| 567 | chr1: 38941919-38942404 |
| 568 | chr2: 176971706-176972305 |
| 569 | chr2: 119607378-119607910 |
| 570 | chr5: 76934581-76935296 |
| 571 | chr12: 103696090-103696418 |
| 572 | chr5: 63255044-63255407 |
| 573 | chr1: 221067447-221068185 |
| 574 | chr2: 119611296-119611881 |
| 575 | chr10: 124907283-124911035 |
| 576 | chr12: 114878143-114879155 |
| 577 | chr12: 49371690-49375550 |
| 578 | chr17: 36719544-36719938 |
| 579 | chr17: 46696553-46696926 |
| 580 | chr3: 147142181-147142391 |
| 581 | chr8: 9762661-9764748 |
| 582 | chr14: 74706188-74708192 |
| 583 | chr3: 12837992-12838359 |
| 584 | chr20: 37352130-37357372 |
| 585 | chr10: 8077829-8078378 |
| 586 | chr4: 4864456~4864834 |
| 587 | chr4: 13524062-13526083 |
| 588 | chr1: 66258440-66258918 |
| 589 | chr11: 17740789-17743779 |
| 590 | chr12: 106975195-106975714 |
| 591 | chr9: 91792662-91793611 |
| 592 | chr1: 149333785-149334111 |
| 593 | chr3: 170303532-170303768 |
| 594 | chr5: 72594147-72595808 |
| 595 | chr5: 145725286-145725852 |
| 596 | chr10: 23462224-23463889 |
| 597 | chr20: 21689758-21690048 |
| 598 | chr15: 53080458-53083699 |
| 599 | chr2: 154727906-154728271 |
| 600 | chr5: 170743178-170744107 |
| 601 | chr10: 102899822-102900263 |
| 602 | chr5: 134368578-134370466 |
| 603 | chr2: 66808568-66809404 |
| 604 | chr7: 96651963-96652246 |
| 605 | chr1: 91190489-91192804 |
| 606 | chr17: 75368688-75370506 |
| 607 | chr4: 185939222-185942747 |
| 608 | chr7: 43152020-43153340 |
| 609 | chr13: 84453664-84453897 |
| 610 | chr2: 176956504-176956707 |
| 611 | chr7: 87563342-87564571 |
| 612 | chr20: 17208550-17208756 |
| 613 | chr22: 19746924-19747141 |
| 614 | chr2: 223159725-223160487 |
| 615 | chr12: 131200509-131200726 |
| 616 | chr18: 44336183-44337110 |
| 617 | chr2: 63285949-63287097 |
| 618 | chr4: 13526553-13526770 |
| 619 | chr15: 89949373-89951130 |
| 620 | chr19: 55815940-55816277 |
| 621 | chr17: 50235175-50236466 |
| 622 | chr19: 58545115-58545897 |
| 623 | chr12: 113592203-113592620 |
| 624 | chr12: 115109503-115110061 |

TABLE 1-continued

List of CGIs

| Reference | Pos (hg19 coordinates) |
|---|---|
| 625 | chr4: 164264821-164265772 |
| 626 | chr1: 2772126-2772665 |
| 627 | chr3: 71834068-71834653 |
| 628 | chr12: 5018585-5021171 |
| 629 | chr15: 74419870-74423044 |
| 630 | chr3: 147108511-147111703 |
| 631 | chr5: 88185224-88185589 |
| 632 | chr12: 54354529-54355491 |
| 633 | chr10: 101290625-101291178 |
| 634 | chr8: 11557852-11558252 |
| 635 | chr8: 105478672-105479340 |
| 636 | chr11: 20181200-20182325 |
| 637 | chr19: 54483021-54483572 |
| 638 | chr13: 112707804-112708696 |
| 639 | chr16: 22824616-22826459 |
| 640 | chr4: 66536065-66536674 |
| 641 | chr4: 154713537-154714240 |
| 642 | chr7: 12151220-12151559 |
| 643 | chr12: 119212110-119212393 |
| 644 | chr17: 14201726-14202052 |
| 645 | chr20: 21376358-21378245 |
| 646 | chr13: 36045931-36046143 |
| 647 | chr15: 60287107-60287663 |
| 648 | chr9: 100613938-100614622 |
| 649 | chr10: 102475276-102475579 |
| 650 | chr7: 121940006-121940648 |
| 651 | chr5: 37834671-37835128 |
| 652 | chr1: 197887088-197887791 |
| 653 | chr12: 99139386-99139769 |
| 654 | chr6: 1619093-1621094 |
| 655 | chr12: 113917394-113918107 |
| 656 | chr14: 24044886-24046760 |
| 657 | chr5: 77253832-77254049 |
| 658 | chr4: 85403830-85404524 |
| 659 | chr6: 166666837-166667541 |
| 660 | chr18: 77547965-77549038 |
| 661 | chr2: 219848919-219850541 |
| 662 | chr17: 7832532-7833164 |
| 663 | chr5: 134363092-134365146 |
| 664 | chr10: 103043990-103044480 |
| 665 | chr8: 97171805-97172022 |
| 666 | chr20: 57089460-57090237 |
| 667 | chr12: 114840853-114841063 |
| 668 | chr4: 66535193-66535620 |
| 669 | chr8: 85096759-85097247 |
| 670 | chr6: 10881846-10882051 |
| 671 | chr13: 28498226-28499046 |
| 672 | chr1: 161695637-161697298 |
| 673 | chr11: 2890388-2891337 |
| 674 | chr17: 5000369-5001205 |
| 675 | chr13: 27334226-27335205 |
| 676 | chr10: 22623350-22625875 |
| 677 | chr2: 157185557-157186355 |
| 678 | chr7: 20370003-20371504 |
| 679 | chr4: 961347-962155 |
| 680 | chr12: 49485766-49485977 |
| 681 | chr3: 62356119-62356378 |
| 682 | chr11: 14995128-14995908 |
| 683 | chr12: 53359192-53359507 |
| 684 | chr16: 51168266-51169110 |
| 685 | chr14: 57278709-57279116 |
| 686 | chr6: 37616722-37617179 |
| 687 | chr18: 11750953-11752756 |
| 688 | chr19: 45260352-45261809 |
| 689 | chr1: 119531991-119532196 |
| 690 | chr19: 36523391-36523887 |
| 691 | chr12: 52652018-52652743 |
| 692 | chr8: 49468683-49468959 |
| 693 | chr8: 9760750-9761643 |
| 694 | chr7: 19146923-19147308 |
| 695 | chr13: 32889533-32889900 |
| 696 | chr5: 140797162-140797701 |
| 697 | chr21: 42218489-42219222 |
| 698 | chr19: 54411376-54411968 |
| 699 | chr3: 62354291-62355012 |
| 700 | chr12: 113590806-113591304 |
| 701 | chr1: 225865068-225865328 |
| 702 | chr7: 130790358-130792773 |
| 703 | chr15: 53076187-53077926 |
| 704 | chr1: 214158726-214159080 |
| 70.5 | chr12: 3308812-3310270 |
| 706 | chr1: 39044059-39044561 |
| 707 | chr10: 119312766-119313563 |
| 708 | chr12: 65514878-65515863 |
| 709 | chr12: 54366815-54369103 |
| 710 | chr12: 114885105-114885418 |
| 711 | chr16: 2228190-2230946 |
| 712 | chr11: 68622722-68623252 |
| 713 | chr2: 25499763-25500429 |
| 714 | chr5: 172661486-172662228 |
| 715 | chr17: 46691520-46692097 |
| 716 | chr12: 75602991-75603344 |
| 717 | chr2: 80531367-80531719 |
| 718 | chr5: 158478378-158478630 |
| 719 | chr2: 177017266-177017489 |
| 720 | chr2: 63282514-63283122 |
| 721 | chr7: 155595926-155599414 |
| 722 | chr5: 172665306-172666072 |
| 723 | chr12: 114843022-114843610 |
| 724 | chr13: 112758598-112760491 |
| 725 | chr4: 4858389-4858893 |
| 726 | chr16: 55365814-55366022 |
| 727 | chr9: 96108466-96108992 |
| 728 | chr12: 3475010-3475654 |
| 729 | chr9: 86152353-86153777 |
| 730 | chr6: 10384965-10385492 |
| 731 | chr22: 31500396-31501239 |
| 732 | chr5: 179228283-179229003 |
| 733 | chr6: 137816474-137817223 |
| 734 | chr2: 106681982-106682403 |
| 735 | chr14: 95239375-95239679 |
| 736 | chr7: 154001964-154002281 |
| 737 | chr1: 1476093-1476669 |
| 738 | chr15: 89904822-89906050 |
| 739 | chr11: 89224416-89224718 |
| 740 | chr9: 100615234-100617510 |
| 741 | chr3: 172165372-172166738 |
| 742 | chr1: 202678924-202679769 |
| 743 | chr14: 37053134-37053690 |
| 744 | chr4: 41875445-41875794 |
| 745 | chr2: 162273294-162273725 |
| 746 | chr1: 181287300-181287873 |
| 747 | chr13: 79181327-79181614 |
| 748 | chr8: 145103285-145108027 |
| 749 | chr22: 42305617-42307254 |
| 750 | chr8: 102505512-102506430 |
| 751 | chr17: 74533281-74534566 |
| 752 | chr1: 214156000-214156851 |
| 753 | chr20: 2780978-2781497 |
| 754 | chr4: 4861227-4862241 |
| 755 | chr19: 13215244-13215543 |
| 756 | chr7: 121943867-121944538 |
| 757 | chr17: 71948478-71949255 |
| 758 | chr2: 127413696-127414171 |
| 759 | chr1: 113286332-113287172 |
| 760 | chr1: 47009575-47010132 |
| 761 | chr16: 62069121-62070634 |
| 762 | chr16: 3013651-3015131 |
| 763 | chr18: 76732970-76734765 |
| 764 | chr4: 155664819-155665833 |
| 765 | chr6: 72298274-72298528 |
| 766 | chr15: 89147660-89149198 |
| 767 | chr17: 33775294-33775794 |
| 768 | chr18: 44337510-44338100 |
| 769 | chr10: 8076002-8077261 |
| 770 | chr13: 112717125-112717421 |
| 771 | chr15: 89914363-89915061 |
| 772 | chr1: 228785986-228786204 |
| 773 | chr1: 156358050-156358252 |
| 774 | chr7: 751712-752150 |
| 775 | chr3: 137489051-137489409 |
| 776 | chr17: 7905927-7907445 |

TABLE 1-continued

List of CGIs

| Reference | Pos (hg19 coordinates) |
|---|---|
| 777 | chr18: 35144907-35147628 |
| 778 | chr3: 9177691-9178189 |
| 779 | chr6: 10390888-10391098 |
| 780 | chr14: 37052537-37052838 |
| 781 | chr1: 47909712-47911020 |
| 782 | chr13: 93879245-93880877 |
| 783 | chr1: 50893468-50893745 |
| 784 | chr7: 27282086-27283136 |
| 785 | chr4: 147558231-147558583 |
| 786 | chr19: 13124569-13124788 |
| 787 | chr17: 46619087-46619314 |
| 788 | chr3: 44596535-44597018 |
| 789 | chr14: 24803678-24804353 |
| 790 | chr2: 3286324-3286530 |
| 791 | chr12: 14134626-14135242 |
| 792 | chr12: 114881649-114881937 |
| 793 | chr20: 22548967-22549720 |
| 794 | chr8: 37822486-37824008 |
| 795 | chr13: 100641334-100642188 |
| 796 | chr4: 206377-206892 |
| 797 | chr3: 11034446-11035384 |
| 798 | chr7: 152622343-152623305 |
| 799 | chr10: 22629360-22630328 |
| 800 | chr4: 140201064-140201449 |
| 801 | chr19: 46318490-46319266 |
| 802 | chr3: 121902742-121903645 |
| 803 | chr9: 77112712-77113583 |
| 804 | chr2: 114256775-114258043 |
| 805 | chr10: 15761423-15762101 |
| 806 | chr1: 115880167-115881332 |
| 807 | chr6: 50791110-50791573 |
| 808 | chr6: 55039170-55039392 |
| 809 | chr2: 176980765-176981423 |
| 810 | chr8: 86350765-86351196 |
| 811 | chr8: 24812946-24814299 |
| 812 | chr7: 19184818-19185033 |
| 813 | chr5: 76936126-76936984 |
| 814 | chr5: 87980878-87981272 |
| 815 | chr9: 77111778-77112042 |
| 816 | chr11: 20622720-20623399 |
| 817 | chr1: 50882433-50882660 |
| 818 | chr17: 35291899-35300875 |
| 819 | chr17: 46675044-46675589 |
| 820 | chr20: 5296266-5297798 |
| 821 | chr7: 156871054-156871297 |
| 822 | chr4: 681313-681514 |
| 823 | chr2: 177039551-177039951 |
| 824 | chr17: 46695325-46695553 |
| 825 | chr1: 41283840-41284591 |
| 826 | chr9: 16726859-16727273 |
| 827 | chr1: 65991001-65991811 |
| 828 | chr1: 181452706-181453073 |
| 829 | chr8: 120428398-120429178 |
| 830 | chr3: 32863174-32863415 |
| 831 | chr4: 134069162-134070442 |
| 832 | chr12: 123754049-123754373 |
| 833 | chr5: 63256548-63257886 |
| 834 | chr5: 1879689-1879928 |
| 835 | chr10: 118899247-118900329 |
| 836 | chr20: 2731063-2731395 |
| 837 | chr5: 134385967-134386370 |
| 838 | chr2: 177014948-177015214 |
| 839 | chr1: 67218079-67218293 |
| 840 | chr11: 65408344-65408631 |
| 841 | chr7: 156801418-156801632 |
| 842 | chr18: 54788959-54789194 |
| 843 | chr2: 220173870-220174283 |
| 844 | chr2: 220173021-220173271 |
| 845 | chr12: 113908887-113910681 |
| 846 | chr6: 100897080-100897621 |
| 847 | chr1: 155290606-155291001 |
| 848 | chr2: 130763483-130763764 |
| 849 | chr12: 129337870-129338653 |
| 850 | chr21: 34395128-34400245 |
| 851 | chr12: 52115410-52115679 |
| 852 | chr3: 126113547-126113967 |
| 853 | chr16: 3220438-3221356 |
| 854 | chr1: 119543056-119543454 |
| 855 | chr14: 62279476-62280019 |
| 856 | chr1: 636906-640628 |
| 857 | chr10: 102893660-102895059 |
| 858 | chr3: 3840513-3842772 |
| 859 | chr1: 119529819-119530712 |
| 860 | chr9: 32782936-32783625 |
| 861 | chr19: 1064897-1065191 |
| 862 | chr5: 54527319-54527760 |
| 863 | chr7: 156795355-156799394 |
| 864 | chr1: 155147185-155147444 |
| 865 | chr9: 37002489-37002957 |
| 866 | chr11: 69831571-69832484 |
| 867 | chr2: 128421719-128422182 |
| 868 | chr22: 38476836-38478839 |
| 869 | chr19: 54412710-54413087 |
| 870 | chr9: 123656750-123656972 |
| 871 | chr7: 129422997-129423355 |
| 872 | chr19: 36336275-36337138 |
| 873 | chr2: 50574045-50574817 |
| 874 | chr10: 102975969-102978096 |
| 875 | chr6: 5996185-5996486 |
| 876 | chr3: 26664104-26664796 |
| 877 | chr7: 155170623-155170939 |
| 878 | chr8: 65286067-65286659 |
| 879 | chr14: 37125219-37125661 |
| 880 | chr11: 65816404-65816665 |
| 881 | chr6: 41908745-41909711 |
| 882 | chr17: 46620367-46621373 |
| 883 | chr2: 142887724-142888553 |
| 884 | chr1: 221050448-221050864 |
| 885 | chr12: 106974412-106974951 |
| 886 | chr14: 57278068-57278287 |
| 887 | chr1: 67773329-67773767 |
| 888 | chr17: 40936445-40936668 |
| 889 | chr20: 2729997-2730797 |
| 890 | chr12: 113013099-113013529 |
| 891 | chr7: 155244046-155244357 |
| 892 | chr1: 214153214-214153668 |
| 893 | chr1: 156863415-156863711 |
| 894 | chr1: 114695136-114696672 |
| 895 | chr14: 85996494-85996958 |
| 896 | chr7: 100823307-100823701 |
| 897 | chr20: 52789252-52790986 |
| 898 | chr5: 178421225-178422337 |
| 899 | chr11: 36397926-36399398 |
| 900 | chr13: 36052553-36053119 |
| 901 | chr14: 57283967-57284558 |
| 902 | chr4: 25090106-25090510 |
| 903 | chr2: 5831187-5831413 |
| 904 | chr6: 117869097-117869530 |
| 905 | chr19: 58094739-58095764 |
| 906 | chr4: 85422929-85423190 |
| 907 | chr13: 100547172-100547431 |
| 908 | chr8: 68864584-68864946 |
| 909 | chr16: 49311413-49312308 |
| 910 | chr7: 19184221-19184686 |
| 911 | chr2: 19562749-19562965 |
| 912 | chr19: 54481412-54481955 |
| 913 | chr10: 124901907-124902617 |
| 914 | chr3: 62357639-62359774 |
| 915 | chr11: 31827696-31827921 |
| 916 | chr17: 43037166-43037740 |
| 917 | chr7: 37955622-37956555 |
| 918 | chr6: 106429111-106429772 |
| 919 | chr6: 50682334-50683214 |
| 920 | chr5: 76923887-76924502 |
| 921 | chr6: 168841818-168843100 |
| 922 | chr7: 19145872-19146256 |
| 923 | chr20: 32856659-32857248 |
| 924 | chr17: 79859808-79860963 |
| 925 | chr7: 95225503-95226194 |
| 926 | chr14: 105167663-105168129 |
| 927 | chr17: 14248391-14248721 |
| 928 | chr16: 84002269-84002860 |

TABLE 1-continued

List of CGIs

| Reference | Pos (hg19 coordinates) |
|---|---|
| 929 | chr9: 104499849-104501076 |
| 930 | chr17: 46604362-46604881 |
| 931 | chr2: 87015974-87018182 |
| 932 | chr14: 36990873-36991209 |
| 933 | chr5: 52777788-52777996 |
| 934 | chr19: 35633847-35634629 |
| 935 | chr1: 221055492-221055800 |
| 936 | chr1: 146551476-146551764 |
| 937 | chr13: 100642774-100643094 |
| 938 | chr14: 85999532-86000478 |
| 939 | chr13: 36049570-36050159 |
| 940 | chr2: 119606038-119606313 |
| 941 | chr11: 123065426-123066184 |
| 942 | chr3: 172167526-172167866 |
| 943 | chr4: 41882450-41882964 |
| 944 | chr8: 142528185-142529029 |
| 945 | chr9: 79637814-79638169 |
| 946 | chr3: 19189688-19190100 |
| 947 | chr4: 122301567-122302290 |
| 948 | chr10: 130339526-130339777 |
| 949 | chr9: 35846310-35846638 |
| 950 | chr15: 53097561-53098476 |
| 951 | chr2: 157184389-157184632 |
| 952 | chr5: 145718289-145720095 |
| 953 | chr11: 105481126-105481422 |
| 954 | chr5: 170741603-170742751 |
| 955 | chr3: 62355315-62355534 |
| 956 | chr1: 38219702-38220012 |
| 957 | chr4: 41881177-41881418 |
| 958 | chr13: 112715359-112716234 |
| 959 | chr17: 1880789-1881116 |
| 960 | chr18: 56887091-56887665 |
| 961 | chr6: 10390038-10390565 |
| 962 | chr11: 69516931-69517218 |
| 963 | chr19: 39737689-39739288 |
| 964 | chr3: 157812053-157812764 |
| 965 | chr14: 37049333-37051726 |
| 966 | chr7: 156409023-156409294 |
| 967 | chr11: 46366876-46367101 |
| 968 | chr5: 50685453-50686148 |
| 969 | chr4: 41883492-41884570 |
| 970 | chr13: 112709884-112712665 |
| 971 | chr22: 44287497-44288061 |
| 972 | chr22: 46440393-46441019 |
| 973 | chr8: 23562475-23565175 |
| 974 | chr2: 207506774-207507422 |
| 975 | chr4: 169799086-169799625 |
| 976 | chr3: 133393118-133393657 |
| 977 | chr8: 41424341-41425300 |
| 978 | chr4: 100870377-100871994 |
| 979 | chr4: 107956555-107957453 |
| 980 | chr17: 79314962-79320653 |
| 981 | chr2: 30453566-30455655 |
| 982 | chr1: 18956895-18959829 |
| 983 | chr12: 41086522-41087102 |
| 984 | chr22: 42685894-42686095 |
| 985 | chr6: 100914946-100915245 |
| 986 | chr1: 46951168-46951792 |
| 987 | chr4: 41749184-41749811 |
| 988 | chr11: 128419198-128419513 |
| 989 | chr2: 171671598-171671804 |
| 990 | chr1: 170630456-170630851 |
| 991 | chr20: 44657463-44659243 |
| 992 | chr9: 139096665-139096993 |
| 993 | chr7: 155174128-155175248 |
| 994 | chr14: 36993488-36994488 |
| 995 | chr3: 138654837-138655363 |
| 996 | chr4: 5709985-5710495 |
| 997 | chr15: 23157794-23158624 |
| 998 | chr20: 9496471-9496893 |
| 999 | chr4: 174437914-174438346 |
| 1000 | chr5: 140305712-140307193 |
| 1001 | chr15: 79576059-79576270 |
| 1002 | chr14: 38678245-38680937 |
| 1003 | chr10: 102473206-102474026 |
| 1004 | chr17:59486727-59487132 |
| 1005 | chr3: 64253533-64253819 |
| 1006 | chr10: 102484200-102484476 |
| 1007 | chr7: 27198182-27198514 |
| 1008 | chr2: 97192977-97193383 |
| 1009 | chr9: 77113709-77113927 |
| 1010 | chr6: 154360586-154361008 |
| 1011 | chr11:44324875-44325087 |
| 1012 | chr2: 182521221-182521927 |
| 1013 | chr7: 124404700-124406189 |
| 1014 | chr2: 132182327-132183101 |
| 1015 | chr7: 101005899-101007443 |
| 1016 | chr7: 149744402-149746469 |
| 1017 | chr8: 50822270-50822860 |
| 1018 | chr7: 27227520-27229043 |
| 1019 | chr6: 134212690-134213098 |
| 1020 | chr13: 36044844-36045481 |
| 1021 | chr11: 132934059-132934291 |
| 1022 | chr16: 51189800-51190260 |
| 1023 | chr1: 155145342-155145938 |
| 1024 | chr4: 682724-683079 |
| 1025 | chr5: 92939795-92940216 |
| 1026 | chr10: 134597357-134602649 |
| 1027 | chr1: 200009807-200010036 |
| 1028 | chr19: 12666243-12666682 |
| 1029 | chr9: 97401286-97402067 |
| 1030 | chr2: 107103833-107104053 |
| 1031 | chr15: 89910521-89912177 |
| 1032 | chr5: 140789094-140789762 |
| 1033 | chr2: 114033359-114033617 |
| 1034 | chr17: 12568667-12569335 |
| 1035 | chr11: 68622108-68622339 |
| 1036 | chr1: 160340604-160340843 |
| 1037 | chr7: 103085710-103086132 |
| 1038 | chr15: 76628998-76629207 |
| 1039 | chr20: 10198135-10198984 |
| 1040 | chr20: 44660342-44660948 |
| 1041 | chr17: 35290403-35290663 |
| 1042 | chr17: 933026-933236 |
| 1043 | chr4: 128544031-128544903 |
| 1044 | chr1: 50881884-50882103 |
| 1045 | chr10: 125425495-125426642 |
| 1046 | chr17: 46801784-46802071 |
| 1047 | chr1: 25255527-25259005 |
| 1048 | chr3: 32861141-32861429 |
| 1049 | chr17: 70116274-70119998 |
| 1050 | chr10: 75407413-75407706 |
| 1051 | chr2: 467849-468659 |
| 1052 | chr11: 132952538-132953307 |
| 1053 | chr3: 6904133-6904641 |
| 1054 | chr10: 120353692-120355821 |
| 1055 | chr7: 20830567-20830817 |
| 1056 | chr11: 71950815-71951408 |
| 1057 | chr14: 95240083-95240341 |
| 1058 | chr19: 5829048-5829474 |
| 1059 | chr20: 9495253-9495597 |
| 1060 | chr9: 112083333-112083549 |
| 1061 | chr15: 96873408-96877721 |
| 1062 | chr16: 67208067-67208678 |
| 1063 | chr1: 175568376-175568808 |
| 1064 | chr6: 5999149-5999787 |
| 1065 | chr3: 129693127-129694841 |
| 1066 | chr6: 10383525-10384114 |
| 1067 | chr11: 636435-636668 |
| 1068 | chr1: 181451311-181452049 |
| 1069 | chr9: 135464586-135466240 |
| 1070 | chr15: 60289325-60289533 |
| 1071 | chr16: 49309123-49309353 |
| 1072 | chr1: 243646394-243646888 |
| 1073 | chr12: 54071053-54071265 |
| 1074 | chr1: 91176404-91176701 |
| 1075 | chr5: 140864527-140864748 |
| 1076 | chr4: 47034427-47034940 |
| 1077 | chr10: 102489343-102491011 |
| 1078 | chr10: 102419147-102419668 |
| 1079 | chr12: 81471569-81472119 |
| 1080 | chr6: 50813314-50813699 |

TABLE 1-continued

List of CGIs

| Reference | Pos (hg19 coordinates) |
|---|---|
| 1081 | chr5: 1585 2 6133-1585 26431 |
| 1082 | chr1: 119543821-119544339 |
| 1083 | chr5: 77140542-77140914 |
| 1084 | chr8: 23567180-23567678 |
| 1085 | chr1: 41831976-41832542 |
| 1086 | chr2: 139537692-139538650 |
| 1087 | chr7: 100075303-100075551 |
| 1088 | chr2: 176969217-176969895 |
| 1089 | chr7: 27284639-27286237 |
| 1090 | chr5: 31193952-31194419 |
| 1091 | chr6: 37616393-37616621 |
| 1092 | chr19: 1748167-1750243 |
| 1093 | chr10: 101281181-101282116 |
| 1094 | chr21: 31311386-31312106 |
| 1095 | chr2: 176973427-176973718 |
| 1096 | chr15: 96900142-96900644 |
| 1097 | chr7: 158936507-158938492 |
| 1098 | chr3: 63263989-63264205 |
| 1099 | chr16: 71459781-71460338 |
| 1100 | chr7: 155601175-155603235 |
| 1101 | chr12: 54447744-54448091 |
| 1102 | chr12: 53491572-53491955 |
| 1103 | chr10: 16561604-16563822 |
| 1104 | chr11: 133994709-133995090 |
| 1105 | chr2: 137522460-137523696 |
| 1106 | chr17: 12877270-12877773 |
| 1107 | chr8: 98289604-98290404 |
| 1108 | chr4: 185937242-185937750 |
| 1109 | chr3: 185911344-185912228 |
| 1110 | chr12: 54378696-54380102 |
| 1111 | chr1: 221060850-221061071 |
| 1112 | chr12: 63543636-63544967 |
| 1113 | chr6: 6006689-6007043 |
| 1114 | chr19: 51169659-51172023 |
| 1115 | chr1: 1474962-1475220 |
| 1116 | chr14: 54418677-54418881 |
| 1117 | chr6: 108497595-108497996 |
| 1118 | chr17: 37764092-37764304 |
| 1119 | chr4: 109092578-109092839 |
| 1120 | chr1: 91182097-91182364 |
| 1121 | chr13: 112760865-112761113 |
| 1122 | chr12: 122018170-122018457 |
| 1123 | chr7: 142494563-142495248 |
| 1124 | chr13: 58203586-58204322 |
| 1125 | chr1: 92945907-92952609 |
| 1126 | chr12: 106977388-106977713 |
| 1127 | chr5: 76925445-76926875 |
| 1128 | chr16: 3190765-3191389 |
| 1129 | chr1: 12123488-12124148 |
| 1130 | chr17: 48545570-48546900 |
| 1131 | chr12: 113916433-113916717 |
| 1132 | chr4: 41747508-41747944 |
| 1133 | chr19: 46916587-46916862 |
| 1134 | chr15: 49254984-49255564 |
| 1135 | chr19: 8674332-8674764 |
| 1136 | chr2: 223167205-223167560 |
| 1137 | chr17: 1173535-1174733 |
| 1138 | chr3: 75955759-75956308 |
| 1139 | chr5: 115697134-115697589 |
| 1140 | chr8: 21644908-21647845 |
| 1141 | chr5: 59189046-59189894 |
| 1142 | chr12:54338761-54339168 |
| 1143 | chr16: 31053479-31053800 |
| 1144 | chr1: 50892437-50893243 |
| 1145 | chr17: 40935964-40936180 |
| 1146 | chr19: 44203558-44203987 |
| 1147 | chr4: 81109887-81110460 |
| 1148 | chr1: 2979275-2980758 |
| 1149 | chr16: 49872449-49872926 |
| 1150 | chr1: 200008392-200009047 |
| 1151 | chr16: 49316997-49317263 |
| 1152 | chr2: 114034594-114036041 |
| 1153 | chr2: 105480197-105480760 |
| 1154 | chr18: 44777632-44778084 |
| 1155 | chr19: 13213450-13213821 |
| 1156 | chr17: 6616422-6617471 |
| 1157 | chr14: 36977518-36977996 |
| 1158 | chr1: 214160798-214161034 |
| 1159 | chr1: 91182509-91182857 |
| 1160 | chr10: 130508443-130508658 |
| 1161 | chr2: 154728944-154729328 |
| 1162 | chr15: 89952271-89953061 |
| 1163 | chr18: 55102427-55102708 |
| 1164 | chr22: 31198491-31199033 |
| 1165 | chr10: 50821487-50821688 |
| 1166 | chr7: 100076454-100076785 |
| 1167 | chr8: 13641584-13642415 |
| 1168 | chr18: 13868532-13869026 |
| 1169 | chr6: 168841438-168841699 |
| 1170 | chr1: 61515875-61516831 |
| 1171 | chr7: 32110063-32110910 |
| 1172 | chr7: 56355508-56355798 |
| 1173 | chr19: 12767749-12767980 |
| 1174 | chr19: 19371675-19372393 |
| 1175 | chr14: 69256676-69257036 |
| 1176 | chr17: 75447477-75447821 |
| 1177 | chr14: 24801680-24802153 |
| 1178 | chr5: 148033472-148034080 |
| 1179 | chr10: 125650820-125651373 |
| 1180 | chr11: 43568921-43569854 |
| 1181 | chr22: 37212769-37213467 |
| 1182 | chr2: 162283581-162284677 |
| 1183 | chr8: 130995921-130996149 |
| 1184 | chr11: 70508328-70508617 |
| 1185 | chr16: 88943427-88943669 |
| 1186 | chr19: 42891311-42891646 |
| 1187 | chr15: 53079220-53079579 |
| 1188 | chr17: 46690390-46691055 |
| 1189 | chr4: 41880224-41880500 |
| 1190 | chr1: 156105707-156106171 |
| 1191 | chr6: 5997027-5997414 |
| 1192 | chr1: 18964180-18964401 |
| 1193 | chr14: 36983440-36983738 |
| 1194 | chr12: 54445876-54446113 |
| 1195 | chr5: 87968635-87968907 |
| 1196 | chr1: 29587087-29587412 |
| 1197 | chr11: 60718428-60718888 |
| 1198 | chr2: 66672431-66673636 |
| 1199 | chr4: 81119095-81119391 |
| 1200 | chr10: 76573195-76573507 |
| 1201 | chr22: 42322043-42322909 |
| 1202 | chr19: 45898879-45900315 |
| 1203 | chr14: 95826675-95826941 |
| 1204 | chr17: 48194634-48195085 |
| 1205 | chr19: 49669275-49669552 |
| 1206 | chr15: 96897596-96898046 |
| 1207 | chr19: 40314926-40315144 |
| 1208 | chr9: 120507227-120507642 |
| 1209 | chr5: 145722467-145722925 |
| 1210 | chr3: 19188246-19188772 |
| 1211 | chr5: 140787447-140788044 |
| 1212 | chr9: 50881418-50881664 |
| 1213 | chr10: 102896342-102896665 |
| 1214 | chr7: 53286851-53287192 |
| 1215 | chr15: 89903446-89903720 |
| 1216 | chr10: 23461300-23461610 |
| 1217 | chr2: 127783081-127783311 |
| 1218 | chr11: 72532612-72533774 |
| 1219 | chr2: 119605200-119605620 |
| 1220 | chr18: 12254147-12255089 |
| 1221 | chr7: 100817759-100817975 |
| 1222 | chr14: 77736733-77737772 |
| 1223 | chr12: 127212279-127212529 |
| 1224 | chr2: 119606569-119606826 |
| 1225 | chr1: 155264318-155265536 |
| 1226 | chr12: 131199824-131200157 |
| 1227 | chr1: 91300979-91301891 |
| 1228 | chr6: 100909210-100909444 |
| 1229 | chr6: 4079052~4079443 |
| 1230 | chr2: 233251361-233253414 |
| 1231 | chr4: 960505-960836 |
| 1232 | chr19: 21769189-21769786 |

TABLE 1-continued

List of CGIs

| Reference | Pos (hg19 coordinates) |
|---|---|
| 1233 | chr10: 102279162-102279730 |
| 1234 | chr12: 127210778-127211651 |
| 12.35 | chr12: 54069625-54070177 |
| 1236 | chr15: 53087211-53087488 |
| 1237 | chr13:28365545-28365785 |
| 1238 | chr12: 113913615-113914322 |
| 1239 | chr14: 51338712-51339146 |
| 1240 | chr7: 155604725-155605095 |
| 1241 | chr3: 62364017-62364316 |
| 1242 | chr6: 6008857~6009299 |
| 1243 | chr3: 46618307-46618669 |
| 1244 | chr17: 33776553-33776888 |
| 1245 | chr12: 58158855-58160000 |
| 1246 | chr2: 219857682-219858917 |
| 1247 | chr19: 44278273-44278777 |
| 1248 | chr10: 101282725-101282934 |
| 1249 | chr20: 2539133-2539877 |
| 1250 | chr12: 58003880-58004249 |
| 1251 | chr16: 51147490-51147944 |
| 1252 | chr1: 179544720-179545307 |
| 1253 | chr2: 71787430-71787897 |
| 1254 | chr10: 129534410-129537366 |
| 1255 | chr6: 42145847-42146053 |
| 1256 | chr14: 24802927-24803159 |
| 1257 | chr22: 29707479-29707797 |
| 1258 | chr9: 132459587-132460017 |
| 1259 | chr17: 40937258-40937480 |
| 1260 | chr4: 151504011-151505085 |
| 1261 | chr1: 18967251-18968119 |
| 1262 | chr19: 56598038-56600296 |
| 1263 | chr19: 35633409-35633697 |
| 1264 | chr2: 171678546-171680358 |
| 1265 | chr6: 134638797-134639021 |
| 1266 | chr1: 36549554-36549965 |
| 1267 | chr19: 12833104-12833574 |
| 1268 | chr3: 137487429-137488021 |
| 1269 | chr9: 139715663-139716441 |
| 1270 | chr6: 37617863-37618147 |
| 1271 | chr17: 32484007-32484280 |
| 1272 | chr7: 156409577-156409865 |
| 1273 | chr5: 11384681-11385521 |
| 1274 | chr8: 102504478-102504841 |
| 1275 | chr20: 33296514-33298242 |
| 1276 | chr20: 57415135-57417153 |
| 1277 | chr10: 71331449-71331691 |
| 1278 | chr3: 75667777-75669067 |
| 1279 | chr16: 67571252-67572728 |
| 1280 | chr19: 36500169-36500530 |
| 1281 | chr2: 154729613-154729918 |
| 1282 | chr12: 48399168-48399372 |
| 1283 | chr4: 41867385-41867586 |
| 1284 | chr17: 46800533-46800746 |
| 1285 | chr20: 44685771-44687610 |
| 1286 | chr19: 10406934-10407342 |
| 1287 | chr6: 108496715-108497320 |
| 1288 | chr5: 158523906-158524598 |
| 1289 | chr9: 124413512-124414193 |
| 1290 | chr20: 57427691-57427995 |
| 1291 | chr16: 10912159-10912719 |
| 1292 | chr7: 149389654-149389976 |
| 1293 | chr1: 173638662-173639045 |
| 1294 | chr19: 55597977-55598887 |
| 1295 | chr14: 62279037-62279339 |
| 1296 | chr3: 13114627-13115245 |
| 1297 | chr2: 3750828-3751927 |
| 1298 | chr4: 85402764-85403175 |
| 1299 | chr17: 74017769-74018658 |
| 1300 | chr5: 54523676-54523901 |
| 1301 | chr7: 89747892-89749036 |
| 1302 | chr18: 72916107-72917233 |
| 1303 | chr9: 136294738-136295236 |
| 1304 | chr1: 201252452-201253648 |
| 1305 | chr5: 146888750-146889840 |
| 1306 | chr14: 52734207-52735486 |
| 1307 | chr13: 20875518-20876214 |
| 1308 | chr18: 77560088-77560292 |
| 1309 | chr2: 102803672-102804556 |
| 1310 | chr2: 176982107-176982402 |
| 1311 | chr17: 6679205-6679710 |
| 1312 | chr19: 10463626-10464378 |
| 1313 | chr5: 140810494-140812617 |
| 1314 | chr11: 46299544-46300216 |
| 1315 | chr11: 64136814-64138187 |
| 1316 | chr6: 6007387-6007797 |
| 1317 | chr17: 37321482-37322099 |
| 1318 | chr10: 94455524-94455896 |
| 1319 | chr13: 51417371-51418149 |
| 1320 | chr8: 11565217-11567212 |
| 1321 | chr1: 226127112-226127695 |
| 1322 | chr2: 3287874-3288228 |
| 1323 | chr6: 10882926-10883149 |
| 1324 | chr22: 19746155-19746369 |
| 1325 | chr3: 12838471-12838782 |
| 1326 | chr9: 36739534-36739782 |
| 1327 | chr9: 134429866-134430491 |
| 1328 | chr11: 70672834-70673055 |
| 1329 | chr14: 24641053-24642220 |
| 1330 | chr7: 27283408-27283614 |
| 1331 | chr12: 49182421-49182658 |
| 1332 | chr1: 44031286-44031853 |
| 1333 | chr1: 114696886-114697185 |
| 1334 | chr15: 89901914-89902785 |
| 1335 | chr11: 65352231-65353134 |
| 1336 | chr7: 72838383-72838815 |
| 1337 | chr22: 38379093-38379964 |
| 1338 | chr4: 155663809-155664315 |
| 1339 | chr9: 100619984-100620192 |
| 1340 | chr7: 143582125-143582610 |
| 1341 | chr7: 23287221-23287508 |
| 1342 | chr11: 64815040-64815722 |
| 1343 | chr2: 87088816-87089037 |
| 1344 | chr20: 57426729-57427047 |
| 1345 | chr10: 43428167-43429460 |
| 1346 | chr10: 121577529-121578385 |
| 1347 | chr4: 190939801-190940591 |
| 1348 | chr6: 100037323-100037544 |
| 1349 | chr19: 12880574-12880888 |
| 1350 | chr2: 171670110-171670549 |
| 1351 | chr7: 124404174-124404432 |
| 1352 | chr7: 97840559-97840845 |
| 1353 | chr19: 50879606-50880094 |
| 1354 | chr1: 113265573-113265787 |
| 1355 | chr19: 2424005-2427983 |
| 1356 | chr3: 127633993-127634588 |
| 1357 | chr10: 50817095-50817309 |
| 1358 | chr2: 171676552-171676980 |
| 1359 | chr1: 86621278-86622871 |
| 1360 | chr1: 164545540-164545917 |
| 1361 | chr22: 19967279-19967808 |
| 1362 | chr11: 67350928-67351953 |
| 1363 | chr20: 36226617-36226841 |
| 1364 | chr19: 14089570-14089796 |
| 1365 | chr19: 38700333-38700577 |
| 1366 | chr1: 18435566-18435904 |
| 1367 | chr8: 21905461-21905757 |
| 1368 | chr2: 176950595-176950846 |
| 1369 | chr17: 75251958-75252180 |
| 1370 | chr15: 37390175-37390380 |
| 1371 | chr9: 98113447-98113662 |
| 1372 | chr1: 40235767-40237190 |
| 1373 | chr8: 144811237-144811446 |
| 1374 | chr8: 99984584-99985072 |
| 1375 | chr7: 152621916-152622149 |
| 1376 | chr1: 40769186-40769871 |
| 1377 | chr19: 2428349-2428731 |
| 1378 | chr17: 15820620-15821325 |
| 1379 | chr22: 25081850-25082112 |
| 1380 | chr1: 19203874-19204234 |
| 1381 | chr20: 61703526-61704022 |
| 1382 | chr2: 237080188-237080432 |
| 1383 | chr1: 156338758-156339251 |
| 1384 | chr1: 149332993-149333389 |

TABLE 1-continued

List of CGIs

| Reference | Pos (hg19 coordinates) |
|---|---|
| 1385 | chr22: 50496441-50497393 |
| 1386 | chr7: 27146069-27146600 |
| 1387 | chr13: 100547633-100548911 |
| 1388 | chr4: 190939007-190939274 |
| 1389 | chr7: 73894815-73895110 |
| 1390 | chr19: 35632356-35632572 |
| 1391 | chr16: 67918679-67918909 |
| 1392 | chr2: 108602824-108603467 |
| 1393 | chr2: 238864315-238865170 |
| 1394 | chr8: 144808221-144810978 |
| 1395 | chr8: 145101631-145101834 |
| 1396 | chr12: 132905449-132906206 |
| 1397 | chr6: 99275763-99276038 |
| 1398 | chr5: 140800760-140801072 |
| 1399 | chr17: 75242871-75243613 |
| 1400 | chr17: 41278134-41278460 |
| 1401 | chr12: 122016170-122017693 |
| 1402 | chr10: 131264948-131265710 |
| 1403 | chr17: 46631800-46632212 |
| 1404 | chr14: 105167277-105167501 |
| 1405 | chr10: 23982382-23982589 |
| 1406 | chr19: 50931270-50931638 |
| 1407 | chr3: 27771638-27771942 |
| 1408 | chr18: 74799144-74800038 |
| 1409 | chr1: 21616380-21617101 |
| 1410 | chr1: 147782066-147782473 |
| 1411 | chr7: 6590563-6590957 |
| 1412 | chr7: 97839862-97840222 |
| 1413 | chr12: 113914440-113914657 |
| 1414 | chr19: 7933263-7934898 |
| 1415 | chr20: 22559553-22560001 |
| 1416 | chr15: 53086629-53086858 |
| 1417 | chr10: 94180315-94180754 |
| 1418 | chr5: 140052059-140053381 |
| 1419 | chr10: 101287162-101287920 |
| 1420 | chr14: 38677154-38677787 |
| 1421 | chr22: 39262338-39263211 |
| 1422 | chr18: 74153239-74155073 |
| 1423 | chr15: 59157045-59157594 |
| 1424 | chr4: 963804-964115 |
| 1425 | chr11: 624780-625053 |
| 1426 | chr7: 1362811-1363643 |
| 1427 | chr19: 36246328-36247982 |
| 1428 | chr5: 54528095-54528404 |
| 1429 | chr12: 54359658-54359906 |
| 1430 | chr2: 127782613-127782829 |
| 1431 | chr19: 406131-406611 |
| 1432 | chr17: 46697413-46697701 |
| 1433 | chr18: 43608140-43608510 |
| 1434 | chr16: 23724270-23724775 |
| 1435 | chr18: 55922987-55924068 |
| 1436 | chr15: 60291879-60292167 |
| 1437 | chr14: 92788913-92789204 |
| 1438 | chr19: 1108394-1109610 |
| 1439 | chr11: 124628367-124629590 |
| 1440 | chr1: 32052471-32052771 |
| 1441 | chr19: 11594372-11594987 |
| 1442 | chr19: 870774-871318 |
| 1443 | chr2: 54086776-54087266 |
| 1444 | chr2: 241459632-241460047 |
| 1445 | chr7: 127990926-127992616 |
| 1446 | chr1: 208132327-208133117 |
| 1447 | chr7: 90893567-90896683 |
| 1448 | chr1: 41284847-41285149 |
| 1449 | chr11: 32452144-32452708 |
| 1450 | chr5: 77146998-77147785 |
| 1451 | chr19: 45901452-45901688 |
| 1452 | chr7: 6661875-6662695 |
| 1453 | chr6: 161188084-161188639 |
| 1454 | chr17: 934417-935088 |
| 1455 | chr11: 65409636-65410127 |
| 1456 | chr17: 19883325-19883610 |
| 1457 | chr18: 77549524-77550299 |
| 1458 | chr1: 38461584-38461988 |
| 1459 | chr19: 10464666-10464927 |
| 1460 | chr17: 70120139-70120442 |
| 1461 | chr7: 27147589-27148389 |
| 1462 | chr2: 31806545-31806782 |
| 1463 | chr11: 119292689-119292891 |
| 1464 | chr19: 18979351-18981200 |
| 1465 | chr6: 42879279-42879623 |
| 1466 | chr12: 130908777-130909191 |
| 1467 | chr17: 46629553-46629816 |
| 1468 | chr1: 202162958-202163390 |
| 1469 | chr17: 21367114-21367592 |
| 1470 | chr16: 84001805-84002011 |
| 1471 | chr1: 221057463-221057757 |
| 1472 | chr17: 27899511-27900067 |
| 1473 | chr15: 40268581-40269061 |
| 1474 | chr22: 37465056-37465331 |
| 1475 | chr17: 77805866-77809046 |
| 1476 | chr19: 13198699-13198999 |
| 1477 | chr3: 184056419-184056671 |
| 1478 | chr22: 37911979-37912258 |
| 1479 | chr19: 19368708-19369681 |
| 1480 | chr11: 64135815-64136381 |
| 1481 | chr18: 77552401-77552603 |
| 1482 | chr19: 58554354-58554587 |
| 1483 | chr20: 57414595-57414896 |
| 1484 | chr4: 190938106-190938848 |
| 1485 | chr5: 172110282-172111166 |
| 1486 | chr16: 68480864-68482822 |
| 1487 | chr9: 139395020-139395287 |
| 1488 | chr12: 113515164-113515970 |
| 1489 | chr1: 221054554-221054888 |
| 1490 | chr8: 144990270-145002135 |
| 1491 | chr9: 131154346-131155923 |
| 1492 | chr6: 150335525-150336278 |
| 1493 | chr9: 115824684-115825033 |
| 1494 | chr12: 54519768-54520457 |
| 1495 | chr6: 35479872-35480154 |
| 1496 | chr19: 3870788-3871043 |
| 1497 | chr19: 48965002-48965792 |
| 1498 | chr6: 35479388-35479678 |
| 1499 | chr12: 52408381-52408675 |
| 1500 | chr1: 221068782-221069159 |
| 1501 | chr6: 46655262-46656738 |
| 1502 | chr3: 55508336-55508708 |
| 1503 | chr1: 39980365-39981768 |
| 1504 | chr16: 3067521-3068358 |
| 1505 | chr1: 1473107-1473342 |
| 1506 | chr10: 105362549-105362827 |
| 1507 | chr17: 46698880-46699083 |
| 1508 | chr2: 198029068-198029438 |
| 1509 | chr20: 17209418-17209622 |
| 1510 | chr12: 49183049-49183282 |
| 1511 | chr16: 58030214-58031633 |
| 1512 | chr10: 94820026-94823252 |
| 1513 | chr11: 725596-726870 |
| 1514 | chr6: 170732119-170732442 |
| 1515 | chr12: 120835586-120835927 |
| 1516 | chr20: 36012595-36013439 |
| 1517 | chr8: 143545445-143546178 |
| 1518 | chr6: 27228100-27228364 |
| 1519 | chr21: 32624144-32624382 |
| 1520 | chr9: 95477296-95477708 |
| 1521 | chr10: 105420685-105421076 |
| 1522 | chr1: 1470604-1471450 |
| 1523 | chr1: 146552328-146552577 |
| 1524 | chr19: 33625467-33625805 |
| 1525 | chr11: 64478843-64479598 |
| 1526 | chr20: 57428308-57428516 |
| 1527 | chr7: 27182613-27185562 |
| 1528 | chr9: 51815157-51815458 |
| 1529 | chr17: 46607804-46608390 |
| 1530 | chr12: 52408860-52409121 |
| 1531 | chr19: 10405924-10406398 |
| 1532 | chr11: 14993452-14993661 |
| 1533 | chr19: 13135317-13136169 |
| 1534 | chr7: 750788-751237 |
| 1535 | chr1: 53742297-53742845 |
| 1536 | chr1: 200010625-200010832 |

TABLE 1-continued

List of CGIs

| Reference | Pos (hg19 coordinates) |
|---|---|
| 1537 | chr5: 139138875-139139242 |
| 1538 | chr17: 45949676-45949885 |
| 1539 | chr3: 128722283-128723036 |
| 1540 | chr15: 89312719-89313183 |
| 1541 | chr9: 135039673-135039978 |
| 1542 | chr19: 12831793-12832225 |
| 1543 | chr20: 51589707-51590020 |
| 1544 | chr20: 3145121-3145746 |
| 1545 | chr8: 65710990-65711722 |
| 1546 | chr11: 128694084-128694688 |
| 1547 | chr2: 20870006-20871280 |
| 1548 | chr19: 18977466-18977833 |
| 1549 | chr3: 49947621-49948430 |
| 1550 | chr6: 30139718-30140263 |
| 1551 | chr12: 104697348-104697984 |
| 1552 | chr10: 105361784-105362188 |
| 1553 | chr6: 29894140-29895117 |
| 1554 | chr4: 187219320-187219745 |
| 1555 | chr15: 67073306-67073943 |
| 1556 | chr2: 220412341-220412678 |
| 1557 | chr6: 170730395-170730887 |
| 1558 | chr9: 115822071-115823416 |
| 1559 | chr1: 10764449-10764925 |
| 1560 | chr17: 46627787-46628444 |
| 1561 | chr19: 51601822-51602260 |
| 1562 | chr19: 55814067-55814278 |
| 1563 | chr6: 138745348-138745593 |
| 1564 | chr9: 124987743-124991086 |
| 1565 | chr2: 46318693-46319087 |
| 1566 | chr16: 3013016-3013228 |
| 1567 | chr4: 114900355-114900810 |
| 1568 | chr19: 1063544-1064265 |
| 1569 | chr19: 1110399-1110701 |
| 1570 | chr7: 97841636-97842005 |
| 1571 | chr8: 57359899-57360114 |
| 1572 | chr17: 72915568-72916510 |
| 1573 | chr1: 16860873-16862296 |
| 1574 | chr17: 75398284-75398527 |
| 1575 | chr9: 139397412-139397710 |
| 1576 | chr6: 33393592-33393908 |
| 1577 | chr6: 29595298-29595795 |
| 1578 | chr12: 6438272-6438931 |
| 1579 | chr3: 113160299-113160641 |
| 1580 | chr1: 55505060-55506015 |
| 1581 | chr11: 132951692-132952260 |
| 1582 | chr4: 81118137-81118603 |
| 1583 | chr19: 38876070-38876332 |
| 1584 | chr19: 58549305-58549712 |
| 1585 | chr17: 43472527-43474343 |
| 1586 | chr9: 139396205-139397040 |
| 1587 | chr16: 3192181-3192669 |
| 1588 | chr6: 33048416-33048814 |
| 1589 | chr7: 128555329-128556650 |
| 1590 | chr19: 46915311-46915802 |
| 1591 | chr6: 30095173-30095610 |

TABLE 2

Example CGIs
Human CGI (hg19)

| | |
|---|---|
| chr1: 1181756-1182470 | chr12: 103696090-103696418 |
| chr1: 1470604-1471450 | chr12: 104697348-104697984 |
| chr1: 2772126-2772665 | chr12: 106974412-106974951 |
| chr1: 4713989-4716555 | chr12: 113013099-113013529 |
| chr1: 18436551-18437673 | chr12: 113515164-113515970 |
| chr1: 18956895-18959829 | chr12: 113916433-113916717 |
| chr1: 18962842-18963481 | chr12: 114833911-114834210 |
| chr1: 18967251-18968119 | chr12: 114838312-114838889 |
| chr1: 19203874-19204234 | chr12: 114843022-114843610 |
| chr1: 21616380-21617101 | chr12: 114845861-114847650 |
| chr1: 25255527-25259005 | chr12: 114851957-114852360 |
| chr1: 29585897-29586598 | chr12: 114881649-114881937 |

TABLE 2-continued

Example CGIs
Human CGI (hg19)

| | |
|---|---|
| chr1: 34628783-34630976 | chr12: 114885105-114885418 |
| chr1: 39980365-39981768 | chr12: 119212110-119212393 |
| chr1: 40235767-40237190 | chr12: 123754049-123754373 |
| chr1: 41831976-41832542 | chr12: 127210778-127211651 |
| chr1: 46951168-46951792 | chr12: 127940451-127940907 |
| chr1: 47909712-47911020 | chr12: 129337870-129338653 |
| chr1: 53742297-53742845 | chr12: 131199824-131200157 |
| chr1: 55505060-55506015 | chr12: 132905449-132906206 |
| chr1: 61515875-61516831 | chr13: 20875518-20876214 |
| chr1: 63782394-63790471 | chr13: 28366549-28368505 |
| chr1: 65731411-65731849 | chr13: 28549839-28550246 |
| chr1: 66258440-66258918 | chr13: 36044844-36045481 |
| chr1: 77747314-77748224 | chr13: 51417371-51418149 |
| chr1: 91172102-91172771 | chr13: 53419897-53422872 |
| chr1: 91176404-91176701 | chr13: 58203586-58204322 |
| chr1: 92945907-92952609 | chr13: 58206526-58208930 |
| chr1: 115880167-115881332 | chr13: 79181944-79182222 |
| chr1: 116380359-116382364 | chr13: 93879245-93880877 |
| chr1: 156105707-156106171 | chr13: 100547633-100548911 |
| chr1: 156338758-156339251 | chr13: 100641334-100642188 |
| chr1: 156358050-156358252 | chr13: 102568425-102569495 |
| chr1: 156390403-156391581 | chr13: 112707804-112708696 |
| chr1: 160340604-160340843 | chr13: 112709884-112712665 |
| chr1: 161695637-161697298 | chr13: 112715359-112716234 |
| chr1: 177133392-177133846 | chr13: 112717125-112717421 |
| chr1: 180198119-180204975 | chr13: 112720564-112723582 |
| chr1: 197887088-197887791 | chr13: 112726281-112728419 |
| chr1: 201252452-201253648 | chr13: 112758598-112760491 |
| chr1: 202678881-202679769 | chr13: 112760865-112761113 |
| chr1: 214156000-214156851 | chr14: 24044886-24046760 |
| chr1: 214158726-214159080 | chr14: 24641053-24642220 |
| chr1: 221057463-221057757 | chr14: 24803678-24804353 |
| chr1: 221067447-221068185 | chr14: 29236835-29237832 |
| chr1: 226075150-226075680 | chr14: 29254365-29255069 |
| chr1: 248020330-248021252 | chr14: 33402094-33404079 |
| chr10: 50602989-50606783 | chr14: 36973169-36973740 |
| chr10: 50817601-50820356 | chr14: 36983440-36983738 |
| chr10: 71331926-71333392 | chr14: 36990873-36991209 |
| chr10: 88122924-88127364 | chr14: 36993488-36994488 |
| chr10: 94820026-94823252 | chr14: 37053134-37053690 |
| chr10: 101279941-101280382 | chr14: 37126786-37128274 |
| chr10: 101281181-101282116 | chr14: 37135513-37136348 |
| chr10: 102419147-102419668 | chr14: 38724254-38725537 |
| chr10: 102473206-102474026 | chr14: 48143433-48145589 |
| chr10: 102484200-102484476 | chr14: 51338712-51339146 |
| chr10: 102489343-102491011 | chr14: 52734207-52735486 |
| chr10: 102507482-102509646 | chr14: 57260878-57262123 |
| chr10: 102893660-102895059 | chr14: 57264638-57265561 |
| chr10: 102896342-102896665 | chr14: 57278709-57279116 |
| chr10: 102899822-102900263 | chr14: 58331676-58333121 |
| chr10: 102975969-102978096 | chr14: 60973772-60974123 |
| chr10: 105361784-105362188 | chr14: 60975732-60978180 |
| chr10: 105420685-105421076 | chr14: 61103978-61104663 |
| chr10: 106399567-106402812 | chr14: 62279476-62280019 |
| chr10: 118899247-118900329 | chr14: 77736733-77737772 |
| chr10: 119000435-119001530 | chr14: 85997468-85998637 |
| chr10: 119311204-119312104 | chr14: 85999532-86000478 |
| chr10: 119312766-119313563 | chr14: 92789494-92790712 |
| chr10: 124905634-124906161 | chr14: 95239375-95239679 |
| chr10: 124907283-124911035 | chr14: 95826675-95826941 |
| chr10: 129534410-129537366 | chr14: 101192851-101193499 |
| chr11: 725596-726870 | chr14: 101923575-101925995 |
| chr11: 8190226-8190671 | chr14: 103655241-103655928 |
| chr11: 17740789-17743779 | chr15: 23157794-23158624 |
| chr11: 20181200-20182325 | chr15: 27112030-27113479 |
| chr11: 20622720-20623399 | chr15: 27215951-27216856 |
| chr11: 31825743-31826967 | chr15: 33602816-33604003 |
| chr11: 31839363-31839813 | chr15: 35046443-35047480 |
| chr11: 31848487-31848776 | chr15: 37390175-37390380 |
| chr11: 32452144-32452708 | chr15: 53076187-53077926 |
| chr11: 32454874-32457311 | chr15: 53079220-53079579 |
| chr11: 36397926-36399398 | chr15: 53080458-53083699 |
| chr11: 44327240-44327932 | chr15: 53087211-53087488 |
| chr11: 46299544-46300216 | chr15: 53097561-53098476 |
| chr11: 46366876-46367101 | chr15: 59157045-59157594 |
| chr11: 64136814-64138187 | chr15: 76630029-76630970 |
| chr11: 65352231-65353134 | chr15: 79574830-79575211 |

TABLE 2-continued

Example CGIs
Human CGI (hg19)

| | | | |
|---|---|---|---|
| chr11: 69517840-69519929 | chr15: 89147660-89149198 | chr15: 96873408-96877721 | chr18: 56887091-56887665 |
| chr11: 69831571-69832484 | chr15: 89312719-89313183 | chr16: 2228190-2230946 | chr18: 56939624-56941540 |
| chr11: 70672834-70673055 | chr15: 89903446-89903720 | chr16: 3013016-3013228 | chr18: 70533965-70536871 |
| chr11: 72532612-72533774 | chr15: 89910521-89912177 | chr16: 3190765-3191389 | chr18: 72916107-72917233 |
| chr11: 79148358-79152200 | chr15: 89952271-89953061 | chr16: 22824616-22826459 | chr18: 73167402-73167920 |
| chr11: 124629723-124629926 | chr15: 96895306-96895729 | chr16: 48844551-48845264 | chr18: 74799144-74800038 |
| chr12: 3475010-3475654 | chr15: 96903311-96903711 | chr16: 49311413-49312308 | chr18: 76732970-76734765 |
| chr12: 5018585-5021171 | chr15: 96904722-96905050 | chr16: 49314037-49316543 | chr18: 76737005-76741244 |
| chr12: 6438272-6438931 | chr15: 96909815-96910030 | chr16: 49872449-49872926 | chr18: 77547965-77549038 |
| chr12: 15475318-15475901 | chr15: 96959341-96960531 | chr16: 51147490-51147944 | chr18: 77557780-77558948 |
| chr12: 29302034-29302954 | chr15: 100913438-100914022 | chr16: 51168266-51169110 | chr19: 870774-871318 |
| chr12: 45444202-45445386 | chr16: 3067521-3068358 | chr16: 54970301-54972846 | chr19: 3868586-3869217 |
| chr12: 49183049-49183282 | chr16: 3220438-3221356 | chr16: 55513220-55513526 | chr19: 5829048-5829474 |
| chr12: 49371690-49375550 | chr16: 6068914-6070401 | chr16: 58030214-58031633 | chr19: 8674332-8674764 |
| chr12: 49484920-49485178 | chr16: 10912159-10912719 | chr16: 62069121-62070634 | chr19: 10406934-10407342 |
| chr12: 53491572-53491955 | chr16: 20084707-20085305 | chr16: 67208067-67208678 | chr19: 10463626-10464378 |
| chr12: 54338761-54339168 | chr16: 23724270-23724775 | chr16: 67571252-67572728 | chr19: 12666243-12666682 |
| chr12: 54366815-54369103 | chr16: 24267040-24267527 | chr16: 68480864-68482822 | chr19: 12767749-12767980 |
| chr12: 54378696-54380102 | chr16: 31053479-31053800 | chr16: 86530747-86532994 | chr19: 12831793-12832225 |
| chr12: 54423427-54423712 | chr16: 49309123-49309353 | chr16: 86549069-86550512 | chr19: 12880574-12880888 |
| chr12: 54440642-54441543 | chr16: 49316997-49317263 | chr16: 86612188-86613821 | chr19: 13124959-13125259 |
| chr12: 54447744-54448091 | chr16: 51183699-51188763 | chr16: 88943427-88943669 | chr19: 13616752-13617267 |
| chr12: 54519768-54520457 | chr16: 54325040-54325703 | chr17: 12568667-12569335 | chr19: 14089570-14089796 |
| chr12: 57618769-57619402 | chr16: 55364823-55365483 | chr17: 14248391-14248721 | chr19: 19371675-19372393 |
| chr12: 58003880-58004249 | chr16: 66612749-66613412 | chr17: 32484007-32484280 | chr19: 21769189-21769786 |
| chr12: 58158855-58160000 | chr16: 67918629-67918909 | chr17: 35291899-35300875 | chr19: 33625467-33625805 |
| chr12: 63543636-63544967 | chr16: 71459781-71460338 | chr17: 37764092-37764304 | chr19: 36246328-36247982 |
| chr12: 75602991-75603344 | chr16: 82660651-82661813 | chr17: 40937258-40937480 | chr19: 36523391-36523887 |
| chr12: 99139386-99139769 | chr16: 84002269-84002860 | chr17: 43472527-43474343 | chr19: 38700333-38700577 |
| chr12: 101109863-101111622 | chr17: 934417-935088 | chr17: 45949676-45949988 | chr19: 39737689-39737908 |
| chr12: 106979429-106981086 | chr17: 1173535-1174733 | chr17: 46607804-46608390 | chr19: 39754973-39756540 |
| chr12: 113590806-113591304 | chr17: 1880789-1881116 | chr17: 46620367-46621373 | chr19: 40314926-40315144 |
| chr12: 113900750-113906442 | chr17: 5000369-5001205 | chr17: 46631800-46632212 | chr19: 44203558-44203987 |
| chr12: 113908887-113910681 | chr17: 6616422-6617471 | chr17: 46669434-46669811 | chr19: 44278273-44278777 |
| chr12: 113913615-113914322 | chr17: 6679205-6679710 | chr17: 46691520-46692097 | chr19: 45260352-45261809 |
| chr12: 114878143-114879155 | chr17: 7832532-7833164 | chr17: 48194634-48195085 | chr19: 46001830-46002686 |
| chr12: 114886354-114886579 | chr17: 7905927-7907445 | chr17: 50235175-50236466 | chr19: 46318490-46319266 |
| chr12: 115109503-115110061 | chr17: 12877270-12877773 | chr17: 59485573-59485780 | chr19: 46915311-46915802 |
| chr12: 117798076-117799448 | chr17: 14201726-14202052 | chr17: 59528979-59530266 | chr19: 47151768-47153125 |
| chr12: 120835586-120835927 | chr17: 15820620-15821325 | chr17: 70116274-70119998 | chr19: 49669275-49669552 |
| chr12: 122016170-122017693 | chr17: 19883325-19883610 | chr17: 70120139-70120442 | chr19: 51601822-51602260 |
| chr12: 130387609-130389139 | chr17: 21367114-21367592 | chr17: 72855621-72858012 | chr19: 51815157-51815458 |
| chr12: 130908777-130909191 | chr17: 27899511-27900067 | chr17: 72915568-72916510 | chr19: 54412710-54413087 |
| chr13: 27334226-27335205 | chr17: 33776553-33776888 | chr17: 74017769-74018658 | chr19: 54481412-54481955 |
| chr13: 28498226-28499046 | chr17: 36717727-36718593 | chr17: 77805866-77809046 | chr19: 54483021-54483572 |
| chr13: 36049570-36050159 | chr17: 37321482-37322099 | chr17: 79314962-79320653 | chr19: 55597977-55598887 |
| chr13: 36052553-36053119 | chr17: 43037166-43037740 | chr17: 79859808-79860963 | chr19: 56988313-56989741 |
| chr13: 79182859-79183880 | chr17: 46604362-46604881 | chr18: 19744936-19752363 | chr19: 58094739-58095764 |
| chr13: 84453664-84453897 | chr17: 46627787-46628444 | chr18: 30349690-30352302 | chr19: 58545115-58545897 |
| chr13: 108518334-108518633 | chr17: 46673532-46674181 | chr18: 35144907-35147628 | chr19: 58554354-58554587 |
| chr13: 109147798-109149019 | chr17: 46697413-46697701 | chr18: 55103154-55108853 | chr2: 467849-468659 |
| chr14: 36974548-36975425 | chr17: 46796234-46797292 | chr18: 55922987-55924068 | chr2: 3286324-3286530 |
| chr14: 36986362-36990576 | chr17: 46800533-46800746 | chr18: 59000683-59001692 | chr2: 5831187-5831413 |
| chr14: 37049333-37051726 | chr17: 46824785-46825372 | chr18: 74153239-74155073 | chr2: 19560963-19561650 |
| chr14: 37116188-37117628 | chr17: 48041282-48043064 | chr18: 74961556-74963822 | chr2: 20870006-20871280 |
| chr14: 38678245-38680937 | chr17: 48545570-48546900 | chr19: 407011-409511 | chr2: 25499763-25500429 |
| chr14: 54418677-54418881 | chr17: 59531723-59535254 | chr19: 1063544-1064265 | chr2: 31805293-31806403 |
| chr14: 57274607-57276840 | chr17: 70111979-70112308 | chr19: 1108394-1109610 | chr2: 45169505-45171884 |
| chr14: 57283967-57284558 | chr17: 70112824-70114271 | chr19: 1748167-1750243 | chr2: 45227644-45228783 |
| chr14: 69256676-69257036 | chr17: 71948478-71949255 | chr19: 2424005-2427798 | chr2: 45240372-45241579 |
| chr14: 74706188-74708192 | chr17: 73749618-73750178 | chr19: 7933263-7934898 | chr2: 54086776-54087266 |
| chr14: 95237622-95238211 | chr17: 74533281-74534566 | chr19: 11594372-11594987 | chr2: 63282514-63283122 |
| chr14: 105167663-105168129 | chr18: 904578-909574 | chr19: 13135317-13136169 | chr2: 63283936-63284147 |
| chr15: 33009530-33011696 | chr18: 11148307-11149936 | chr19: 13198699-13198999 | chr2: 63285949-63287097 |
| chr15: 40268581-40269061 | chr18: 11750953-11752756 | chr19: 13213450-13213821 | chr2: 66652691-66654218 |
| chr15: 45408573-45409528 | chr18: 12254147-12255089 | chr19: 18979351-18981200 | chr2: 66672431-66673636 |
| chr15: 47476369-47477499 | chr18: 13641584-13642415 | chr19: 19368708-19369681 | chr2: 80549578-80549798 |
| chr15: 49254984-49255564 | chr18: 13868532-13869026 | chr19: 30715549-30715753 | chr2: 87015974-87018182 |
| chr15: 60287107-60287663 | chr18: 43608140-43608510 | chr19: 35633409-35633697 | chr2: 87088816-87089037 |
| chr15: 60296135-60298520 | chr18: 44336183-44337110 | chr19: 36336275-36337138 | chr2: 97192977-97193383 |
| chr15: 67073306-67073943 | chr18: 44337510-44338100 | chr19: 36500169-36500530 | chr2: 105480197-105480760 |
| chr15: 74419870-74423044 | chr18: 44772992-44775573 | chr19: 38876070-38876332 | chr2: 106681982-106682403 |
| chr15: 79724099-79725643 | chr18: 44777632-44778084 | chr19: 42891311-42891646 | chr2: 107103833-107104053 |
| chr15: 89914363-89915061 | chr18: 44789742-44790678 | chr19: 45898879-45900315 | chr2: 114033359-114033617 |
| chr15: 89920793-89922768 | chr18: 54788959-54789194 | chr19: 48965002-48965792 | chr2: 114034594-114036041 |
| chr15: 89949373-89951130 | chr18: 55019707-55021605 | chr19: 50881418-50881664 | chr2: 114256775-114258043 |
| chr15: 91642908-91643702 | chr18: 55094825-55096310 | chr19: 50931270-50931638 | chr2: 118981769-118982466 |

TABLE 2-continued

Example CGIs
Human CGI (hg19)

| | | | |
|---|---|---|---|
| chr19: 51169659-51172023 | chr2: 119592602-119593845 | chr3: 137482964-137484454 | chr3: 238391-240140 |
| chr19: 55815940-55816277 | chr2: 119599059-119599299 | chr3: 137489594-137491004 | chr3: 6904133-6904641 |
| chr19: 56598038-56600296 | chr2: 119602616-119604486 | chr3: 147108511-147111703 | chr3: 9177691-9178189 |
| chr2: 3750828-3751927 | chr2: 119606569-119606826 | chr3: 147113608-147114479 | chr3: 11034446-11035384 |
| chr2: 30453566-30455655 | chr2: 119611296-119611881 | chr3: 147130342-147130577 | chr3: 12838471-12838782 |
| chr2: 38301276-38304518 | chr2: 119616133-119616826 | chr3: 147131066-147131333 | chr3: 22413492-22414365 |
| chr2: 45155195-45157049 | chr2: 119914126-119916663 | chr3: 154146347-154146965 | chr3: 26664104-26664796 |
| chr2: 45395869-45398186 | chr2: 124782252-124783255 | chr3: 157821232-157821604 | chr3: 27771638-27771942 |
| chr2: 50574045-50574817 | chr2: 127413696-127414171 | chr3: 170303044-170303249 | chr3: 32861141-32861429 |
| chr2: 66808568-66809404 | chr2: 127782613-127782829 | chr3: 172165372-172166738 | chr3: 44063314-44063837 |
| chr2: 71787430-71787897 | chr2: 128421719-128422182 | chr4: 4868440-4869173 | chr3: 44596535-44597018 |
| chr2: 73143055-73148260 | chr2: 130763483-130763764 | chr4: 25090106-25090510 | chr3: 46618307-46618669 |
| chr2: 80529677-80530846 | chr2: 132182327-132183101 | chr4: 41749184-41749811 | chr3: 62356119-62356378 |
| chr2: 102803672-102804556 | chr2: 139537692-139538650 | chr4: 47034427-47034940 | chr3: 62356773-62357315 |
| chr2: 105459127-105461770 | chr2: 154727906-154728271 | chr4: 54966163-54968063 | chr3: 62362610-62363082 |
| chr2: 105468851-105473488 | chr2: 154728944-154729328 | chr4: 81119095-81119391 | chr3: 63263989-63264205 |
| chr2: 108602824-108603467 | chr2: 162279835-162280709 | chr4: 90228714-90229010 | chr3: 64253533-64253819 |
| chr2: 119599458-119600966 | chr2: 162283581-162284677 | chr4: 94755786-94756310 | chr3: 75667777-75669067 |
| chr2: 137522460-137523696 | chr2: 171671598-171671804 | chr4: 100870377-100871994 | chr3: 75955759-75956308 |
| chr2: 142887724-142888553 | chr2: 171678546-171680358 | chr4: 107956555-107957453 | chr3: 113160299-113160641 |
| chr2: 144694666-144695180 | chr2: 176931575-176932663 | chr4: 109093038-109094546 | chr3: 121902742-121903645 |
| chr2: 157185557-157186355 | chr2: 176936246-176936809 | chr4: 114900355-114900810 | chr3: 126113547-126113967 |
| chr2: 162273294-162273725 | chr2: 176944087-176948446 | chr4: 122301567-122302290 | chr3: 127633993-127634588 |
| chr2: 176949511-176949795 | chr2: 176949993-176950336 | chr4: 128544031-128544903 | chr3: 127794369-127796136 |
| chr2: 176964062-176965509 | chr2: 176956504-176956707 | chr4: 144620822-144622218 | chr3: 128719865-128721245 |
| chr2: 176969217-176969895 | chr2: 177012371-177012675 | chr4: 147559205-147561901 | chr3: 129693127-129694841 |
| chr2: 176977284-176977540 | chr2: 177016416-177016632 | chr4: 156680095-156681386 | chr3: 133393118-133393657 |
| chr2: 176982107-176982402 | chr2: 177024501-177025692 | chr4: 164264821-164265772 | chr3: 138656627-138659107 |
| chr2: 177036254-177037213 | chr2: 198029068-198029438 | chr4: 172733734-172735118 | chr3: 147126988-147128999 |
| chr2: 177042751-177043444 | chr2: 200333687-200334172 | chr4: 174430386-174430861 | chr3: 147138916-147139564 |
| chr2: 182321761-182323029 | chr2: 207506774-207507422 | chr4: 185939222-185942747 | chr3: 147142181-147142391 |
| chr2: 182521221-182521927 | chr2: 220173870-220174283 | chr5: 1879689-1879928 | chr3: 157812053-157812764 |
| chr2: 219736132-219736592 | chr2: 223159725-223160487 | chr5: 1881924-1887743 | chr3: 170303532-170303768 |
| chr2: 219848919-219850541 | chr2: 223162946-223163912 | chr5: 2748368-2757024 | chr3: 184056419-184056671 |
| chr2: 219857682-219858917 | chr2: 223167205-223167560 | chr5: 37834671-37835128 | chr3: 185911344-185912228 |
| chr2: 220299483-220300243 | chr2: 223168653-223169008 | chr5: 38257825-38259136 | chr3: 186078710-186080111 |
| chr2: 220412341-220412678 | chr2: 223176493-223177515 | chr5: 52777788-52777996 | chr3: 192125821-192127994 |
| chr2: 223183013-223185468 | chr2: 233251361-233253414 | chr5: 54527319-54527760 | chr4: 107146-107898 |
| chr2: 237071794-237078762 | chr2: 237068071-237068834 | chr5: 59189046-59189894 | chr4: 206377-206892 |
| chr2: 241758141-241760783 | chr2: 238864315-238865170 | chr5: 63256548-63257886 | chr4: 682724-683079 |
| chr20: 3145121-3145746 | chr2: 241459632-241460047 | chr5: 71014917-71015715 | chr4: 961347-962155 |
| chr20: 21485932-21496714 | chr20: 690575-691099 | chr5: 72529099-72529976 | chr4: 4859632-4860191 |
| chr20: 21686199-21687689 | chr20: 2539133-2539877 | chr5: 76932317-76933523 | chr4: 5709985-5710495 |
| chr20: 22557517-22559240 | chr20: 2729997-2730797 | chr5: 76934581-76935296 | chr4: 5891981-5892365 |
| chr20: 33296514-33298242 | chr20: 2780978-2781497 | chr5: 77805753-77806313 | chr4: 5894071-5895116 |
| chr20: 37352130-37357372 | chr20: 5296266-5297798 | chr5: 92923487-92924497 | chr4: 13524062-13526083 |
| chr20: 39994545-39995810 | chr20: 9496471-9496893 | chr5: 92939795-92940216 | chr4: 15779998-15780729 |
| chr20: 44657463-44659243 | chr20: 10198135-10198984 | chr5: 134363092-134365146 | chr4: 24801109-24801902 |
| chr20: 44685771-44687610 | chr20: 17206528-17206952 | chr5: 134366913-134367438 | chr4: 41869174-41869459 |
| chr20: 51589707-51590020 | chr20: 17208550-17208756 | chr5: 134374385-134376751 | chr4: 41875445-41875794 |
| chr20: 52789252-52790986 | chr20: 21376358-21378245 | chr5: 139138875-139139242 | chr4: 41880224-41880520 |
| chr20: 57415135-57417153 | chr20: 21694472-21695344 | chr5: 140052059-140053381 | chr4: 41882450-41882964 |
| chr21: 31311386-31312106 | chr20: 22548967-22549720 | chr5: 140305712-140307193 | chr4: 46995128-46995872 |
| chr21: 32624144-32624382 | chr20: 25063838-25065525 | chr5: 140798757-140799359 | chr4: 54975387-54976202 |
| chr21: 38065179-38066185 | chr20: 32856659-32857248 | chr5: 140810494-140812617 | chr4: 57521621-57522703 |
| chr22: 19967279-19967808 | chr20: 36012595-36013439 | chr5: 145718289-145720095 | chr4: 66535193-66535620 |
| chr22: 29709281-29712013 | chr20: 36226617-36226841 | chr5: 145725286-145725852 | chr4: 81109887-81110460 |
| chr22: 31198491-31199033 | chr20: 41817475-41819212 | chr5: 158523906-158524598 | chr4: 85403830-85404524 |
| chr22: 31500396-31501239 | chr20: 48184193-48184833 | chr5: 172665306-172666072 | chr4: 85413997-85414594 |
| chr22: 37212769-37213467 | chr20: 57089460-57090237 | chr5: 179228283-179229003 | chr4: 85422929-85423190 |
| chr22: 37911979-37912258 | chr20: 57426729-57427047 | chr6: 391188-393790 | chr4: 93226348-93227007 |
| chr22: 38476836-38478839 | chr20: 61703526-61704022 | chr6: 1381743-1385211 | chr4: 110222970-110224257 |
| chr22: 42305617-42307254 | chr21: 19617098-19617874 | chr6: 5997027-5997414 | chr4: 111554965-111555504 |
| chr22: 42322043-42322909 | chr21: 34395128-34400245 | chr6: 6007387-6007797 | chr4: 134069162-134070442 |
| chr22: 44726724-44727590 | chr21: 38076762-38077685 | chr6: 7229877-7230865 | chr4: 140201064-140201449 |
| chr22: 46318693-46319087 | chr21: 38079941-38081833 | chr6: 10390038-10390565 | chr4: 151504011-151505085 |
| chr22: 46440393-46441019 | chr21: 42218489-42219222 | chr6: 29894140-29895117 | chr4: 154709512-154710827 |
| chr3: 3840513-3842772 | chr22: 19746125-19746369 | chr6: 33393592-33393908 | chr4: 154712073-154712706 |
| chr3: 6902823-6903516 | chr22: 25081850-25082112 | chr6: 33655966-33656238 | chr4: 154713537-154714240 |
| chr3: 13114627-13115245 | chr22: 37465056-37465331 | chr6: 41908745-41909711 | chr4: 155663809-155664315 |
| chr3: 19189688-19190100 | chr22: 38379093-38379964 | chr6: 42072032-42072701 | chr4: 156129168-156130209 |
| chr3: 49947621-49948430 | chr22: 39262338-39263211 | chr6: 46655262-46656738 | chr4: 158143296-158144053 |
| chr3: 55508336-55508708 | chr22: 42685894-42686095 | chr6: 50682334-50683214 | chr4: 169799086-169799625 |
| chr3: 62354291-62355012 | chr22: 44257942-44258612 | chr6: 50791110-50791573 | chr4: 174422024-174422443 |
| chr3: 62357639-62359774 | chr22: 44287497-44288061 | chr6: 55039170-55039392 | chr4: 174427891-174428192 |
| chr3: 71834068-71834653 | chr22: 48884884-48887043 | chr6: 99275763-99276038 | chr4: 174437914-174438346 |
| chr3: 87841796-87842563 | chr22: 50496441-50497393 | chr6: 101846766-101847135 | chr4: 174439812-174440249 |

TABLE 2-continued

Example CGIs
Human CGI (hg19)

| | | | |
|---|---|---|---|
| chr6: 108485671-108490539 | chr4: 174448333-174448845 | chr1: 2979275-2980758 | chr6: 70992040-70992912 |
| chr6: 108491033-108491410 | chr4: 174450046-174451469 | chr1: 10764449-10764925 | chr6: 72298274-72298528 |
| chr6: 108497595-108497996 | chr4: 174451828-174452962 | chr1: 12123488-12124148 | chr6: 78172231-78174088 |
| chr6: 117198089-117198705 | chr4: 174459200-174460054 | chr1: 16860873-16862296 | chr6: 85472702-85474132 |
| chr6: 117591533-117592279 | chr4: 185937242-185937750 | chr1: 18964180-18964401 | chr6: 99290279-99290771 |
| chr6: 134210639-134211218 | chr4: 187219320-187219745 | chr1: 24229115-24229537 | chr6: 100038655-100039477 |
| chr6: 134638797-134639021 | chr4: 188916605-188916876 | chr1: 32052471-32052771 | chr6: 100897080-100897621 |
| chr6: 137242315-137245442 | chr4: 190938106-190938848 | chr1: 34642382-34643024 | chr6: 100903491-100903713 |
| chr6: 137814355-137815202 | chr4: 190939801-190940591 | chr1: 36549554-36549965 | chr6: 100905444-100905697 |
| chr6: 138745348-138745593 | chr5: 1874907-1879032 | chr1: 38219702-38220012 | chr6: 100905952-100906686 |
| chr7: 1362811-1363643 | chr5: 2738953-2741237 | chr1: 38461584-38461988 | chr6: 100914946-100915245 |
| chr7: 6590563-6590957 | chr5: 3590644-3592000 | chr1: 38941919-38942404 | chr6: 106429111-106429772 |
| chr7: 6661875-6662695 | chr5: 3594467-3603054 | chr1: 39044059-39044561 | chr6: 106433984-106434459 |
| chr7: 19145872-19146256 | chr5: 11384681-11385521 | chr1: 40769186-40769871 | chr6: 108495654-108495986 |
| chr7: 20370003-20371504 | chr5: 31193952-31194419 | chr1: 41284847-41285149 | chr6: 110299365-110301267 |
| chr7: 20830567-20830817 | chr5: 45695394-45696510 | chr1: 44031286-44031853 | chr6: 117869097-117869530 |
| chr7: 26415746-26416891 | chr5: 50685453-50686148 | chr1: 47009575-47010132 | chr6: 127441553-127441760 |
| chr7: 27146069-27146600 | chr5: 54519054-54519628 | chr1: 50880916-50881516 | chr6: 137809342-137810204 |
| chr7: 27182613-27185562 | chr5: 63255044-63255407 | chr1: 50881884-50882103 | chr6: 137816474-137817223 |
| chr7: 27227520-27229043 | chr5: 72526203-72526497 | chr1: 50892437-50893243 | chr6: 150335525-150336278 |
| chr7: 27278945-27279469 | chr5: 72594147-72595808 | chr1: 53527572-53528974 | chr6: 150358872-150359394 |
| chr7: 27282086-27283136 | chr5: 72676210-72678421 | chr1: 63795363-63796140 | chr6: 154360586-154361008 |
| chr7: 30721372-30722445 | chr5: 76923887-76924502 | chr1: 65991001-65991811 | chr6: 161188084-161188639 |
| chr7: 37955622-37956555 | chr5: 76936126-76936984 | chr1: 67218079-67218293 | chr6: 166579973-166583423 |
| chr7: 49813008-49815752 | chr5: 77140542-77140914 | chr1: 67773329-67773767 | chr6: 166666837-166667541 |
| chr7: 56355508-56355798 | chr5: 77146998-77147785 | chr1: 86621278-86622871 | chr6: 168841438-168841699 |
| chr7: 87563342-87564571 | chr5: 77253832-77254049 | chr1: 91183240-91184540 | chr6: 170732119-170732442 |
| chr7: 90893567-90896683 | chr5: 77268350-77268787 | chr1: 91185156-91185577 | chr7: 751712-752150 |
| chr7: 95225503-95226194 | chr5: 87968635-87968907 | chr1: 91190489-91192804 | chr7: 12151220-12151559 |
| chr7: 96650221-96651551 | chr5: 87980878-87981272 | chr1: 91300979-91301891 | chr7: 19184818-19185033 |
| chr7: 96651963-96652246 | chr5: 87985470-87985810 | chr1: 110610265-110613303 | chr7: 23287221-23287508 |
| chr7: 97841636-97842005 | chr5: 88185224-88185589 | chr1: 113265573-113265787 | chr7: 27134097-27134303 |
| chr7: 113724924-113727795 | chr5: 115697134-115697589 | chr1: 113286332-113287172 | chr7: 27147589-27148389 |
| chr7: 130790358-130792773 | chr5: 122430676-122431443 | chr1: 114695136-114696672 | chr7: 27198182-27198439 |
| chr7: 136553854-136556194 | chr5: 134385967-134386370 | chr1: 119526782-119527192 | chr7: 27203915-27206462 |
| chr7: 155595692-155599414 | chr5: 140346105-140346931 | chr1: 119529819-119530712 | chr7: 27260101-27260467 |
| chr7: 155604725-155605095 | chr5: 140787447-140788044 | chr1: 119543056-119543454 | chr7: 27291119-27292197 |
| chr7: 156795355-156799394 | chr5: 140864527-140864748 | chr1: 119549144-119551320 | chr7: 32110063-32110910 |
| chr8: 21905461-21905757 | chr5: 146888750-146889840 | chr1: 145075483-145075845 | chr7: 35296921-35298218 |
| chr8: 25900562-25905842 | chr5: 148033472-148034080 | chr1: 146552328-146552577 | chr7: 42267546-42267823 |
| chr8: 55366180-55367628 | chr5: 158478378-158478630 | chr1: 147782066-147782473 | chr7: 43152020-43153340 |
| chr8: 65710990-65711722 | chr5: 159399004-159399928 | chr1: 149332993-149333389 | chr7: 53286851-53287192 |
| chr8: 70981873-70984888 | chr5: 170735169-170739863 | chr1: 155147185-155147444 | chr7: 54612324-54612558 |
| chr8: 105478672-105479340 | chr5: 170741603-170742751 | chr1: 155264318-155265536 | chr7: 70596228-70598382 |
| chr8: 120428398-120429178 | chr5: 170743178-170744107 | chr1: 155290606-155291001 | chr7: 71800757-71802768 |
| chr8: 143545445-143546178 | chr5: 172110282-172111166 | chr1: 156863415-156863711 | chr7: 72838383-72838815 |
| chr8: 144808221-144810978 | chr5: 172659049-172660277 | chr1: 164545540-164545917 | chr7: 73894815-73895110 |
| chr8: 144990270-145002135 | chr5: 172660720-172661133 | chr1: 165324191-165326328 | chr7: 89747892-89749036 |
| chr9: 17906419-17907488 | chr5: 172661486-172662228 | chr1: 170630456-170630851 | chr7: 97361132-97363018 |
| chr9: 21970913-21971190 | chr5: 172672311-172672971 | chr1: 173638662-173639045 | chr7: 100075303-100075551 |
| chr9: 22005887-22006229 | chr5: 174158376-174159729 | chr1: 175568376-175568808 | chr7: 100817759-100817975 |
| chr9: 86152353-86153777 | chr5: 175085004-175085756 | chr1: 179544720-179545307 | chr7: 100823307-100823701 |
| chr9: 95477296-95477708 | chr5: 178421225-178422337 | chr1: 181287300-181287873 | chr7: 101005899-101007443 |
| chr9: 96713326-96718186 | chr5: 180486154-180486892 | chr1: 181452706-181453073 | chr7: 103085710-103086132 |
| chr9: 97401286-97402067 | chr6: 1378445-1379318 | chr1: 200009807-200010036 | chr7: 103968783-103969959 |
| chr9: 102590742-102591303 | chr6: 1393049-1394170 | chr1: 202162958-202163390 | chr7: 121940006-121940648 |
| chr9: 112081402-112082905 | chr6: 1619093-1621094 | chr1: 203044722-203045390 | chr7: 121950249-121950927 |
| chr9: 120175253-120177496 | chr6: 4079052-4079443 | chr1: 208132327-208133117 | chr7: 121956543-121957341 |
| chr9: 122131086-122132214 | chr6: 5999149-5999787 | chr1: 214153214-214153668 | chr7: 124404174-124404432 |
| chr9: 124413512-124414193 | chr6: 10381558-10382354 | chr1: 217310749-217311178 | chr7: 127990926-127992616 |
| chr9: 124987743-124991086 | chr6: 10881846-10882051 | chr1: 221050448-221050864 | chr7: 128555329-128556650 |
| chr9: 126773246-126780953 | chr6: 26614013-26614851 | chr1: 221060850-221061071 | chr7: 129422997-129423355 |
| chr9: 129372737-129378106 | chr6: 27228100-27228364 | chr1: 225865068-225865328 | chr7: 142494563-142495248 |
| chr9: 129386112-129389231 | chr6: 29595298-29595795 | chr1: 226127112-226127695 | chr7: 143582125-143582610 |
| chr9: 131154346-131155923 | chr6: 30095173-30095610 | chr1: 228785986-228786204 | chr7: 149389654-149389976 |
| chr9: 132459587-132460017 | chr6: 30139718-30140263 | chr1: 231296559-231297345 | chr7: 149744402-149746469 |
| chr9: 133534534-133542394 | chr6: 33048416-33048814 | chr1: 243646394-243646888 | chr7: 152621916-152622149 |
| chr9: 135039673-135039978 | chr6: 35479388-35479678 | chr10: 1778784-1780018 | chr7: 153748407-153750444 |
| chr9: 135455164-135458586 | chr6: 37616722-37617179 | chr10: 8076002-8077261 | chr7: 154001964-154002281 |
| chr9: 135461934-135462909 | chr6: 38682949-38683265 | chr10: 8077829-8078378 | chr7: 155164557-155167854 |
| chr9: 135464586-135466240 | chr6: 41528266-41528900 | chr10: 15761423-15762101 | chr7: 155174128-155175248 |
| chr9: 139096665-139096993 | chr6: 42145847-42146053 | chr10: 16561604-16563832 | chr7: 155241323-155243757 |
| chr9: 139396205-139397040 | chr6: 42879279-42879623 | chr10: 22623350-22625875 | chr7: 155258827-155261403 |
| chrX: 67352650-67352923 | chr6: 50787286-50788091 | chr10: 22634000-22634862 | chr7: 155302253-155303158 |
| chrX: 99891299-99891794 | chr6: 50810642-50810994 | chr10: 22764708-22767050 | chr7: 156409023-156409294 |
| chrX: 152612775-152613464 | chr6: 50813314-50813699 | chr10: 23461300-23461610 | chr7: 156409577-156409865 |
| chr1: 1474962-1475220 | chr6: 50818180-50818431 | chr10: 23462224-23463889 | chr7: 156801418-156801632 |

TABLE 2-continued

Example CGIs
Human CGI (hg19)

| | | | |
|---|---|---|---|
| chr10: 23480697-23482455 | chr7: 156871054-156871297 | chr11: 31827696-31827921 | chr9: 36739534-36739782 |
| chr10: 23983366-23984978 | chr7: 158936507-158938492 | chr11: 31841315-31842003 | chr9: 37002489-37002957 |
| chr10: 26504383-26507434 | chr8: 4848968-4852635 | chr11: 31847132-31847958 | chr9: 77112712-77113583 |
| chr10: 27547668-27548402 | chr8: 9760750-9761643 | chr11: 43568921-43569854 | chr9: 77113709-77113927 |
| chr10: 43428167-43429460 | chr8: 9762661-9764748 | chr11: 44325657-44326517 | chr9: 79633326-79636030 |
| chr10: 48438411-48439320 | chr8: 11536767-11538961 | chr11: 60718428-60718888 | chr9: 79637814-79638169 |
| chr10: 63212495-63213009 | chr8: 11557852-11558252 | chr11: 64478843-64479598 | chr9: 91792662-91793611 |
| chr10: 71331449-71331691 | chr8: 11565217-11567212 | chr11: 64815040-64815722 | chr9: 96108466-96108992 |
| chr10: 75407413-75407706 | chr8: 21644908-21647845 | chr11: 65409636-65410127 | chr9: 96710811-96711717 |
| chr10: 76573195-76573507 | chr8: 23562475-23565175 | chr11: 65816404-65816665 | chr9: 98111364-98112362 |
| chr10: 94180315-94180754 | chr8: 23567180-23567678 | chr11: 68622108-68622339 | chr9: 100610696-100611517 |
| chr10: 94455524-94455896 | chr8: 24812946-24814299 | chr11: 70508328-70508617 | chr9: 100619984-100620192 |
| chr10: 94828102-94829040 | chr8: 26721642-26724566 | chr11: 71952112-71952528 | chr9: 104499849-104501076 |
| chr10: 99789614-99791320 | chr8: 37822486-37824008 | chr11: 88241710-88242562 | chr9: 115822071-115823416 |
| chr10: 100992156-100992687 | chr8: 41424341-41425300 | chr11: 89224416-89224718 | chr9: 120507227-120507642 |
| chr10: 101282725-101282934 | chr8: 49468683-49468959 | chr11: 105481126-105481422 | chr9: 123656750-123656972 |
| chr10: 101290025-101290338 | chr8: 50822270-50822860 | chr11: 115630398-115631117 | chr9: 134429866-134430491 |
| chr10: 102279162-102279730 | chr8: 53851701-53854426 | chr11: 119293320-119293943 | chr9: 136294738-136295236 |
| chr10: 102475276-102475579 | chr8: 55370170-55372525 | chr11: 123066517-123066986 | chr9: 137967110-137967727 |
| chr10: 102891010-102891794 | chr8: 55378928-55380186 | chr11: 128419198-128419513 | chr9: 139715663-139716441 |
| chr10: 102905714-102906693 | chr8: 57358126-57359415 | chr11: 128694084-128694688 | |
| chr10: 102996034-102996646 | chr8: 65281903-65283028 | chr11: 131780328-131781532 | |
| chr10: 103043990-103044480 | chr8: 65286067-65286659 | chr11: 132813562-132814395 | |
| chr10: 108923780-108924805 | chr8: 65290108-65290946 | chr11: 132934059-132934291 | |
| chr10: 109674196-109674964 | chr8: 68864584-68864946 | chr11: 132952538-132953307 | |
| chr10: 110671724-110672326 | chr8: 72468560-72469561 | chr11: 133994709-133995090 | |
| chr10: 111216604-111217083 | chr8: 85096759-85097247 | chr12: 186863-187610 | |
| chr10: 118030732-118034230 | chr8: 86350765-86351196 | chr12: 3308812-3310270 | |
| chr10: 118892161-118892639 | chr8: 87081653-87082046 | chr12: 5153012-5154346 | |
| chr10: 118893527-118894432 | chr8: 97169731-97170432 | chr12: 14134626-14135242 | |
| chr10: 119494493-119494991 | chr8: 97171805-97172022 | chr12: 41086522-41087102 | |
| chr10: 120353692-120355821 | chr8: 98289604-98290404 | chr12: 48399168-48399372 | |
| chr10: 121577529-121578385 | chr8: 99960497-99961438 | chr12: 52115410-52115679 | |
| chr10: 123922850-123923542 | chr8: 99984584-99985052 | chr12: 52408381-52408675 | |
| chr10: 124901907-124902617 | chr8: 99985733-99986983 | chr12: 52652018-52652743 | |
| chr10: 125425495-125426642 | chr8: 101117922-101118693 | chr12: 53107912-53108471 | |
| chr10: 125650820-125651373 | chr8: 130995921-130996149 | chr12: 53359192-53359507 | |
| chr10: 125732220-125732843 | chr8: 132052203-132054749 | chr12: 54071053-54071265 | |
| chr10: 130338695-130338994 | chr8: 139508795-139509774 | chr12: 54321301-54321721 | |
| chr10: 130508443-130508658 | chr8: 142528185-142529029 | chr12: 54354529-54355491 | |
| chr10: 134597357-134602649 | chr8: 145103285-145108027 | chr12: 54359658-54359906 | |
| chr11: 626728-628037 | chr8: 145925410-145926101 | chr12: 54424610-54425173 | |
| chr11: 636435-636668 | chr9: 969529-973276 | chr12: 65218245-65219143 | |
| chr11: 636906-640628 | chr9: 16726859-16727273 | chr12: 65514878-65515863 | |
| chr11: 2890388-2891337 | chr9: 19788215-19789288 | chr12: 72665683-72667551 | |
| chr11: 14995128-14995908 | chr9: 23820691-23822135 | chr12: 81102034-81102716 | |
| chr11: 20618197-20619920 | chr9: 23850910-23851522 | chr12: 81471569-81472119 | |
| chr11: 27743472-27744564 | chr9: 32782936-32783625 | | |

TABLE 3

Additional Example CGIs

| | | |
|---|---|---|
| chr1: 1072370-1072847 | chr11: 65190825-65191058 | chr16: 72821141-72821592 |
| chr1: 10895896-10896117 | chr11: 65222491-65222750 | chr16: 73099813-73100791 |
| chr1: 109203594-109204378 | chr11: 65341621-65342501 | chr16: 743925-745943 |
| chr1: 1093212-1093476 | chr11: 65343330-65343849 | chr16: 78079753-78080166 |
| chr1: 110185962-110186164 | chr11: 65553750-65555573 | chr16: 80574742-80575090 |
| chr1: 110626529-110627484 | chr11: 65779312-65779767 | chr16: 80965953-80966478 |
| chr1: 110880395-110880624 | chr11: 66034752-66035054 | chr16: 84029457-84029710 |
| chr1: 111505882-111507007 | chr11: 66035217-66035447 | chr16: 84328520-84328720 |
| chr1: 111746338-111747303 | chr11: 66049751-66050229 | chr16: 84346477-84346931 |
| chr1: 113044411-113044992 | chr11: 66314208-66314455 | chr16: 84401958-84402497 |
| chr1: 113392143-113392807 | chr11: 66335576-66336151 | chr16: 85171020-85171323 |
| chr1: 113497987-113498206 | chr11: 67232299-67232558 | chr16: 85783863-85785131 |
| chr1: 1141671-1142150 | chr11: 67770427-67771629 | chr16: 85863382-85863601 |
| chr1: 11538670-11540342 | chr11: 67806252-67806611 | chr16: 85932122-85932942 |
| chr1: 116694665-116694983 | chr11: 68611251-68611807 | chr16: 86546360-86546632 |
| chr1: 116710838-116711260 | chr11: 69258150-69258544 | chr16: 87902455-87903460 |
| chr1: 11710460-11710788 | chr11: 69924339-69925197 | chr16: 88292764-88293010 |
| chr1: 11779567-11780016 | chr11: 705795-706534 | chr16: 88716990-88717606 |
| chr1: 118727817-118728097 | chr11: 70962174-70964161 | chr16: 88803803-88804112 |
| chr1: 120835962-120839391 | chr11: 71954817-71955659 | chr16: 88850205-88850537 |
| chr1: 12655927-12656248 | chr11: 720562-721369 | chr16: 89070647-89070904 |
| chr1: 1362955-1363299 | chr11: 72301303-72301746 | chr16: 89267824-89268087 |

TABLE 3-continued

Additional Example CGIs

| | | |
|---|---|---|
| chr1: 1370768-1371449 | chr11: 72463093-72463717 | chr16: 89268493-89268865 |
| chr1: 13839506-13840613 | chr11: 72492282-72492644 | chr16: 89323281-89323661 |
| chr1: 13909607-13909842 | chr11: 74022429-74022703 | chr16: 89632593-89632799 |
| chr1: 14026482-14027200 | chr11: 75236190-75237781 | chr16: 90014251-90014613 |
| chr1: 14219351-14219737 | chr11: 75917272-75917926 | chr17: 10632790-10633490 |
| chr1: 146556313-146556676 | chr11: 77122737-77123088 | chr17: 11501632-11502328 |
| chr1: 14924611-14925993 | chr11: 78673008-78673213 | chr17: 1163342-1163773 |
| chr1: 149605515-149605903 | chr11: 789872-790133 | chr17: 12692738-12693690 |
| chr1: 150254366-150254637 | chr11: 8102359-8102913 | chr17: 1390457-1390786 |
| chr1: 150266477-150266689 | chr11: 826942-827625 | chr17: 1395120-1395372 |
| chr1: 151300523-151300724 | chr11: 8284103-8285032 | chr17: 14212364-14212788 |
| chr1: 151445872-151446142 | chr11: 86382696-86383586 | chr17: 15244706-15245126 |
| chr1: 151693992-151694282 | chr11: 87908244-87908614 | chr17: 15466360-15466843 |
| chr1: 151812254-151812525 | chr11: 9025096-9026315 | chr17: 1546743-1547324 |
| chr1: 151966633-151966893 | chr11: 93583375-93583717 | chr17: 1551731-1553249 |
| chr1: 152079998-152081705 | chr11: 94473536-94474338 | chr17: 15847758-15849513 |
| chr1: 154298206-154298544 | chr11: 94501367-94502696 | chr17: 16283928-16284768 |
| chr1: 154732823-154733436 | chr11: 9634970-9636065 | chr17: 17685017-17687240 |
| chr1: 154971871-154972404 | chr11: 9779593-9780470 | chr17: 18965478-18965728 |
| chr1: 155043413-155043922 | chr11: 98891544-98891821 | chr17: 2627241-2628302 |
| chr1: 155830196-155830489 | chr12: 103350090-103350422 | chr17: 26578273-26578682 |
| chr1: 156051240-156051461 | chr12: 103351580-1032695 | chr17: 26645291-26645614 |
| chr1: 156616554-156616946 | chr12: 103359249-103359629 | chr17: 26698360-26699557 |
| chr1: 156646293-156647260 | chr12: 104850254-104852395 | chr17: 26711384-26712311 |
| chr1: 156814882-156815792 | chr12: 105478090-105478517 | chr17: 27038085-27038919 |
| chr1: 156893520-156894232 | chr12: 106532107-106533696 | chr17: 27332269-27333188 |
| chr1: 157963541-157963947 | chr12: 107711604-107714107 | chr17: 27503599-27504014 |
| chr1: 158119489-158119704 | chr12: 108297427-108297743 | chr17: 27942533-27945388 |
| chr1: 159141203-159141718 | chr12: 109162409-109162722 | chr17: 27949430-27950277 |
| chr1: 15929824-15930289 | chr12: 109729573-109729826 | chr17: 29298047-29298606 |
| chr1: 160040129-160040668 | chr12: 110150048-110150262 | chr17: 29718231-29719291 |
| chr1: 16085148-16085862 | chr12: 110156268-110156496 | chr17: 29814615-29815662 |
| chr1: 161228478-161229028 | chr12: 111471961-111473546 | chr17: 30593199-30594033 |
| chr1: 162760251-162760722 | chr12: 112204499-112204979 | chr17: 30845904-30846702 |
| chr1: 162792177-162792574 | chr12: 115104849-115105548 | chr17: 32953154-32953801 |
| chr1: 16543684-16544307 | chr12: 115120775-115122945 | chr17: 33787402-33787845 |
| chr1: 166134259-166136448 | chr12: 115135926-115136350 | chr17: 33814235-33814947 |
| chr1: 167789397-167789647 | chr12: 115889598-115889995 | chr17: 34091137-34091919 |
| chr1: 17033769-17034728 | chr12: 116354788-116355187 | chr17: 3438842-3439046 |
| chr1: 171810468-171811325 | chr12: 116946196-116946607 | chr17: 35060323-35060692 |
| chr1: 179555402-179555770 | chr12: 117316390-117317611 | chr17: 35303285-35303572 |
| chr1: 180881317-180882592 | chr12: 117536291-117537421 | chr17: 36102034-36104766 |
| chr1: 182584178-182584545 | chr12: 120031495-120033212 | chr17: 36105335-36105583 |
| chr1: 184633224-184633663 | chr12: 12079933-120799912 | chr17: 36575500-36575782 |
| chr1: 1875618-1875877 | chr12: 122277302-122277539 | chr17: 36584421-36585453 |
| chr1: 18971730-18972097 | chr12: 122667649-122668038 | chr17: 36728634-36729284 |
| chr1: 19970256-19971923 | chr12: 123380334-123380894 | chr17: 37365987-37366539 |
| chr1: 200860077-200860576 | chr12: 126018101-126018365 | chr17: 37856449-37856891 |
| chr1: 200992283-200992839 | chr12: 128850550-128850755 | chr17: 38020382-38020645 |
| chr1: 201368561-201369032 | chr12: 129787736-129788160 | chr17: 38347534-38347765 |
| chr1: 201450881-201451105 | chr12: 130526916-130527117 | chr17: 38497528-38498963 |
| chr1: 201475886-201476516 | chr12: 13152820-13153084 | chr17: 38501397-38501839 |
| chr1: 201708788-201709429 | chr12: 132312440-132315739 | chr17: 39683909-39684599 |
| chr1: 202936046-202936252 | chr12: 132689881-132690197 | chr17: 39705046-39705332 |
| chr1: 203456785-203457059 | chr12: 132690340-132690571 | chr17: 40250273-40250591 |
| chr1: 203598472-203598853 | chr12: 133463808-133464858 | chr17: 40332598-40333471 |
| chr1: 204159599-204159833 | chr12: 14927292-14928023 | chr17: 40440189-40441014 |
| chr1: 204797611-204797930 | chr12: 175667-176400 | chr17: 40805675-40805957 |
| chr1: 20512361-20512797 | chr12: 1770702-1771476 | chr17: 40912817-40913553 |
| chr1: 205537752-205538443 | chr12: 1905278-1906765 | chr17: 40932330-40933299 |
| chr1: 206223538-206224028 | chr12: 20521617-20523122 | chr17: 41723220-41723826 |
| chr1: 2064629-2064855 | chr12: 21680409-21680982 | chr17: 41791111-41791476 |
| chr1: 206730398-206730908 | chr12: 21810489-21810766 | chr17: 41984149-41985012 |
| chr1: 20810463-20813511 | chr12: 22486836-22488666 | chr17: 42015422-42015707 |
| chr1: 209848444-209849428 | chr12: 24714957-24716243 | chr17: 42015844-42016069 |
| chr1: 209979317-209979666 | chr12: 26348261-26349130 | chr17: 42030174-42030941 |
| chr1: 210465710-210466212 | chr12: 2800140-2801062 | chr17: 42061047-42061643 |
| chri: 211306668-211307675 | chr12: 28127891-28128575 | chr17: 42082028-42084972 |
| chr1: 211688462-211689104 | chr12: 29935996-29937433 | chr17: 42091713-42091948 |
| chr1: 213123648-213125092 | chr12: 3862069-3862606 | chr17: 42092144-42092432 |
| chr1: 214161198-214161415 | chr12: 4273820-4274491 | chr17: 42287693-42288392 |
| chr1: 2144200-2144497 | chr12: 4378367-4382222 | chr17: 42392324-42393079 |
| chr1: 215256052-215256636 | chr12: 4383194-4384405 | chr17: 42402788-42403266 |
| chr1: 219347110-219347572 | chr12: 49318487-49319476 | chr17: 44026528-44026738 |
| chr1: 220960017-220960603 | chr12: 49363665-49364443 | chr17: 44848309-44849912 |
| chr1: 2222199-2222569 | chr12: 49390618-49392441 | chr17: 45400875-45401440 |
| chr1: 225117221-225117781 | chr12: 49487964-49488202 | chr17: 45928212-45928710 |
| chr1: 226270724-226271841 | chr12: 49688874-49691360 | chr17: 46089637-46089851 |

TABLE 3-continued

Additional Example CGIs

| | | |
|---|---|---|
| chr1: 22668639-22668862 | chr12: 49735720-49736875 | chr17: 46114574-46115059 |
| chr1: 226736355-226737412 | chr12: 50297581-50297988 | chr17: 46507345-46507778 |
| chr1: 227729516-227730492 | chr12: 50349080-50349525 | chr17: 46655216-46655604 |
| chr1: 228565950-228567121 | chr12: 51785280-51785821 | chr17: 46687528-46688730 |
| chr1: 230561104-230562702 | chr12: 51818461-51819166 | chr17: 46710813-46711419 |
| chr1: 231175063-231176317 | chr12: 52444554-52445421 | chr17: 46719361-46720234 |
| chr1: 231176786-231177009 | chr12: 52545938-52546363 | chr17: 46723732-46724383 |
| chr1: 232941055-232941707 | chr12: 52701963-52702560 | chr17: 46755566-46756006 |
| chr1: 233749374-233750314 | chr12: 53267860-53268290 | chr17: 46827436-46827641 |
| chr1: 236687072-236687608 | chr12: 53273232-53273498 | chr17: 47209812-47210740 |
| chr1: 23750509-23751663 | chr12: 53297443-53297824 | chr17: 47572346-47575316 |
| chr1: 23884843-23885087 | chr12: 53441385-53441706 | chr17: 47647377-47647660 |
| chr1: 240254960-240257063 | chr12: 53448009-53448406 | chr17: 47967874-47968409 |
| chr1: 244012713-244013245 | chr12: 53613717-53615103 | chr17: 48619112-48619794 |
| chr1: 244213398-244213619 | chr12: 53718633-53719778 | chr17: 49021857-49022279 |
| chr1: 2460761-2462010 | chr12: 54332806-54333731 | chr17: 4981358-4981979 |
| chr1: 24648203-24648985 | chr12: 54343623-54343848 | chr17: 52977867-52978307 |
| chr1: 24739858-24740262 | chr12: 54346778-54347101 | chr17: 53315619-53316198 |
| chr1: 2477564-2478363 | chr12: 54387826-54388732 | chr17: 53342199-53343061 |
| chr1: 26490523-26491015 | chr12: 54389114-54389520 | chr17: 54674159-54674366 |
| chr1: 26686517-26687281 | chr12: 54393375-54394648 | chr17: 54910497-54912470 |
| chr1: 27338880-27339441 | chr12: 54399413-54399654 | chr17: 55939089-55939591 |
| chr1: 27854417-27854963 | chr12: 54399907-54400495 | chr17: 56832962-56833986 |
| chr1: 27894928-27895524 | chr12: 54408427-54408713 | chr17: 58228062-58228361 |
| chr1: 27960568-27961023 | chr12: 54784901-54785238 | chr17: 58498712-58499332 |
| chr1: 27986306-27986808 | chr12: 5541211-5542973 | chr17: 59473061-59483266 |
| chr1: 29101791-29102069 | chr12: 56522944-56523285 | chr17: 59539363-59539834 |
| chr1: 2929156-2929376 | chr12: 56881402-56882702 | chr17: 5973316-5974449 |
| chr1: 31158010-31158261 | chr12: 58013172-58013652 | chr17: 60704543-60705943 |
| chr1: 31380845-31381078 | chr12: 58021295-58022037 | chr17: 60729646-60730269 |
| chr1: 32169538-32169869 | chr12: 58258987-58259496 | chr17: 60885409-60885857 |
| chr1: 32180132-32180487 | chr12: 59989652-59990507 | chr17: 61523001-61524470 |
| chr1: 32226147-32226535 | chr12: 63025589-63026213 | chr17: 61615393-61616035 |
| chr1: 32237828-32238661 | chr12: 6419604-6420024 | chr17: 6460072-6460302 |
| chr1: 3239916-3240261 | chr12: 6472661-6473322 | chr17: 64961008-64962321 |
| chr1: 32410189-32410630 | chr12: 6472890-6493522 | chr17: 68164914-68165720 |
| chr1: 32892429-32892835 | chr12: 65672392-65673250 | chr17: 6945390-6947521 |
| chr1: 3310103-3311035 | chr12: 6664426-6665336 | chr17: 7108305-7108654 |
| chr1: 33219428-33220028 | chr12: 71003625-71004057 | chr17: 71639029-71641670 |
| chr1: 33358470-33359449 | chr12: 8123347-8123561 | chr17: 7164286-7166245 |
| chr1: 33438459-33438979 | chr12: 81330609-81331514 | chr17: 71897971-71898420 |
| chr1: 33938026-33938328 | chr12: 82152321-82152674 | chr17: 72270302-72270512 |
| chr1: 3447450-3447950 | chr12: 8849964-8851403 | chr17: 72352828-72353798 |
| chr1: 35331704-35332409 | chr12: 96883287-96883737 | chr17: 72442928-72443194 |
| chr1: 35350879-35351854 | chr12: 98850691-98851002 | chr17: 72449983-72450617 |
| chr1: 35394748-35396206 | chr12: 99288223-99289374 | chr17: 72667196-72667710 |
| chr1: 36042433-36043444 | chr13: 100631753-100635526 | chr17: 72732849-72733545 |
| chr1: 3662964-3664085 | chr13: 102068117-102069258 | chr17: 72848167-72848901 |
| chr1: 36771831-36773009 | chr13: 107186469-107189024 | chr17: 72889350-72890060 |
| chr1: 3688554-3689684 | chr13: 110958892-110960590 | chr17: 72931730-72932601 |
| chr1: 37498378-37500624 | chr13: 110960925-110961143 | chr17: 73030677-73031160 |
| chr1: 38229839-38230888 | chr13: 113548644-113549127 | chr17: 73083867-73084495 |
| chr1: 41847265-41849204 | chr13: 113597554-113598303 | chr17: 73520957-73522540 |
| chr1: 43832815-43833073 | chr13: 113622738-113623660 | chr17: 74496993-74497632 |
| chr1: 44401758-44402423 | chr13: 113807289-113807865 | chr17: 74706466-74707067 |
| chr1: 44871110-44874047 | chr13: 114017867-114018463 | chr17: 75524590-75525152 |
| chr1: 44883137-44884272 | chr13: 20175967-20176766 | chr17: 7608377-7608956 |
| chr1: 46767426-46769036 | chr13: 20702852-20703122 | chr17: 76127522-76128406 |
| chr1: 46859725-46860291 | chr13: 20806017-20806867 | chr17: 77093292-77093805 |
| chr1: 46913787-46914343 | chr13: 23489631-23490058 | chr17: 77783810-77789842 |
| chr1: 47489227-47489633 | chr13: 26760422-26760892 | chr17: 78977614-78978447 |
| chr1: 47690981-47691727 | chr13: 28491489-28492518 | chr17: 79366807-79374742 |
| chr1: 47915640-47915952 | chr13: 28501860-28502090 | chr17: 79448219-79448827 |
| chr1: 47998900-47999517 | chr13: 28542222-28543544 | chr17: 79485600-79486913 |
| chr1: 48058794-48059230 | chr13: 28554428-28555065 | chr17: 79614851-79615559 |
| chr1: 48190757-48190992 | chr13: 29105412-29105676 | chr17: 79917287-79920022 |
| chr1: 48449871-48450144 | chr13: 29292671-29293329 | chr17: 80329067-80330208 |
| chr1: 48462132-48462976 | chr13: 30995686-30995947 | chr17: 8054551-8055835 |
| chr1: 48937305-48937683 | chr13: 31019861-31020137 | chr17: 9142981-9143839 |
| chr1: 49242372-49242810 | chr13: 31377146-31377493 | chr18: 10131854-10132080 |
| chr1: 50513645-50514320 | chr13: 36705041-36705707 | chr18: 12271658-12271920 |
| chr1: 50798668-50799536 | chr13: 36871668-36872059 | chr18: 12407716-12408242 |
| chr1: 53386618-53387523 | chr13: 36919738-36921004 | chr18: 13136597-13137564 |
| chr1: 55446088-55446846 | chr13: 37005582-37006453 | chr18: 13824002-13824215 |
| chr1: 57110664-57111337 | chr13: 37247950-37248463 | chr18: 14132001-14132482 |
| chr1: 57887964-57890637 | chr13: 43597505-43597856 | chr18: 14430639-14431567 |
| chr1: 59280952-59281194 | chr13: 44359859-44361696 | chr18: 19928417-19929329 |
| chr1: 60280625-60281048 | chr13: 44453208-44454295 | chr18: 20139485-20140246 |

TABLE 3-continued

Additional Example CGIs

| | | |
|---|---|---|
| chr1: 6086245-6086494 | chr13: 45885755-45886103 | chr18: 21199432-21199798 |
| chr1: 61508643-61509282 | chr13: 50070023-50070719 | chr18: 21269270-21270349 |
| chr1: 61519353-61519971 | chr13: 53174029-53174674 | chr18: 22006311-22007007 |
| chr1: 6208717-6209039 | chr13: 53424942-53425995 | chr18: 24443201-24443458 |
| chr1: 6241032-6241251 | chr13: 67804594-67805459 | chr18: 25755415-25758175 |
| chr1: 6265826-6266778 | chr13: 88323570-88324640 | chr18: 2846566-2848175 |
| chr1: 6301696-6302856 | chr13: 95201561-95202293 | chr18: 28681321-28682455 |
| chr1: 6484504-6485327 | chr13: 95354190-95355184 | chr18: 2905951-2907348 |
| chr1: 6507208-6509186 | chr13: 95619884-95620977 | chr18: 29077553-29078526 |
| chr1: 6545144-6545559 | chr13: 96204692-96205496 | chr18: 31802359-31803792 |
| chr1: 65468273-65468828 | chr13: 98794399-98796241 | chr18: 31804481-31804875 |
| chr1: 68696640-68697628 | chr14: 100204041-100204262 | chr18: 34823799-34824017 |
| chr1: 70032968-70034495 | chr14: 100625320-100626461 | chr18: 3498942-3499358 |
| chr1: 72748472-72749736 | chr14: 100680270-100680947 | chr18: 42258984-42260795 |
| chr1: 76080455-76080808 | chr14: 101012841-101013117 | chr18: 43355319-43355698 |
| chr1: 76540148-76540653 | chr14: 101121009-101121365 | chr18: 43913346-43914477 |
| chr1: 77333112-77334534 | chr14: 102247661-102248279 | chr18: 44526867-44527137 |
| chr1: 8002409-8002699 | chr14: 103010785-103011625 | chr18: 45662315-45663520 |
| chr1: 8013994-8014651 | chr14: 103389017-103390248 | chr18: 47087076-47087446 |
| chr1: 805199-805628 | chr14: 103394398-103397070 | chr18: 47087880-47088528 |
| chr1: 82265999-82269048 | chr14: 103589354-103590246 | chr18: 48085839-48087589 |
| chr1: 8277196-8277822 | chr14: 103739579-103740892 | chr18: 5237724-5238674 |
| chr1: 84326268-84326838 | chr14: 105293561-15293879 | chr18: 52495605-52496007 |
| chr1: 85462586-85463435 | chr14: 105309691-105310500 | chr18: 52626518-52626849 |
| chr1: 87617154-87617417 | chr14: 105330515-105332186 | chr18: 53447075-53447842 |
| chr1: 87617693-87617986 | chr14: 105512056-105512307 | chr18: 5542848-5543054 |
| chr1: 90308840-90309606 | chr14: 105662778-105663403 | chr18: 55862654-55862873 |
| chr1: 9258566-9258956 | chr14: 105952604-105954296 | chr18: 56932714-56932994 |
| chr1: 94702691-94703344 | chr14: 21100839-21101043 | chr18: 56934834-56936827 |
| chr1: 95285603-95286319 | chr14: 21537083-21537355 | chr18: 5890293-5891682 |
| chr1: 9749296-9750228 | chr14: 21539712-21540045 | chr18: 59992070-59993556 |
| chr1: 999679-999911 | chr14: 23355739-23356402 | chr18: 63417776-63418640 |
| chr10: 100227439-100227832 | chr14: 24457865-24458100 | chr18: 65183238-65184014 |
| chr10: 101293016-101293238 | chr14: 24550318-24551148 | chr18: 70208975-70211790 |
| chr10: 102416497-102416716 | chr14: 24835811-24836220 | chr18: 72123607-72124717 |
| chr10: 102430698-102431119 | chr14: 24837873-24838324 | chr18: 74514041-74514292 |
| chr10: 102440601-102441011 | chr14: 24898780-24899288 | chr18: 74843361-74845426 |
| chr10: 102469807-102470341 | chr14: 25518425-25519612 | chr18: 7566558-7568830 |
| chr10: 102501701-102502232 | chr14: 27066314-27066578 | chr18: 77724353-77724836 |
| chr10: 102586126-102588109 | chr14: 32670418-32671092 | chr18: 811650-812709 |
| chr10: 102590123-102590402 | chr14: 34419509-34420438 | chr18: 8367274-8367599 |
| chr10: 102778605-102778922 | chr14: 37641233-37641879 | chr18: 9333897-9334244 |
| chr10: 102792043-102792266 | chr14: 38052646-38054166 | chr19: 10077032-10077444 |
| chr10: 102807775-102808271 | chr14: 38057139-38057798 | chr19: 10120751-10121231 |
| chr10: 102809888-102810282 | chr14: 38060842-38062119 | chr19: 10526983-10527755 |
| chr10: 102882978-102883551 | chr14: 38063664-38065665 | chr19: 10529628-10532004 |
| chr10: 103326283-103326712 | chr14: 38067447-38069207 | chr19: 1068439-1068764 |
| chr10: 103538816-103539988 | chr14: 45431629-45432115 | chr19: 10697787-10698099 |
| chr10: 103985853-103986246 | chr14: 52780688-52781969 | chr19: 1074727-1075071 |
| chr10: 104000255-104001741 | chr14: 54413305-54413764 | chr19: 11353961-11354362 |
| chr10: 105211951-105212306 | chr14: 55595698-55596692 | chr19: 11491560-11492740 |
| chr10: 106028543-106029047 | chr14: 58862542-58863209 | chr19: 11529214-11529588 |
| chr10: 110225928-110226465 | chr14: 60097209-60097553 | chr19: 11529723-11529966 |
| chr10: 11059443-11060524 | chr14: 60794577-60794867 | chr19: 11531279-11531590 |
| chr10: 11207179-11207980 | chr14: 61114103-61116552 | chr19: 11533199-11533619 |
| chr10: 113943284-113943657 | chr14: 61746805-61748141 | chr19: 11689418-11689768 |
| chr10: 115860680-115861093 | chr14: 61787881-61789467 | chr19: 11909403-11909841 |
| chr10: 116391467-116391827 | chr14: 62583680-62584279 | chr19: 11959578-11960064 |
| chr10: 116527525-116528474 | chr14: 67878535-67879167 | chr19: 11998805-11999131 |
| chr10: 116852262-116854094 | chr14: 70041214-70041662 | chr19: 12076030-12076366 |
| chr10: 118976050-118976706 | chr14: 73704055-73705106 | chr19: 12098572-12098950 |
| chr10: 119293918-119297675 | chr14: 73706300-73706677 | chr19: 12146031-12146649 |
| chr10: 122708511-122708899 | chr14: 73957751-73958889 | chr19: 12163327-12163560 |
| chr10: 122739053-122739391 | chr14: 74036128-74036662 | chr19: 12175461-12176057 |
| chr10: 124638744-124639793 | chr14: 74058401-74059116 | chr19: 12266999-12267686 |
| chr10: 125851152-125853233 | chr14: 74100344-74101230 | chr19: 12305553-12306304 |
| chr10: 126135810-126138896 | chr14: 75389713-75390133 | chr19: 12444033-12444548 |
| chr10: 133879006-133879255 | chr14: 75894309-75895469 | chr19: 12476050-12476372 |
| chr10: 134973511-134974311 | chr14: 76819146-76819379 | chr19: 12943347-12943661 |
| chr10: 135075002-135075452 | chr14: 88789601-88790493 | chr19: 12978360-12978785 |
| chr10: 135089970-135090491 | chr14: 89493136-89494382 | chr19: 13207376-13207621 |
| chr10: 13933483-13934184 | chr14: 90167783-90168352 | chr19: 13208344-13210525 |
| chr10: 17270431-17272617 | chr14: 91883362-91883566 | chr19: 1324970-1325349 |
| chr10: 17495408-17496721 | chr14: 92302202-92303078 | chr19: 13266390-13267030 |
| chr10: 18429126-18430234 | chr14: 92413582-92414324 | chr19: 1401093-1401784 |
| chr10: 20104452-20106105 | chr14: 96505312-96506402 | chr19: 14168143-14168512 |
| chr10: 20106644-20106946 | chr14: 96890431-96890633 | chr19: 14542769-14543102 |
| chr10: 21462129-21463808 | chr14: 97685060-97685946 | chr19: 1455227-1455544 |

TABLE 3-continued

Additional Example CGIs

| | | |
|---|---|---|
| chr10: 22518027-22518334 | chr14: 99711840-99713431 | chr19: 1456078-1456347 |
| chr10: 25241111-25241900 | chr14: 99739802-99740920 | chr19: 1456886-1457312 |
| chr10: 25463757-25465639 | chr15: 100880958-100882438 | chr19: 1503512-1503791 |
| chr10: 26222922-26224022 | chr15: 100890243-100890494 | chr19: 15090017-15090873 |
| chr10: 26500608-26501126 | chr15: 101389733-101390260 | chr19: 15288315-15288911 |
| chr10: 26680635-26680999 | chr15: 101548676-101548898 | chr19: 15334123-15334822 |
| chr10: 28030183-28035211 | chr15: 23207950-23208796 | chr19: 15619224-15619613 |
| chr10: 29698363-29699044 | chr15: 24123232-24123432 | chr19: 15662114-15662358 |
| chr10: 31422710-31423316 | chr15: 28982670-28983497 | chr19: 15695299-15695535 |
| chr10: 35103125-35105243 | chr15: 30113706-30113940 | chr19: 16186790-16188275 |
| chr10: 43571940-43573434 | chr15: 31733082-31733489 | chr19: 1675922-1676137 |
| chr10: 44185040-44186132 | chr15: 32828333-32829181 | chr19: 17007102-17008857 |
| chr10: 45470023-45470291 | chr15: 34728788-34729495 | chr19: 1725416-1726154 |
| chr10: 45914375-45914883 | chr15: 37179517-37179782 | chr19: 17346166-17346886 |
| chr10: 49812853-49813352 | chr15: 37393667-37394248 | chr19: 17392384-17393775 |
| chr10: 51572199-51572620 | chr15: 40728263-40728466 | chr19: 17403040-17403570 |
| chr10: 52177725-52178182 | chr15: 41851724-41851970 | chr19: 17487896-17488125 |
| chr10: 57390344-57391215 | chr15: 41913334-41914360 | chr19: 17501956-17502250 |
| chr10: 60272468-60273456 | chr15: 41952536-41953222 | chr19: 17580198-17580598 |
| chr10: 60935828-60937049 | chr15: 45427297-45428206 | chr19: 1762373-1762848 |
| chr10: 62492786-62493376 | chr15: 45722562-45722939 | chr19: 1766145-1766364 |
| chr10: 62703308-62704290 | chr15: 48009419-48011044 | chr19: 17716645-17717531 |
| chr10: 64133790-64134420 | chr15: 48470008-48470628 | chr19: 1776028-1776730 |
| chr10: 71077947-71079377 | chr15: 51633725-51634318 | chr19: 17791068-17791301 |
| chr10: 71812319-71813693 | chr15: 52587354-52588172 | chr19: 17905580-17906317 |
| chr10: 71892093-71892802 | chr15: 60690709-60690930 | chr19: 18059850-18060148 |
| chr10: 72043447-72043886 | chr15: 61519622-61520031 | chr19: 18209912-18210268 |
| chr10: 72218131-72218484 | chr15: 61520424-61521716 | chr19: 18319146-18319363 |
| chr10: 72647739-72648317 | chr15: 62456016-62457648 | chr19: 18499098-18499697 |
| chr10: 72977124-72977774 | chr15: 64443588-64444821 | chr19: 18539782-18540341 |
| chr10: 734708-735606 | chr15: 65066917-65068352 | chr19: 1862257-1862600 |
| chr10: 74020774-74021023 | chr15: 65127965-65128185 | chr19: 18722359-18724001 |
| chr10: 74079337-74079861 | chr15: 65669311-65670617 | chr19: 18811562-18811791 |
| chr10: 75670697-75671379 | chr15: 65714743-65715571 | chr19: 19280999-19281560 |
| chr10: 77191062-77191571 | chr1S: 66274584-66274838 | chr19: 19335772-19336151 |
| chr10: 79396096-79398495 | chr15: 66544433-66546134 | chr19: 19729128-19729814 |
| chr10: 8091375-8098329 | chr15: 68126023-68126569 | chr19: 19738573-19739821 |
| chr10: 81892223-81892640 | chr15: 68723368-68724691 | chr19: 19843483-19843943 |
| chr10: 85954200-85955303 | chr15: 69366322-69366796 | chr19: 19971578-19971863 |
| chr10: 86300400-86300953 | chr15: 71145996-71146820 | chr19: 20011911-20012238 |
| chr10: 88730555-88731632 | chr15: 72476677-72476969 | chr19: 20149856-20150175 |
| chr10: 90342529-90343221 | chr15: 72564443-72565165 | chr19: 20162773-20163107 |
| chr10: 93647053-93647393 | chr15: 72611947-72612802 | chr19: 2041824-2042593 |
| chr10: 94351357-94351615 | chr15: 74044562-74045885 | chr19: 21949904-21950217 |
| chr10: 94459255-94459591 | chr15: 74425092-74428821 | chr19: 22018595-22018827 |
| chr10: 94831513-94832312 | chr1S: 74537810-74538114 | chr19: 22034395-22034943 |
| chr10: 95326230-95327108 | chr15: 75470912-75471212 | chr19: 22193331-22193583 |
| chr10: 95360390-95361387 | chr15: 75628251-75628677 | chr19: 2273694-2274047 |
| chr10: 95753348-95754201 | chr15: 78633323-78634089 | chr19: 2302467-2302999 |
| chr10: 97802872-97804262 | chr15: 79102716-79104628 | chr19: 23253797-23254382 |
| chr10: 98479726-98480487 | chr15: 83348840-83349865 | chr19: 23386650-23387069 |
| chr10: 99473085-99473291 | chr15: 83620951-83621727 | chr19: 23456575-23456868 |
| chr11: 100998031-100999774 | chr15: 83775862-83776922 | chr19: 2478866-2479244 |
| chr11: 101918074-101918493 | chr15: 83875649-83877079 | chr19: 2613933-2614133 |
| chr11: 102188180-102188440 | chr15: 84047823-84048105 | chr19: 267086-267660 |
| chr11: 106888324-106890203 | chr15: 84115763-84116921 | chr19: 28284529-28285129 |
| chr11: 109963241-109964677 | chr15: 84322323-84323771 | chr19: 295115-295354 |
| chr11: 112832525-112834490 | chr15: 84976071-84977044 | chr19: 30215233-30215594 |
| chr11: 113185333-113185663 | chr15: 89438177-89438850 | chr19: 30363203-30363527 |
| chr11: 113258444-113258821 | chr15: 89942593-89943853 | chr19: 31839636-31843049 |
| chr11: 113345069-113346328 | chr15: 89959743-89959990 | chr19: 31843881-31844183 |
| chr11: 113929634-113932190 | chr15: 90039465-90039984 | chr19: 31847947-31848209 |
| chr11: 113953621-113953839 | chr15: 91427541-91427905 | chr19: 3275609-3275970 |
| chr11: 116371183-116371606 | chr15: 93198375-93199181 | chr19: 33685147-33686085 |
| chr11: 116706629-116706910 | chr15: 93615623-93617185 | chr19: 34112280-34114353 |
| chr11: 119227097-119227758 | chr15: 96883942-96884533 | chr19: 3434930-3435417 |
| chr11: 119455154-119456102 | chr15: 96888959-96889417 | chr19: 34396472-34398079 |
| chr11: 119612092-119612476 | chr15: 99091356-99091812 | chr19: 34850072-34850587 |
| chr11: 120039602-120040210 | chr15: 99557979-99559170 | chr19: 35531781-35531991 |
| chr11: 120110498-120110719 | chr16: 10479687-10480254 | chr19: 36164078-36164286 |
| chr11: 120856726-120857174 | chr16: 1098523-1098875 | chr19: 36351441-36352167 |
| chr11: 121322539-121323302 | chr16: 11327009-11327234 | chr19: 3671903-3672121 |
| chr11: 122854931-122855582 | chr16: 1202415-1204624 | chr19: 3687787-3688262 |
| chr11: 123301050-123302149 | chr16: 12897366-12897889 | chr19: 36909282-36909854 |
| chr11: 124709223-124709957 | chr16: 1392545-1392753 | chr19: 37063893-37064749 |
| chr11: 124713006-124713395 | chr16: 1429051-1430104 | chr19: 37095681-37096589 |
| chr11: 124932731-124933657 | chr16: 1458144-1458435 | chr19: 37157633-37158119 |
| chr11: 1:26225356-126226073 | chr16: 19421817-19422498 | chr19: 3721465-3721788 |

TABLE 3-continued

Additional Example CGIs

| | | |
|---|---|---|
| chr11: 126286452-126286870 | chr16: 203754-204866 | chr19: 37263382-37264083 |
| chr11: 12695415-12696981 | chr16: 2054012-2054288 | chr19: 37328897-37329518 |
| chr11: 128391713-128392611 | chr16: 2069719-2070865 | chr19: 37340919-37341262 |
| chr11: 129243999-129244567 | chr16: 2077043-2077470 | chr19: 37341732-37342000 |
| chr11: 129245109-129246395 | chr16: 21294981-21295414 | chr19: 37568953-37569549 |
| chr11: 129685738-129686211 | chr16: 21831483-21831944 | chr19: 37803517-37803822 |
| chr11: 130029659-130030262 | chr16: 2245867-2247100 | chr19: 37957727-37958390 |
| chr11: 130297402-130298517 | chr16: 25078048-25078532 | chr19: 37959853-37960615 |
| chr11: 133825338-133827457 | chr16: 2835064-2835958 | chr19: 38145827-38147219 |
| chr11: 134201785-134202407 | chr16: 28634441-28635031 | chr19: 38182794-38183327 |
| chr11: 13689589-13690724 | chr16: 28752083-28752332 | chr19: 38210108-38210692 |
| chr11: 15094958-15095872 | chr16: 29624388-29625391 | chr19: 3821975-3822278 |
| chr11: 1592499-1592810 | chr16: 29887789-29888316 | chr19: 38754847-38755699 |
| chr11: 16632509-16632725 | chr16: 30428871-30429799 | chr19: 38852312-38853485 |
| chr11: 17373020-17373665 | chr16: 3078142-3078553 | chr19: 39359917-39361160 |
| chr11: 17565767-17566052 | chr16: 3079537-3079954 | chr19: 39440405-39441011 |
| chr11: 18067717-18067928 | chr16: 30913356-30913942 | chr19: 39574701-39575137 |
| chr11: 18415923-18416680 | chr16: 31008833-31009036 | chr19: 39687598-39687964 |
| chr11: 18727321-18727727 | chr16: 31117102-31117435 | chr19: 39810993-39811293 |
| chr11: 19798538-19798949 | chr16: 31213567-31214287 | chr19: 39894559-39894768 |
| chr11: 20385162-20385673 | chr16: 31342453-31343140 | chr19: 39993358-39993765 |
| chr11: 2165136-2165672 | chr16: 31483277-31483646 | chr19: 39997591-39998291 |
| chr11: 22362863-22363377 | chr16: 31580071-31580317 | chr19: 40323908-40325005 |
| chr11: 22850766-22851367 | chr16: 31580560-31581023 | chr19: 40732076-40732665 |
| chr11: 2290105-2292932 | chr16: 3199653-3199937 | chr19: 41025315-41026106 |
| chr11: 2465172-2465648 | chr16: 3225355-3225594 | chr19: 41055125-41055331 |
| chr11: 2466248-2466818 | chr16: 32822902-32823585 | chr19: 41060059-41060565 |
| chr11: 27740645-27741236 | chr16: 3355021-3356012 | chr19: 41106059-41106415 |
| chr11: 30040073-30040294 | chr16: 4166656-4167012 | chr19: 41109614-41110075 |
| chr11: 30606005-30608128 | chr16: 4357553-4357955 | chr19: 41111084-41111767 |
| chr11: 3181575-3182120 | chr16: 4363936-4364151 | chr19: 41115446-41115767 |
| chr11: 32354761-32355484 | chr16: 4377509-4378162 | chr19: 41119032-41120394 |
| chr11: 32448262-32449744 | chr16: 4421643-4422240 | chr19: 41633777-41634047 |
| chr11: 35547140-35547396 | chr16: 4587837-4588890 | chr19: 41698744-41699325 |
| chr11: 416420-417650 | chr16: 46823933-46824263 | chr19: 42419339-42419564 |
| chr11: 43596991-43597336 | chr16: 47176788-47178446 | chr19: 42501262-42501486 |
| chr11: 43902:255-43902528 | chr16: 48399731-48400040 | chr1 9: 42720827-42722132 |
| chr11: 45307442-45307975 | chr16: 50581476-50582735 | chr19: 42901017-42901375 |
| chr11: 45686161-45687495 | chr16: 52579637-52580845 | chr19: 42905724-42906350 |
| chr11: 45921388-45922167 | chr16: 52581294-52581610 | chr19: 42927286-42928598 |
| chr11: 46316876-46317485 | chr16: 54316904-54317149 | chr19: 43979360-43979684 |
| chr11: 46389075-46389378 | chr16: 54962423-54967805 | chr19: 44324437-44325009 |
| chr11: 47736740-47737106 | chr16: 55357522-55359040 | chr19: 44405818-44406053 |
| chr11: 49229718-49230040 | chr16: 56224732-56224980 | chr19: 44763979-44764312 |
| chr11: 504190-504659 | chr16: 56225256-56226351 | chr19: 44952417-44952809 |
| chr11: 57117316-57117575 | chr16: 56677121-56677598 | chr19: 45257704-45257918 |
| chr11: 57243682-57244463 | chr16: 56701864-56702208 | chr19: 45281134-45281355 |
| chr11: 57249947-57250848 | chr16: 56703388-56703648 | chr19: 4535070-4535339 |
| chr11: 58940831-58941052 | chr16: 57835956-57836989 | chr19: 4558364-4558579 |
| chr11: 61061752-61063063 | chr16: 58058713-58058928 | chr19: 45655294-45657246 |
| chr11: 61159837-61160285 | chr16: 58535041-58535596 | chr19: 45843871-45844418 |
| chr11: 61283865-61284147 | chr16: 66638255-66639561 | chr19: 45888769-45889465 |
| chr11: 61322733-61323285 | chr16: 66982435-66982945 | chr19: 45947711-45948047 |
| chr11: 61335113-61335340 | chr16: 67034471-67035340 | chr19: 46032305-46032855 |
| chr11: 61355039-61355363 | chr16: 67188614-67189652 | chr19: 4607080-4607350 |
| chr11: 61519742-61519972 | chr16: 67193006-67193:219 | chr19: 46144873-46145631 |
| chr11: 61722745-61723483 | chr16: 67196793-67199988 | chr19: 46282545-46283127 |
| chr11: 62476771-62477481 | chr16: 67204209-67204637 | chr19: 46379884-46380207 |
| chr11: 62690975-62691488 | chr16: 67211934-67212509 | chr19: 46456210-46456503 |
| chr11: 62693374-62694772 | chr16: 67312897-67313731 | chr19: 46518284-46520080 |
| chr11: 63685490-63685968 | chr16: 67564501-67564332 | chr19: 46974558-46975073 |
| chr11: 63775347-63775613 | chr16: 67700010-67701354 | chr19: 46996328-46998437 |
| chr11: 63803376-63804365 | chr16: 68002838-68003039 | chr19: 47137781-47138070 |
| chr11: 64038965-64039306 | chr16: 68:273546-68274084 | chr19: 47614409-47614661 |
| chr11: 64409878-64411253 | chr16: 68678687-68680149 | chr19: 47910108-47910563 |
| chr11: 64993281-64993484 | chr16: 69760294-69760506 | chr19: 47922252-47922777 |
| chr19: 48216487-48216837 | chr22: 23522551-23524465 | chr6: 10410110-10410690 |
| chr19: 48833395-48833720 | chr22: 23908323-23909178 | chr6: 10414217-10414498 |
| chr19: 48837142-48837549 | chr22: 24110030-24110995 | chr6: 10415019-10415318 |
| chr19: 48901805-48902123 | chr22: 24551814-24552696 | chr6: 10417385-10417842 |
| chr19: 49061546-49061769 | chr22: 26565200-26565986 | chr6: 10419400-10420323 |
| chr19: 49199965-49200184 | chr22: 27152698-27153133 | chr6: 10421415-10421727 |
| chr19: 49242019-49242962 | chr22: 29426511-29426843 | chr6: 10422322-10422648 |
| chr19: 49255779-49256495 | chr22: 29467292-29467817 | chr6: 10426201-10426638 |
| chr19: 49340489-49340774 | chr22: 31218227-31218893 | chr6: 105627407-105627830 |
| chr19: 49522774-49523093 | chr22: 32026298-32026874 | chr6: 106958233-106958718 |
| chr19: 49575130-49576076 | chr22: 33453893-33454505 | chr6: 106959765-106960985 |
| chr19: 49646093-49646308 | chr22: 37655606-37655839 | chr6: 108436110-108436522 |

TABLE 3-continued

Additional Example CGIs

| | | |
|---|---|---|
| chr19: 49655103-49655395 | chr22: 37730552-37731415 | chr6: 108455061-108455273 |
| chr19: 49935752-49936275 | chr22: 38073038-38073412 | chr6: 112575092-112575483 |
| chr19: 49939611-49940045 | chr22: 38453188-38453503 | chr6: 117584585-117584816 |
| chr19: 50016532-50016851 | chr22: 38808785-38809017 | chr6: 118241348-118241569 |
| chr19: 50030982-50031300 | chr22: 39745984-39746634 | chr6: 124124178-124125309 |
| chr19: 50037079-50037670 | chr22: 39853324-39854065 | chr6: 125283125-125284389 |
| chr19: 50096610-50096912 | chr22: 40057942-40058844 | chr6: 125420744-125421141 |
| chr19: 50183923-50184172 | chr22: 40390485-40391490 | chr6: 127836731-127837706 |
| chr19: 50312012-50312821 | chr22: 42062791-42063002 | chr6: 1311069-1314220 |
| chr19: 50651174-50651535 | chr22: 42470036-42470669 | chr6: 132271357-132271658 |
| chr19: 50706483-50707196 | chr22: 43505952-43506167 | chr6: 134159127-134159349 |
| chr19: 50708602-50708855 | chr22: 45015934-45016488 | chr6; 134213960-134214351 |
| chr19: 50831455-50832070 | chr22: 45403037-45406372 | chr6: 13873766-13874262 |
| chr19: 50833814-50834128 | chr22: 46262066-46263747 | chr6: 13925100-13925510 |
| chr19: 50836391-50837447 | chr22: 46366727-46368726 | chr6: 146136326-146136564 |
| chr19: 51069360-51069600 | chr22: 50328694-50329178 | chr6: 150246753-150247257 |
| chr19: 51161924-51162514 | chr22: 50453057-50454137 | chr6: 150284683-150286515 |
| chr19: 51198809-51199347 | chr22: 50628950-50629249 | chr6: 150463772-150465002 |
| chr19: 51227662-51228883 | chr22: 50982571-50982994 | chr6: 151561284-151562550 |
| chr19: 51321268-51321781 | chr3: 101497831-101498648 | chr6: 151646669-151646958 |
| chr19: 51416003-51416249 | chr3: 101568108-101569046 | chr6: 152128823-152129771 |
| chr19: 51522005-51522803 | chr3: 10206450-10207024 | chr6: 152623280-152623480 |
| chr19: 51568155-51568412 | chr3: 112930438-112931506 | chr6: 152957811-152958472 |
| chr19: 51842129-51842353 | chr3: 113251700-113252290 | chr6: 155316300-155317197 |
| chr19: 52206245-52206726 | chr3: 117716101-117716564 | chr6: 158957221-158958677 |
| chr19: 52207133-52207731 | chr3: 119041383-119042255 | chr6: 159290674-159291195 |
| chr19: 52222424-52223208 | chr3: 119421856-119422334 | chr6: 1604607-1615866 |
| chr19: 52452317-52452543 | chr3: 120003884-120004426 | chr6: 166267510-166268461 |
| chr19: 52531324-52531724 | chr3: 120626881-120627579 | chr6: 166401527-166402659 |
| chr19: 52800400-52800871 | chr3: 122640714-122641355 | chr6: 17102310-17102539 |
| chr19: 52839445-52839937 | chr3: 12328995-12329227 | chr6: 19837505-19839314 |
| chr19: 52900956-52901158 | chr3: 124303530-124304092 | chr6: 21594614-21596437 |
| chr19: 5293011-5294211 | chr3: 124931162-124931747 | chr6: 21664508-21665178 |
| chr19: 53030825-53031359 | chr3: 126242784-126243358 | chr6: 21665716-21666031 |
| chr1 9: 53073309-53074039 | chr3: 127391012-127392434 | chr6: 21666656-21666862 |
| chr19: 53104385-53105149 | chi-3: 128145258-128145656 | chr6: 24360030-24360411 |
| chr19: 53141176-53141813 | chr3: 128205496-128212274 | chr6: 25652381-25652709 |
| chr19: 53193140-53193945 | chr3: 128336407-128337113 | chr6: 26020672-26021125 |
| chr19: 5339641-5341061 | chr3: 128564772-128565007 | chr6: 26021958-26022193 |
| chr19: 53400461-53401205 | chr3: 129323916-129325332 | chr6: 26044204-26044469 |
| chr19: 53426079-53426389 | chr3: 129345668-129346521 | chr6: 26045645-26046033 |
| chr19: 53496733-53497028 | chr3: 129721369-129722131 | chr6: 26172034-26172398 |
| chr19: 53606060-53606784 | chr3: 13008649-13009210 | chr6: 26184037-26184336 |
| chr19: 53635626-53636230 | chr3: 131753881-131754139 | chr6: 26197071-26197537 |
| chr19: 53661431-53661848 | chr3: 133464950-133465420 | chr6: 26199198-26199466 |
| chr19: 53662190-53662500 | chr3: 134082861-134083201 | chr6: 26204765-26205213 |
| chr19: 53696030-53696650 | chr3: 134125488-134125871 | chr6: 26217212-26217521 |
| chr19: 54023869-54024560 | chr3: 136751342-136751683 | chr6: 26240698-26240951 |
| chr19: 54024646-54024923 | chr3: 138153270-138154621 | chr6: 26250437-26250827 |
| chr19: 54369388-54369809 | chr3: 140769887-140771080 | chr6: 26251899-26252233 |
| chr19: 54382665-54382951 | chr3: 145878431-145879287 | chr6: 26271346-26271588 |
| chr19: 54409967-54410200 | chr3: 145968335-145969008 | chr6: 26272471-26272696 |
| chr19: 54599161-54599456 | chr3: 150802997-150805168 | chr6: 26273291-26273557 |
| chr19: 54665922-54666377 | chr3: 152552603-152553712 | chr6: 26987599-26988074 |
| chr19: 54982389-54982897 | chr3: 156533840-156535131 | chr6: 27100175-27101124 |
| chr19: 5536532-5536789 | chr3: 157155268-157155826 | chr6: 27107139-27107394 |
| chr19: 55591434-55591644 | chr3: 158288801-158289271 | chr6: 27598688-27599146 |
| chr19: 55591906-55593980 | chr3: 159756633-159756997 | chr6: 27777856-27778251 |
| chr19: 55667533-55668465 | chr3: 160822495-160823260 | chr6: 27782248-27782485 |
| chr19: 55672024-55673212 | chr3: 168864031-168864449 | chr6: 27791781-27792217 |
| chr19: 5567519-5567939 | chr3: 169482339-169483052 | chr6: 27798991-27799427 |
| chr19: 55865017-55865434 | chr3: 169487146-169487522 | chr6: 27835191-27835461 |
| chr19: 55865825-55866324 | chr3: 173113271-173113681 | chr6: 28367125-28367651 |
| chr19: 55953372-55954641 | chr3: 179168736-179169593 | chr6: 2841811-2842273 |
| chr19: 56159258-56159937 | chr3: 179754231-179755245 | chr6: 2875602-2875811 |
| chr19: 56728589-56729375 | chr3: 181413015-181414022 | chr6: 2971087-2971962 |
| chr19: 56879418-56879995 | chr3: 181430142-181431076 | chr6: 3231596-3232289 |
| chr19: 56904637-56905355 | chr3: 181437185-181437478 | chr6: 32632159-32633027 |
| chr19: 56915357-56915856 | chr3: 182896921-182897381 | chr6: 33539023-33539339 |
| chr19: 57049676-57050646 | chr3: 182971430-182972635 | chr6: 36098040-36098621 |
| chr19: 57078366-57079301 | chr3: 183542497-183543804 | chr6: 39196818-39197517 |
| chr19: 57106576-57106896 | chr3: 184319377-184319822 | chr6: 40554596-40555928 |
| chr19: 57149424-57149631 | chr3: 184320006-184320218 | chr6: 40995803-40996241 |
| chr19: 57276615-57276942 | chr3: 184321784-184322277 | chr6: 41339237-41340027 |
| chr19: 57702697-57703425 | chr3: 18485113-18487056 | chr6: 41410590-41411140 |
| chr19: 57831600-57832250 | chr3: 184971642-184972002 | chr6: 41438063-41438594 |
| chr19: 57862442-57863236 | chr3: 185000558-185000896 | chr6: 42109905-42110361 |
| chr19: 57874764-57875110 | chr3: 186490603-186490813 | chr6: 4282005-4282310 |

TABLE 3-continued

Additional Example CGIs

| | | |
|---|---|---|
| chr19: 57999026-57999613 | chr3: 186648175-186649103 | chr6: 42928219-42928810 |
| chr19: 58011125-58011743 | chr3: 187455331-187455843 | chr6: 43021126-43021694 |
| chr19: 5802235-5802569 | chr3: 187456251-187456580 | chr6: 43044045-43045057 |
| chr19: 58038573-58039208 | chr3: 187457732-187457948 | chr6: 43142014-43142217 |
| chr19: 58070554-58071273 | chr3: 188665276-188665552 | chr6: 43237261-43237643 |
| chr19: 58111230-58111770 | chr3: 193720954-193721291 | chr6: 43970074-43970922 |
| chr19: 58125531-58125902 | chr3: 193776092-193776308 | chr6: 44119527-44119781 |
| chr19: 58175624-58176104 | chr3: 193858771-193859695 | chr6: 44187187-44187400 |
| chr19: 58220190-58220517 | chr3: 194117602-194118988 | chr6: 45387347-45388164 |
| chr19: 58280927-58281486 | chr3: 194207386-194208785 | chr6: 4775132-4777550 |
| chr19: 58446337-58446800 | chr3: 196255496-196256013 | chr6: 49518316-49519186 |
| chr19: 58458687-58459219 | chr3: 197281606-197283128 | chr6: 52441270-52441793 |
| chr19: 58609339-58609988 | chr3: 197391890-197392481 | chr6: 53212618-53214043 |
| chr19: 58661738-58662287 | chr3: 23244051-23245071 | chr6: 54711154-54712033 |
| chr19: 58666024-58666833 | chr3: 24535845-24537436 | chr6: 56407465-56407926 |
| chr19: 58739944-58740554 | chr3: 24870675-24871369 | chr6: 56818874-56820308 |
| chr19: 58858454-58859223 | chr3: 27410613-27411066 | chr6: 69345217-69345483 |
| chr19: 58951215-58952250 | chr3: 27756213-27756422 | chr6: 70576975-70577572 |
| chr19: 59025309-59025705 | chr3: 27756661-27756941 | chr6: 710835-711297 |
| chr19: 6199293-6199551 | chr3: 32021970-32023364 | chr6: 7141037-7141576 |
| chr19: 6463992-6464780 | chr3: 32443153-32443455 | chr6: 72129509-72130756 |
| chr19: 6530827-6531552 | chr3: 38035702-38036000 | chr6: 73972820-73973027 |
| chr19: 6740670-6741203 | chr3: 38040290-38040535 | chr6: 74019429-74020053 |
| chr19: 675672-675881 | chr3: 38080629-38081187 | chr6: 74024403-74025020 |
| chr19: 6767946-6768160 | chr3: 38179858-38180689 | chr6: 74161087-74162090 |
| chr19: 681346-681576 | chr3: 40428652-40429015 | chr6: 74233269-74233546 |
| chr19: 7953281-7953708 | chr3: 40657160-40657395 | chr6: 75794881-75795088 |
| chr19: 8273531-8273920 | chr3: 44690127-44690587 | chr6: 75914706-75916387 |
| chr19: 8274242-8275045 | chr3: 44726929-44727237 | chr6: 83073417-83075319 |
| chr19: 9473590-9474001 | chr3: 44754100-44754399 | chr6: 87647254-87647707 |
| chr19: 9896564-9896994 | chr3: 44770937-44771137 | chr6: 94126273-94129677 |
| chr2: 100937780-100939059 | chr3: 45187027-45187946 | chr6: 96463870-96464136 |
| chr2: 101033607-101034296 | chr3: 46734732-46735717 | chr6: 99279318-99283842 |
| chr2: 10260280-10260931 | chr3: 46742765-46743086 | chr7: 100091181-100091598 |
| chr2: 102758807-102759577 | chr3: 46887629-46887919 | chr7: 100167137-100168144 |
| chr2: 105488369-105489991 | chr3: 46940055-46940394 | chr7: 100201615-100203652 |
| chr2: 105760110-105761018 | chr3: 50275394-50275645 | chr7: 100224271-100224558 |
| chr2: 106886119-106886738 | chr3: 50377804-50378540 | chr7: 100230650-100231320 |
| chr2: 107502354-107504216 | chr3: 50402104-50402942 | chr7: 100434983-100435193 |
| chr2: 10861207-10862382 | chr3: 50604906-50605359 | chr7: 100845051-100845726 |
| chr2: 110370907-110373301 | chr3: 51989764-51990639 | chr7: 102157824-102158510 |
| chr2: 110518072-110518913 | chr3: 52279602-52280140 | chr7: 102329951-102330654 |
| chr2: 112656187-112656918 | chr3: 53190510-53190764 | chr7: 104624338-104624848 |
| chr2: 119981080-119981818 | chr3: 54155240-54157025 | chr7: 106684814-106685765 |
| chr2: 121101047-121101432 | chr3: 55515153-55515613 | chr7: 108095402-108097206 |
| chr2: 121101801-121104534 | chr3: 55517659-55517939 | chr7: 114562171-114563193 |
| chr2: 121104713-121104935 | chr3: 55519090-55519623 | chr7: 115850371-115851028 |
| chr2: 121199724-121199993 | chr3: 55520227-55522344 | chr7: 116139775-116140352 |
| chr2: 121200504-121200788 | chr3: 55522561-55522836 | chr7: 121513047-121513911 |
| chr2: 121499229-121499578 | chr3: 56501869-56502345 | chr7: 12610166-12610834 |
| chr2: 121624828-121625209 | chr3: 57198244-57199378 | chr7: 126891301-126894205 |
| chr2: 127643801-127644104 | chr3: 57994922-57995218 | chr7: 126987644-126988233 |
| chr2: 127729673-127729905 | chr3: 59035407-59035944 | chr7: 127880751-127881375 |
| chr2: 128173476-128173793 | chr3: 62304515-62304780 | chr7: 128509207-128510201 |
| chr2: 128180295-128181381 | chr3: 62859618-62861190 | chr7: 128530630-128531356 |
| chr2: 130691703-130692102 | chr3: 64430586-64431192 | chr7: 128809090-128809393 |
| chr2: 131129719-131130511 | chr3: 65534685-65535344 | chr7: 128828334-128829366 |
| chr2: 131513364-131514183 | chr3: 69129059-69129515 | chr7: 130126018-130126801 |
| chr2: 131720820-131721867 | chr3: 69434927-69435583 | chr7: 130417913-130419378 |
| chr2: 131792238-131793189 | chr3: 69591012-69592050 | chr7: 132260475-132262527 |
| chr2: 132121264-132121762 | chr3: 72788073-72788416 | chr7: 1329382-1329673 |
| chr2: 132285409-132285992 | chr3: 73673231-73674375 | chr7: 133812006-133812233 |
| chr2: 133173533-133174369 | chr3: 74663507-74664121 | chr7: 138666359-138666972 |
| chr2: 133426653-133428870 | chr3: 75834255-75834761 | chr7: 138720045-138721019 |
| chr2: 134023948-134024467 | chr3: 77088499-77089198 | chr7: 139167481-139168712 |
| chr2: 134785626-134785845 | chr3: 85008285-85008837 | chr7: 14029379-14029593 |
| chr2: 145273457-145275378 | chr3: 96532024-96533625 | chr7: 1408517-1408878 |
| chr2: 145281737-145282269 | chr3: 98451287-98452225 | chr7: 148036495-148036848 |
| chr2: 14772378-14775809 | chr3: 98620132-98620910 | chr7: 148982080-148982675 |
| chr2: 154334450-154335458 | chr3: 9904332-9904811 | chr7: 149119399-149120307 |
| chr2: 155554006-155556069 | chr3: 9956823-9957664 | chr7: 149495-150038 |
| chr2: 160654230-160654631 | chr3: 99594970-99595215 | chr7: 150019951-150020752 |
| chr2: 160918675-160919177 | chr3: 9993731-9994136 | chr7: 150655109-150655643 |
| chr2: 161263872-161264460 | chr4: 1005931-1006282 | chr7: 150675207-150675866 |
| chr2: 162930234-162930879 | chr4: 102711830-102712199 | chr7: 150676179-150676585 |
| chr2: 164592918-164593511 | chr4: 103997209-103998007 | chr7: 151078463-151079536 |
| chr2: 166649910-166650966 | chr4: 10462833-10463689 | chr7: 151136934-151137273 |
| chr2: 168149034-168150797 | chr4: 1049653-1049923 | chr7: 154861798-154862074 |

TABLE 3-continued

Additional Example CGIs

| | | |
|---|---|---|
| chr2: 171569878-171573904 | chr4: 109683730-109684362 | chr7: 155579869-155580392 |
| chr2: 172944989-172945384 | chr4: 111532648-111533391 | chr7: 156810573-156814593 |
| chr2: 172945912-172946212 | chr4: 113435899-113438002 | chr7: 158785262-158785771 |
| chr2: 172947844-172948200 | chr4: 113445023-113445350 | chr7: 16460779-16461265 |
| chr2: 172949243-172950126 | chr4: 1161128-1161682 | chr7: 1703862-1710517 |
| chr2: 172951290-172952159 | chr4: 118006539-118006859 | chr7: 191876-193799 |
| chr2: 172952810-172953160 | chr4: 119273306-119274458 | chr7: 20817456-20818227 |
| chr2: 172959268-172962054 | chr4: 123747741-123748980 | chr7: 20823308-20825662 |
| chr2: 172971046-172971387 | chr4: 124333-124841 | chr7: 21582444-21583313 |
| chr2: 173600282-173600970 | chr4: 124426781-124427157 | chr7: 21985072-21985842 |
| chr2: 1746834-1748971 | chr4: 126235896-126238930 | chr7: 22893795-22894577 |
| chr2: 174877566-174877778 | chr4: 13529255-13529865 | chr7: 23513535-23514412 |
| chr2: 175193399-175193764 | chr4: 13548571-13549956 | chr7: 24323559-24325080 |
| chr2: 175199464-175202639 | chr4: 1396292-1401730 | chr7: 25891957-25892615 |
| chr2: 175204844-175207553 | chr4: 141294667-141295274 | chr7: 25898238-25898771 |
| chr2: 176989338-176989587 | chr4: 142053328-142054601 | chr7: 26191795-26192757 |
| chr2: 176993480-176995557 | chr4: 154143933-154144463 | chr7: 27190275-27191115 |
| chr2: 177001222-177001783 | chr4: 154170369-154170600 | chr7: 27194584-27194827 |
| chr2: 177005365-177005666 | chr4: 154605087-154606052 | chr7: 27208872-27209616 |
| chr2: 177029414-177029941 | chr4: 156588298-156589292 | chr7: 27212417-27214396 |
| chr2: 177052958-177054350 | chr4: 15704641-15705000 | chr7: 27219310-27219750 |
| chr2: 177502241-177502910 | chr4: 157892686-157893286 | chr7: 27224268-27224596 |
| chr2: 180725718-180726465 | chr4: 157997167-157997686 | chr7: 27275056-27275626 |
| chr2: 183902403-183903625 | chr4: 166299976-166300668 | chr7: 29603110-29603328 |
| chr2: 185463209-185463589 | chr4: 166794546-166795341 | chr7: 30028519-30029822 |
| chr2: 189156417-189157719 | chr4: 168155006-168155765 | chr7: 31232678-31232900 |
| chr2: 191044980-191045829 | chr4: 170946767-170947925 | chr7: 35301151-35301731 |
| chr2: 192109829-192110940 | chr4: 171010944-171011503 | chr7: 37487355-37488672 |
| chr2: 197457393-197458522 | chr4: 175750331-175750584 | chr7: 37960317-37961046 |
| chr2: 200320503-200329681 | chr4: 176922474-176922820 | chr7: 38670440-38671008 |
| chr2: 201450527-201451027 | chr4: 176923076-176923630 | chr7: 42276004-42277850 |
| chr2: 201983199-201983709 | chr4: 176986922-176987360 | chr7: 42533077-42533283 |
| chr2: 207308267-207308907 | chr4: 183369277-183370459 | chr7: 44079718-44080568 |
| chr2: 20865290-20867589 | chr4: 184319565-184320198 | chr7: 44364433-44365328 |
| chr2: 21022565-21022934 | chr4: 184643915-184644414 | chr7: 48128047-48128499 |
| chr2: 213402181-213403867 | chr4: 186455984-186456864 | chr7: 5111621-5112088 |
| chr2: 214148958-214149426 | chr4: 187476280-187476844 | chr7: 51383312-51384938 |
| chr2: 217236026-217237129 | chr4: 190942735-190944898 | chr7: 5336514-5336894 |
| chr2: 217497812-217498847 | chr4: 21950086-21950346 | chr7: 54731780-54732479 |
| chr2: 217556803-217557174 | chr4: 26030421-26030692 | chr7: 55000877-55001135 |
| chr2: 218621280-218621498 | chr4: 2765639-2766063 | chr7: 56183578-56184165 |
| chr2: 219156978-219157380 | chr4: 298804-299312 | chr7: 63767751-63767991 |
| chr2: 219252422-219252631 | chr4: 30718854-30719847 | chr7: 64349425-64350151 |
| chr2: 219748277-219748805 | chr4: 30721205-30724842 | chr7: 64407590-64408299 |
| chr2: 219762988-219763537 | chr4: 330163-332068 | chr7: 65037625-65037864 |
| chr2: 219773547-219774103 | chr4: 3464800-3465440 | chr7: 65509075-65509594 |
| chr2: 219827660-219828205 | chr4: 379900-380399 | chr7: 65878464-65878977 |
| chr2: 219866132-219868054 | chr4: 38869402-38869780 | chr7: 6654746-6655860 |
| chr2: 219922155-219923130 | chr4: 4108735-4109499 | chr7: 69062375-69065037 |
| chr2: 219924820-219926130 | chr4: 41218315-41218768 | chr7: 70060835-70061456 |
| chr2: 220159439-220159977 | chr4: 41646293-41646582 | chr7: 73021487-73021720 |
| chr2: 220196432-220196768 | chr4: 41753670-41753947 | chr7: 73867788-73868061 |
| chr2: 220348956-220349784 | chr4: 42399153-42400802 | chr7: 74202334-74203629 |
| chr2: 220361463-220363254 | chr4: 4577005-4577448 | chr7: 74572475-74573770 |
| chr2: 220377744-220377946 | chr4: 46391904-46392572 | chr7: 75889087-75889345 |
| chr2: 220406364-220406840 | chr4: 48271363-48271846 | chr7: 75889498-75889760 |
| chr2: 223288923-223290013 | chr4: 48272027-48272298 | chr7: 75896511-75896944 |
| chr2: 223536123-223536565 | chr4: 48492118-48493589 | chr7: 76026791-76027223 |
| chr2: 224701963-224702790 | chr4: 4854614-4855210 | chr7: 77649015-77649543 |
| chr2: 225906654-225907464 | chr4: 4873263-4873613 | chr7: 82072022-82073520 |
| chr2: 228582486-228582821 | chr4: 48908293-48908850 | chr7: 82791675-82792412 |
| chr2: 228736231-228736544 | chr4: 52917389-52918280 | chr7: 8473140-8475199 |
| chr2: 229045958-229046553 | chr4: 53617119-53617607 | chr7: 84814840-84816242 |
| chr2: 230135709-230136004 | chr4: 55991403-55992171 | chr7: 852961-853230 |
| chr2: 231692698-231693496 | chr4: 5713036-5713451 | chr7: 87256679-87258444 |
| chr2: 231712776-231712982 | chr4: 57687611-57687906 | chr7: 88388489-88389283 |
| chr2: 231902027-231903122 | chr4: 62065884-62068801 | chr7: 90225083-90226364 |
| chr2: 232276743-232277135 | chr4: 667274-667601 | chr7: 915754-916644 |
| chr2: 232765247-232765491 | chr4: 7194538-7195467 | chr7: 94536850-94537477 |
| chr2: 232791576-232792016 | chr4: 74486045-74486258 | chr7: 95025560-95026122 |
| chr2: 233367781-233368577 | chr4: 74702421-74702627 | chr7: 96631384-96631800 |
| chr2: 233740669-233741879 | chr4: 74809870-74810089 | chr7: 96746768-96747190 |
| chr2: 234776883-234777098 | chr4: 74864114-74864329 | chr7: 98971650-98973170 |
| chr2: 236578081-236580153 | chr4: 74964657-74965279 | chr7: 993402-994574 |
| chr2: 238395062-238396241 | chr4: 77507078-77507339 | chr7: 99768885-99769559 |
| chr2: 238599858-238601430 | chr4: 77610325-77610943 | chr8: 102092795-102093240 |
| chr2: 238768074-238768831 | chr4: 786119-786341 | chr8: 103822615-103823263 |
| chr2: 239755097-239758310 | chr4: 7940564-7941853 | chr8: 104310810-104311620 |

TABLE 3-continued

Additional Example CGIs

| | | |
|---|---|---|
| chr2: 241391877-241393598 | chr4: 79472807-79473177 | chr8: 104383410-104384109 |
| chr2: 241395249-241395802 | chr4: 81123509-81124318 | chr8: 104510871-104513913 |
| chr2: 241771656-241772194 | chr4: 81124469-81124845 | chr8: 105235385-105235979 |
| chr2: 241855375-241855631 | chr4: 81951942-81952808 | chr8: 105600454-105601704 |
| chr2: 241922778-241923143 | chr4: 8594413-8594777 | chr8: 10586614-10586886 |
| chr2: 242498014-242499274 | chr4: 87515184-87515735 | chr8: 107669778-107670591 |
| chr2: 242742599-242743758 | chr4: 8869045-8870067 | chr8: 110374553-110374793 |
| chr2: 242785912-242786616 | chr4: 8893372-8896268 | chr8: 11058625-11058844 |
| chr2: 242808406-242808618 | chr4: 89378224-89378948 | chr8: 11059012-11059242 |
| chr2: 242823447-242823970 | chr4: 91048412-91049682 | chr8: 110986114-110986983 |
| chr2: 24300061-24300294 | chr4: 95678799-95679809 | chr8: 11555100-11555603 |
| chr2: 26396103-26397204 | chr5: 102201584-102201912 | chr8: 11759863-11760212 |
| chr2: 26401696-26402099 | chr5: 10307521-10307913 | chr8: 119963947-119964178 |
| chr2: 26407423-26408253 | chr5: 112630220-112630624 | chr8: 119964390-119964637 |
| chr2: 26726190-26726710 | chr5: 112823257-112824304 | chr8: 120220389-120221222 |
| chr2: 26785115-26785687 | chr5: 113391072-113392005 | chr8: 12990091-12990914 |
| chr2: 27341568-27341923 | chr5: 113696517-113699195 | chr8: 13133843-13134312 |
| chr2: 27958208-27958723 | chr5: 115151349-115152713 | chr8: 131455249-131456285 |
| chr2: 31360322-31361821 | chr5: 11903551-11904703 | chr8: 133492399-133493586 |
| chr2: 31456741-31457653 | chr5: 121412501-121414077 | chr8: 142318354-142319155 |
| chr2: 38763115-38763564 | chr5: 121647451-121648147 | chr8: 143530646-143530872 |
| chr2: 42068364-42068594 | chr5: 122424906-122425958 | chr8: 143531119-143534495 |
| chr2: 43864323-43864956 | chr5: 122426126-122426836 | chr8: 143556715-143556997 |
| chr2: 45161428-45163058 | chr5: 122433879-122435551 | chr8: 144099457-144099731 |
| chr2: 45235512-45237792 | chr5: 125930602-125931049 | chr8: 144503421-144503808 |
| chr2: 47499465-47499813 | chr5: 126564998-126565580 | chr8: 144640397-144640772 |
| chr2: 47796924-47799166 | chr5: 127872564-127874945 | chr8: 144798488-144799038 |
| chr2: 48757212-48757785 | chr5: 128300801-128301329 | chr8: 144822012-144822805 |
| chr2: 54785027-54785969 | chr5: 128795504-128797417 | chr8: 144842965-144843542 |
| chr2: 56410866-56412539 | chr5: 131346893-131347776 | chr8: 145555343-145562310 |
| chr2: 58273643-58274422 | chr5: 132155289-132155497 | chr8: 145697880-145698784 |
| chr2: 64836207-64836765 | chr5: 132946745-132948467 | chr8: 145700239-145700822 |
| chr2: 65086805-65087180 | chr5: 134824932-134825224 | chr8: 145806259-145806713 |
| chr2: 66660453-66660794 | chr5: 134827286-134827644 | chr8: 145909677-145912846 |
| chr2: 66661119-66661657 | chr5: 135170272-135171156 | chr8: 15397637-15398287 |
| chr2: 68870352-68871055 | chr5: 135527057-135528978 | chr8: 16884364-16885339 |
| chr2: 69240084-69241004 | chr5: 139017134-139017668 | chr8: 17354322-17355250 |
| chr2: 70351316-70351550 | chr5: 139040820-139041028 | chr8: 1771362-1772760 |
| chr2: 7057531-7058433 | chr5: 139047906-139048235 | chr8: 22089368-22089668 |
| chr2: 70994448-70995385 | chr5: 139076543-139077179 | chr8: 22408673-22409635 |
| chr2: 71192095-71192495 | chr5: 139081002-139081202 | chr8: 22456092-22456508 |
| chr2: 71503548-71504233 | chr5: 139135590-139135976 | chr8: 22457124-22457753 |
| chr2: 71680559-71681276 | chr5: 139174905-139176172 | chr8: 22960385-22960927 |
| chr2: 71693165-71694127 | chr5: 139227606-139228279 | chr8: 23081957-23082975 |
| chr2: 73151201-73152060 | chr5: 139742900-139743148 | chr8: 23260443-23261867 |
| chr2: 74347274-74347777 | chr5: 139927158-139927491 | chr8: 24770909-24772547 |
| chr2: 74425445-74426423 | chr5: 140011483-140012739 | chr8: 25897201-25897612 |
| chr2: 74725040-74727038 | chr5: 140167092-140168139 | chr8: 26371173-26372830 |
| chr2: 74776017-74776897 | chr5: 140207726-140208078 | chr8: 27183091-27183390 |
| chr2: 74781495-74782685 | chr5: 140261885-140262153 | chr8: 27348659-27348883 |
| chr2: 75147006-75147336 | chr5: 140531158-140532017 | chr8: 29210484-29210801 |
| chr2: 75426593-75428030 | chr5: 140568217-140569118 | chr8: 33371898-33372526 |
| chr2: 7571072-7571642 | chr5: 140573424-140574316 | chr8: 35092680-35093559 |
| chr2: 75787718-75788312 | chr5: 140604454-140605304 | chr8: 35093901-35094111 |
| chr2: 79220193-79220592 | chr5: 140615392-140616353 | chr8: 38325092-38326374 |
| chr2: 79739697-79740243 | chr5: 140620865-140621698 | chr8: 38644474-38645760 |
| chr2: 85359957-85362593 | chr5: 140741175-140741738 | chr8: 40755165-40755404 |
| chr2: 85640970-85641259 | chr5: 140750051-140750264 | chr8: 41624556-41625380 |
| chr2: 85811341-85811855 | chr5: 140762402-140762768 | chr8: 41654876-41655984 |
| chr2: 85980500-85982198 | chr5: 140767197-140767695 | chr8: 49231523-49231810 |
| chr2: 8818293-8818503 | chr5: 140777443-140777938 | chr8: 494156-496083 |
| chr2: 88316234-88316859 | chr5: 140802400-140802832 | chr8: 49647703-49647988 |
| chr2: 88469692-88470386 | chr5: 141132812-141133338 | chr8: 54569668-54570010 |
| chr2: 96054895-96055143 | chr5: 141228931-141230084 | chr8: 54789582-54790665 |
| chr2: 96192056-96193068 | chr5: 141705392-141705648 | chr8: 54791846-54795141 |
| chr2: 96314996-96315230 | chr5: 142782072-142785071 | chr8: 57232371-57232795 |
| chr2: 98703355-98703889 | chr5: 145316146-145316354 | chr8: 58907002-58907822 |
| chr20: 1206680-1207119 | chr5: 146257347-146258575 | chr8: 60030135-60032356 |
| chr20: 13200671-13202616 | chr5: 146614284-146614560 | chr8: 61193313-61194195 |
| chr20: 13975769-13976287 | chr5: 149681703-149682601 | chr8: 65491084-65491319 |
| chr20: 13976701-13977068 | chr5: 150004671-150004984 | chr8: 65492936-65494452 |
| chr20: 18039533-18039928 | chr5: 150284386-150284635 | chr8: 6691834-6693135 |
| chr20: 1874934-1875718 | chr5: 150325905-150326194 | chr8: 67089250-67089962 |
| chr20: 19738040-19739773 | chr5: 150537020-150537418 | chr8: 6949350-6950039 |
| chr20: 22562737-22566104 | chr5: 151304227-151304824 | chr8: 70946891-70947299 |
| chr20: 23028404-23032218 | chr5: 153853057-153853551 | chr8: 72917306-72917641 |
| chr20: 24898955-24899181 | chr5: 153862143-153862451 | chr8: 74005022-74005856 |
| chr20: 30196119-30196585 | chr5: 154026819-154027257 | chr8: 7543874-7544385 |

TABLE 3-continued

Additional Example CGIs

| | | |
|---|---|---|
| chr20: 30582789-30583099 | chr5: 15500077-15500923 | chr8: 80695831-80696458 |
| chr20: 30605745-30605970 | chr5: 155107505-155108934 | chr8: 81805956-81806327 |
| chr20: 3229239-3229693 | chr5: 157002175-157003182 | chr8: 82192379-82193685 |
| chr20: 32450501-32450765 | chr5: 157285770-157286254 | chr8: 82644604-82644849 |
| chr20: 33865768-33866091 | chr5: 158758475-158758839 | chr8: 8820767-8821112 |
| chr20: 3387966-3388901 | chr5: 159343216-159343574 | chr8: 89339966-89340481 |
| chr20: 34188720-34190267 | chr5: 159738782-159739913 | chr8: 95651207-95651760 |
| chr20: 36793550-36793867 | chr5: 160974693-160975384 | chr8: 95652456-95652873 |
| chr20: 37230524-37230742 | chr5: 16179065-16180420 | chr8: 95653899-95654733 |
| chr20: 37274692-37275134 | chr5: 168727430-168728275 | chr8: 97156764-97158030 |
| chr20: 39311379-39312435 | chr5: 170288880-170289737 | chr8: 97505748-97507607 |
| chr20: 39316551-39319987 | chr5: 170877799-170878210 | chr8: 9756178-9756993 |
| chr20: 4202149-4202765 | chr5: 172068287-172069174 | chr8: 99305904-99306726 |
| chr20: 42285962-42286535 | chr5: 172385523-172385912 | chr9: 103173890-103174153 |
| chr20: 43438738-43439546 | chr5: 172710766-172711062 | chr9: 103790613-103791764 |
| chr20: 44098281-44099536 | chr5: 172754057-172757098 | chr9: 103791945-103792173 |
| chr20: 44452577-44453162 | chr5: 174151479-174152364 | chr9: 104248248-104249501 |
| chr20: 44539730-44540099 | chr5: 175223610-175224679 | chr9: 1051820-1052240 |
| chr20: 44642095-44642406 | chr5: 175621334-175621827 | chr9: 10612636-10613333 |
| chr20: 44746823-44747060 | chr5: 176236762-176238081 | chr9: 107509907-107510768 |
| chr20: 44935933-44937310 | chr5: 176789979-176790296 | chr9: 110249749-110252660 |
| chr20: 45142001-45142337 | chr5: 176830276-176831639 | chr9: 112262011-112262317 |
| chr20: 45523251-45524020 | chr5: 177098635-177099525 | chr9: 112402768-112403349 |
| chr20: 47443735-47445181 | chr5: 177366539-177366973 | chr9: 114287381-114287695 |
| chr20: 48598960-48599657 | chr5: 177433282-177434067 | chr9: 116111664-116112189 |
| chr20: 50158905-50159509 | chr5: 177540208-177541234 | chr9: 116450146-116450454 |
| chr20: 55500348-55501102 | chr5: 178016559-178017670 | chr9: 116860474-116860695 |
| chr20: 55839288-55839766 | chr5: 178322714-178323538 | chr9: 123631107-123631672 |
| chr20: 55840217-55841794 | chr5: 178367621-178368725 | chr9: 123690772-123691675 |
| chr20: 55964273-55964656 | chr5: 178770725-178772794 | chr9: 124061806-124062229 |
| chr20: 55964917-55965271 | chr5: 180479586-180480959 | chr9: 124461798-124462190 |
| chr20: 56323974-56324254 | chr5: 180542154-180542402 | chr9: 124498514-124498962 |
| chr20: 56725858-56726113 | chr5: 2038528-2038949 | chr9: 124975754-124976692 |
| chr20: 57224696-57226322 | chr5: 31855004-31855426 | chr9: 125109008-125109644 |
| chr20: 57581903-57582595 | chr5: 36690208-36690658 | chr9: 126135408-126136193 |
| chr20: 57797224-57797441 | chr5: 373843-374426 | chr9: 126762469-126762683 |
| chr20: 59826978-59828978 | chr5: 38556223-38557563 | chr9: 126807511-126808181 |
| chr20: 6103437-6103970 | chr5: 38845503-38846476 | chr9: 129677707-129678009 |
| chr20: 61147458-61147787 | chr5: 41510325-41510651 | chr9: 130461544-130461839 |
| chr20: 61200973-61201272 | chr5: 42423531-42423740 | chr9: 131012455-131013429 |
| chr20: 61456340-61456565 | chr5: 42424339-42425047 | chr9: 131965038-131965636 |
| chr20: 61884645-61886387 | chr5: 42994627-42994936 | chr9: 132020630-132021038 |
| chr20: 61927195-61927482 | chr5: 42995123-42995415 | chr9: 132082872-132083582 |
| chr20: 61937483-61937738 | chr5: 43017969-43018668 | chr9: 132099124-132099616 |
| chr20: 61992187-61993599 | chr5: 43040346-43040633 | chr9: 132145577-132146328 |
| chr20: 62600654-62601676 | chr5: 43040846-43041161 | chr9: 132331219-132331458 |
| chr20: 62673793-62674131 | chr5: 43396898-43397364 | chr9: 132359673-132360061 |
| chr20: 62714764-62715761 | chr5: 472601-474261 | chr9: 132382433-132383004 |
| chr20: 62958974-62959513 | chr5: 474959-475319 | chr9: 132499969-132500553 |
| chr20: 708602-709290 | chr5: 49736608-49737300 | chr9: 13278313-13279805 |
| chr20: 8112885-8113592 | chr5: 55776605-55777233 | chr9: 132934214-132934483 |
| chr20: 9048959-9050018 | chr5: 57878726-57879177 | chr9: 133308594-133309448 |
| chr20: 9819272-9819861 | chr5: 58334837-58335881 | chr9: 133412891-133413096 |
| chr21: 18984536-18985697 | chr5: 60921535-60922472 | chr9: 134151854-134153015 |
| chr21: 27011625-27012398 | chr5: 6448754-6449629 | chr9: 134158161-134158682 |
| chr21: 28216559-28218117 | chr5: 66299769-66300083 | chr9: 136451013-136451276 |
| chr21: 32929928-32932017 | chr5: 67584214-67584451 | chr9: 137217063-137218078 |
| chr21: 36041306-36043224 | chr5: 68710808-68711520 | chr9: 137299191-137299437 |
| chr21: 38119794-38120742 | chr5: 691081-691376 | chr9: 137533360-137534397 |
| chr21: 38352857-38353274 | chr5: 72415612-72416766 | chr9: 138985838-138987846 |
| chr21: 38362016-38362868 | chr5: 72715408-72715997 | chr9: 139014622-139014848 |
| chr21: 40032244-40033665 | chr5: 72732366-72733732 | chr9: 139159210-139159560 |
| chr21: 40760627-40760829 | chr5: 74349801-74350239 | chr9: 139551255-139551559 |
| chr21: 42878752-42880674 | chr5: 75378975-75380796 | chr9: 139552948-139553269 |
| chr21: 43373136-43374062 | chr5: 76011121-76012292 | chr9: 139553660-139553915 |
| chr21: 43917047-43917268 | chr5: 76115511-76116089 | chr9: 139595846-139596130 |
| chr21: 44073202-44074650 | chr5: 76941396-76941888 | chr9: 139872238-139873143 |
| chr21: 45148455-45149262 | chr5: 78365299-78365711 | chr9: 140051063-140051730 |
| chr21: 46129392-46129689 | chr5: 87437096-87437505 | chr9: 140317161-140318663 |
| chr21: 46351329-46352911 | chr5: 87976095-87976546 | chr9: 14348685-14349074 |
| chr21: 46706692-46707049 | chr5: 92906240-92908875 | chr9: 14349308-14349515 |
| chr22: 17849475-17850733 | chr5: 94619460-94621121 | chr9: 17134822-17135706 |
| chr22: 18923471-18923840 | chr5: 95170618-95170855 | chr9: 214587-215431 |
| chr22: 19753313-19755013 | chr5: 9544693-9546715 | chr9: 21559134-21559816 |
| chr22: 21319179-21319912 | chr5: 96038210-96038884 | chr9: 2241892-2242102 |
| chr22: 22862624-22863220 | chr6: 101841426-101841905 | chr9: 27528358-27528725 |
| chr9: 27528977-27529885 | | |
| chr9: 33044246-33044612 | | |

TABLE 3-continued

Additional Example CGIs chr9: 33447447-33447824
chr9: 33750520-33751160
chr9: 34377402-34377610
chr9: 34379542-34380017
chr9: 34577867-34578258
chr9: 34589114-34591978
chr9: 35756949-35757339
chr9: 36036799-36037564
chr9: 36258171-36258886
chr9: 37575919-37576445
chr9: 38069785-38069991
chr9: 38423948-38424584
chr9: 4297818-4300182
chr9: 46148701-46149726
chr9: 4662253-4662951
chr9: 707022-707420
chr9: 71788716-71789542
chr9: 72658837-72659277
chr9: 77502094-77502518
chr9: 79073908-79074561
chr9: 79520804-79521508
chr9: 80911780-80912611
chr9: 85677016-85678321
chr9: 86571048-86572027
chr9: 8857486-8858708
chr9: 88713706-88714908
chr9: 89560585-89562647
chr9: 90112515-90113817
chr9: 90340716-90341542
chr9: 90589210-90589807
chr9: 93563776-93564546
chr9: 93955501-93956420
chr9: 94183408-94183994
chr9: 95569430-95572255
chr9: 95896008-95897016
chr9: 97021465-97021967
chr9: 97766650-97767955
chr9: 97810766-97811272
chr9: 99145525-99145849

TABLE 4

Additional Example CGIs

| | | |
|---|---|---|
| chr1: 10762450-10766925 | chr12: 101107864-101113622 | chr17: 48039283-48045064 |
| chr1: 110608266-110615303 | chr12: 103694091-103698418 | chr17: 48192635-48197085 |
| chr1: 113263574-113267787 | chr12: 104695349-104699984 | chr17: 48543571-48548900 |
| chr1: 113284333-113289172 | chr12: 106972413-106983086 | chr17: 4998370-5003205 |
| chr1: 114693137-114698672 | chr12: 113011100-113015529 | chr17: 50233176-50238466 |
| chr1: 115878168-115883332 | chr12: 113513165-113517970 | chr17: 59483574-59487780 |
| chr1: 116378360-116384364 | chr12: 113588807-113593304 | chr17: 59526980-59537254 |
| chr1: 1179757-1184470 | chr12: 113898751-113918717 | chr17: 6614423-6619471 |
| chr1: 119524783-119532712 | chr12: 114831912-114854360 | chr17: 6677206-6681710 |
| chr1: 119541057-119553320 | chr12: 114876144-114888579 | chr17: 70109980-70122442 |
| chr1: 12121489-12126148 | chr12: 115107504-115112061 | chr17: 71946479-71951255 |
| chr1: 145073484-145077845 | chr12: 117796077-117801448 | chr17: 72853622-72860012 |
| chr1: 146550329-146554577 | chr12: 119210111-119214393 | chr17: 72913569-72918510 |
| chr1: 1468605-1477220 | chr12: 120833587-120837927 | chr17: 73747619-73752178 |
| chr1: 147780067-147784473 | chr12: 122014171-122019693 | chr17: 74015770-74020658 |
| chr1: 149330994-149335389 | chr12: 123752050-123756373 | chr17: 74531282-74536566 |
| chr1: 155145186-155149444 | chr12: 127208779-127213651 | chr17: 75240872-75254180 |
| chr1: 155262319-155267536 | chr12: 127938452-127942907 | chr17: 75275318-75280172 |
| chr1: 155288607-155293001 | chr12: 129335871-129340653 | chr17: 75366689-75372506 |
| chr1: 156103708-156108171 | chr12: 130385610-130391139 | chr17: 75396285-75400527 |
| chr1: 156336759-156341251 | chr12: 130906778-130911191 | chr17: 75445478-75449821 |
| chr1: 156356051-156360252 | chr12: 131197825-131202157 | chr17: 77803867-77811046 |
| chr1: 156388404-156393581 | chr12: 132903450-132908206 | chr17: 7830533-7835164 |
| chr1: 156861416-156865711 | chr12: 14132627-14137242 | chr17: 78997641-79001641 |
| chr1: 160338605-160342843 | chr12: 15473319-15477901 | chr17: 7903928-7909445 |
| chr1: 161693638-161699298 | chr12: 184864-189610 | chr17: 79312963-79322653 |
| chr1: 164543541-164547917 | chr12: 29300035-29304954 | chr17: 79857809-79862963 |
| chr1: 165321704-165328328 | chr12: 3306813-3312270 | chr17: 932418-937088 |
| chr1: 16858874-16864296 | chr12: 3473011-3477654 | chr18: 11146308-11151936 |
| chr1: 170628457-170632851 | chr12: 41084523-41089102 | chr18: 11748954-11754756 |
| chr1: 173636663-173641045 | chr12: 45442203-45447386 | chr18: 12252148-12257089 |

TABLE 4-continued

Additional Example CGIs

| | | |
|---|---|---|
| chr1: 175566377-175570808 | chr12: 48397169-48401372 | chr18: 13639585-13644415 |
| chr1: 177131393-177135846 | chr12: 49181050-49185282 | chr18: 13866533-13871026 |
| chr1: 179542721-179547307 | chr12: 49369691-49377550 | chr18: 19742937-19754363 |
| chr1: 180196120-180206975 | chr12: 49482921-49487178 | chr18: 30347691-30354302 |
| chr1: 181285301-181289873 | chr12: 5016586-5023171 | chr18: 35142908-35149628 |
| chr1: 181450707-181455073 | chr12: 5151013-5156346 | chr18: 43606141-43610510 |
| chr1: 18434552-18439673 | chr12 : 52113411-52117679 | chr18: 44334184-44340100 |
| chr1: 18954896-18970739 | chr12: 52406382-52410675 | chr18: 44770993-44780084 |
| chr1: 19201875-19206234 | chr12: 52650019-52654743 | chr18: 44787407-44792678 |
| chr1: 197885089-197889791 | chr12: 53105913-53110471 | chr18: 54786960-54791194 |
| chr1: 200007808-200012036 | chr12: 53357193-53361507 | chr18: 55017708-55023605 |
| chr1: 201250453-201255648 | chr12: 53489573-53493955 | chr18: 55092826-55110853 |
| chr1: 202160959-202165390 | chr12: 54069054-54073265 | chr18: 55920988-55926068 |
| chr1: 202676882-202681769 | chr12: 54319302-54323721 | chr18: 56885092-56889665 |
| chr1: 203042723-203047390 | chr12: 54336762-54341168 | chr18: 56937625-56943540 |
| chr1: 208130328-208135117 | chr12: 54352530-54382102 | chr18: 58998684-59003692 |
| chr1: 214151215-214161080 | chr12: 54421428-54428709 | chr18: 61141927-61145927 |
| chr1: 21614381-21619101 | chr12: 54438643-54450091 | chr18: 70531966-70538871 |
| chr1: 217308750-217313178 | chr12: 54517769-54522457 | chr18: 72914108-72919233 |
| chr1: 221048449-221070185 | chr12: 57616770-57621402 | chr18: 73165403-73169920 |
| chr1: 225863069-225867328 | chr12: 58001881-58006249 | chr18: 74151240-74157073 |
| chr1: 226073151-226077680 | chr12: 58156856-58162000 | chr18: 74797145-74802038 |
| chr1: 226125113-226129695 | chr12: 63541637-63546967 | chr18: 74959557-74965822 |
| chr1: 228783987-228788204 | chr12: 6436273-6440931 | chr18: 76730971-76743244 |
| chr1: 231294560-231299345 | chr12: 65216246-65221143 | chr18: 77545966-77560948 |
| chr1: 24227116-24231537 | chr12: 65512879-65517863 | chr18: 902579-911574 |
| chr1: 243644395-243648888 | chr12: 72663684-72669551 | chr19: 10404935-10409342 |
| chr1: 248018331-248023252 | chr12: 75600992-75605344 | chr19: 10461627-10466378 |
| chr1: 25253528-25261005 | chr12: 81100035-81104716 | chr19: 1061545-1066265 |
| chr1: 2770127-2774665 | chr12: 81469570-81474119 | chr19: 1106395-1111610 |
| chr1: 29583898-29588598 | chr12: 99137387-99141769 | chr19: 11592373-11596987 |
| chr1: 2977276-2982758 | chr13: 100545634-100550911 | chr19: 12664244-12668682 |
| chr1: 32050472-32054771 | chr13: 100639335-100644188 | chr19: 12765750-12769980 |
| chr1: 34626784-34632976 | chr13: 102566426-102571495 | chr19: 12829794-12834225 |
| chr1: 34640383-34645024 | chr13: 108516335-108521063 | chr19: 12878575-12882888 |
| chr1: 36547555-36551965 | chr13: 109145799-109151019 | chr19: 13122960-13127259 |
| chr1: 38217703-38222012 | chr13: 112705805-112730419 | chr19: 13133318-13138169 |
| chr1: 38459585-38463988 | chr13: 112756599-112763113 | chr19: 13196700-13200999 |
| chr1: 38939920-38944404 | chr13: 20873519-20878214 | chr19: 13211451-13215821 |
| chr1: 39042060-39046561 | chr13: 27332227-27337205 | chr19: 13614753-13619267 |
| chr1: 39978366-39983768 | chr13: 28364550-28370505 | chr19: 14087571-14091796 |
| chr1: 40233768-40239190 | chr13: 28496227-28501046 | chr19: 15290400-15294632 |
| chr1: 40767187-40771871 | chr13: 28547840-28552246 | chr19: 1746168-1752243 |
| chr1: 41282848-41287149 | chr13: 32887117-32892116 | chr19: 18977352-18983200 |
| chr1: 41829977-41834542 | chr13: 36042845-36055119 | chr19: 19366709-19374393 |
| chr1: 44029287-44033853 | chr13: 51415372-51420149 | chr19: 21767190-21771786 |
| chr1: 46949169-46953792 | chr13: 53417898-53424872 | chr19: 2422006-2429983 |
| chr1: 47007576-47012132 | chr13: 58201587-58210930 | chr19: 30713550-30719970 |
| chr1: 4711990-4718555 | chr13: 79179945-79185880 | chr19: 33623468-33627805 |
| chr1: 47907713-47913020 | chr13: 84451665-84455897 | chr19: 35631410-35635697 |
| chr1: 50878917-50884103 | chr13: 93877246-93882877 | chr19: 36244329-36249982 |
| chr1: 50890438-50895243 | chr14: 101190852-101195499 | chr19: 36334276-36339138 |
| chr1: 53525573-53530974 | chr14: 101921576-101927995 | chr19: 36498170-36502530 |
| chr1: 53740298-53744845 | chr14: 103653242-103657928 | chr19: 36521392-36525887 |
| chr1: 55503061-55508015 | chr14: 105165664-105170129 | chr19: 3866587-3871217 |
| chr1: 61513876-61518831 | chr14: 24042887-24048760 | chr19: 38698334-38702577 |
| chr1: 63780395-63798140 | chr14: 24639054-24644220 | chr19: 38874071-38878332 |
| chr1: 65729412-65733849 | chr14: 24801679-24806353 | chr19: 39735690-39741288 |
| chr1: 65989002-65993811 | chr14: 29234836-29239832 | chr19: 39752974-39758540 |
| chr1: 66256441-66260918 | chr14: 29252366-29257069 | chr19: 40312927-40317144 |
| chr1: 67216080-67220293 | chr14: 33400095-33406079 | chr19: 405012-411511 |
| chr1: 67771330-67775767 | chr14: 36971170-36996488 | chr19: 42889312-42893646 |
| chr1: 77745315-77750224 | chr14: 37047334-37055690 | chr19: 44201559-44205987 |
| chr1: 86619279-86624871 | chr14: 37114189-37138348 | chr19: 44276274-44280777 |
| chr1: 91170103-91194804 | chr14: 38676246-38682937 | chr19: 45258353-45263809 |
| chr1: 91298980-91303891 | chr14: 38722255-38727537 | chr19: 45896880-45902315 |
| chr1: 92943908-92954609 | chr14: 48141434-48147589 | chr19: 45999831-46004686 |
| chr10: 100990157-100994687 | chr14: 51336713-51341146 | chr19: 46316491-46321266 |
| chr10: 101277942-101292338 | chr14: 52732208-52737486 | chr19: 46913312-46917802 |
| chr10: 102277163-102281730 | chr14: 54416678-54420881 | chr19: 47149769-47155125 |
| chr10: 102417148-102421668 | chr14: 57258879-57286558 | chr19: 48963003-48967792 |
| chr10: 102471207-102493011 | chr14: 58329677-58335121 | chr19: 49667276-49671552 |
| chr10: 102505483-102511646 | chr14: 60971773-60980180 | chr19: 50879419-50883664 |
| chr10: 102889011-102908693 | chr14: 61101979-61106663 | chr19: 50929271-50933638 |
| chr10: 102973970-102980096 | chr14: 62277477-62282019 | chr19: 51167660-51174023 |
| chr10: 102994035-102998646 | chr14: 69254677-69259036 | chr19: 51599823-51604260 |
| chr10: 103041991-103046480 | chr14: 74704189-74710192 | chr19: 51813158-51817458 |
| chr10: 105359785-105364188 | chr14: 77734734-77739772 | chr19: 54410711-54415087 |

TABLE 4-continued

Additional Example CGIs

| | | |
|---|---|---|
| chr10: 105418686-105423076 | chr14: 85995469-86002478 | chr19: 54479413-54485572 |
| chr10: 105525044-105529044 | chr14: 92787495-92792712 | chr19: 55595978-55600887 |
| chr10: 106397568-106404812 | chr14: 95235623-95241679 | chr19: 55813941-55818277 |
| chr10: 108921781-108926805 | chr14: 95824676-95828941 | chr19: 56596039-56602296 |
| chr10: 109672197-109676964 | chr15: 100911439-100916022 | chr19: 56986314-56991741 |
| chr10: 110669725-110674326 | chr15: 23155795-23160624 | chr19: 58092740-58097764 |
| chr10: 111214605-111219083 | chr15: 27110031-27115479 | chr19: 5827049-5831474 |
| chr10: 118028733-118036230 | chr15: 27213952-27218856 | chr19: 58543116-58556587 |
| chr10: 118890162-118902329 | chr15: 33007531-33013696 | chr19: 7931264-7936898 |
| chr10: 118998436-119003530 | chr15: 33600817-33606003 | chr19: 8672333-8676764 |
| chr10: 119309205-119315563 | chr15: 35044444-35049480 | chr19: 868775-873318 |
| chr10: 119492494-119496991 | chr15: 37388176-37392380 | chr2: 102801673-102806556 |
| chr10: 120351693-120357821 | chr15: 40266582-40271061 | chr2: 105457128-105482760 |
| chr10: 121575530-121580385 | chr15: 45406468-45411528 | chr2: 106679983-106684403 |
| chr10: 123920851-123925542 | chr15: 47474370-47479499 | chr2: 107101834-107106053 |
| chr10: 124899908-124913035 | chr15: 49252985-49257564 | chr2: 108600825-108605467 |
| chr10: 125423496-125428642 | chr15: 53074188-53089488 | chr2: 114031360-114038041 |
| chr10: 125648821-125653373 | chr15: 53095562-53100476 | chr2: 114254776-114260043 |
| chr10: 125730221-125734843 | chr15: 59155046-59159594 | chr2: 118979770-118984466 |
| chr10: 129532411-129539366 | chr15: 60285108-60300520 | chr2: 119590603-119618826 |
| chr10: 130336696-130340994 | chr15: 67071307-67075943 | chr2: 119912127-119918663 |
| chr10: 130506444-130510658 | chr15: 74417871-74425044 | chr2: 124780253-124785255 |
| chr10: 131262948-131267947 | chr15: 76628030-76635515 | chr2: 127411697-127416171 |
| chr10: 134595358-134604649 | chr15: 79572831-79577211 | chr2: 127780614-127784829 |
| chr10: 15759424-15764101 | chr15: 79722100-79727643 | chr2: 128419720-128424182 |
| chr10: 16559605-16565822 | chr15: 89145661-89151198 | chr2: 130761484-130765764 |
| chr10: 1776785-1782018 | chr15: 89310720-89315183 | chr2: 132180328-132185101 |
| chr10: 22621351-22636862 | chr15: 89901447-89924768 | chr2: 137520461-137525696 |
| chr10: 22762709-22769050 | chr15: 89947374-89955182 | chr2: 139535693-139540650 |
| chr10: 23459301-23465889 | chr15: 91640909-91645702 | chr2: 142885725-142890553 |
| chr10: 23478698-23484455 | chr15: 96871409-96879721 | chr2: 144692667-144697180 |
| chr10: 23981367-23986978 | chr15: 96893307-96912030 | chr2: 154725907-154731328 |
| chr10: 26502384-26509434 | chr15: 96957342-96962531 | chr2: 157183558-157188355 |
| chr10: 27545669-27550402 | chr16: 10910160-10914719 | chr2: 162271295-162286677 |
| chr10: 43426168-43431460 | chr16: 20082708-20087305 | chr2: 171669599-171682358 |
| chr10: 48436412-48441320 | chr16: 2226191-2232946 | chr2: 176929576-176984402 |
| chr10: 50600990-50608783 | chr16: 22822617-22828459 | chr2: 177010372-177027692 |
| chr10: 50815602-50822356 | chr16: 23722271-23726775 | chr2: 177034255-177045444 |
| chr10: 63210496-63215009 | chr16: 24265041-24269527 | chr2: 182319762-182325029 |
| chr10: 71329450-71335392 | chr16: 3011017-3015228 | chr2: 182519222-182523927 |
| chr10: 75405414-75409706 | chr16: 3065522-3070358 | chr2: 19558964-19563650 |
| chr10: 76571196-76575507 | chr16: 31051480-31055800 | chr2: 198027069-198031438 |
| chr10: 8074003-8080378 | chr16: 3188766-3193389 | chr2: 200331688-200336172 |
| chr10: 88120925-88129364 | chr16: 3218439-3223356 | chr2: 207504775-207509422 |
| chr10: 94178316-94182754 | chr16: 48842552-48847264 | chr2: 20868007-20873280 |
| chr10: 94453525-94457896 | chr16: 49307124-49319263 | chr2: 219734133-219738788 |
| chr10: 94818027-94831040 | chr16: 49870450-49874926 | chr2: 219846292-219860917 |
| chr10: 99787615-99793320 | chr16: 51145491-51149944 | chr2: 220171871-220176283 |
| chr11: 105479127-105483422 | chr16: 51166267-51171110 | chr2: 220297484-220302243 |
| chr11: 115628399-115633117 | chr16: 51181700-51190763 | chr2: 220410342-220414678 |
| chr11: 119291321-119295943 | chr16: 54323041-54327703 | chr2: 223157726-223187468 |
| chr11: 123064518-123068986 | chr16: 54968302-54974846 | chr2: 233249362-233255414 |
| chr11: 124627724-124631926 | chr16: 55362824-55367483 | chr2: 237066072-237080762 |
| chr11: 128417199-128421513 | chr16: 55511221-55515526 | chr2: 238862316-238867170 |
| chr11: 128692085-128696688 | chr16: 58028215-58033633 | chr2: 241457633-241462047 |
| chr11: 131778329-131783532 | chr16: 6066915-6072401 | chr2: 241756142-241762783 |
| chr11: 132811563-132816395 | chr16: 62067122-62072634 | chr2: 25497764-25502429 |
| chr11: 132932060-132936291 | chr16: 66610750-66615412 | chr2: 30451567-30457655 |
| chr11: 132950539-132955307 | chr16: 67206068-67210678 | chr2: 31803294-31808403 |
| chr11: 133992710-133997090 | chr16: 67569253-67574728 | chr2: 3284325-3288530 |
| chr11: 14993129-14997908 | chr16: 67916680-67920909 | chr2: 3748829-3753927 |
| chr11: 17738790-17745779 | chr16: 68478865-68484822 | chr2: 38299277-38306518 |
| chr11: 20179201-20184325 | chr16: 71457782-71462338 | chr2: 45153196-45159049 |
| chr11: 20616198-20625399 | chr16: 82658652-82663813 | chr2: 45167506-45173884 |
| chr11: 27741473-27746564 | chr16: 84000270-84004860 | chr2: 45225645-45230783 |
| chr11: 2888389-2893337 | chr16: 86528748-86534994 | chr2: 45238373-45243579 |
| chr11: 31823744-31850776 | chr16: 86547070-86552512 | chr2: 45393870-45400186 |
| chr11: 32450145-32459311 | chr16: 86609389-86615821 | chr2: 465850-470659 |
| chr11: 36395927-36401398 | chr16: 88941428-88945669 | chr2: 50572046-50576817 |
| chr11: 43566922-43571854 | chr17: 1171536-1176733 | chr2: 54084777-54089266 |
| chr11: 44323658-44329932 | chr17: 12566668-12571335 | chr2: 5829188-5834208 |
| chr11: 46297545-46302216 | chr17: 12875271-12879773 | chr2: 63280515-63289097 |
| chr11: 46364877-46369101 | chr17: 14199727-14204052 | chr2: 66650692-66656218 |
| chr11: 60716429-60720888 | chr17: 14246392-14250721 | chr2: 66670432-66675636 |
| chr11:61535001-61539001 | chr17: 15818621-15823325 | chr2: 66806569-66811404 |
| chr11: 624729-642628 | chr17: 1878790-1883116 | chr2: 71785431-71789897 |
| chr11: 64134815-64140187 | chr17: 19881326-19885610 | chr2: 73141056-73150260 |
| chr11: 64476844-64481598 | chr17: 21365115-21369592 | chr2: 80527678-80532846 |

TABLE 4-continued

Additional Example CGIs

| | | |
|---|---|---|
| chr11: 64813041-64817722 | chr17: 27897512-27902067 | chr2: 80547579-80551798 |
| chr11: 65350232-65355134 | chr17: 32482008-32486280 | chr2: 87013975-87020182 |
| chr11: 65407637-65412127 | chr17: 33774554-33778888 | chr2: 87086817-87091037 |
| chr11: 65814405-65818665 | chr17: 35289900-35302875 | chr2: 97190978-97195383 |
| chr11: 67348566-67353565 | chr17: 36715692-36720593 | chr20: 10196136-10200984 |
| chr11: 68620109-68624339 | chr17: 37319483-37324099 | chr20: 17204529-17210756 |
| chr11: 69515841-69521929 | chr17: 37761692-37766304 | chr20: 21374359-21380245 |
| chr11: 69829572-69834484 | chr17: 40935259-40939480 | chr20: 21483933-21498714 |
| chr11: 70209532-70213532 | chr17: 41275001-41280000 | chr20: 21684200-21697344 |
| chr11: 70506329-70510617 | chr17: 43035167-43039740 | chr20: 22546968-22561240 |
| chr11: 70670835-70675055 | chr17: 43470528-43476343 | chr20: 25061839-25067525 |
| chr11: 71950113-71954528 | chr17: 45947677-45951885 | chr20: 2537134-2541877 |
| chr11: 723597-728870 | chr17: 46602363-46610390 | chr20: 2727998-2733630 |
| chr11: 72530613-72535774 | chr17: 46618368-46634212 | chr20: 2778979-2783497 |
| chr11: 79146359-79154200 | chr17: 46667435-46676181 | chr20: 3143122-3147746 |
| chr11: 8188227-8192671 | chr17: 46689521-46699701 | chr20: 32854660-32859248 |
| chr11: 88239711-88244562 | chr17: 46794235-46802746 | chr20: 33294515-33300242 |
| chr11: 89222417-89226718 | chr17: 46822786-46827372 | chr20: 36010596-36015439 |
| chr20: 36224618-36228841 | chr6: 161186085-161190639 | chr20: 44655464-44661243 |
| chr20: 37350131-37359372 | chr6: 1617094-1623094 | |
| chr20: 39992546-39997810 | chr6: 166577974-166585423 | |
| chr20: 41815476-41821212 | chr6: 166664838-166669541 | |
| chr20: 44683772-44689610 | chr6: 170730120-170734442 | |
| chr20: 48182194-48186833 | chr6: 26612014-26616851 | |
| chr20: 51587708-51592020 | chr6: 27226101-27230364 | |
| chr20: 52787253-52792986 | chr6: 29593299-29597795 | |
| chr20: 5294267-5299798 | chr6: 29892141-29897117 | |
| chr20: 57087461-57092237 | chr6: 30093174-30097610 | |
| chr20: 57413136-57429047 | chr6: 30137719-30142263 | |
| chr20: 61701527-61706022 | chr6: 33046417-33050814 | |
| chr20: 688576-693099 | chr6: 33391593-33395908 | |
| chr20: 9494472-9498893 | chr6: 33653967-33658238 | |
| chr21: 19615099-19619874 | chr6: 35477389-35481678 | |
| chr21: 31309387-31314106 | chr6: 37614723-37619179 | |
| chr21: 32622145-32626382 | chr6: 38680950-38685265 | |
| chr21: 34393129-34402245 | chr6: 389189-395790 | |
| chr21: 38063180-38068185 | chr6: 4077053-4081443 | |
| chr21: 38074763-38083833 | chr6: 41526267-41530900 | |
| chr21: 42216490-42221222 | chr6: 41906746-41911711 | |
| chr22: 19744156-19748369 | chr6: 42070033-42074701 | |
| chr22: 19965280-19969808 | chr6: 42143848-42148053 | |
| chr22: 25079851-25084112 | chr6: 42877280-42881623 | |
| chr22: 29707282-29714013 | chr6: 46653263-46658738 | |
| chr22: 31196492-31201033 | chr6: 50680335-50685214 | |
| chr22: 31498397-31503239 | chr6: 50785287-50793573 | |
| chr22: 37210770-37215467 | chr6: 50808643-50820431 | |
| chr22: 37463057-37467331 | chr6: 55037171-55041392 | |
| chr22: 37909980-37914258 | chr6: 5995028-6009797 | |
| chr22: 38377094-38381964 | chr6: 70990041-70994912 | |
| chr22: 38474837-38480839 | chr6: 7227878-7232865 | |
| chr22: 39260339-39265211 | chr6: 72296275-72300528 | |
| chr22: 42303618-42309254 | chr6: 78170232-78176088 | |
| chr22: 42320044-42324909 | chr6: 85470703-85476132 | |
| chr22: 42683895-42688095 | chr6: 99273764-99278038 | |
| chr22: 44255943-44260612 | chr6: 99288280-99292771 | |
| chr22: 44285498-44290061 | chr7: 100073304-100077551 | |
| chr22: 44724725-44729590 | chr7: 100815485-100825701 | |
| chr22: 46316694-46321087 | chr7: 101003900-101009443 | |
| chr22: 46438394-46443019 | chr7: 103083711-103088132 | |
| chr22: 48882885-48889043 | chr7: 103966784-103971959 | |
| chr22: 50494442-50499393 | chr7: 113722925-113729795 | |
| chr3: 11032447-11037384 | chr7: 12149221-12153559 | |
| chr3: 113158300-113162641 | chr7: 121938007-121959341 | |
| chr3: 121900743-121905645 | chr7: 124402175-124406432 | |
| chr3: 126111548-126115967 | chr7: 127988927-127994616 | |
| chr3: 127631994-127636588 | chr7: 128553330-128558650 | |
| chr3: 127792370-127798136 | chr7: 129418287-129425355 | |
| chr3: 12836472-12840782 | chr7: 130788359-130794773 | |
| chr3: 128717866-128723245 | chr7: 1360812-1365643 | |
| chr3: 129691128-129696841 | chr7: 136551855-136558194 | |
| chr3: 13112628-13117245 | chr7: 142492564-142497248 | |
| chr3: 133391119-133395657 | chr7: 143580126-143584610 | |
| chr3: 137480965-137493004 | chr7: 149387655-149391976 | |
| chr3: 138654628-138661107 | chr7: 149742403-149748469 | |
| chr3: 147106512-147116479 | chr7: 152619917-152624149 | |
| chr3: 147124989-147144391 | chr7: 153746408-153752444 | |
| chr3: 154144348-154148965 | chr7: 153999965-154004281 | |
| chr3: 157810054-157823836 | chr7: 155162558-155177248 | |

TABLE 4-continued

Additional Example CGIs

| | |
|---|---|
| chr3: 170301045-170305768 | chr7: 155239324-155245757 |
| chr3: 172163373-172168738 | chr7: 155256828-155263403 |
| chr3: 184054420-184058671 | chr7: 155300254-155305158 |
| chr3: 185909345-185914228 | chr7: 155593693-155607095 |
| chr3: 186076711-186082111 | chr7: 156407024-156411865 |
| chr3: 19187689-19192100 | chr7: 156793356-156803632 |
| chr3: 192123822-192129994 | chr7: 156869055-156873297 |
| chr3: 22411493-22416365 | chr7: 158934508-158940492 |
| chr3: 236392-242140 | chr7: 19143873-19148256 |
| chr3: 26662105-26666796 | chr7: 19182819-19187033 |
| chr3: 27769639-27773942 | chr7: 20368004-20373504 |
| chr3: 32859142-32863429 | chr7: 20828568-20832817 |
| chr3: 3838514-3844772 | chr7: 23285222-23289508 |
| chr3: 44061315-44065837 | chr7: 26413747-26418891 |
| chr3: 44594536-44599018 | chr7: 27132098-27136736 |
| chr3: 46616308-46620669 | chr7: 27144070-27150389 |
| chr3: 49945622-49950430 | chr7: 27180614-27187562 |
| chr3: 55506337-55510708 | chr7: 27195602-27208462 |
| chr3: 62352292-62365082 | chr7: 27225521-27231043 |
| chr3: 63261990-63266205 | chr7: 27258102-27262467 |
| chr3: 64251534-64255819 | chr7: 27276946-27294197 |
| chr3: 6900824-6906641 | chr7: 30719373-30724445 |
| chr3: 71832069-71836653 | chr7: 32108064-32112910 |
| chr3: 75665778-75671067 | chr7: 35294922-35300218 |
| chr3: 75953760-75958308 | chr7: 37953623-37958555 |
| chr3: 87839797-87844563 | chr7: 42265547-42269823 |
| chr3: 9175692-9180189 | chr7: 43150021-43155340 |
| chr4: 100868378-100873994 | chr7: 49811009-49817752 |
| chr4: 105147-109898 | chr7: 53284852-53289192 |
| chr4: 107954556-107959453 | chr7: 54610325-54614558 |
| chr4: 109091039-109096546 | chr7: 56353509-56357798 |
| chr4: 110220971-110226257 | chr7: 6588564-6592957 |
| chr4: 111552966-111557504 | chr7: 6659876-6664695 |
| chr4: 114898356-114902810 | chr7: 70594229-70600382 |
| chr4: 122299568-122304290 | chr7: 71798758-71804768 |
| chr4: 128542032-128546903 | chr7: 72836384-72840815 |
| chr4: 134067163-134072442 | chr7: 73892816-73897110 |
| chr4: 13522063-13528083 | chr7: 749713-754150 |
| chr4: 140199065-140203449 | chr7: 87561343-87566571 |
| chr4: 144618823-144624218 | chr7: 89745893-89751036 |
| chr4: 147557206-147563901 | chr7: 90891568-90898683 |
| chr4: 151502012-151507085 | chr7: 95223504-95228194 |
| chr4: 154707513-154716240 | chr7: 96648222-96654246 |
| chr4: 155661810-155666315 | chr7: 97359133-97365018 |
| chr4: 156127169-156132209 | chr7: 97839637-97844005 |
| chr4: 156678096-156683386 | chr8: 101115923-101120693 |
| chr4: 15777999-15782729 | chr8: 102502479-102506841 |
| chr4: 158141297-158146053 | chr8: 105476673-105481340 |
| chr4: 164262822-164267772 | chr8: 11534768-11540961 |
| chr4: 169797087-169801625 | chr8: 11555853-11569212 |
| chr4: 172731735-172737118 | chr8: 120426399-120431178 |
| chr4: 174420025-174462054 | chr8: 130993922-130998149 |
| chr4: 185935243-185944747 | chr8: 132050204-132056749 |
| chr4: 187217321-187221745 | chr8: 139506796-139511774 |
| chr4: 188914606-188918876 | chr8: 142526186-142531029 |
| chr4: 190935926-190942591 | chr8: 143543446-143548178 |
| chr4: 204378-208892 | chr8: 144806222-144812978 |
| chr4: 24799110-24803902 | chr8: 144988271-145004135 |
| chr4: 25088107-25092510 | chr8: 145101286-145110027 |
| chr4: 41747185-41751811 | chr8: 145923411-145928101 |
| chr4: 41867175-41884964 | chr8: 21642909-21649845 |
| chr4: 46993129-46997872 | chr8: 21903462-21907757 |
| chr4: 47032428-47036940 | chr8: 23560476-23569678 |
| chr4: 4857633-4871173 | chr8: 24810947-24816299 |
| chr4: 54964164-54978202 | chr8: 25898563-25907842 |
| chr4: 5707986-5712495 | chr8: 26719643-26726566 |
| chr4: 57519622-57524703 | chr8: 37820487-37826008 |
| chr4: 5889204-5897116 | chr8: 41422342-41427300 |
| chr4: 66533194-66537620 | chr8: 4846969-4854635 |
| chr4: 680725-685079 | chr8: 49466684-49470959 |
| chr4: 81107888-81121391 | chr8: 50820271-50824860 |
| chr4: 85401831-85425190 | chr8: 53849702-53856426 |
| chr4: 90226715-90231010 | chr8: 55364181-55382186 |
| chr4: 93224349-93229007 | chr8: 57356127-57361415 |
| chr4: 94753787-94758310 | chr8: 65279904-65292946 |
| chr4: 959348-964155 | chr8: 65708991-65713722 |
| chr5: 11382682-11387521 | chr8: 68862585-68866946 |
| chr5: 115695135-115699589 | chr8: 70979874-70986888 |

TABLE 4-continued

| Additional Example CGIs | |
|---|---|
| chr5: 122428677-122433443 | chr8: 72466561-72471561 |
| chr5: 134361093-134388370 | chr8: 85094760-85099247 |
| chr5: 139136876-139141242 | chr8: 86348766-86353196 |
| chr5: 140050060-140055381 | chr8: 87079654-87084046 |
| chr5: 140303713-140309193 | chr8: 97167732-97174022 |
| chr5: 140344106-140348931 | chr8: 9758751-9766748 |
| chr5: 140785448-140790044 | chr8: 98287605-98292404 |
| chr5: 140796758-140801359 | chr8: 99958498-99963438 |
| chr5: 140808495-140814617 | chr8: 99982585-99988983 |
| chr5: 140862528-140866748 | chr9: 100608697-100622192 |
| chr5: 145716290-145727852 | chr9: 102588743-102593303 |
| chr5: 146886751-146891840 | chr9: 104497850-104503076 |
| chr5: 148031473-148036080 | chr9: 112079403-112084905 |
| chr5: 158476379-158480630 | chr9: 115820072-115825416 |
| chr5: 158521907-158526598 | chr9: 120173254-120179496 |
| chr5: 159397005-159401928 | chr9: 120505228-120509642 |
| chr5: 170733170-170746107 | chr9: 122129087-122134214 |
| chr5: 172108283-172113166 | chr9: 123654751-123658972 |
| chr5: 172657050-172674971 | chr9: 124411513-124416193 |
| chr5: 174156681-174161729 | chr9: 124985744-124993086 |
| chr5: 175083005-175087756 | chr9: 126771247-126782953 |
| chr5: 178419226-178424337 | chr9: 129370738-129391231 |
| chr5: 179226284-179231003 | chr9: 131152347-131157923 |
| chr5: 180484155-180488892 | chr9: 132457588-132462017 |
| chr5: 1872908-1889743 | chr9: 133532535-133544394 |
| chr:5 2736954-2759024 | chr9: 134427867-134432491 |
| chr:5 31191953-31196419 | chr9: 135036714-135041978 |
| chr5: 3588645-3605054 | chr9: 135453165-135468240 |
| chr5: 37832672-37837128 | chr9: 136292739-136297236 |
| chr5: 38255826-38261136 | chr9: 137965111-137969727 |
| chr5: 45693395-45698510 | chr9: 139094666-139098993 |
| chr5: 50683454-50688148 | chr9: 139394206-139399040 |
| chr5: 52775789-52779996 | chr9: 139713664-139718441 |
| chr5: 54517055-54529760 | chr9: 16724860-16729273 |
| chr5: 59187047-59191894 | chr9: 17904420-17909488 |
| chr5: 63253045-63259886 | chr9: 19786216-19791288 |
| chr5: 71012918-71017715 | chr9: 21968914-21973190 |
| chr5: 72524204-72531976 | chr9: 22003888-22008229 |
| chr5: 72592148-72597808 | chr9: 23818692-23824135 |
| chr5: 72674121-72680421 | chr9: 23848911-23853522 |
| chr5: 76921888-76938984 | chr9: 32780937-32785625 |
| chr5: 77138543-77149785 | chr9: 35842850-35846850 |
| chr5: 77251833-77256049 | chr9: 36737535-36741782 |
| chr5: 77266351-77270787 | chr9: 37000490-37004957 |
| chr5: 77803754-77808313 | chr9: 77110713-77115927 |
| chr5: 87966636-87972070 | chr9: 79631327-79640169 |
| chr5: 87978879-87987810 | chr9: 86150354-86155777 |
| chr5: 88183225-88187589 | chr9: 91790663-91795611 |
| chr5: 92921488-92926497 | chr9: 95475297-95479708 |
| chr5: 92937796-92942216 | chr9: 96106467-96110992 |
| chr6: 100036542-100041477 | chr9: 96708812-96720186 |
| chr6: 100895008-100917245 | chr9: 967530-975276 |
| chr6: 101844767-101849135 | chr9: 97399287-97404067 |
| chr6: 10379559-10392565 | chr9: 98109365-98114362 |
| chr6: 106427112-106436459 | chrX: 152610776-152615464 |
| chr6: 108483672-108499996 | chrX: 67350651-67354923 |
| chr6: 10879847-10884051 | chrX: 99889300-99893794 |
| chr6: 110297366-110303267 | |
| chr6: 117196090-117200705 | |
| chr6: 117589534-117594279 | |
| chr6: 117867098-117871530 | |
| chr6: 127439554-127443760 | |
| chr6: 134208640-134213218 | |
| chr6: 134636798-134641021 | |
| chr6: 137240316-137247442 | |
| chr6: 1376446-1396170 | |
| chr6: 137807343-137819223 | |
| chr6: 138743349-138747593 | |
| chr6: 150333526-150338278 | |
| chr6: 150356873-150361394 | |
| chr6: 154358587-154363008 | |
| chr6: 168839439-168843699 | |

The invention claimed is:

1. A tiered, multipart method for detecting circulating tumor DNA in a biological sample of a subject, the method comprising:

performing a first analysis of nucleic acid sequence information that was derived from a first assay performed on the biological sample to identify whether the biological sample is not at risk of containing circulating tumor DNA, wherein the first analysis comprises analyzing methylation statuses of fewer than 1000 CGIs of nucleic acids from the biological sample each selected from Tables 1-4, wherein the first analysis achieves at least 80% specificity that the biological sample indicates the subject is not at risk of a disease, and then if the biological sample is not identified as not at risk:

performing an intra-individual analysis for the subject comprising:

obtaining target nucleic acids and reference nucleic acids from the biological sample or an additional biological sample obtained from the subject, wherein the reference nucleic acids comprise genomic DNA from peripheral blood mononuclear cells (PBMCs) or polymorphonuclear cells of the subject;

performing bisulfite conversion of the target nucleic acids and the reference nucleic acids;

selectively amplifying at least 1000 CGIs selected from Tables 1-4 of the bisulfite converted target nucleic acids and reference nucleic acids;

generating a dataset comprising methylation information of the at least 1000 CGIs selected from Tables 1-4 from the target nucleic acids and methylation information of the at least 1000 CGIs selected from Tables 1-4 from the reference nucleic acids;

using a computer processor, combining the methylation information of the at least 1000 CGIs selected from Tables 1-4 from the target nucleic acids and the methylation information of the at least 1000 CGIs selected from Tables 1-4 from the reference nucleic acids to generate background-corrected methylation information of the at least 1000 CGIs selected from Tables 1-4 for the target nucleic acids;

performing a second analysis comprising analyzing the background-corrected methylation information of the at least 1000 CGIs selected from Tables 1-4 to detect the presence of the circulating tumor DNA in the biological sample, wherein the second analysis achieves at least a 70% positive predictive value; and performing a third analysis comprising determining a longitudinal change between the background-corrected methylation information of the second analysis and methylation information of a further additional sample obtained from the subject.

2. The method of claim 1, wherein the biological sample or the additional biological sample is a blood sample of the subject.

3. The method of claim 1, wherein obtaining target nucleic acids and reference nucleic acids comprises fractionating the biological sample or the additional sample, wherein the target nucleic acids are obtained from a first fraction of the biological sample or the additional biological sample, and wherein the reference nucleic acids are obtained from a second fraction of the biological sample or the additional biological sample.

4. The method of claim 1, wherein the target nucleic acids comprise cell free DNA (cfDNA).

5. The method of claim 1, wherein combining the methylation information from the target nucleic acids and the methylation information from the reference nucleic acids comprises:

aligning the methylation information from the target nucleic acids and the methylation information from the reference nucleic acids; and determining a difference between the methylation information from the target nucleic acids and the methylation information from the reference nucleic acids.

6. The method of claim 1, wherein selectively amplifying the at least 1000 CGIs selected from Tables 1-4 of the bisulfite converted target nucleic acids and reference nucleic acids comprises performing hybrid capture of both the bisulfite converted target nucleic acids and reference nucleic acids.

7. The method of claim 6, wherein performing the hybrid capture comprises providing hybrid capture probe sets designed to hybridize with sequences comprising one or more CGIs of the at least 1000 CGIs selected from Tables 1-4 of both the bisulfite converted target nucleic acids and reference nucleic acids.

8. The method of claim 1, further comprising providing one of a surgical intervention, therapeutic intervention, or lifestyle intervention to the subject subsequent to having identified presence of circulating tumor DNA in the biological sample or further additional sample.

9. A tiered, multipart method for detecting circulating tumor DNA in a blood sample of a subject, the method comprising:
   performing a first analysis of nucleic acid sequence information that was derived from a first assay performed on the blood sample to identify whether the blood sample is not at risk of containing circulating tumor DNA, wherein the first analysis comprises analyzing methylation statuses of fewer than 1000 CGIs of nucleic acids from the biological sample each selected from Tables 1-4, wherein the first analysis achieves at least 80% specificity that the biological sample indicates the subject is not at risk of a disease,
and then if the blood sample is not identified as not at risk:
   performing an intra-individual analysis for the subject comprising:
      obtaining target nucleic acids and reference nucleic acids from the blood sample or an additional blood sample obtained from the subject, wherein the reference nucleic acids comprise genomic DNA from peripheral blood mononuclear cells (PBMCs) or polymorphonuclear cells of the subject;
      performing bisulfite conversion of the target nucleic acids and the reference nucleic acids;
      selectively amplifying at least 1000 CGIs selected from Tables 1-4 of the bisulfite converted target nucleic acids and reference nucleic acids;
      generating a dataset comprising methylation information of the at least 1000 CGIs selected from Tables 1-4 from the target nucleic acids and methylation information of the at least 1000 CGIs selected from Tables 1-4 from the reference nucleic acids;
      using a computer processor, combining the methylation information of the at least 1000 CGIs selected from Tables 1-4 from the target nucleic acids and the methylation information of the at least 1000 CGIs selected from Tables 1-4 from the reference nucleic acids to generate background-corrected methylation information of the at least 1000 CGIs selected from Tables 1-4 for the target nucleic acids; and
   performing a second analysis comprising analyzing the background-corrected methylation information of the at least 1000 CGIs selected from Tables 1-4 to detect the presence of the circulating tumor DNA in the blood sample, wherein the second analysis achieves at least a 70% positive predictive value, thereby diagnosing whether the subject is at risk of the disease.

10. The method of claim 9, wherein the disease is an early stage of cancer.

* * * * *